US012310950B2

(12) United States Patent
Powala et al.

(10) Patent No.: US 12,310,950 B2
(45) Date of Patent: May 27, 2025

(54) FORMULATIONS OF PYRROLOPYRIDINE-ANILINE COMPOUNDS

(71) Applicant: NFLECTION THERAPEUTICS, INC., Boston, MA (US)

(72) Inventors: Christopher Powala, Wayne, PA (US); Elaine Morefield, Boston, MA (US); Charles Rodney Greenaway Evans, Godalming (GB); Cameron Robert Stevenson, Guildford (GB); Brendan Philip Brady, Guildford (GB)

(73) Assignee: NFLECTION THERAPEUTICS, INC., Boston, MA (US)

( * ) Notice: Subject to any disclaimer, the term of this patent is extended or adjusted under 35 U.S.C. 154(b) by 168 days.

(21) Appl. No.: 17/992,859

(22) Filed: Nov. 22, 2022

(65) Prior Publication Data

US 2023/0255945 A1 Aug. 17, 2023

Related U.S. Application Data

(60) Provisional application No. 63/282,395, filed on Nov. 23, 2021.

(51) Int. Cl.
| | |
|---|---|
| *A61K 31/437* | (2006.01) |
| *A61K 9/06* | (2006.01) |
| *A61K 31/381* | (2006.01) |
| *A61K 47/10* | (2017.01) |
| *A61K 47/38* | (2006.01) |
| *A61P 17/00* | (2006.01) |
| *B64D 1/12* | (2006.01) |
| *B64U 101/60* | (2023.01) |

(52) U.S. Cl.
CPC .............. *A61K 31/437* (2013.01); *A61K 9/06* (2013.01); *A61K 31/381* (2013.01); *A61K 47/10* (2013.01); *A61K 47/38* (2013.01); *A61P 17/00* (2018.01); *B64D 1/12* (2013.01); *B64U 2101/60* (2023.01)

(58) Field of Classification Search
None
See application file for complete search history.

(56) References Cited

U.S. PATENT DOCUMENTS

| | | | |
|---|---|---|---|
| 7,803,839 | B2 | 9/2010 | Aay et al. |
| 7,915,250 | B2 | 3/2011 | Aay et al. |
| 8,211,921 | B2 | 7/2012 | Blake et al. |
| 8,252,838 | B2 | 8/2012 | Kisak et al. |
| 8,470,821 | B2 | 6/2013 | Ibrahim et al. |
| 11,161,845 | B2 | 11/2021 | Kincaid et al. |
| 2005/0202001 | A1 | 9/2005 | Koo et al. |
| 2009/0082328 | A1 | 3/2009 | Li et al. |
| 2010/0075947 | A1 | 3/2010 | Aftab et al. |
| 2010/0215579 | A1 | 8/2010 | Kung et al. |
| 2014/0213598 | A1 | 7/2014 | Liu et al. |
| 2015/0023915 | A1 | 1/2015 | Morrison et al. |
| 2015/0335644 | A1 | 11/2015 | Seykora |
| 2018/0256570 | A1 | 9/2018 | Peterson et al. |
| 2021/0275495 | A1 | 9/2021 | Vivier |
| 2022/0033399 | A1 | 2/2022 | Kincaid et al. |
| 2022/0087989 | A1 | 3/2022 | Tsai et al. |
| 2022/0110862 | A1 | 4/2022 | Powala et al. |
| 2022/0204486 | A1 | 6/2022 | Kincaid et al. |
| 2023/0013227 | A1 | 1/2023 | Kincaid et al. |

FOREIGN PATENT DOCUMENTS

| | | |
|---|---|---|
| WO | WO-1999001421 A1 | 1/1999 |
| WO | WO-2000042029 A1 | 7/2000 |
| WO | WO-2007002433 A1 | 1/2007 |
| WO | WO-2007088345 A1 | 8/2007 |
| WO | WO-2008021389 A2 | 2/2008 |
| WO | WO-2008067481 A1 | 6/2008 |

(Continued)

OTHER PUBLICATIONS

Akinleye et al., "MEK and the Inhibitors: From Bench to Bedside," Journal of Hematology & Oncology, 2013, 6(27), 11 pages.
International Search Report and Written Opinion for International PCT Application No. PCT/US2018/033547, mailed Aug. 9, 2018, 10 pages.
International Search Report and Written Opinion for International PCT Application No. PCT/US2019/000067, mailed Apr. 24, 2020, 11 pages.
International Search Report and Written Opinion for International PCT Application No. PCT/US2019/000066, mailed Feb. 7, 2020, 16 pages.

(Continued)

*Primary Examiner* — Zinna Northington Davis
(74) *Attorney, Agent, or Firm* — Mintz Levin Cohn Ferris Glovsky & Popeo, P.C.

(57) ABSTRACT

Provided herein are topical formulations including a compound of formula (I) and methods of using these topical formulations for the treatment of skin diseases, wherein the topical formulations include non-aqueous gel, aqueous gel, and emulsion-based formulations; and the compound of formula (I) is represented by

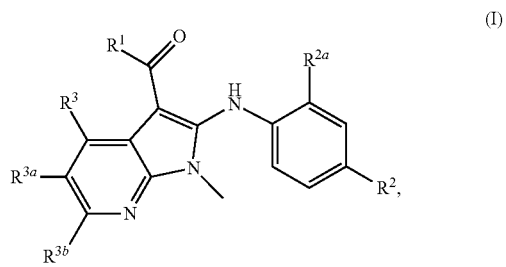

wherein $R^1$, $R^2$, $R^{2a}$, $R^3$, $R^{3a}$, and $R^{3b}$ are as defined and described herein.

25 Claims, 10 Drawing Sheets

(56) References Cited

FOREIGN PATENT DOCUMENTS

| WO | WO-2018213810 A1 | 11/2018 |
| WO | WO-2019139970 A1 | 7/2019 |
| WO | WO-2020106303 A1 | 5/2020 |
| WO | WO-2020106304 A1 | 5/2020 |
| WO | WO-2020106305 A1 | 5/2020 |
| WO | WO-2020106307 A1 | 5/2020 |

OTHER PUBLICATIONS

International Search Report and Written Opinion for International PCT Application No. PCT/US2019/000065, mailed Apr. 24, 2020, 10 pages.
International Search Report and Written Opinion for International PCT Application No. PCT/US2019/000069, mailed Mar. 20, 2020, 9 pages.
International Search Report and Written Opinion for International application No. PCT/US2022/050794, mailed Apr. 24, 2023, 13 pages.
PUBCHEM-CID; 131273078, Create Date; Oct. 9, 2017, pp. 1-7, p. 2, structure.
PUBCHEM-CID; 69072648, Create Date; Nov. 30, 2012, pp. 1-9, p. 2, structure.

FORMULATIONS OF PYRROLOPYRIDINE-ANILINE COMPOUNDS

CROSS-REFERENCES TO RELATED APPLICATIONS

This application claims priority to U.S. Provisional Application No. 63/282,395 filed Nov. 23, 2021, which is incorporated herein in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE DISCLOSURE

Neurofibromatosis type 1 (NF1) occurs in approximately 1:3, 500 births, and is one of the most common autosomal dominant single-gene disorders affecting neurological function in humans. Clinically, NF1 disease is characterized by the presence of benign peripheral nerve tumors, called neurofibromas, involving Schwann cells with biallelic mutations in the NF1 gene, as well as other tumor and non-tumor manifestations. See Jousma et al. Pediatr. Blood Cancer 62: 1709-1716, 2015. NF1 is associated with several dermal disorders, including dermal neurofibromas; plexiform neurofibromas; café au lait spots; and axillary and inguinal freckling. Dermal neurofibromas occur in over 95% of NF1 patients, and can appear anywhere on the body, causing itching, irritation, infection, physical pain, and disfigurement. Moreover, dermal neurofibromas are associated with social isolation and anxiety.

NF1 is caused by one or more germ line mutations in NF1, a gene that inactivates the RAS pathway. Because the NF1 gene encodes a Ras-GAP protein, NF1 loss results in high Ras-GTP. Therefore, NF1 research has focused intensively on testing inhibitors in the Ras signaling pathway, including the Ras-MAPK cascade. See Jousma et al. Pediatr. Blood Cancer 62: 1709-1716, 2015. Four distinct MAPK cascades have been identified and named according to their MAPK module. See Akinleye et al. Journal of Hematology & Oncology 6:27, 2013. MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras, and thus provide a strong rationale for targeting MEK in the treatment of NF1. See Rice et al. Medicinal Chemistry Letters 3:416-421, 2012.

Currently available MEK inhibitors are designed to have oral bioavailability for systemic delivery, and are associated with significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown side effects with prolonged high-dose administration of MEK inhibitors. See Huang et al. J. Ocul. Pharmacol. Ther. 25:519-530, 2009. For example, PD0325901, a MEK inhibitor currently in clinical trials, has exhibited neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that inhibit MEK to treat NF1 associated dermal neurofibromas, which limit these serious side effects.

Benign cutaneous tumors of the vascular, keratinocytic, and melanocytic compartments often occur at birth or during childhood. These lesions, referred in this application as "birthmarks", can cause cosmetic distress, disfigurement and social anxiety. In some cases, these lesions can predispose individuals to functional impairment or future malignancies. These birthmarks can be sporadic or arise as part of an underlying neurocutaneous syndrome.

Vascular birthmarks include, for example port wine stain/capillary malformation, angiomas, lobular capillary hemangiomas, arteriovascular malformation, lymphatic malformation, vascular malformation, hemangiomas, and other angioma. Keratinocytic nevi refers to Keratinocytic epidermal nevi and nevi sebacei. Melanocytic nevi (commonly known as moles) include, for example congenital nevi, multiple lentigines (which can occur in syndromes such as LEOPARD), ephiledes (freckles), and nevus spiilus.

Neurocutaneous syndromes, also referred to as birthmarks, such as port-wine stains, are associated with congenital low-flow vascular malformations (capillary malformation) in the skin which, if left untreated, can hypertrophy and develop nodularity (Minkis, K. et al, *Lasers Surg Med*. (2009) 41(6): pp 423-426). Laser therapy is typically used for treatment of port-wine stains, but often without full resolution. Epidermal nevi are common cutaneous mosaic disorders, subdivided into keratinocytic and organoid nevi. Organoid nevi include nevus sebaceus (NS). Immunolabelling of NS is reportedly associated with increased phosphorylated ERK staining (Aslam, A, et al., *Clinical and Experimental Dermatology* (2014) 39: pp 1-6). Non-organoid keratinocytic epidermal nevus (KEN) is characterized by benign congenital hyperpigmented skin lesions. Epidermal nevi with localized epidermal thickening are present at birth or become visible during childhood. Other cutaneous disorders that also occur in childhood birthmarks include nevus cellular nevus, lobulary capillary hemangioma, congenital nevi, ephiledes (freckles), multiple lentigines (which can occur in multiple syndromes including LEOPARD syndrome), capillary angioma, nevus spilus, arterio-venous malformations, lymphatic malformations, and congenital melanocytic nevus. Lentigines can occur in childhood (in syndromes such as LEOPARD syndrome), which has mutations that activate RAS/MAPK pathway, as well as can be acquired in adults. In some cases birthmarks are not amenable to surgical excision and/or laser treatment. In some cases birthmarks, when untreated, can progress to lesions and/or proliferative skin conditions.

Modulation of ERK/MEK pathways may have a therapeutic effect on birthmarks. RAS mutations have been reported in mosaic RASopathies i.e. non-organoid KEN, and sebaceous nevus (Farschtschi S, et al., *BMC Medical Genetics*. (2015); 16: pp 6; and Sun, B. K. et. Al, Journal of Investigative Dermatology, (2013); 3: pp 824-827). Thus, inhibition of Ras signaling pathway, including the Ras-MAPK cascade, may be useful in treating birthmarks.

Four distinct MAPK cascades have been identified and named according to their MAPK module. See Akinleye et al. *Journal of Hematology & Oncology* 6:27, 2013. MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras (Rice et al. *Medicinal Chemistry Letters* 3:416-421, 2012), and thus provide a rationale for targeting MEK in the treatment of birthmarks.

Currently available MEK pathway inhibitors are designed to have oral bioavailability for systemic delivery, but are associated with one or more significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown one or more side effects with prolonged high-dose administration of MEK inhibitors. (Huang et al. *J. Ocul. Pharmacol. Ther.* 25:519-530, 2009). For example, PD0325901, a clinically-tested MEK inhibitor, has exhibited one or more neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that treat birthmarks and also limit one or more side effects associated with systemic exposure to MEK/ERK pathway inhibitors.

Topical formulations including a MEK inhibitor and ethanol in an amount of >40% by weight of the base formulation are disclosed in International Application No. PCT/US2019/000066. While having good skin permeability, the formulations are found to cause certain degree of unwanted dermal irritation.

In view of the above, there is urgent need for the development of a topical formulation including MEK inhibitors that can be delivered topically with reduced dermal irritation to treat skin disorders such as MEK-inhibitor responsive dermal disorders or MEK-mediated dermal disorders, and birthmarks.

BRIEF SUMMARY OF THE DISCLOSURE

In one aspect, the present disclosure provides a gel formulation useful for the treatment of skin disorders, the gel formulation including:
a) a compound represented by formula (I)

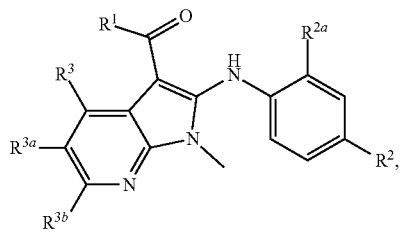

or a stereoisomer, a mixture of stereoisomers, and/or a pharmaceutically acceptable salt thereof, wherein $R^1$, $R^2$, $R^{2a}$, $R^3$, $R^{3a}$, and $R^{3b}$ are as defined and described herein;

b) a polyethylene glycol, an antioxidant, and optionally a preservative;
c) one or more organic solvents; and
d) a gelling agent,
wherein:
the polyethylene glycol has an average molecular weight of from about 200 Da to about 900 Da and is present in an amount of at least about 30% by weight;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof,
the gelling agent is hydroxypropyl cellulose or polyvinylpyrrolidone, each of which has an average molecular weight of from about 80,000 Da to about 1,700,000 Da;
the gel formulation has a pH value of no more than about 7; and
water, when present, is no more than about 5% by weight.

In some embodiments, the compound of formula (I) is represented by formula (Ib):

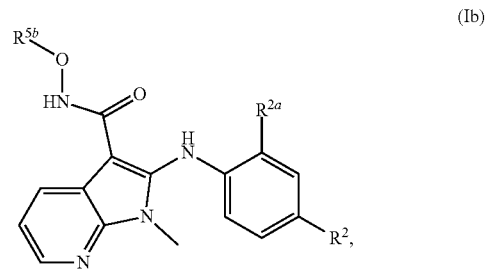

or a stereoisomer, a mixture of stereoisomers, and/or a pharmaceutically acceptable salt thereof, wherein $R^2$, $R^{2a}$, and $R^{5b}$ are as defined and described herein.

In another aspect, the present disclosure provides a gel formulation useful for the treatment of skin disorders, the gel formulation including:
a) a compound represented by formula (II):

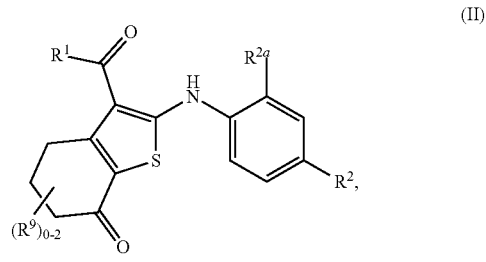

or a stereoisomer, a mixture of stereoisomers, and/or a pharmaceutically acceptable salt thereof, wherein $R^1$, $R^2$, $R^{2a}$, and $R^9$ are as defined and described herein;
b) a polyethylene glycol, an antioxidant, and optionally a preservative;
c) one or more organic solvents; and
d) a gelling agent,
wherein:
the polyethylene glycol has an average molecular weight of from about 200 Da to about 900 Da and is present in an amount of at least about 30% by weight;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof, the gelling agent is hydroxypropyl cellulose or polyvinylpyrrolidone, each of which has an average molecular weight of from about 80,000 Da to about 1,700,000 Da;

the gel formulation has a pH value of no more than about 7; and water, when present, is no more than about 5% by weight.

In some embodiments, the compound of formula (II) is represented by formula (IIb):

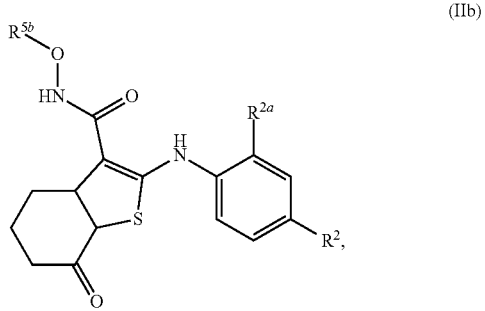

(IIb)

or a stereoisomer, a mixture of stereoisomers, and/or a pharmaceutically acceptable salt thereof, wherein $R^2$, $R^{2a}$, and $R^{5b}$ are as defined and described herein.

In another aspect, the present disclosure provides an aqueous gel formulation, including a compound of formula (I), useful for the treatment of skin disorders, wherein the aqueous gel formulation is as defined and described herein.

In yet another aspect, the present disclosure provides an emulsion-based formulation, including a compound of formula (I), useful for the treatment of skin disorders, wherein the emulsion-based formulation is as defined and described herein.

In a further aspect, the present disclosure provides a method of treating a skin disorder. The method includes administering a topical formulation (e.g., a non-aqueous gel, an aqueous gel, or an emulsion-based formulation) including a compound of formula (I) or (II), thereby treating the skin disease, wherein the topical formulation and the compound of formula (I) or (II) are as defined and described herein.

BRIEF DESCRIPTION OF THE DRAWINGS

FIG. 6A: Substantial tumor regression and tumor suppression on the treated side as compared to the untreated side of the mouse; and FIG. 6B: 65% or greater suppression of p-ERK levels in mouse skin treated with Compound 1.003.

DETAILED DESCRIPTION OF THE DISCLOSURE

I. General

Figure 1:
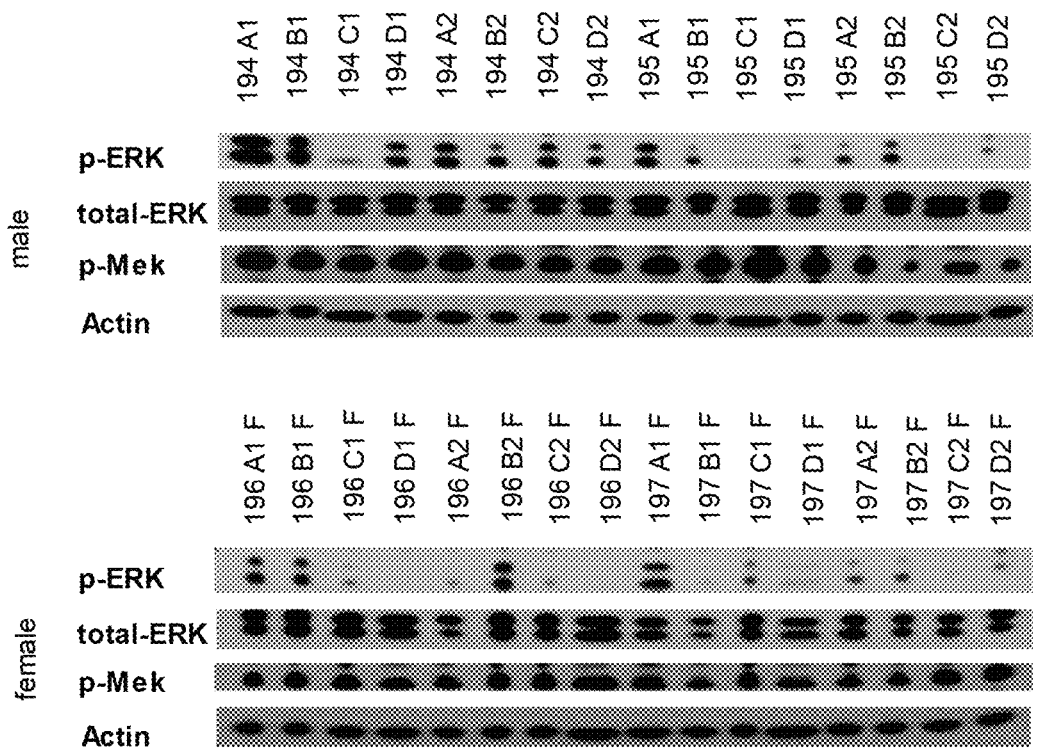
FIG. 1 shows dose dependent suppression of p-ERK by Compound 1.003 in gel formulation (NA-1a) in minipig skin. A: vehicle (NA-1a without Compound 1.003) at 30 uL/cm$^2$; B: NA-1a-0.01% at 10 uL/cm$^2$; C: NA-1a-0.1% at 30 uL/cm$^2$; and D: NA-1a-0.1% at 10 uL/cm$^2$.

Provided herein are topical formulations (e.g., non-aqueous gel, aqueous gel, and/or emulsion-based formulations) including compounds of formula (I) or (II) as MEK inhibitors and methods of using these topical formulations for the treatment of skin diseases. The topical formulations are administered topically, thereby treating the skin diseases. The skin diseases are MEK-inhibitor responsive dermal disorders or diseases, MEK-mediated dermal disorder or disease, birthmarks, or skin cancers.

II. Definition

The abbreviations used herein have their conventional meaning within the chemical and biological arts.

Where substituent groups are specified by their conventional chemical formulae, written from left to right, they equally encompass the substituents that would result from writing the structure from right to left, e.g., —CH$_2$O— is meant to include —OCH$_2$—.

Unless specifically indicated otherwise, compounds of formula (I) are 1-methyl-1H-pyrrolo[2,3-b]pyridine compounds, where the nitrogen (N) atom (with "*") of the pyrrolo[2,3-b]pyridine core is substituted with methyl:

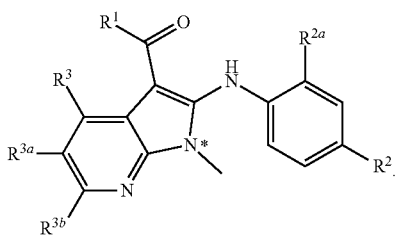

(I)

"Alkyl" refers to a straight or branched, saturated, aliphatic radical having the number of carbon atoms indicated (i.e., $C_1$-$C_6$ means one to six carbons). Alkyl can include any number of carbons, such as $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

"Alkylene" refers to a straight or branched, saturated, aliphatic radical having the number of carbon atoms indicated (i.e., $C_1$-$C_6$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkenyl" refers to a straight chain or branched hydrocarbon having at least 2 carbon atoms and at least one double bond and having the number of carbon atom indicated (i.e., $C_2$-$C_6$ means to two to six carbons). Alkenyl can include any number of carbons, such as $C_2$, $C_2$-$C_3$, $C_2$-$C_4$, $C_2$-$C_5$, $C_2$-$C_6$, $C_2$-$C_7$, $C_2$-$C_8$, $C_2$-$C_9$, $C_2$-$C_{10}$, $C_3$, $C_3$-$C_4$, $C_3$-$C_5$, $C_3$-$C_6$, $C_4$, $C_4$-$C_5$, $C_4$-$C_6$, $C_5$, $C_5$-$C_6$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkynyl" refers to either a straight chain or branched hydrocarbon having at least 2 carbon atoms and at least one triple bond and having the number of carbon atom indicated (i.e., $C_2$-$C_6$ means to two to six carbons). Alkynyl can include any number of carbons, such as $C_2$, $C_2$-$C_3$, $C_2$-$C_4$, $C_2$-$C_5$, $C_2$-$C_6$, $C_2$-$C_7$, $C_2$-$C_8$, $C_2$-$C_9$, $C_2$-$C_{10}$, $C_3$, $C_3$-$C_4$, $C_3$-$C_5$, $C_3$-$C_6$, $C_4$, $C_4$-$C_5$, $C_4$-$C_6$, $C_5$, $C_5$-$C_6$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_3$-$C_6$, $C_4$-$C_6$, $C_5$-$C_6$, $C_3$-$C_8$, $C_4$-$C_8$, $C_5$-$C_8$, $C_6$-$C_8$, $C_3$-$C_9$, $C_3$-$C_{10}$, $C_3$-$C_{11}$, and $C_3$-$C_{12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_3$-$C_8$ cycloalkyl, exemplary groups include, but are not limited to cyclopropyl, cyclobutyl, cyclopentyl, cyclohexyl, cycloheptyl and cyclooctyl.

"Cycloalkylalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_1$-$C_6$, $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. The cycloalkyl component is as defined above. Exemplary cycloalkyl-alkyl groups include, but are not limited to, cyclopropylmethyl, cyclobutylmethyl, cyclopentylmethyl and cyclohexylmethyl.

"Alkoxy" refers to an alkyl group having an oxygen atom that connects the alkyl group to the point of attachment: alkyl-O—. Alkoxy groups can have any suitable number of carbon atoms, such as $C_1$-$C_6$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Hydroxyalkyl" refers to an alkyl group, as defined above, where at least one of the hydrogen atoms is replaced with a hydroxy group. As for the alkyl group, a hydroxyalkyl group can have any suitable number of carbon atoms, such as $C_1$-$C_6$. As for the hydroxy group, a hydroxyalkyl group can have 1, 2, 3, or 4 hydroxy groups. "Monohydroxyalkyl" refers to a hydroxyalkyl group having one hydroxy group. "Dihydroxyalkyl" refers to a hydroxyalkyl group having two hydroxy groups. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_1$-$C_2$, $C_1$-$C_3$, $C_1$-$C_4$, $C_1$-$C_5$, $C_1$-$C_6$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. The alkoxy component is as defined above. Examples of the alkoxy-alkyl group include, but are not limited to, 2-ethoxyethyl and methoxymethyl.

"Halogen" or "halo" refers to fluoro, chloro, bromo, or iodo.

"Alcohol" refers to an alkyl group (e.g., $C_{2-6}$ alkyl), as defined within, having a hydroxy group attached to a carbon of the chain. For example, alcohols useful in the present disclosure include, but are not limited to, ethanol, propanol, isopropanol, butanol, isobutanol, tert-butanol, pentanol and hexanol, among others. Alcohols useful in the present disclosure are fully saturated. In some embodiments, the alcohol is $C_{2-6}$ alcohol.

"Alkylene glycol" refers to a compound having the formula of H—[O-alkylene]-OH, wherein the alkylene group has 2 to 6, 2 to 4, or 2 to 3 carbon atoms. In some embodiments, the alkylene glycol is a $C_{2-6}$ alkylene glycol. In some embodiments, the $C_{2-6}$ alkylene glycol is propylene glycol (1,2-propanediol).

"Di-alkylene glycol" refers to a compound having the formula of HO-(alkylene-O)$_2$—H, wherein the alkylene group has 2 to 6, 2 to 4, or 2 to 3 carbon atoms. In some embodiments, the di-alkylene glycol is a di-($C_{2-6}$ alkylene) glycol. In some embodiments, the di-($C_{2-6}$ alkylene) glycol is dipropylene glycol. Dipropylene glycol can include one or more isomers, for example 4-oxa-2,6-heptandiol, 2-(2-hydroxy-propoxy)-propan-1-ol, 2-(2-hydroxy-1-methyl-ethoxy)-propan-1-ol, and 3,3'-oxybis(propan-1-ol).

"Polyethylene glycol" refers to a polymer having the formula of HO—(CH$_2$CH$_2$O)$_n$—OH with variations in subscript "n". Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present disclosure can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to PEG200, PEG300, PEG400, PEG600, and PEG900, PEG-1500. The number following the "PEG" in the name refers to the average molecular weight of the polymer.

"Super refined" excipients refer to excipients that are stripped of their impurities. Super refining removes polar impurities (including primary and secondary oxidation products) from an excipient without altering its chemical composition. The removal of these impurities helps to reduce excipient-Active Pharmaceutical Ingredient (API) interaction and subsequent API degradation, thereby maintaining both the stability of the drug and the final formulation. In addition, the removal of these impurities can minimize cellular irritation, ideal for various drug administration routes. Super Refined excipients of the present disclosure include a super refined PEG-400 and a super refined propylene glycol.

"Super refined PEG-400" or "S.R. PEG-400" refers to a high purity grade of polyethylene glycol 400 that can enhance drug active and formulation stability. S.R. PEG-400 meets or exceeds requirements of one or more of, for example FDA-IIG listed, the Japanese Pharmacopoeia (JP), the European Pharmacopoeia (PhEur), the United States Pharmacopeia (USP), the National Formulary (NF), and/or the United States Pharmacopeia-National Formulary (USP-NF). In some embodiments, S.R. PEG-400 has a purity of no less than about 99.5%, 99.6%, 99.7%, 99.8%, or 99.9%. In some embodiments, S.R. PEG-400 has a purity of no less than about 99.8% or 99.9%.

"Super refined propylene glycol" or "S.R. propylene glycol" refers to a highly purified propylene glycol that can enhance drug activity and composition (or formulation) stability. S.R. propylene glycol meets or exceeds requirements of one or more of, for example FDA-IIG listed, the Japanese Pharmacopoeia (JP), the European Pharmacopoeia (PhEur), the United States Pharmacopeia (USP), the National Formulary (NF), and/or the United States Pharmacopeia-National Formulary (USP-NF). In some embodiments, S.R. propylene glycol has a purity of no less than about 99.5%, 99.6%, 99.7%, 99.8%, or 99.9%. In some embodiments, S.R. propylene glycol has a purity of no less than about 99.8% or 99.9%.

The product sold under the name Transcutol® is represented by the formula: $CH_3CH_2OCH_2CH_2OCH_2CH_2OH$, which has a preferred IUPAC name of 2-(2-ethoxyethoxy) ethanol. Other names for 2-(2-ethoxyethoxy)ethanol includes diethylene glycol monoethyl ether (abbreviated as DGME or DEGEE), diethylene glycol ethyl ether (abbreviated as DEGEE), ethyldiglycol, etc. The product sold under the name Transcutol® includes Transcutol® P and Transcutol® HP.

The product sold under the name Transcutol® P refers to a high purity grade of 2-(2-ethoxyethoxy)ethanol. The product sold under the name Transcutol® HP refers to a highly purified grade of 2-(2-ethoxyethoxy)ethanol that can enhance drug activity and composition (or formulation) stability. In some embodiments, the product sold under the name Transcutol® P or HP has a purity of no less than about 99.5%, 99.6%, 99.7%, 99.8%, or 99.9%. In some embodiments, the product sold under the name Transcutol® P or HP has a purity of no less than about 99.8% or 99.9%. In some embodiments, the product sold under the name Transcutol® HP has a purity of about 99.90%.

"Fatty acid" refers to a carboxylic acid with a long aliphatic chain, which is straight or branched and saturated or unsaturated. Most naturally occurring fatty acids have an unbranched chain of an even number of carbon atoms, from 8 to 24.

"Saturated fatty acid" refers to a fatty acid having an alkyl chain. The alkyl component is as defined above. The saturated fatty acid having 8-24 carbon atoms includes caprylic acid, pelargonic acid, capric acid, neodecanoic acid, undecylic acid, lauric acid, tridecylic acid, myristic acid, pentadecylic acid, palmitic acid, margaric acid, stearic acid, isostearic acid, nonadecylic acid, arachidic acid, heneicosylic acid, behenic acid, tricosylic acid, and lignoceric acid. In some embodiments, the saturated fatty acid having 8-18 carbon atoms is caprylic acid, pelargonic acid, capric acid, neodecanoic acid, undecylic acid, lauric acid, tridecylic acid, myristic acid, pentadecylic acid, palmitic acid, margaric acid, stearic acid, or isostearic acid.

"Unsaturated fatty acid" refers to a carboxylic acid with a long aliphatic chain having one or more C=C double bonds. The C=C double bonds can give either cis or trans isomers. A cis configuration means that the two hydrogen atoms adjacent to the double bond lie on the same side of the chain. A trans configuration, by contrast, means that the adjacent two hydrogen atoms lie on opposite sides of the chain. Unsaturated fatty acid can include 10 to 24 carbons. Unsaturated fatty acids useful in the present disclosure include mono-unsaturated fatty acids and di-unsaturated fatty acids.

Mono-unsaturated fatty acids include, but are not limited to, caproleic acid, lauroleic acid, myristoleic acid, palmitoleic acid, sapienic acid, oleic acid, elaidic acid, vaccenic acid, gadoleic acid, eicosenoic acid, erucic acid, brassidic acid, and nervonic acid. In some embodiments, the unsaturated fatty acid having 10-18 carbon atoms is caproleic acid, lauroleic acid, myristoleic acid, palmitoleic acid, sapienic acid, oleic acid, elaidic acid, vaccenic acid, linoleic acid, alpha-linolenic acid, gamma-linolenic acid, columbinic acid, pinolenic acid, or stearidonic acid.

Di-unsaturated fatty acids include, but are not limited to, linoleic acid, eicosadienoic acid, and docosadienoic acid. The di-unsaturated fatty acid having 18 carbon atoms is linoleic acid.

"Fatty alcohol" refers to a primary alcohol with a long aliphatic chain, which is either saturated or unsaturated. The fatty alcohol can also range from as few as 4-6 carbons to as many as 22-26 carbons. The fatty alcohol includes, but is not limited to, capric alcohol, undecyl alcohol, lauryl alcohol, tridecyl alcohol, myristyl alcohol, pentadecyl alcohol, cetyl alcohol, palmitoleyl alcohol (unsaturated), heptadecyl alcohol, stearyl alcohol, oleyl alcohol (unsaturated), nonadecyl alcohol, arachidyl alcohol, heneicosyl alcohol, behenyl alcohol, erucyl alcohol (unsaturated), and lignoceryl alcohol.

"Fatty ester" or "fatty acid ester" refers to a type of ester that results from the combination of a fatty acid with an alcohol. When the alcohol is a polyethylene glycol, the fatty ester refers to a polyoxyethylene fatty ester or a polyoxyethylene fatty acid ester.

"Fatty ether" refers to a type of ether that results from the combination of a fatty alcohol with a second alcohol. When the second alcohol is a polyethylene glycol, the fatty ether refers to a polyoxyethylene fatty ether.

"Polysorbate" refers a type of fatty ester that results from an ethoxylated sorbitan (a polyethylene glycol derivative of sorbitol) with a fatty acid. Examples of polysorbates include Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), and Polysorbate 80 (polyoxyethylene (20) sorbitan monooleate). Suitable polysorbates include, but are not limited to the Tween® series, which includes Tween® 20 (polyoxyethylene (20) sorbitan monolaurate), Tween® 40 (polyoxyethylene (20) sorbitan monopalmitate), Tween® 60 (polyoxyethylene (20) sorbitan monostearate), and Tween® 80 (polyoxyethylene (20) sorbitan monooleate). Other suitable polysorbates include the ones listed in R. C. Rowe and P. J. Shesky, Handbook of pharmaceutical excipients, (2006), 5th ed., which is incorporated herein by reference in its entirety.

"Poloxamer" refers to a nonionic triblock copolymer consisting of a central hydrophobic block of polypropylene glycol flanked by two hydrophilic blocks of polyethylene glycol (PEG). Poloxamer 407 refers to a poloxamer wherein the approximate lengths of the two PEG blocks is 101 repeat units while the approximate length of the propylene glycol block is 56 repeat units. Poloxamer 407 is also known by the BASF trade name Pluronic™ F127 or by the Croda trade name Synperonic™ PE/F 127.

"Glyceride" refers to a fatty ester when the alcohol component is glycerol. The glyceryl fatty esters (or glycerides) produced can be monoglycerides, diglycerides, or triglycerides. "Monoglyceride" is glyceride consisting of one fatty acid chain covalently bonded to a glycerol molecule through an ester linkage. "Diglyceride" is glyceride consisting of two fatty acid chains covalently bonded to a glycerol molecule through ester linkages. "Triglyceride" is glyceride consisting of three fatty acid chains covalently bonded to a glycerol molecule through ester linkages.

"Cyclomethicone" refers to a cyclic polydimethylsiloxane polymer. Examples of cyclomethicones include decamethylcyclopentasiloxane ($D_5$), an organosilicon compound with the formula $[(CH_3)_2SiO]_5$.

"Dimethicone", also known as polydimethylsiloxane (PDMS) or dimethylpolysiloxane, belongs to a group of polymeric organosilicon compounds that are commonly referred to as silicones. Dimethicone is one of several types of silicone oil (polymerized siloxane).

"Salt" refers to acid or base salts of the compounds of the present disclosure. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomer" refers to compounds with the same chemical formula but which are structurally distinguishable. Certain compounds of the present disclosure possess asymmetric carbon atoms (optical centers) or double bonds; the racemates, diastereomers, geometric isomers and individual isomers are all intended to be encompassed within the scope of the present disclosure.

"Tautomer" refers to one of two or more structural isomers which exist in equilibrium and which are readily converted from one form to another.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound that is complexed to a water molecule. The compounds of the present disclosure can be complexed with 12 water molecule or from 1 to 10 water molecules.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present disclosure include, but are not limited to, binders, fillers, disintegrants, lubricants, coatings, sweeteners, flavors and colors. Pharmaceutical excipients useful in the present disclosure for transdermal/topical delivery include, but are not limited to, enhancers, solubilizers, antioxidants, plasticizers, thickeners, polymers, and pressure sensitive adhesives. One of skill in the art will recognize that other pharmaceutical excipients are useful in the present disclosure.

For any one of topical formulations as described herein, the content of the polyethylene glycol having an average molecular weight of from about 200 to about 900 Da (e.g., PEG-400 or a super refined PEG-400) refers to a total amount by weight including the portion from a pH adjusting solution (e.g., 0.1 M citric acid in PEG-400 or a super refined PEG-400) and the final Q.S. 100 (Q.S stands for quantum satis). Similarly, the content of $C_{1-3}$ alkyl-$(OCH_2CH_2)_{1-5}$—OH (e.g., 2-(2-ethoxyethoxy)ethanol or Transcutol® HP) refers to a total amount by weight including the portion from a pH adjusting solution (e.g., 0.1 M citric acid in 2-(2-ethoxyethoxy)ethanol or Transcutol® HP) and the final Q.S. 100. Similarly, the content of water refers to a total amount by weight including the portion from a pH adjusting solution (e.g., 0.1 M NaOH solution in water) and the final Q.S. 100.

Unless specifically indicated otherwise, for any one of topical formulations as described herein, the content by weight of any one of excipients (e.g., polyethylene glycol, organic solvents, antioxidant, preservative, gelling agent, etc.) and the compound of formula (I) (e.g., Compound 1.003) or (II) (e.g., Compound 2.003) is based on a total weight of the topical formulation.

"A relative purity of the compound of formula (I) in the topical formulation" refers to the purity of the compound of formula (I) at a certain time point (e.g., 8 weeks) stored under stressed conditions (e.g., 40° C.) or under normal storage conditions (e.g., room temperature or 25° C.) as compared to an initial purity of the compound of formula (I) at time zero (i.e., day 0). As always, the relative purity of the compound of formula (I) at time zero (i.e., day 0) is set as 100%. This definition also applies to a relative purity of the compound of formula (II) in the topical formulation.

Unless specifically indicated otherwise, a pH value of a formulation described herein refers to an apparent pH value. A topical formulation can be an non-aqueous formulation or include water, however the formulation includes substantial amounts of other excipients (e.g., one or more absorption enhancers). Therefore, the pH value of the non-aqueous formulation or the partially aqueous solution is regarded only as an apparent pH value. According to USP chapter <791>, the apparent pH value of a non-aqueous solution or suspension or the apparent pH value of a partially aqueous solution is anticipated for variability, which may be up to approximately 1 pH unit). See USP chapter <791>, the entirety of which is incorporated herein by reference for all purposes.

"Substantially free of . . . " refers to a formulation containing no more than about 1% by weight of other excipients, such as a $C_{2-6}$ alcohol, a $C_{2-6}$ alkylene glycol, a fatty alcohol, glycerol, or combinations thereof, each of which is defined and described herein. Polyethylene glycol (e.g., PEG-400) and/or $C_{1-3}$ alkyl-$(OCH_2CH_2)_{1-5}$—OH (e.g., 2-(2-ethoxyethoxy)ethanol or Transcutol® HP) contain impurities including ethylene glycol and/or diethylene glycol. When the polyethylene glycol (e.g., PEG-400) and/or $C_{1-3}$ alkyl-$(OCH_2CH_2)_{1-5}$—OH (e.g., 2-(2-ethoxyethoxy) ethanol or Transcutol® HP) are present in a formulation, the formulation contains no more than about 0.5% by weight of ethylene glycol and/or diethylene glycol as impurities. In some embodiments, when the polyethylene glycol (e.g., PEG-400) and/or $C_{1-3}$ alkyl-$(OCH_2CH_2)_{1-5}$—OH (e.g., 2-(2-ethoxyethoxy)ethanol or Transcutol® HP) are present in a formulation, the formulation contains no more than about 0.25% by weight of ethylene glycol and/or diethylene glycol as impurities.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

"Inhibition", "inhibits" and "inhibitor" refer to a compound that prohibits or a method of prohibiting, a specific action or function.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Topical" means application of a suitable compound (e.g. active agent) or composition comprising a compound (e.g. active agent) to the skin to treat a skin disorder (e.g., birthmark). "Subcutaneous" means application of a suitable compound (e.g. active agent) or composition comprising a compound (e.g. active agent) to the layers below the epidermis and dermis. "Intradermal" means application of a suitable compound (e.g. active agent) or composition comprising a compound (e.g. active agent) in the dermal or hypodermal layers. Intralesional" means injection of a suitable compound (e.g. active agent) or composition comprising a compound (e.g. active agent) at the site of the lesion (e.g. birthmark).

In some embodiments, "topical" means application of a suitable compound (e.g. active agent) or composition comprising a compound (e.g. active agent) to the skin with adequate penetration of the epidermis or dermis to treat a skin disorder (e.g., birthmark) of the epidermis and/or dermis. In some embodiments of topical application, the compound or composition penetrates the epidermis or dermis without significant systemic exposure nor intent to treat or prevent a disease of another organ system. In some embodiments, "subcutaneous" means injection of a suitable compound (e.g. active agent) or composition comprising a compound (e.g. active agent) into the layers below the epidermis and dermis. In some embodiments, "intradermal" means injection of a compound (e.g. active agent) or composition comprising a compound (e.g. active agent) into the dermal layers. In some embodiments, "intralesional" means injection of a compound (e.g. active agent) or composition comprising a compound (e.g. active agent) directly into a lesion, such as a birthmark, with the objective of treating a birthmark or a lesion.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, the patient or subject is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The disclosure provides "soft" MEK inhibitors, compositions comprising "soft" MEK inhibitors, and methods of treating and/or preventing a dermal disorder (e.g., a MEK-inhibitor responsive dermal disorder or a MEK mediated dermal disorder, e.g., a dermal rasopathy, e.g., a dermal disorder associated with neurofibromatosis type 1 (NF1), e.g., a dermal neurofibroma, a subdermal neurofibroma, or a superficial plexiform neurofibroma) with MEK inhibitors e.g., "soft" MEK inhibitors. For example, the methods described herein provide administration, e.g., local or non-systemic, e.g., topical, intradermal, or intralesional administration, of MEK inhibitors, e.g., "soft" MEK inhibitors, e.g., "soft" MEK inhibitors described herein, whereby the side effects exhibited with systemic exposure, e.g., known side effects exhibited with MEK inhibitors designed for systemic delivery, are significantly reduced.

In some embodiments, "soft MEK inhibitor" is a compound which inhibits MEK1 and/or 2 and is characterized by a predictable and controllable metabolism/degradation to non-toxic and biologically less active or inactive (i.e. does not inhibit, or inhibits to a lesser degree, MEK1 and/or 2) products after they have achieved their therapeutic role in the skin.

"Hard MEK inhibitor" refers to a MEK inhibitor known in the art. In some embodiments, a hard MEK inhibitor is designed for oral bioavailability. This is necessary to deliver therapeutically effective levels of MEK inhibitor to peripheral lesions with systemic delivery. Hard MEK inhibitor include, for example, PD0325901; PD184161; SMK-17; AS703026 (Pimasertib, MSC1936369); RO-4987655; Selumetinib (AZD6244, ARRY142886); Binimetinib (MEK162, ARRY-162, ARRY-438162); Refametinib; Cobimetinib (GDC-0973, XL518); GDC-0623; AZD8330 (ARRY-424704); CI-1040 (PD184352); PD198306; PD318088; Trametinib; RO-4987655; GDC-0623; TAK-733; WX-554; CH5126766 (also as RO5126766); G-573; Arry 300; SHR 7390; MSC2015103B (also known as AS-703988); CS 3006; and LY 2228820 (also known as Ralimetinib).

While not wishing to be bound by theory, it is believed that soft MEK inhibitors, e.g., such as the "soft" MEK inhibitors described herein, are more metabolically labile than known "hard" MEK inhibitors. Due to their inherent metabolic instability, e.g., for degradation upon reaching the systemic circulation, "soft" MEK inhibitors, e.g., such as the "soft" MEK inhibitors described herein, are dermally active but have low systemic exposure upon local or non-systemic administration, e.g., topical, intradermal, or intralesional administration, because they rapidly degrade upon exposure to plasma or blood or hepatic metabolic enzymes. Unlike "soft" MEK inhibitors, known MEK inhibitors have been historically designed for oral bioavailability, which requires good stability in plasma or blood and good stability to hepatic metabolism necessary to permit systemic delivery at therapeutically effective levels, and are more prone to unwanted side effects and increased toxicity. As a result, "soft" MEK inhibitors, e.g., such as the soft MEK inhibitors described herein, are less systemically toxic.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Topical Formulations

As will be appreciated, some excipients of the topical formulations (e.g., non-aqueous gel, aqueous gel, and/or emulsion-based formulations) described herein can possess multiple functions. For example, a given substance may act as both a solvent and an enhancer, both an antioxidant and a stabilizer, both an emulsifier and a surfactant, both an emulsifier and a thickening agent, and so on. In some such cases, the function of a given substance can be considered singular, even though its properties may allow multiple functionality.

III-A. Gel Formulations (Non-Aqueous) Including a Compound of Formula (I)

In one aspect, the present disclosure provides a gel formulation useful for the treatment of skin disorders. The gel formulation includes:

a) a compound represented by formula (I):

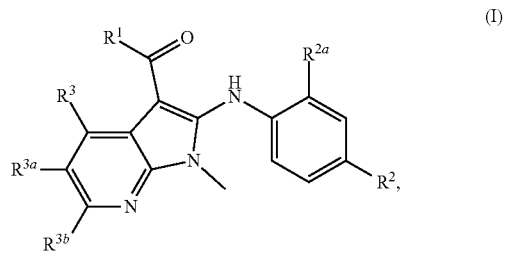

or a stereoisomer, a mixture of stereoisomers, and/or a pharmaceutically acceptable salt thereof, wherein:

$R^1$ is —$OR^4$, —$NR^5R^{5a}$, or —$N(OR^{5b})R^{5a}$;

$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;

$R^{2a}$ is halo or $C_1$-$C_6$ alkyl;

$R^3$, $R^{3a}$, and $R^{3b}$ are independently hydrogen, halo, $C_1$-$C_6$ alkyl, or $C_1$-$C_6$ alkoxy;

$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

$R^{5a}$ is hydrogen or $C_1$-$C_6$ alkyl; and $R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

b) a polyethylene glycol, an antioxidant, and optionally a preservative;
c) one or more organic solvents; and
d) a gelling agent, wherein:
the polyethylene glycol has an average molecular weight of from about 200 Da to about 900 Da and is present in an amount of at least about 30% by weight;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof,
the gelling agent is hydroxypropyl cellulose or polyvinylpyrrolidone, each of which has an average molecular weight of from about 80,000 Da to about 1,700,000 Da;
the gel formulation has a pH value of no more than about 7; and water, when present, is no more than about 5% by weight.

Compounds of Formula (I)

Compounds of formula (I) are described herein according to Section IV.

Compounds.

In some embodiments, the compound of formula (I) is represented by formula (Ia):

(Ia)

wherein $R^1$, $R^2$, and $R^{2a}$ are as defined and described herein.

In some embodiments, the compound is represented by formula (Ib):

(Ib)

wherein:
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, or $C_1$-$C_6$ hydroxyalkyl.

In some embodiments, $R^2$ and $R^{2a}$ are each halo. In some embodiments, $R^{5b}$ is $C_3$-$C_8$ cycloalkyl-$C_1$-$C_6$ alkyl or $C_1$-$C_6$ hydroxyalkyl. In some embodiments, $R^{5b}$ is $C_1$-$C_6$ hydroxyalkyl. In some embodiments, $R^{5b}$ is unbranched $C_1$-$C_6$ hydroxyalkyl. In some embodiments, $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy. In some embodiments, $R^2$ and $R^{2a}$ are each halo; and $R^{5b}$ is $C_1$-$C_6$ hydroxyalkyl. In some embodiments, $R^2$ and $R^{2a}$ are each halo; and $R^{5b}$ is unbranched $C_1$-$C_6$ hydroxyalkyl. In some embodiments, $R^2$ and $R^{2a}$ are each halo; and $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy.

In some embodiments, the compound is represented by formula (Ib-1):

(Ib-1)

wherein $R^{5b}$ is defined and described herein.

In some embodiments, the compound is represented by the formula:

(Compound 1.003)

Viscosity of Gel Formulations

In some embodiments, the gel formulation has a viscosity of from about 10,000 to about 200,000 cps, from about 15,000 to about 200,000 cps, from about 25,000 to about 200,000 cps, from about 50,000 to about 200,000 cps, from about 75,000 to about 200,000 cps, or from about 100,000 to about 200,000 cps. In some embodiments, the viscosity is from about 15,000 to about 150,000 cps, from about 25,000 to about 150,000 cps, from about 50,000 to about 150,000 cps, from about 75,000 to about 150,000 cps, or from about 100,000 to about 150,000 cps. In some embodiments, the viscosity is from about 15,000 to about 120,000 cps, from about 25,000 to about 120,000 cps, from about 50,000 to about 120,000 cps, or from about 75,000 to about 120,000 cps. In some embodiments, the viscosity is from about 15,000 to about 100,000 cps, from about 25,000 to about 100,000 cps, from about 50,000 to about 100,000 cps, or from about 75,000 to about 100,000 cps. In some embodiments, the viscosity is from about 50,000 to about 200,000 cps. In some embodiments, the viscosity is from about 50,000 to about 150,000 cps. In some embodiments, the viscosity is from about 75,000 to about 150,000 cps. In some embodiments, the viscosity is from about 50,000 to about 100,000 cps. In some embodiments, the viscosity is from about 50,000 to about 75,000 cps. In some embodiments, the viscosity is from about 75,000 to about 100,000 cps. In some embodiments, the viscosity is from about 100,000 to about 200,000 cps. In some embodiments, the viscosity is from about 100,000 to about 150,000 cps. In some embodiments, the viscosity is from about 120,000 to about 170,000 cps.

In some embodiments, the gel formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

In some embodiments, the gel formulation has a viscosity of from about 10,000 to about 25,000 cps, from about 15,000 to about 25,000 cps, from about 15,000 to about 50,000 cps, or from about 25,000 to about 50,000 cps. In some embodiments, the viscosity is from about 15,000 to about 25,000 cps. In some embodiments, the viscosity is from about 15,000 to about 50,000 cps. In some embodiments, the viscosity is from about 20,000 to about 50,000 cps. In some embodiments, the viscosity is from about 20,000 to about 40,000 cps. In some embodiments, the viscosity is from about 25,000 to about 50,000 cps. In some embodiments, the viscosity is from about 25,000 to about 40,000 cps.

Polyethylene Glycol and Organic Solvents

In some embodiments, the polyethylene glycol and the one or more organic solvents are present in a total amount of from about 90 to about 99% by weight. In some embodiments, the polyethylene glycol and the one or more organic solvents are present in a total amount of from about 95 to about 98% by weight.

In some embodiments, the polyethylene glycol is PEG-200, PEG-300, PEG-400, PEG-600, or PEG-900. In some embodiments, the polyethylene glycol is PEG-400. In some embodiments, PEG-400 is a super refined PEG-400.

In some embodiments, PEG-400 is present in an amount of from about 30% to about 80% by weight. In some embodiments, PEG-400 is present in an amount of from about 40% to about 80% by weight. In some embodiments, PEG-400 is present in an amount of from about 40% to about 70%, from about 40% to about 60%, from about 50% to about 60%, or from about 60% to about 80% by weight. In some embodiments, PEG-400 is present in an amount of from about 40% to about 60% by weight. In some embodiments, PEG-400 is present in an amount of from about 50% to about 60% by weight. In some embodiments, PEG-400 is present in an amount of from about 60% to about 80% by weight.

In some embodiments, the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof. In some embodiments, the one or more organic solvents are a $C_{2-6}$ alkylene glycol, $C_{1-3}$ alkyl-$(OCH_2CH_2)_{1-5}$—OH, or combinations thereof. In some embodiments, the one or more organic solvents are $C_{1-3}$ alkyl-$(OCH_2CH_2)_{1-5}$—OH. In some embodiments, the one or more organic solvents are $C_{1-3}$ alkyl-$(OCH_2CH_2)_{1-5}$—OH; and the gel formulation is substantially free of a $C_{2-6}$ alcohol, a $C_{2-6}$ alkylene glycol, a fatty alcohol, glycerol, or combinations thereof. In some embodiments, the $C_{2-6}$ alcohol is ethanol. In some embodiments, the $C_{2-6}$ alkylene glycol is propylene glycol. In some embodiments, $C_{1-3}$ alkyl-$(OCH_2CH_2)_{1-5}$—OH is 2-(2-ethoxyethoxy)ethanol.

In some embodiments, the one or more organic solvents are ethanol, propylene glycol, 2-(2-ethoxyethoxy)ethanol, or combinations thereof. In some embodiments, the one or more organic solvents include 2-(2-ethoxyethoxy)ethanol. In some embodiments, the one or more organic solvents are 2-(2-ethoxyethoxy)ethanol. In some embodiments, the one or more organic solvents include ethanol and propylene glycol. In some embodiments, the one or more organic solvents are a mixture of ethanol and propylene glycol. In some embodiments, the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol. In some embodiments, the one or more organic solvents are 2-(2-ethoxyethoxy)ethanol; and the gel formulation is substantially free of ethanol and/or propylene glycol. In some embodiments, the one or more organic solvents are 2-(2-ethoxyethoxy)ethanol; and the gel formulation is substantially free of ethanol, propylene glycol, diethylene glycol, or combinations thereof.

In some embodiments, the one or more organic solvents are present in an amount of from about 20% to about 60% by weight, wherein the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof. In some embodiments, the one or more organic solvents are $C_{1-3}$ alkyl-$(OCH_2CH_2)_{1-5}$—OH in an amount of from about 40% to about 60% by weight. In some embodiments, the one or more organic solvents are $C_{1-3}$ alkyl-$(OCH_2CH_2)_{1-5}$—OH in an amount of from about 40% to about 50% by weight. In some embodiments, the one or more organic solvents are 2-(2-ethoxyethoxy)ethanol in an amount of from about 40% to about 60% by weight. In some embodiments, the one or more organic solvents are 2-(2-ethoxyethoxy)ethanol in an amount of from about 40% to about 50% by weight.

In some embodiments, propylene glycol is a super refined propylene glycol.

In some embodiments, 2-(2-ethoxyethoxy)ethanol is Transcutol® HP. In some embodiments, 2-(2-ethoxyethoxy)ethanol is Transcutol® HP having a purity of >about 99.90%.

Antioxidant

In some embodiments, the antioxidant is butylated hydroxytoluene, butylated hydroxyanisole, an ascorbyl ester, or combinations thereof. In some embodiments, the antioxidant is butylated hydroxytoluene, butylated hydroxyanisole, or a combination thereof. In some embodiments, the antioxidant is a mixture of butylated hydroxytoluene and butylated hydroxyanisole. In some embodiments, the antioxidant is butylated hydroxytoluene. In some embodiments, the antioxidant is butylated hydroxyanisole. In some embodiments, the antioxidant is an ascorbyl ester including ascorbyl palmitate.

In some embodiments, the antioxidant is present in an amount of from about 0.01% to about 1% by weight. In some embodiments, the antioxidant is present in an amount of from about 0.01% to about 0.5% by weight. In some embodiments, the antioxidant is present in an amount of from about 0.01% to about 0.1% by weight. In some embodiments, the antioxidant is present in an amount of from about 0.1% to about 0.5% by weight. In some embodiments, the antioxidant is present in an amount of from about 0.1% to about 0.3% by weight. In some embodiments, the antioxidant is butylated hydroxytoluene in an amount of from about 0.1% to about 0.5% by weight, from about 0.1% to about 0.4%, or from about 0.1% to about 0.3% by weight. In some embodiments, the antioxidant is butylated hydroxytoluene in an amount of from about 0.1% to about 0.3% by weight. In some embodiments, the antioxidant is butylated hydroxytoluene in an amount of about 0.2% by weight. In some embodiments, the antioxidant is an ascorbyl ester including ascorbyl palmitate in an amount of from about 0.01% to about 0.1% by weight. In some embodiments, the antioxidant is ascorbyl palmitate in an amount of from about 0.01% to about 0.1% by weight. In some embodiments, the antioxidant is ascorbyl palmitate in an amount of about 0.05% by weight.

Stabilizer

In some embodiments, the gel formulation further includes a stabilizer. In some embodiments, the stabilizer is alpha tocopherol or alpha tocopherol acetate. When the antioxidant is an ascorbyl ester including ascorbyl palmitate, in some embodiments, the stabilizer is alpha tocopherol or alpha tocopherol acetate. In some embodiments, the stabilizer is present in an amount of from about 0.001% to about 0.1% by weight. In some embodiments, the stabilizer is present in an amount of from about 0.001% to about 0.05% by weight. In some embodiments, the stabilizer is present in an amount of from about 0.001% to about 0.01% by weight. When the antioxidant is an ascorbyl ester including ascorbyl palmitate, in some embodiments, the stabilizer is alpha tocopherol or alpha tocopherol acetate in an amount of from about 0.001% to about 0.05% by weight. When the antioxidant is an ascorbyl ester including ascorbyl palmitate, in some embodiments, the stabilizer is alpha tocopherol in an amount of about 0.002% by weight. When the antioxidant is an ascorbyl ester including ascorbyl palmitate, in some embodiments, the stabilizer is alpha tocopherol acetate in an amount of about 0.002% by weight. When the antioxidant is an ascorbyl ester including ascorbyl palmitate, in some embodiments, the stabilizer is alpha tocopherol acetate in an amount of about 0.02% by weight.

Preservative

In some embodiments, the preservative is absent in the gel formulation. In some embodiments, the preservative is present in the gel formulation.

In some embodiments, the preservative, when present, is benzyl alcohol, phenoxyethanol, potassium sorbate, or combinations thereof. In some embodiments, the preservative, when present, is benzyl alcohol, phenoxyethanol, or a combination thereof. In some embodiments, the preservative, when present, is benzyl alcohol. In some embodiments, the preservative, when present, is phenoxyethanol. In some embodiments, the preservative, when present, is a mixture of benzyl alcohol and phenoxyethanol. In some embodiments, the preservative, when present, is potassium sorbate.

In some embodiments, the preservative, when present, is in an amount of from about 0.1% to about 5% by weight. In some embodiments, the preservative, when present, is in an amount of from about 0.5% to about 2% by weight. In some embodiments, the preservative, when present, is in an amount of from about 0.02% to about 1% by weight. In some embodiments, the preservative, when present, is phenoxyethanol in an amount of from about 0.5% to about 5%, from about 0.5% to about 4%, from about 0.5% to about 3%, or from about 0.5% to about 2% by weight. In some embodiments, the preservative, when present, is phenoxyethanol in an amount of from about 0.5% to about 2% by weight. In some embodiments, the preservative, when present, is phenoxyethanol in an amount of about 1% by weight. In some embodiments, the preservative, when present, is potassium sorbate in an amount of from about 0.05% to about 0.5%, from about 0.05% to about 0.4%, from about 0.05% to about 0.3%, or from about 0.05% to about 0.2% by weight. In some embodiments, the preservative, when present, is potassium sorbate in an amount of from about 0.05% to about 0.2% by weight. In some embodiments, the preservative, when present, is potassium sorbate in an amount of about 0.1% by weight.

Formulations (NA-1) and (NA-2)

In some embodiments, the gel formulation (NA-1) includes:
  a) the compound of any one of formulae (I), (Ia), (Ib), (Ib-1), and Compound 1.003;
  b) PEG-400, the antioxidant, optionally the preservative, and optionally a stabilizer;
  c) $C_{1-3}$ alkyl-$(OCH_2CH_2)_{1-5}$—OH; and
  d) the gelling agent.

In some embodiments, the gel formulation (NA-1) is substantially free of a $C_{2-6}$ alcohol, a $C_{2-6}$ alkylene glycol, a fatty alcohol, glycerol, or combinations thereof, each of which is defined and described herein. In some embodiments, the gel formulation (NA-1) is substantially free of ethanol, propylene glycol, diethylene glycol, or combinations thereof.

In some embodiments of gel formulation (NA-1), PEG-400 is present in an amount of from about 30% to about 70%, from about 40% to about 70%, from about 40% to about 60%, from about 40% to about 50%, or from about 50% to about 60% by weight. In some embodiments, PEG-400 is present in an amount of from about 40% to about 70%, from about 40% to about 60%, or from about 50% to about 60% by weight. In some embodiments, PEG-400 is present in an amount of from about 40% to about 70% by weight. In some embodiments, PEG-400 is present in an amount of from about 40% to about 60% by weight. In some embodiments, PEG-400 is present in an amount of from about 50% to about 60% by weight. In some embodiments, PEG-400 is present in an amount of from about 50% to about 55% by weight. In some embodiments, PEG-400 is present in an amount of about 53% by weight.

In some embodiments of gel formulation (NA-1), $C_{1-3}$ alkyl-$(OCH_2CH_2)_{1-5}$—OH is 2-(2-ethoxyethoxy)ethanol. In some embodiments, 2-(2-ethoxyethoxy)ethanol is present in an amount of from about 30% to about 60%, from about 40% to about 60%, or from about 40% to about 50% by weight. In some embodiments, 2-(2-ethoxyethoxy)ethanol is present in an amount of from about 40% to about 60% by weight. In some embodiments, 2-(2-ethoxyethoxy)ethanol is present in an amount of from about 40% to about 50% by weight. In some embodiments, 2-(2-ethoxyethoxy)ethanol is present in an amount of about 45% by weight.

In some embodiments of gel formulation (NA-1), the antioxidant is butylated hydroxytoluene. In some embodiments, butylated hydroxytoluene is present in an amount of from about 0.1% to about 0.5%, from about 0.1% to about 0.4%, or from about 0.1% to about 0.3% by weight. In some embodiments, butylated hydroxytoluene is present in an amount of from about 0.1% to about 0.3% by weight. In some embodiments, butylated hydroxytoluene is present in an amount of about 0.2% by weight.

In some embodiments of gel formulation (NA-1), the antioxidant is an ascorbyl ester including ascorbyl palmitate. In some embodiments, ascorbyl palmitate is present in an amount of from about 0.01% to about 0.1% by weight. In some embodiments, ascorbyl palmitate is present in an amount of from about 0.01% to about 0.1%, from about 0.02% to about 0.08%, or from about 0.03% to about 0.07% by weight. In some embodiments, ascorbyl palmitate is present in an amount of from about 0.03% to about 0.07% by weight. In some embodiments, ascorbyl palmitate is present in an amount of about 0.05% by weight.

In some embodiments of gel formulation (NA-1), stabilizer is present. In some embodiments, when the antioxidant is an ascorbyl ester including ascorbyl palmitate, the stabilizer is alpha tocopherol. In some embodiments, when the antioxidant is an ascorbyl ester including ascorbyl palmitate, the stabilizer is alpha tocopherol acetate. In some embodiments, alpha tocopherol is present in an amount of from about 0.001% to about 0.005% by weight. In some embodiments, alpha tocopherol is present in an amount of about 0.002% by weight. In some embodiments, alpha tocopherol acetate is present in an amount of from about 0.001% to about 0.05% by weight. In some embodiments, alpha tocopherol acetate is present in an amount of about 0.002% by weight. In some embodiments, alpha tocopherol acetate is present in an amount of about 0.02% by weight.

In some embodiments of gel formulation (NA-1), the preservative is present. In some embodiments, the preservative is phenoxyethanol. In some embodiments, phenoxyethanol is present in an amount of from 0.5% to 5%, from 0.5% to 4%, from 0.5% to 3%, or from 0.5% to 2% by weight. In some embodiments, phenoxyethanol is present in an amount of from 0.5% to 2% by weight. In some embodiments, phenoxyethanol is present in an amount of about 1% by weight. In some embodiments, the preservative is potassium sorbate. In some embodiments, potassium sorbate is present in an amount of from 0.05% to 0.5%, from 0.05% to 0.4%, from 0.05% to 0.3%, or from 0.05% to 0.2% by weight. In some embodiments, potassium sorbate is present in an amount of from 0.05% to 0.2% by weight. In some embodiments, potassium sorbate is present in an amount of about 0.1% by weight.

In some embodiments, the gel formulation (NA-2) includes:
  a) the compound of any one of formulae (I), (Ia), (Ib), (Ib-1), and Compound 1.003;
  b) PEG-400, the antioxidant, and the preservative;
  c) the one or more organic solvents; and
  c) the gelling agent,
wherein:
  the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof.

In some embodiments of gel formulation (NA-2), PEG-400 is present in an amount of from about 40% to about 80%, from about 50% to about 75%, or from about 60% to about 70% by weight. In some embodiments, PEG-400 is present in an amount of from about 40% to about 80% by weight. In some embodiments, PEG-400 is present in an amount of from about 50% to about 75% by weight. In some embodiments, PEG-400 is present in an amount of from about 60% to about 70% by weight. In some embodiments, PEG-400 is present in an amount of about 67% by weight.

In some embodiments of gel formulation (NA-2), the one or more organic solvents include ethanol and propylene glycol. In some embodiments, the one or more organic solvents are a mixture of ethanol and propylene glycol. In some embodiments, the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol.

In some embodiments of gel formulation (NA-2), ethanol is present in an amount of from about 5% to about 20% or from about 5% to about 15% by weight. In some embodiments, ethanol is present in an amount of from about 5% to about 15% by weight. In some embodiments, ethanol is present in an amount of about 10% by weight.

In some embodiments of gel formulation (NA-2), propylene glycol is present in an amount of from about 5% to about 30%, from about 5% to about 15%, or from about 10% to about 30% by weight. In some embodiments, propylene glycol is present in an amount of from about 10% to about 30% by weight. In some embodiments, propylene glycol is present in an amount of from about 15% to about 25% by weight. In some embodiments, propylene glycol is present in an amount of about 20% by weight. In some embodiments, propylene glycol is present in an amount of from about 5% to about 15% by weight. In some embodiments, propylene glycol is present in an amount of about 10% by weight.

In some embodiments of gel formulation (NA-2), 2-(2-ethoxyethoxy)ethanol is absent. In some embodiments, 2-(2-ethoxyethoxy)ethanol is present in an amount of from about 5% to about 20% or from about 5% to about 15% by weight. In some embodiments, 2-(2-ethoxyethoxy)ethanol is present in an amount of from about 5% to about 15% by weight. In some embodiments, 2-(2-ethoxyethoxy)ethanol is present in an amount of about 10 by weight.

In some embodiments of gel formulation (NA-2), propylene glycol and 2-(2-ethoxyethoxy)ethanol combined are present in an amount of from about 15% to about 25% by weight. In some embodiments, propylene glycol and 2-(2-ethoxyethoxy)ethanol combined are present in an amount of about 20% by weight. In some embodiments, each of propylene glycol and 2-(2-ethoxyethoxy)ethanol is present in an amount of about 10% by weight.

In some embodiments of gel formulation (NA-2), the antioxidant is butylated hydroxytoluene, butylated hydroxyanisole, or a combination thereof. In some embodiments, the antioxidant includes butylated hydroxytoluene and butylated hydroxyanisole. In some embodiments, the antioxidant is a mixture of butylated hydroxytoluene and butylated hydroxyanisole.

In some embodiments of gel formulation (NA-2), butylated hydroxytoluene is present in an amount of from about 0.1% to about 0.5% by weight. In some embodiments, butylated hydroxytoluene is present in an amount of about 0.2% by weight. In some embodiments, butylated hydroxyanisole is present in an amount of from about 0.1% to about 0.5% by weight. In some embodiments, butylated hydroxyanisole is present in an amount of about 0.2% by weight. In some embodiments, each of butylated hydroxytoluene and butylated hydroxyanisole is present in an amount of about 0.2% by weight.

In some embodiments of gel formulation (NA-2), the preservative is phenoxyethanol. In some embodiments, phenoxyethanol is present in an amount of from about 0.5% to about 2% by weight. In some embodiments, phenoxyethanol is present in an amount of about 1% by weight.

In some embodiments of gel formulation (NA-1) or (NA-2), PEG-400 is a super refined PEG-400. In some embodiments, propylene glycol is a super refined propylene glycol. In some embodiments, 2-(2-ethoxyethoxy)ethanol is Transcutol® HP. In some embodiments, 2-(2-ethoxyethoxy)ethanol is Transcutol® HP having a purity of >about 99.90%.

Gelling Agent

In some embodiments of any one of gel formulations, the gelling agent is hydroxypropyl cellulose. In some embodiments, hydroxypropyl cellulose has an average molecular weight of about 80,000 Da, 95,000 Da, 100,000 Da, 140,000

Da, 180,000 Da, 280,000 Da, 370,000 Da, 700,000 Da, 850,000 Da, 1,000,000 Da, or 1,150,000 Da. In some embodiments, hydroxypropyl cellulose has an average molecular weight of about 140,000 Da, 180,000 Da, 280,000 Da, 370,000 Da, 700,000 Da, 850,000 Da, 1,000,000 Da, or 1,150,000 Da. In some embodiments, hydroxypropyl cellulose has an average molecular weight of about 140,000 Da, 370,000 Da, 850,000 Da, or 1,150,000 Da. In some embodiments, hydroxypropyl cellulose has an average molecular weight of from about 850,000 Da to about 1,150,000 Da. In some embodiments, hydroxypropyl cellulose has an average molecular weight of about 140,000 Da. In some embodiments, hydroxypropyl cellulose has an average molecular weight of about 370,000 Da. In some embodiments, hydroxypropyl cellulose has an average molecular weight of about 850,000 Da. In some embodiments, hydroxypropyl cellulose has an average molecular weight of about 1,150,000 Da.

The hydroxypropyl cellulose (HPC) as described herein includes products sold under the names HY117, HY119, HY121, Nisso SSL, Nisso SL, Nisso L, Nisso LM, Nisso LMM, Nisso M, Nisso H, Nisso VH, Klucel™ ELF, Klucel™ EF, Klucel™ LF, Klucel™ JF, Klucel™ GF, Klucel™ MF, and Klucel™ HF. HY117 has an average molecular weight of about 95,000 Da; HY119 has an average molecular weight of about 370,000 Da; and HY121 has an average molecular weight of about 850,000 Da. Nisso SL has an average molecular weight of about 100,000 Da; Nisso L has an average molecular weight of about 140,000 Da; Nisso LM has an average molecular weight of about 180,000 Da; Nisso LMM has an average molecular weight of about 280,000 Da; Nisso M has an average molecular weight of about 700,000 Da; and Nisso H has an average molecular weight of about 1,000,000 Da. Suitable particle sizes of Nisso HPC (i.e., Nisso SSL, Nisso SL, Nisso L, Nisso LM, Nisso LMM, Nisso M, Nisso H, and Nisso VH) in the gel formulation include regular powder (40 mesh), fine powder (100 mesh), and super fine powder (300 mesh). See Technical date sheets of Nisso HPCs, the entirety of which is incorporated herein by reference for all purposes. Klucel™ EF has an average molecular weight of about 80,000 Da; Klucel™ LF has an average molecular weight of about 95,000 Da; Klucel™ JF has an average molecular weight of about 140,000 Da; Klucel™ GF has an average molecular weight of about 370,000 Da; Klucel™ MF has an average molecular weight of about 850,000 Da; and Klucel™ HTF has an average molecular weight of about 1,150,000 Da. Suitable particle sizes of Klucel™ HPC in the gel formulation include regular grade and fine grade. See Technical date sheets of Klucel™ HPC products, the entirety of which is incorporated herein by reference for all purposes.

In some embodiments of any one of gel formulations, the hydroxypropyl cellulose is Klucel™ JF, Klucel™ GF, Klucel™ MF, or Klucel™ HF. In some embodiments, the hydroxypropyl cellulose is Klucel™ JF, Klucel™ MF, or Klucel™ HF. In some embodiments, the hydroxypropyl cellulose is Klucel™ MF or Klucel™ HF. In some embodiments, the hydroxypropyl cellulose is Klucel™ JF. In some embodiments, the hydroxypropyl cellulose is Klucel™ GF. In some embodiments, the hydroxypropyl cellulose is Klucel™ MF. In some embodiments, the hydroxypropyl cellulose is Klucel™ HF.

In some embodiments of any one of gel formulations, the gelling agent is polyvinylpyrrolidone (PVP). In some embodiments, the gelling agent is polyvinylpyrrolidone (PVP) having an average molecular weight of from about 80,000 Da to about 1,700,000 Da.

The polyvinylpyrrolidone as described herein includes PVP K-60, K-85, and K-90. PVP K-60 has an average molecular weight of from about 390,000 Da to about 470,000 Da; PVP K-85 has an average molecular weight of from about 900,000 Da to about 1,200,000 Da; and PVP K-90 has an average molecular weight of from about 1,000,000 Da to about 1,700,000 Da. See Technical date sheets of PVP products, the entirety of which is incorporated herein by reference for all purposes.

In some embodiments of any one of gel formulations, polyvinylpyrrolidone is PVP K-60, K-85, or K-90. In some embodiments, polyvinylpyrrolidone is PVP K-60. In some embodiments, polyvinylpyrrolidone is PVP K-85. In some embodiments, polyvinylpyrrolidone is PVP K-90.

In some embodiments of any one of gel formulations, the gelling agent is present in an amount of from about 0.2% to about 5% by weight. In some embodiments, the gelling agent is present in an amount of from about 0.2% to about 5% by weight, wherein the viscosity of the gel formulation is from about 10,000 to about 200,000 cps, from about 15,000 to about 200,000 cps, from about 25,000 to about 200,000 cps, from about 50,000 to about 200,000 cps, from about 75,000 to about 200,000 cps, from about 100,000 to about 200,000 cps, from about 50,000 to about 150,000 cps, from about 75,000 to about 150,000 cps, from about 100,000 to about 150,000 cps, from about 50,000 to about 100,000 cps, from about 75,000 to about 100,000 cps, or from about 50,000 to about 75,000 cps. In some embodiments, the gelling agent is present in an amount of from about 0.2% to about 5% by weight, wherein the viscosity of the gel formulation is from about 15,000 to about 200,000 cps. In some embodiments, the gelling agent is present in an amount of from about 0.2% to about 5% by weight, wherein the viscosity of the gel formulation is from about 25,000 to about 200,000 cps. In some embodiments, the gelling agent is present in an amount of from about 0.2% to about 5% by weight, wherein the viscosity of the gel formulation is from about 50,000 to about 200,000 cps. In some embodiments, the gelling agent is present in an amount of from about 0.2% to about 5% by weight, wherein the viscosity of the gel formulation is from about 50,000 to about 150,000 cps. In some embodiments, the gelling agent is present in an amount of from about 0.2% to about 5% by weight, wherein the viscosity of the gel formulation is from about 50,000 to about 100,000 cps. In some embodiments, the gelling agent is present in an amount of from about 0.2% to about 5% by weight, wherein the viscosity of the gel formulation is from about 100,000 to about 200,000 cps. In some embodiments, the gelling agent is present in an amount of from about 0.2% to about 5% by weight, wherein the viscosity of the gel formulation is from about 120,000 to about 170,000 cps.

In some embodiments of any one of gel formulations, the gelling agent is present in an amount of from about 0.2% to about 5% by weight, wherein the viscosity of the gel formulation is from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

In some embodiments of any one of gel formulations, the gelling agent is present in an amount of from about 0.2% to about 5% by weight, wherein the viscosity of the gel formulation is from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the gelling agent is present in an amount of from about 0.2% to about 5% by weight, wherein the viscosity of the gel formulation is from about 10,000 to about 50,000 cps. In some embodiments, the gelling agent is present in an amount of from about 0.2% to about 5% by weight, wherein the viscosity of the gel formulation is from about 15,000 to about 50,000 cps. In some embodiments, the gelling agent is present in an amount of from about 0.2% to about 5% by weight, wherein the viscosity of the gel formulation is from about 20,000 to about 50,000 cps. In some embodiments, the gelling agent is present in an amount of from about 0.2% to about 5% by weight, wherein the viscosity of the gel formulation is from about 25,000 to about 50,000 cps. In some embodiments, the gelling agent is present in an amount of from about 0.2% to about 5% by weight, wherein the viscosity of the gel formulation is from about 10,000 to about 40,000 cps. In some embodiments, the gelling agent is present in an amount of from about 0.2% to about 5% by weight, wherein the viscosity of the gel formulation is from about 15,000 to about 40,000 cps. In some embodiments, the gelling agent is present in an amount of from about 0.2% to about 5% by weight, wherein the viscosity of the gel formulation is from about 20,000 to about 40,000 cps. In some embodiments, the gelling agent is present in an amount of from about 0.2% to about 5% by weight, wherein the viscosity of the gel formulation is from about 25,000 to about 40,000 cps.

In some embodiments of any one of gel formulations, the gelling agent is Klucel™ HF in an amount of from about 0.2% to about 5%, from about 0.5% to about 5%, from about 0.5% to about 3%, or from about 0.5% to about 2% by weight. In some embodiments, the gelling agent is Klucel™ HF in an amount of from about 0.5% to about 5% by weight. In some embodiments, the gelling agent is Klucel™ HF in an amount of from about 0.5% to about 3% by weight. In some embodiments, the gelling agent is Klucel™ HF in an amount of from about 0.5% to about 2% by weight. In some embodiments, the gelling agent is Klucel™ HF in an amount of about 0.75% by weight. In some embodiments, the gelling agent is Klucel™ HF in an amount of about 1% by weight. In some embodiments, the gelling agent is Klucel™ HF in an amount of about 1.5% by weight.

In some embodiments of any one of gel formulations, the gelling agent is PVP K-90 in an amount of from about 3% to about 5% by weight. In some embodiments, the gelling agent is PVP K-90 in an amount of from about 3% to about 5% by weight. In some embodiments, the gelling agent is PVP K-90 in an amount of about 4% by weight.

Additional Thickening Agent

In some embodiments, the gel formulation further includes a thickening agent in addition to the gelling agent. In some embodiments, the thickening agent is a polyethylene glycol having an average molecular weight of from about 1000 to about 3000 Da. In some embodiments, the thickening agent is PEG-1000, PEG-1500, PEG-2000, PEG-2500, or PEG-3000. In some embodiments, the thickening agent is PEG-1500. In some embodiments, the thickening agent is PEG-1500 in an amount of from about 1% to about 5% by weight. In some embodiments, the thickening agent is PEG-1500 in an amount of about 2% by weight.

pH of Formulations

The gel formulation is an non-aqueous formulation, therefore the pH value of the formulation is an apparent pH value. According to USP chapter <791>, the apparent pH value of a non-aqueous solution or suspension is anticipated for variability, which may be up to approximately 1 pH unit). See USP chapter <791>, the entirety of which is incorporated herein by reference for all purposes.

In some embodiments, the gel formulation has a pH value of from about 5 to about 7. In some embodiments, the gel formulation has a pH value of from about 5 to about 6. In some embodiments, the gel formulation has a pH value of from about 6 to about 7.

In some embodiments of any one of gel formulations, a pH of the gel formulation is adjusted with citric acid. In some embodiments, a pH is adjusted with a solution of citric acid in PEG-400. In some embodiments, a pH is adjusted with a solution of citric acid in a super refined PEG-400. In some embodiments, a pH is adjusted with a solution of citric acid in 2-(2-ethoxyethoxy)ethanol. In some embodiments, a pH is adjusted with a solution of citric acid in Transcutol® HP. In some embodiments, a pH is adjusted with 0.1 M to 0.5 M citric acid in a super refined PEG-400. In some embodiments, a pH is adjusted with 0.1 M to 0.5 M citric acid in Transcutol® HP. In some embodiments, a pH is adjusted with 0.1 M citric acid in a super refined PEG-400. In some embodiments, a pH is adjusted with 0.1 M citric acid in Transcutol® HP. In some embodiments, a pH is adjusted with 0.5 M citric acid in a super refined PEG-400. In some embodiments, a pH is adjusted with 0.5 M citric acid in Transcutol® HP.

In some embodiments of any one of gel formulations, a pH of the gel formulation is further adjusted with sodium hydroxide. In some embodiments, a pH is further adjusted with a solution of sodium hydroxide in PEG-400. In some embodiments, a pH is further adjusted with a solution of sodium hydroxide in a super refined PEG-400. In some embodiments, a pH is further adjusted with a solution of sodium hydroxide in 2-(2-ethoxyethoxy)ethanol. In some embodiments, a pH is further adjusted with a solution of sodium hydroxide in Transcutol® HP. In some embodiments, a pH is further adjusted with 0.1 M sodium hydroxide in a super refined PEG-400. In some embodiments, a pH is further adjusted with 0.1 M sodium hydroxide in Transcutol® HP.

Content of Compounds of Formula (I)

In some embodiments of any one of gel formulations, the compound of formula (I) is present in the gel formulation in an amount of from about 0.005% to about 5%, from about 0.01% to about 5%, from about 0.01% to about 3%, or from about 0.1% to about 3% by weight on a salt-free and anhydrous basis. In some embodiments, the compound of formula (I) is present in an amount of from about 0.01% to about 3% by weight on a salt-free and anhydrous basis. In some embodiments, the compound of formula (I) is present in an amount of from about 0.1% to about 3% by weight on a salt-free and anhydrous basis.

In some embodiments of any one of gel formulations, the compound of formula (Ib) is present in the gel formulation in an amount of from about 0.005% to about 5%, from about 0.01% to about 5%, from about 0.01% to about 3%, or from about 0.1% to about 3% by weight on a salt-free and anhydrous basis. In some embodiments, the compound of formula (Ib) is present in an amount of from about 0.01% to about 3% by weight on a salt-free and anhydrous basis. In some embodiments, the compound of formula (Ib) is present in an amount of from about 0.1% to about 3% by weight on a salt-free and anhydrous basis.

In some embodiments of any one of gel formulations, Compound 1.003 is present in the gel formulation in an amount of from about 0.005% to about 5%, from about 0.01% to about 5%, from about 0.005% to about 3%, from about 0.01% to about 3%, or from about 0.1% to about 3% by weight on a salt-free and anhydrous basis. In some embodiments, Compound 1.003 is present in an amount of from about 0.005% to about 3% by weight on a salt-free and anhydrous basis. In some embodiments, Compound 1.003 is present in an amount of from about 0.01% to about 3% by weight on a salt-free and anhydrous basis. In some embodiments, Compound 1.003 is present in an amount of from about 0.1% to about 3% by weight on a salt free and anhydrous basis. In some embodiments, Compound 1.003 is present in an amount of about 0.05% by weight on a salt-free and anhydrous basis. In some embodiments, Compound 1.003 is present in an amount of about 0.1% by weight on a salt-free and anhydrous basis. In some embodiments, Compound 1.003 is present in an amount of about 0.15% by weight on a salt-free and anhydrous basis. In some embodiments, Compound 1.003 is present in an amount of about 0.25% by weight on a salt-free and anhydrous basis. In some embodiments, Compound 1.003 is present in an amount of about 0.5% by weight on a salt-free and anhydrous basis. In some embodiments, Compound 1.003 is present in an amount of about 1% by weight on a salt-free and anhydrous basis. In some embodiments, Compound 1.003 is present in an amount of about 1.5% by weight on a salt-free and anhydrous basis. In some embodiments, Compound 1.003 is present in an amount of about 2% by weight on a salt-free and anhydrous basis.

Water

Water in the gel formulation can be from any one of excipients (e.g., the polyethylene glycol, one or more organic solvents, and/or the gelling agent). In some embodiments of any one of gel formulations, water, when present, is no more than about 5%, 4%, 3%, 2%, or 1% by weight. In some embodiments, water, when present, is no more than about 2% by weight. In some embodiments, water, when present, is no more than about 1% by weight.

Formulations (NA-1a), (NA-1b), and (Na-1c)

In some embodiments, the present disclosure provides a gel formulation (NA-1a), including:
a) a compound represented by the formula:

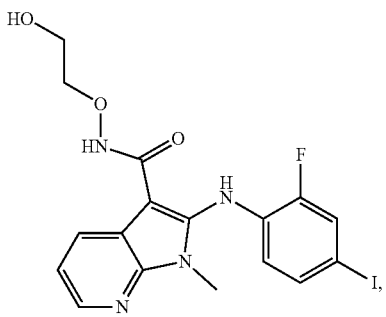 [SMILES: Cn1c(Nc2ccc(I)cc2F)c(C(=O)NOCCO)c2cccnc21]

or a pharmaceutically acceptable salt thereof,
b) PEG-400, 2-(2-ethoxyethoxy)ethanol, ascorbyl palmitate, and alpha tocopherol or alpha tocopherol acetate; and c) a hydroxypropyl cellulose having an average molecular weight of from about 140,000 Da to about 1,150,000 Da,
wherein the gel formulation has a pH value of no more than about 7.

In some embodiments of the gel formulation (NA-1a), PEG-400 is present in an amount of from about 50% to about 55% by weight. In some embodiments, PEG-400 is present in an amount of about 53% by weight. In some embodiments, PEG-400 is a super refined PEG-400.

In some embodiments of the gel formulation (NA-1a), 2-(2-ethoxyethoxy)ethanol is present in an amount of from about 40% to about 50% by weight. In some embodiments, 2-(2-ethoxyethoxy)ethanol is present in an amount of about 45% by weight. In some embodiments, 2-(2-ethoxyethoxy) ethanol is Transcutol® HP having a purity of >about 99.90%.

In some embodiments of the gel formulation (NA-1a), ascorbyl palmitate is present in an amount of about 0.05% by weight. In some embodiments, ascorbyl palmitate is present in an amount of about 0.03% by weight of the gel formulation (e.g., formulation (NA-1aa)).

In some embodiments of the gel formulation (NA-1a), alpha tocopherol is present in an amount of about 0.002% by weight. In some embodiments of the gel formulation (NA-1a), alpha tocopherol acetate is present in an amount of about 0.002% by weight. In some embodiments, alpha tocopherol acetate is present in an amount of about 0.02% by weight of the gel formulation (e.g., formulation (NA-1aa)).

In some embodiments of the gel formulation (NA-1a), the hydroxypropyl cellulose has an average molecular weight of about 1,150,000 Da. In some embodiments, the hydroxypropyl cellulose is Klucel™ HF.

In some embodiments of the gel formulation (NA-1a), Klucel™ HF is present in an amount of from about 0.5% to 2% by weight. In some embodiments, Klucel™ HF is present in an amount of about 0.5% by weight. In some embodiments, Klucel™ HF is present in an amount of about 0.75% by weight. In some embodiments, Klucel™ HF is present in an amount of about 1.0% by weight. In some embodiments, Klucel™ HF is present in an amount of about 1.5% by weight.

In some embodiments of the gel formulation (NA-1a), the formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the formulation has a viscosity of from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the formulation has a viscosity of from about 20,000 to about 50,000 cps, from about 25,000 to about 50,000 cps, from about 20,000 to about 40,000 cps, or from about 25,000 to about 40,000 cps. In some embodiments, the formulation has a viscosity of from about 15,000 to about 50,000 cps. In some embodiments, the formulation has a viscosity of from about 20,000 to about 50,000 cps. In some embodiments, the formulation has a viscosity of from about 25,000 to about 50,000 cps. In some embodiments, the formulation has a viscosity of from about 15,000 to about 40,000 cps. In some embodiments, the formulation has a viscosity of from about 20,000 to about 40,000 cps. In some embodiments, the formulation has a viscosity of from about 25,000 to about 40,000 cps.

In some embodiments, the present disclosure provides a gel formulation (NA-1b), comprising:
a) a compound represented by the formula:

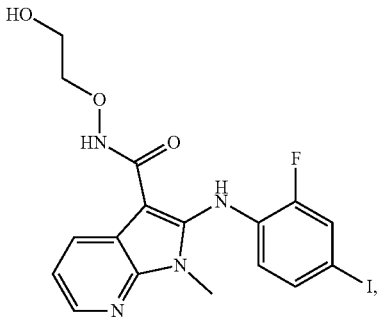 [SMILES: Cn1c(Nc2ccc(I)cc2F)c(C(=O)NOCCO)c2cccnc21]

or a pharmaceutically acceptable salt thereof,
b) PEG-400, 2-(2-ethoxyethoxy)ethanol, butylated hydroxytoluene, and potassium sorbate; and
c) a hydroxypropyl cellulose having an average molecular weight of from about 850,000 Da to about 1,150,000 Da,
wherein the gel formulation has a pH value of no more than about 7.

In some embodiments, the present disclosure provides a gel formulation (NA-1c), comprising:
a) a compound represented by the formula:

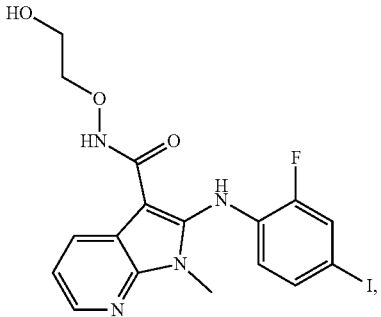 [SMILES: Cn1c(Nc2ccc(I)cc2F)c(C(=O)NOCCO)c2cccnc21]

or a pharmaceutically acceptable salt thereof,
b) PEG-400, 2-(2-ethoxyethoxy)ethanol, butylated hydroxytoluene, and phenoxyethanol; and
c) a hydroxypropyl cellulose having an average molecular weight of from about 850,000 Da to about 1,150,000 Da,
wherein the gel formulation has a pH value of no more than about 7.

In some embodiments of the gel formulation (NA-1b) or (NA-1c), PEG-400 is present in an amount of from about 50% to about 55% by weight. In some embodiments, PEG-400 is a super refined PEG-400.

In some embodiments of the gel formulation (NA-1b) or (NA-1c), 2-(2-ethoxyethoxy)ethanol is present in an amount of from about 40% to about 50% by weight. In some embodiments, 2-(2-ethoxyethoxy)ethanol is present in an amount of about 45% by weight. In some embodiments, 2-(2-ethoxyethoxy)ethanol is Transcutol® HP having a purity of >about 99.90%.

In some embodiments of the gel formulation (NA-1b) or (NA-1c), butylated hydroxytoluene is present in an amount of about 0.2% by weight.

In some embodiments of the gel formulation (NA-1b), potassium sorbate is present in an amount of about 0.1% by weight.

In some embodiments of the gel formulation (NA-1c), phenoxyethanol is present in an amount of about 1% by weight.

In some embodiments of the gel formulation (NA-1b) or (NA-1c), the gel formulation further includes a thickening agent in addition to the hydroxypropyl cellulose. In some embodiments, the thickening agent is PEG-1500 in an amount of from about 1% to about 5% by weight. In some embodiments, the thickening agent is PEG-1500 in an amount of about 2% by weight.

In some embodiments of the gel formulation (NA-1b) or (NA-1c), the hydroxypropyl cellulose has an average molecular weight of about 850,000 Da. In some embodiments, the hydroxypropyl cellulose is Klucel™ MF. In some embodiments, Klucel™ MF is present in an amount of about 4% by weight.

In some embodiments of the gel formulation (NA-1b) or (NA-1c), the hydroxypropyl cellulose has an average molecular weight of about 1,150,000 Da. In some embodiments, the hydroxypropyl cellulose is Klucel™ HF.

In some embodiments of the gel formulation (NA-1b) or (NA-1c), Klucel™ HF is present in an amount of from about 0.5% to 2% by weight. In some embodiments, Klucel™ HF is present in an amount of about 0.5% by weight. In some embodiments, Klucel™ HF is present in an amount of about 0.75% by weight. In some embodiments, Klucel™ HF is present in an amount of about 1% by weight. In some embodiments, Klucel™ HF is present in an amount of about 1.5% by weight.

In some embodiments of the gel formulation (NA-1b) or (NA-1c), Klucel™ HF is present in an amount of from about 0.5% to about 2% by weight; and the thickening agent is PEG-1500 in an amount of from about 1% to about 5% by weight. In some embodiments, Klucel™ HF is present in an amount of from about 0.5% by weight; and PEG-1500 is present in an amount of about 2% by weight.

In some embodiments of the gel formulation (NA-1b) or (NA-1c), the formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the formulation has a viscosity of from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the formulation has a viscosity of from about 20,000 to about 50,000 cps, from about 25,000 to about 50,000 cps, from about 20,000 to about 40,000 cps, or from about 25,000 to about 40,000 cps. In some embodiments, the formulation has a viscosity of from about 15,000 to about 50,000 cps. In some embodiments, the formulation has a viscosity of from about 20,000 to about 50,000 cps. In some embodiments, the formulation has a viscosity of from about 25,000 to about 50,000 cps. In some embodiments, the formulation has a viscosity of from about 15,000 to about 40,000 cps. In some embodiments, the formulation has a viscosity of from about 20,000 to about 40,000 cps. In some embodiments, the formulation has a viscosity of from about 25,000 to about 40,000 cps.

With reference to any one of gel formulations (NA-1a), (NA-1b), and (NA-1c), in some embodiments, a pH is adjusted with a solution of citric acid in PEG-400. In some embodiments, a pH is adjusted with a solution of citric acid in a super refined PEG-400. In some embodiments, a pH is adjusted with a solution of citric acid in 2-(2-ethoxyethoxy) ethanol. In some embodiments, a pH is adjusted with a solution of citric acid in Transcutol® HP.

With reference to any one of gel formulations (NA-1a), (NA-1b), and (NA-1c), in some embodiments, the compound (i.e., Compound 1.003) is present in an amount of from 0.005% to 3% by weight. In some embodiments, the compound is present in an amount of about 0.5% by weight. In some embodiments, the compound is present in an amount of about 1% by weight. In some embodiments, the compound is present in an amount of about 1.5% by weight. In some embodiments, the compound is present in an amount of about 2% by weight.

In some embodiments, the gel formulation (NA-1a) includes:
- a) from about 0.005% to about 3% by weight of Compound 1.003 or a hydrate and/or pharmaceutically acceptable salt thereof, on a salt-free and anhydrous basis;
- b) from about 50% to about 55% by weight of PEG-400;
- c) from about 40% to about 50% by weight of 2-(2-ethoxyethoxy)ethanol;
- d) from about 0.03% to about 0.7% by weight of ascorbyl palmitate;
- e) from about 0.001% to about 0.05% by weight of alpha tocopherol or alpha tocopherol acetate; and
- f) from about 0.2% to about 1% by weight of the hydroxypropyl cellulose having an average molecular weight of about 1,150,000 Da; and
- g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1a-0.05%) includes:
- a) about 0.05% by weight of Compound 1.003 or a hydrate and/or pharmaceutically acceptable salt thereof, on a salt-free and anhydrous basis;
- b) about 54% by weight of PEG-400;
- c) about 45% by weight of 2-(2-ethoxyethoxy)ethanol;
- d) about 0.05% by weight of ascorbyl palmitate;
- e) about 0.002% by weight of alpha tocopherol or alpha tocopherol acetate;
- f) about 0.50% by weight of the hydroxypropyl cellulose having an average molecular weight of about 1,150,000 Da; and
- g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1a-0.15%) includes:
- a) about 0.15% by weight of Compound 1.003 or a hydrate and/or pharmaceutically acceptable salt thereof, on a salt-free and anhydrous basis;
- b) about 54% by weight of PEG-400;
- c) about 45% by weight of 2-(2-ethoxyethoxy)ethanol;
- d) about 0.05% by weight of ascorbyl palmitate;
- e) about 0.002% by weight of alpha tocopherol or alpha tocopherol acetate;
- f) about 0.50% by weight of the hydroxypropyl cellulose having an average molecular weight of about 1,150,000 Da; and
- g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1a-0.5%) includes:
- a) about 0.5% by weight of Compound 1.003 or a hydrate and/or pharmaceutically acceptable salt thereof, on a salt-free and anhydrous basis;
- b) about 54% by weight of PEG-400;
- c) about 45% by weight of 2-(2-ethoxyethoxy)ethanol;
- d) about 0.05% by weight of ascorbyl palmitate;
- e) about 0.002% by weight of alpha tocopherol or alpha tocopherol acetate;
- f) about 0.50% by weight of the hydroxypropyl cellulose having an average molecular weight of about 1,150,000 Da; and
- g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1a-1%) includes:
- a) about 1% by weight of Compound 1.003 or a hydrate and/or pharmaceutically acceptable salt thereof, on a salt-free and anhydrous basis;
- b) about 53% by weight of PEG-400;
- c) about 45% by weight of 2-(2-ethoxyethoxy)ethanol;
- d) about 0.05% by weight of ascorbyl palmitate;
- e) about 0.002% by weight of alpha tocopherol or alpha tocopherol acetate;
- f) about 0.50% by weight of the hydroxypropyl cellulose having an average molecular weight of about 1,150,000 Da; and
- g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1a-2%) includes:
- a) about 2% by weight of Compound 1.003 or a hydrate and/or pharmaceutically acceptable salt thereof, on a salt-free and anhydrous basis;
- b) about 52% by weight of PEG-400;
- c) about 45% by weight of 2-(2-ethoxyethoxy)ethanol;
- d) about 0.05% by weight of ascorbyl palmitate;

e) about 0.002% by weight of alpha tocopherol or alpha tocopherol acetate;
f) about 0.50% by weight of the hydroxypropyl cellulose having an average molecular weight of about 1,150,000 Da; and
g) citric acid and/or sodium hydroxide, wherein the total weight of a) to g) is 100%; and citric acid and sodium hydroxide are each a solution in PEG-400 or 2-(2-ethoxyethoxy)ethanol to adjust a pH.

In some embodiments, the gel formulation (NA-1b) includes:
a) from about 0.005% to about 3% by weight of Compound 1.003 or a hydrate and/or pharmaceutically acceptable salt thereof, on a salt-free and anhydrous basis;
b) from about 50% to about 55% by weight of PEG-400;
c) from about 40% to about 50% by weight of 2-(2-ethoxyethoxy)ethanol;
d) from about 0.1% to about 0.3% by weight of butylated hydroxytoluene;
e) from about 0.05% to about 0.2% by weight of potassium sorbate;
f) optionally from about 1% to about 3% PEG-1500;
g) from about 0.5% to about 2% by weight of the hydroxypropyl cellulose having an average molecular weight of about 1,150,000 Da; and
h) citric acid, and
i) optionally from about 0.001% to about 0.05% by weight of one or more dyes, wherein the total weight of a) to i) is 100%; and citric acid is a solution in PEG-400 or 2-(2-ethoxyethoxy)ethanol to adjust a pH.

In some embodiments, the gel formulation (NA-1b-0.5%) includes:
a) about 0.5% by weight of Compound 1.003 or a hydrate and/or pharmaceutically acceptable salt thereof, on a salt-free and anhydrous basis;
b) from about 50% to about 55% by weight of PEG-400;
c) about 45% by weight of 2-(2-ethoxyethoxy)ethanol;
d) about 0.2% by weight of butylated hydroxytoluene;
e) about 0.1% by weight of potassium sorbate;
f) from about 0.5% to about 2% by weight of the hydroxypropyl cellulose having an average molecular weight of about 1,150,000 Da; and
g) citric acid, and
h) optionally from about 0.001% to about 0.05% by weight of one or more dyes, wherein the total weight of a) to h) is 100%; and citric acid is a solution in PEG-400 or 2-(2-ethoxyethoxy)ethanol to adjust a pH.

In some embodiments, the gel formulation (NA-1b-1.5%) includes:
a) about 1.5% by weight of Compound 1.003 or a hydrate and/or pharmaceutically acceptable salt thereof, on a salt-free and anhydrous basis;
b) from about 50% to about 53% by weight of PEG-400;
c) about 45% by weight of 2-(2-ethoxyethoxy)ethanol;
d) about 0.2% by weight of butylated hydroxytoluene;
e) about 0.1% by weight of potassium sorbate;
f) from about 0.5% to about 2% by weight of the hydroxypropyl cellulose having an average molecular weight of about 1,150,000 Da; and
g) citric acid, wherein the total weight of a) to g) is 100%; and citric acid is a solution in PEG-400 or 2-(2-ethoxyethoxy)ethanol to adjust a pH.

In some embodiments, the gel formulation (NA-1c) includes:
a) from about 0.005% to about 3% by weight of Compound 1.003 or a hydrate and/or pharmaceutically acceptable salt thereof, on a salt-free and anhydrous basis;
b) from about 50% to about 55% by weight of PEG-400;
c) from about 40% to about 50% by weight of 2-(2-ethoxyethoxy)ethanol;
d) from about 0.1% to about 0.3% by weight of butylated hydroxytoluene;
e) from about 0.5% to about 2% by weight of phenoxyethanol;
f) optionally from about 1% to about 3% PEG-1500;
g) from about 0.5% to about 2% by weight of the hydroxypropyl cellulose having an average molecular weight of about 1,150,000 Da;
h) citric acid; and
i) optionally from about 0.001% to about 0.05% by weight of one or more dyes, wherein the total weight of a) to i) is 100%; and citric acid is a solution in PEG-400 or 2-(2-ethoxyethoxy)ethanol to adjust a pH.

In some embodiments, the gel formulation (NA-1c-0.5%) includes:
a) about 0.5% by weight of Compound 1.003 or a hydrate and/or pharmaceutically acceptable salt thereof, on a salt-free and anhydrous basis;
b) about 52% by weight of PEG-400;
c) about 45% by weight of 2-(2-ethoxyethoxy)ethanol;
d) about 0.2% by weight of butylated hydroxytoluene;
e) about 1% by weight of phenoxyethanol;
f) about 1% by weight of the hydroxypropyl cellulose having an average molecular weight of about 1,150,000 Da;
g) citric acid; and
h) optionally about 0.02% by weight of one or more dyes, wherein the total weight of a) to h) is 100%; and citric acid is a solution in PEG-400 or 2-(2-ethoxyethoxy)ethanol to adjust a pH.

In some embodiments, the gel formulation (NA-1c-1.5%) includes:
a) about 1.5% by weight of Compound 1.003 or a hydrate and/or pharmaceutically acceptable salt thereof, on a salt-free and anhydrous basis;
b) about 51% by weight of PEG-400;
c) about 45% by weight of 2-(2-ethoxyethoxy)ethanol;
d) about 0.2% by weight of butylated hydroxytoluene;
e) about 1% by weight of phenoxyethanol;
f) about 1% by weight of the hydroxypropyl cellulose having an average molecular weight of about 1,150,000 Da; and
g) citric acid, wherein the total weight of a) to g) is 100%; and citric acid is a solution in PEG-400 or 2-(2-ethoxyethoxy)ethanol to adjust a pH.

In some embodiments of any one of gel formulations (e.g., NA-1a, NA-1b, and NA-1c) as described herein, the solution of citric acid or sodium hydroxide in PEG-400 or 2-(2-ethoxyethoxy)ethanol has a concentration of from about 0.1 M to about 0.5 M. In some embodiments, the solution of citric acid or sodium hydroxide in PEG-400 or 2-(2-ethoxyethoxy)ethanol has a concentration of about 0.1 M. In some embodiments, the solution of citric acid or sodium hydroxide in PEG-400 or 2-(2-ethoxyethoxy)ethanol has a concentration of about 0.5 M. In some embodiments, the solution of citric acid in 2-(2-ethoxyethoxy) ethanol has a concentration of about 0.5 M.

In some embodiments of any one of gel formulations as described herein, PEG-400 is a super refined PEG-400; 2-(2-ethoxyethoxy)ethanol is Transcutol® HP having a purity of >about 99.90%; and/or the hydroxypropyl cellulose is Klucel™ HF. In some embodiments, PEG-400 is a super refined PEG-400; 2-(2-ethoxyethoxy)ethanol is Transcutol® HP having a purity of >about 99.90%; and the hydroxypropyl cellulose is Klucel™ HF.

Stability of Formulations

In some embodiments, the gel formulations as described herein have a visual appearance as clear, transparent, or monophasic. In some embodiments, the visual appearance of the gel formulation is maintained over a period of 4 weeks at a temperature of about 40° C.

The gel formulations as described herein have stable viscosity for a period of 4 weeks at a temperature of about 40° C.

The compound of formula (I) in the gel formulations as described herein is stable for a period of 6 months at a temperature of about 25° C. In some embodiments, a relative purity of the compound of formula (I) is maintained from 95% to 100% over a period of 6 months at a temperature of about 25° C. The compound of formula (Ib) in the gel formulations as described herein is stable for a period of 6 months at a temperature of about 25° C. In some embodiments, a relative purity of the compound of formula (Ib) is maintained from 95% to 100% over a period of 6 months at a temperature of about 25° C. In some embodiments, a relative purity of Compound 1.003 is maintained from 95% to 100% over a period of 6 months at a temperature of about 25° C.

EMBODIMENTS

Embodiment A1. A gel formulation, comprising:
a) a compound represented by formula (I):

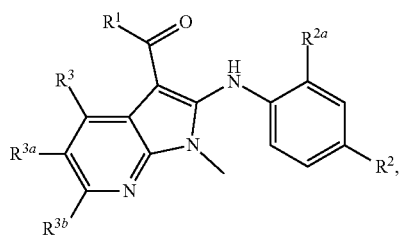

or a stereoisomer, a mixture of stereoisomers, and/or a pharmaceutically acceptable salt thereof,
wherein
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^3$, $R^{3a}$, and $R^{3b}$ are independently hydrogen, halo, $C_1$-$C_6$ alkyl, or $C_1$-$C_6$ alkoxy;
$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^{5a}$ is hydrogen or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
b) a polyethylene glycol, an antioxidant, and optionally a preservative;
c) one or more organic solvents; and
d) a gelling agent,
wherein:
the polyethylene glycol has an average molecular weight of from about 200 Da to about 900 Da and is present in an amount of at least about 30% by weight;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof,
the gelling agent is hydroxypropyl cellulose or polyvinylpyrrolidone, each of which has an average molecular weight of from about 80,000 Da to about 1,700,000 Da;
the gel formulation has a pH value of no more than about 7; and
water, when present, is no more than about 5% by weight.

Embodiment A2. The gel formulation of Embodiment A1, wherein the gel formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

Embodiment A3. The gel formulation of Embodiment A1 or A2, wherein the gel formulation has a viscosity of from about 15,000 to about 50,000 cps.

Embodiment A4. The gel formulation of any one of Embodiments A1 to A3, wherein the compound is represented by formula (Ib):

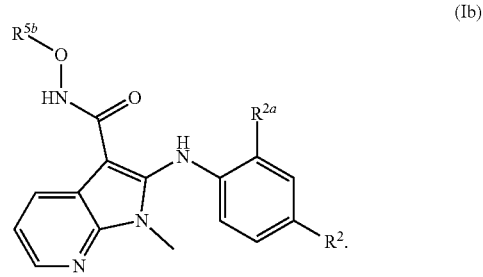

Embodiment A5. The gel formulation of any one of Embodiments A1 to A4, wherein the compound is represented by the formula:

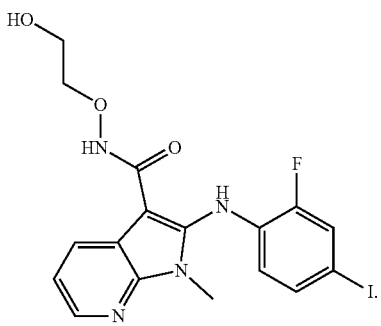 [SMILES: Cn1c(Nc2ccc(I)cc2F)c(C(=O)NOCCO)c2cccnc21]

Embodiment A6. The gel formulation of any one of Embodiments A1 to A5, wherein the polyethylene glycol is PEG-400.

Embodiment A7. The gel formulation of Embodiment A6, wherein PEG-400 is present in an amount of from about 50% to about 60% by weight.

Embodiment A8. The gel formulation of any one of Embodiments A1 to A7, wherein the one or more organic solvents are $C_{1-3}$ alkyl-$(OCH_2CH_2)_{1-5}$—OH; and $C_{1-3}$ alkyl-$(OCH_2CH_2)_{1-5}$—OH is 2-(2-ethoxyethoxy)ethanol.

Embodiment A9. The gel formulation of Embodiment A8, wherein 2-(2-ethoxyethoxy)ethanol is present in an amount of from about 40% to about 50% by weight.

Embodiment A10. The gel formulation of any one of Embodiments A1 to A9, wherein the antioxidant is butylated hydroxytoluene, butylated hydroxyanisole, an ascorbyl ester, or combinations thereof.

Embodiment A11. The gel formulation of any one of Embodiments A1 to A10, wherein the antioxidant is butylated hydroxytoluene in an amount of from about 0.1% to about 0.5%, from about 0.1% to about 0.4%, or from about 0.1% to about 0.3% by weight.

Embodiment A12. The gel formulation of Embodiment A11, wherein butylated hydroxytoluene is present in an amount of about 0.2% by weight.

Embodiment A13. The gel formulation of any one of Embodiments A1 to A10, wherein the antioxidant is an ascorbyl ester comprising ascorbyl palmitate.

Embodiment A14. The gel formulation of Embodiment A13, wherein ascorbyl palmitate is present in an amount of from about 0.01% to about 0.1% by weight.

Embodiment A15. The gel formulation of Embodiment A14, wherein ascorbyl palmitate is present in an amount of about 0.05% by weight.

Embodiment A16. The gel formulation of any one of Embodiments A13 to A15, further comprising a stabilizer, wherein the stabilizer is alpha tocopherol or alpha tocopherol acetate.

Embodiment A17. The gel formulation of Embodiment A16, wherein alpha tocopherol or alpha tocopherol acetate is present in an amount of about 0.002% by weight.

Embodiment A18. The gel formulation of any one of Embodiments A1 to A17, wherein the preservative, when present, is benzyl alcohol, phenoxyethanol, potassium sorbate, or combinations thereof.

Embodiment A19. The gel formulation of any one of Embodiments A1 to A18, wherein the preservative, when present, is phenoxyethanol in an amount of from about 0.5% to about 5%, from about 0.5% to about 4%, from about 0.5% to about 3%, or from about 0.5% to about 2% by weight.

Embodiment A20. The gel formulation of Embodiment A19, wherein phenoxyethanol is present in an amount of about 1% by weight.

Embodiment A21. The gel formulation of any one of Embodiments A1 to A18, wherein the preservative, when present, is potassium sorbate in an amount of from about 0.05% to about 0.5%, from about 0.05% to about 0.4%, from about 0.05% to about 0.3%, or from about 0.05% to about 0.2% by weight.

Embodiment A22. The gel formulation of Embodiment A21, wherein potassium sorbate is present in an amount of about 0.1% by weight.

Embodiment A23. The gel formulation of any one of Embodiments A1 to A22, further comprising a thickening agent, wherein the thickening agent is a polyethylene glycol having an average molecular weight of from about 1000 to about 3000 Da.

Embodiment A24. The gel formulation of any one of Embodiments A6 to A23, wherein PEG-400 is a super refined PEG-400.

Embodiment A25. The gel formulation of any one of Embodiments A8 to A24, wherein 2-(2-ethoxyethoxy)ethanol is Transcutol® HP having a purity of >about 99.90%.

Embodiment A26. The gel formulation of any one of Embodiments A1 to A25, wherein the gelling agent is hydroxypropyl cellulose.

Embodiment A27. The gel formulation of Embodiment A26, wherein the hydroxypropyl cellulose has an average molecular weight of from about 850,000 Da to about 1,150,000 Da.

Embodiment A28. The gel formulation of Embodiment A26, wherein the hydroxypropyl cellulose is Klucel™ MF or Klucel™ HF.

Embodiment A29. The gel formulation of Embodiment A28, wherein the hydroxypropyl cellulose is Klucel™ HF in an amount of from about 0.5% to about 2% by weight.

Embodiment A30. The gel formulation of any one of Embodiments A1 to A29, wherein the compound of formula (I) is present in an amount of from about 0.1% to about 3% by weight.

Embodiment A31. A gel formulation, comprising:
a) a compound represented by the formula:

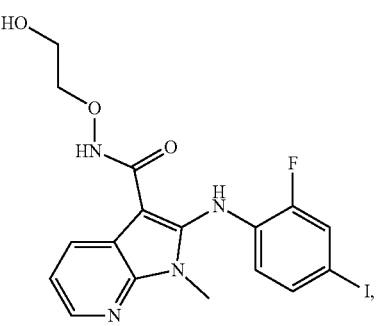

or a pharmaceutically acceptable salt thereof,
b) PEG-400, 2-(2-ethoxyethoxy)ethanol, butylated hydroxytoluene, and potassium sorbate; and
c) a hydroxypropyl cellulose having an average molecular weight of from about 850,000 Da to about 1,150,000 Da, wherein the gel formulation has a pH value of no more than about 7.

Embodiment A32. A gel formulation, comprising:
a) a compound represented by the formula:

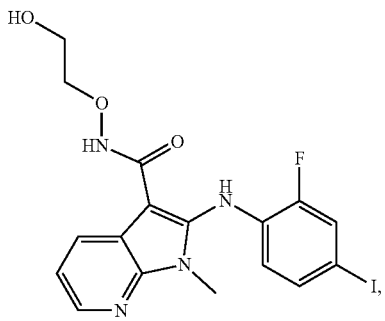 [SMILES: Cn1c(Nc2ccc(I)cc2F)c(C(=O)NOCCO)c2cccnc21]

or a pharmaceutically acceptable salt thereof,
b) PEG-400, 2-(2-ethoxyethoxy)ethanol, butylated hydroxytoluene, and phenoxyethanol; and
c) a hydroxypropyl cellulose having an average molecular weight of from about 850,000 Da to about 1,150,000 Da, wherein the gel formulation has a pH value of no more than about 7.

Embodiment A33. The gel formulation of Embodiment A31 or A32, wherein the gel formulation has a viscosity of from about 15,000 to about 50,000 cps.

Embodiment A34. A method of treating a skin disorder comprising administering a gel formulation of any one of Embodiments A1 to A33, wherein the skin disorder is a MEK-inhibitor responsive dermal disorder or a MEK-mediated dermal disorder, a birthmark, or a skin cancer.

Embodiment A35. The method of Embodiment A34, wherein the MEK-inhibitor responsive dermal disorder or MEK-mediated dermal disorder is selected from the group consisting of neurofibromatosis type 1, dermal neurofibroma, subdermal neurofibroma, superficial plexiform neurofibroma, and dermal rasopathy.

Embodiment A36. The method of Embodiment A35, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

Embodiment A37. The method of Embodiment A34, wherein the birthmark is selected from the group consisting of port-wine stains/capillary malformations, nevus cellular nevus, displastic nevi, capillary angioma, epidermal nevi, nevus sebaceous, nevus spilus, arterio-venous malformations, lymphatic malformations, and congenital melanocytic nevus.

Embodiment A38. The method of Embodiment A34 or A37, wherein the birthmark is associated with activation of p-ERK.

Embodiment A39. The method of Embodiment A38, wherein the birthmark associated with activation of p-ERK is selected from the group consisting of epidermal nevi, nevus sebaceous, nevus spilus, arterio-venous malformations, capillary malformations/port-wine stain, congenital melanocytic nevus, and lymphatic malformations.

Embodiment A40. The method of Embodiment A34, wherein the skin cancer is a cutaneous squamous-cell carcinoma.

Embodiment A41. The method of Embodiment A34, wherein the skin cancer is a MEK-inhibitor responsive or MEK-mediated cutaneous squamous-cell carcinoma.

Embodiment A42. The method of Embodiment A40 or A41, wherein the cutaneous squamous-cell carcinoma is associated with activation of p-ERK.

Embodiment A43. The method of any one of Embodiments A34 to A42, wherein the gel formulation is administered topically.

Embodiment A44. The method of any one of Embodiments A34 to A43, wherein the gel formulation is administered as a paint, a lotion, an ointment, a cream, a gel, or a patch.

III-B. Aqueous Gel Formulations Including a Compound of Formula (I)

In a second aspect, the present disclosure provides an aqueous gel formulation useful for the treatment of skin disorders. The aqueous gel formulation includes:
a) a compound represented by formula (I):

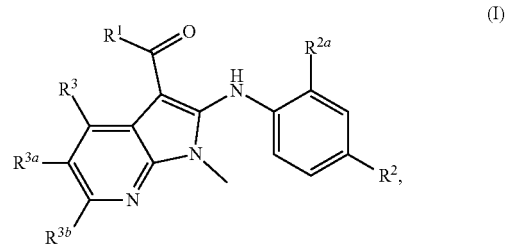

or a stereoisomer, a mixture of stereoisomers, and/or a pharmaceutically acceptable salt thereof,
wherein
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^3$, $R^{3a}$, and $R^{3b}$ are independently hydrogen, halo, $C_1$-$C_6$ alkyl, or $C_1$-$C_6$ alkoxy;
$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^{5a}$ is hydrogen or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
b) water, a polyethylene glycol, an antioxidant, and a preservative; and
c) optionally one or more organic solvents; and
d) a gelling agent,
wherein:
water is present in an amount of at least about 10% by weight;
the polyethylene glycol has an average molecular weight of from about 200 Da to about 900 Da;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof;

the gelling agent is hydroxypropyl cellulose having an average molecular weight of from about 80,000 Da to about 1,700,000 Da, or the gelling agent is poly(acrylic acid); and the aqueous gel formulation has a pH value of no more than about 7.

In some embodiments, the compound of formula (I) is represented by formula (Ia):

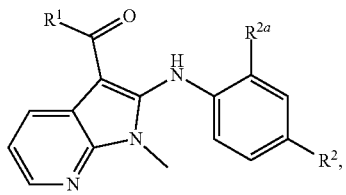

(Ia)

wherein $R^1$, $R^2$, and $R^{2a}$ are as defined and described herein.

In some embodiments, the compound is represented by formula (Ib):

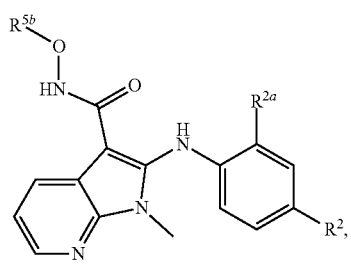

(Ib)

wherein $R^2$, $R^{2a}$, and $R^{5b}$ are defined and described herein.

In some embodiments, $R^2$ and $R^{2a}$ are each halo. In some embodiments, $R^{5b}$ is $C_3$-$C_8$ cycloalkyl-$C_1$-$C_6$ alkyl or $C_1$-$C_6$ hydroxyalkyl. In some embodiments, $R^{5b}$ is $C_1$-$C_6$ hydroxyalkyl. In some embodiments, $R^{5b}$ is unbranched $C_1$-$C_6$ hydroxyalkyl. In some embodiments, $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy. In some embodiments, $R^2$ and $R^{2a}$ are each halo; and $R^{5b}$ is $C_1$-$C_6$ hydroxyalkyl. In some embodiments, $R^2$ and $R^{2a}$ are each halo; and $R^{5b}$ is unbranched $C_1$-$C_6$ hydroxyalkyl. In some embodiments, $R^2$ and $R^{2a}$ are each halo; and $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy.

In some embodiments, the compound is represented by formula (Ib-1):

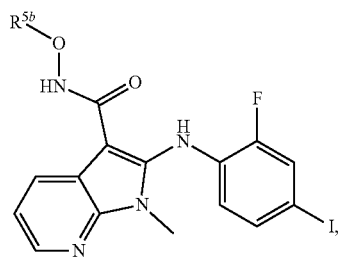

(Ib-1)

wherein $R^{5b}$ is defined and described herein.

In some embodiments, the compound is represented by the formula:

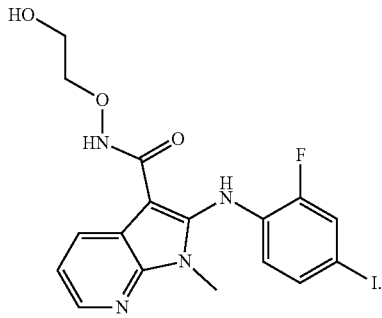 [SMILES: Cn1c(Nc2ccc(I)cc2F)c(C(=O)NOCCO)c2cccnc21]

(Compound 1.003)

In some embodiments, the aqueous gel formulation has a viscosity of from about 1,000 to about 25,000 cps, from about 2,000 to about 25,000 cps, from about 5,000 to about 25,000 cps, or from about 10,000 to about 25,000 cps. In some embodiments, the viscosity is from about 1,000 to about 25,000 cps. In some embodiments, the viscosity is from about 2,000 to about 25,000 cps. In some embodiments, the viscosity is from about 5,000 to about 25,000 cps. In some embodiments, the viscosity is from about 10,000 to about 25,000 cps. In some embodiments, the viscosity is from about 10,000 to about 15,000 cps. In some embodiments, the viscosity is from about 10,000 to about 20,000 cps. In some embodiments, the viscosity is from about 15,000 to about 20,000 cps.

In some embodiments, the aqueous gel formulation has a viscosity of from about 25,000 to about 200,000 cps, from about 50,000 to about 200,000 cps, from about 75,000 to about 200,000 cps, or from about 100,000 to about 200,000 cps. In some embodiments, the viscosity is from about 25,000 to about 150,000 cps, from about 50,000 to about 150,000 cps, from about 75,000 to about 150,000 cps, or from about 100,000 to about 150,000 cps. In some embodiments, the viscosity is from about 25,000 to about 100,000 cps, from about 50,000 to about 100,000 cps, from about 75,000 to about 100,000 cps, from about 50,000 to about 75,000 cps, or from about 25,000 to about 50,000 cps. In some embodiments, the viscosity is from about 50,000 to about 200,000 cps. In some embodiments, the viscosity is from about 100,000 to about 200,000 cps.

In some embodiments, the aqueous gel formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

In some embodiments, the aqueous gel formulation has a viscosity of from about 10,000 to about 25,000 cps, from about 15,000 to about 25,000 cps, from about 15,000 to about 50,000 cps, or from about 25,000 to about 50,000 cps. In some embodiments, the viscosity is from about 15,000 to about 25,000 cps. In some embodiments, the viscosity is from about 15,000 to about 50,000 cps. In some embodiments, the viscosity is from about 20,000 to about 50,000 cps. In some embodiments, the viscosity is from about 20,000 to about 40,000 cps. In some embodiments, the viscosity is from about 25,000 to about 50,000 cps. In some embodiments, the viscosity is from about 25,000 to about 40,000 cps.

In some embodiments, an aqueous solution without the gelling agent is miscible.

In some embodiments, water is present in an amount of at least about 15%, 20%, or 25% by weight. In some embodiments, water is present in an amount of at least about 20% by weight. In some embodiments, water is present in an amount of at least about 25% by weight. In some embodiments, water is present in an amount of from about 15% to about 40% by weight.

In some embodiments, the polyethylene glycol is PEG-200, PEG-300, PEG-400, PEG-600, or PEG-900. In some embodiments, the polyethylene glycol is PEG-400. In some embodiments, PEG-400 is a super refined PEG-400.

In some embodiments, the antioxidant is butylated hydroxytoluene, butylated hydroxyanisole, ascorbic acid, or combinations thereof. In some embodiments, the antioxidant is butylated hydroxytoluene, butylated hydroxyanisole, or a combination thereof. In some embodiments, the antioxidant is butylated hydroxytoluene. In some embodiments, the antioxidant is ascorbic acid.

In some embodiments, the antioxidant is present in an amount of from about 0.01% to about 1% by weight. In some embodiments, the antioxidant is present in an amount of from about 0.01% to about 0.5% by weight. In some embodiments, the antioxidant is present in an amount of from about 0.01% to about 0.1% by weight. In some embodiments, the antioxidant is present in an amount of from about 0.1% to about 0.5% by weight.

In some embodiments, when the antioxidant is ascorbic acid, the aqueous gel formulation further includes a stabilizer. In some embodiments, the stabilizer is a disodium salt of ethylenediaminetetraacetic acid. In some embodiments, the stabilizer is present in an amount of from about 0.01% to about 0.5% by weight.

In some embodiments, the preservative is benzyl alcohol, phenoxyethanol, or a combination thereof. In some embodiments, the preservative is benzyl alcohol. In some embodiments, the preservative is phenoxyethanol. In some embodiments, the preservative is a mixture of benzyl alcohol and phenoxyethanol.

In some embodiments, the preservative is present in an amount of from about 0.1% to about 5% by weight. In some embodiments, the preservative is present in an amount of from about 0.5% to about 3% by weight.

In some embodiments, the aqueous gel formulation further includes one or more surfactants. In some embodiments, the one or more surfactants are a polysorbate, a poloxamer, a polyoxyethylene fatty ether, a polyoxyethylene fatty acid ester, or combinations thereof.

In some embodiments, the one or more surfactants include a polysorbate. In some embodiments, the one or more surfactants include polysorbate 80.

In some embodiments, the one or more surfactants include a poloxamer. In some embodiments, the one or more surfactants include poloxamer 407.

In some embodiments, the one or more surfactants include a polyoxyethylene fatty ether. In some embodiments, the one or more surfactants include polyoxyl 20 cetostearyl ether.

In some embodiments, the one or more surfactants are polysorbate 80, poloxamer 407, polyoxyl 20 cetostearyl ether, or combinations thereof. In some embodiments, the one or more surfactants are a mixture of polysorbate 80 and poloxamer 407. In some embodiments, the one or more surfactants are polyoxyl 20 cetostearyl ether.

In some embodiments, the one or more organic solvents are absent. In some embodiments, the one or more organic solvents are present. In some embodiments, the one or more organic solvents are a $C_{2-6}$ alcohol, a $C_{2-6}$ alkylene glycol, $C_{1-3}$ alkyl-$(OCH_2CH_2)_{1-5}$—OH, glycerol, and combinations thereof. In some embodiments, one or more organic solvents are a $C_{2-6}$ alcohol, a $C_{2-6}$ alkylene glycol, $C_{1-3}$ alkyl-$(OCH_2CH_2)_{1-5}$—OH, or combinations thereof. In some embodiments, the $C_{2-6}$ alcohol is ethanol. In some embodiments, the $C_{2-6}$ alkylene glycol is propylene glycol. In some embodiments, $C_{1-3}$ alkyl-$(OCH_2CH_2)_{1-5}$—OH is 2-(2-ethoxyethoxy)ethanol.

In some embodiments, the one or more organic solvents, when present, are ethanol, propylene glycol, 2-(2-ethoxyethoxy)ethanol, or combinations thereof. In some embodiments, the one or more organic solvents include 2-(2-ethoxyethoxy)ethanol. In some embodiments, the one or more organic solvents are 2-(2-ethoxyethoxy)ethanol. In some embodiments, the one or more organic solvents include propylene glycol and 2-(2-ethoxyethoxy)ethanol. In some embodiments, the one or more organic solvents are a mixture of propylene glycol and 2-(2-ethoxyethoxy)ethanol. In some embodiments, the one or more organic solvents include ethanol and 2-(2-ethoxyethoxy)ethanol. In some embodiments, the one or more organic solvents are a mixture of ethanol and 2-(2-ethoxyethoxy)ethanol. In some embodiments, the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol.

In some embodiments, the one or more organic solvents, when present, are in an amount of from about 20% to about 60% by weight, wherein the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof.

In some embodiments, water, the polyethylene glycol, and the one or more organic solvents (when present) are present in a total amount of from about 90% to about 99% by weight. In some embodiments, water, the polyethylene glycol, and the one or more organic solvents (when present) are present in a total amount of from about 95% to about 98% by weight.

In some embodiments, propylene glycol is a super refined propylene glycol.

In some embodiments, 2-(2-ethoxyethoxy)ethanol is Transcutol® HP. In some embodiments, 2-(2-ethoxyethoxy)ethanol is Transcutol® HP having a purity of >about 99.90%.

In some embodiments, the aqueous gel formulation (AG-1) includes:
a) the compound of any one of formulae (I), (Ia), (Ib), (Ib-1), and Compound 1.003;
b) water, PEG-400, ascorbic acid, a disodium salt of ethylenediaminetetraacetic acid, and phenoxyethanol;
c) one or more surfactants; and
d) the gelling agent,
wherein the one or more surfactants include the polysorbate and the poloxamer.

In some embodiments of aqueous gel formulation (AG-1), water is present in an amount of from about 20% to about 40% or from about 25% to about 35% by weight. In some embodiments, water is present in an amount of from about 25% to about 35% by weight. In some embodiments, water is present in an amount of about 30% by weight.

In some embodiments of aqueous gel formulation (AG-1), PEG-400 is present in an amount of from about 40% to about 80% or from about 50% to about 70% by weight. In some embodiments, PEG-400 is present in an amount of from about 50% to about 70% by weight. In some embodiments, PEG-400 is present in an amount of from about 50% to about 70% by weight. In some embodiments, PEG-400 is present in an amount of about 62% by weight.

In some embodiments of aqueous gel formulation (AG-1), ascorbic acid in an amount of from about 0.05% to about 0.2% by weight. In some embodiments, ascorbic acid in an amount of about 0.1% by weight.

In some embodiments of aqueous gel formulation (AG-1), the disodium salt of ethylenediaminetetraacetic acid is present in an amount of from about 0.01% to about 0.1% by weight. In some embodiments, the disodium salt of ethylenediaminetetraacetic acid is present in an amount of about 0.05% by weight.

In some embodiments of aqueous gel formulation (AG-1), phenoxyethanol is present in an amount of from about 0.5% to about 2% by weight. In some embodiments, phenoxyethanol is present in an amount of about 1% by weight.

In some embodiments of aqueous gel formulation (AG-1), the one or more surfactants are a mixture of polysorbate 80 and poloxamer 407. In some embodiments, polysorbate 80 is present in an amount of from about 3% to about 7% by weight. In some embodiments, polysorbate 80 is present in an amount of about 5% by weight. In some embodiments, poloxamer 407 is present in an amount of from about 0.5% to about 2% by weight. In some embodiments, poloxamer 407 is present in an amount of about 1% by weight.

In some embodiments, the aqueous gel formulation (AG-1) is free of one or more organic solvents, wherein the one or more organic solvents are as defined and described herein.

In some embodiments, the aqueous gel formulation (AG-2) includes:
 a) the compound of any one of formulae (I), (Ia), (Ib), (Ib-1), and Compound 1.003;
 b) water, PEG-400, butylated hydroxytoluene, and phenoxyethanol;
 c) one or more organic solvents; and
 d) the gelling agent,
wherein the one or more organic solvents are a $C_{2-6}$ alcohol, a $C_{2-6}$ alkylene glycol, $C_{1-3}$ alkyl-$(OCH_2CH_2)_{1-5}$—OH, glycerol, or combinations thereof.

In some embodiments of aqueous gel formulation (AG-2), water is present in an amount of from about 10% to about 30% or from about 15% to about 25% by weight. In some embodiments, water is present in an amount of from about 15% to about 25% by weight. In some embodiments, water is present in an amount of about 20% by weight.

In some embodiments of aqueous gel formulation (AG-2), PEG-400 is present in an amount of from about 20% to about 50%, from about 30% to about 50%, or from about 20% to about 40% by weight. In some embodiments, PEG-400 is present in an amount of from about 30% to about 50% by weight. In some embodiments, PEG-400 is present in an amount of about 38% by weight. In some embodiments, PEG-400 is present in an amount of from about 20% to about 40% by weight. In some embodiments, PEG-400 is present in an amount of about 29% by weight.

In some embodiments of aqueous gel formulation (AG-2), butylated hydroxytoluene is present in an amount of from about 0.01% to about 0.1% by weight. In some embodiments, butylated hydroxytoluene is present in an amount of about 0.05% by weight.

In some embodiments of aqueous gel formulation (AG-2), phenoxyethanol is present in an amount of from about 0.5% to about 2% by weight. In some embodiments, phenoxyethanol is present in an amount of about 1% by weight.

In some embodiments of aqueous gel formulation (AG-2), the $C_{2-6}$ alcohol is ethanol; the $C_{2-6}$ alkylene glycol is propylene glycol; and $C_{1-3}$ alkyl-$(OCH_2CH_2)_{1-5}$—OH is 2-(2-ethoxyethoxy)ethanol.

In some embodiments of aqueous gel formulation (AG-2), the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol. In some embodiments, the one or more organic solvents are a mixture of ethanol, propylene glycol, 2-(2-ethoxyethoxy)ethanol, and glycerol.

In some embodiments of aqueous gel formulation (AG-2), the one or more organic solvents are present in an amount of from about 35% to about 55% by weight. In some embodiments, a mixture of ethanol, propylene glycol, and 2-(2-ethoxyethoxy)ethanol is present in an amount of about 35% to about 45% by weight. In some embodiments, a mixture of ethanol, propylene glycol, and 2-(2-ethoxyethoxy)ethanol is present in an amount of about 40% by weight.

In some embodiments of aqueous gel formulation (AG-2), ethanol is present in an amount of from about 2% to about 15% by weight. In some embodiments, ethanol is present in an amount of about 5% by weight. In some embodiments, ethanol is present in an amount of about 10% by weight.

In some embodiments of aqueous gel formulation (AG-2), propylene glycol is present in an amount of from about 5% to about 20% by weight. In some embodiments, propylene glycol is present in an amount of about 10% by weight. In some embodiments, propylene glycol is present in an amount of about 15% by weight.

In some embodiments of aqueous gel formulation (AG-2), 2-(2-ethoxyethoxy)ethanol is present in an amount of from about 10% to about 30% by weight. In some embodiments, 2-(2-ethoxyethoxy)ethanol is present in an amount of about 20% by weight.

In some embodiments of aqueous gel formulation (AG-2), glycerol is absent. In some embodiments, glycerol is present in an amount of from about 5% to about 15% by weight. In some embodiments, glycerol is present in an amount of about 9% by weight.

In some embodiments, the aqueous gel formulation (AG-3) includes:
 a) the compound of any one of formulae (I), (Ia), (Ib), (Ib-1), and Compound 1.003;
 b) water, PEG-400, ascorbic acid, a disodium salt of ethylenediaminetetraacetic acid, and the preservative;
 c) one or more organic solvents, and optionally one or more surfactants; and
 d) the gelling agent,
wherein the preservative is phenoxyethanol or benzyl alcohol;
 the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof, and
 the one or more surfactants include the polyoxyethylene fatty ether.

In some embodiments of the aqueous gel formulation (AG-3), water is present in an amount of from about 20% to about 50%, from about 20% to about 40%, from about 30% to about 50%, from about 20% to about 30%, or from about 30% to about 40% by weight. In some embodiments, water is present in an amount of from about 20% to about 40% by weight. In some embodiments, water is present in an amount of from about 30% to about 40% by weight. In some embodiments, water is present in an amount of from about 20% to about 30% by weight. In some embodiments, water is present in an amount of about 37% by weight. In some embodiments, water is present in an amount of about 33% by weight. In some embodiments, water is present in an amount of about 31% by weight. In some embodiments, water is present in an amount of about 25% by weight.

In some embodiments of the aqueous gel formulation (AG-3), PEG-400 is present in an amount of from about 10% to about 50%, from about 20% to about 50%, from about 20% to about 40%, from about 20% to about 30%, from about 30% to about 40%, or from about 10% to about 20% by weight. In some embodiments, PEG-400 is present in an amount of from about 30% to about 40% by weight. In some embodiments, PEG-400 is present in an amount of from about 10% to about 20% by weight. In some embodiments, PEG-400 is present in an amount of from about 20% to about 30% by weight. In some embodiments, PEG-400 is present in an amount of about 35% by weight. In some embodiments, PEG-400 is present in an amount of about 13% by weight. In some embodiments, PEG-400 is present in an amount of about 25% by weight.

In some embodiments of the aqueous gel formulation (AG-3), ascorbic acid in an amount of from about 0.05% to about 0.2% by weight. In some embodiments, ascorbic acid in an amount of about 0.1% by weight.

In some embodiments of the aqueous gel formulation (AG-3), the disodium salt of ethylenediaminetetraacetic acid is present in an amount of from about 0.01% to about 0.1% by weight. In some embodiments, the disodium salt of ethylenediaminetetraacetic acid is present in an amount of about 0.02% by weight. In some embodiments, the disodium salt of ethylenediaminetetraacetic acid is present in an amount of about 0.05% by weight.

In some embodiments of the aqueous gel formulation (AG-3), the preservative is phenoxyethanol. In some embodiments, phenoxyethanol is present in an amount of from about 0.5% to about 2% by weight. In some embodiments, phenoxyethanol is present in an amount of about 1% by weight. In some embodiments, the preservative is benzyl alcohol. In some embodiments, benzyl alcohol is present in an amount of from about 1% to about 5% by weight. In some embodiments, benzyl alcohol is present in an amount of about 2% by weight.

In some embodiments of the aqueous gel formulation (AG-3), the $C_{2-6}$ alcohol is absent. In some embodiments, the $C_{2-6}$ alkylene glycol is absent. In some embodiments, both the $C_{2-6}$ alcohol and $C_{2-6}$ alkylene glycol are absent. In some embodiments, the $C_{2-6}$ alcohol is ethanol; the $C_{2-6}$ alkylene glycol is propylene glycol; and $C_{1-3}$ alkyl-$(OCH_2CH_2)_{1-5}$—OH is 2-(2-ethoxyethoxy)ethanol.

In some embodiments of aqueous gel formulation (AG-3), the one or more organic solvents include 2-(2-ethoxyethoxy)ethanol. In some embodiments, the one or more organic solvents are 2-(2-ethoxyethoxy)ethanol. In some embodiments, the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol. In some embodiments, the one or more organic solvents include ethanol and 2-(2-ethoxyethoxy)ethanol. In some embodiments, the one or more organic solvents are a mixture of ethanol and 2-(2-ethoxyethoxy)ethanol. In some embodiments, the one or more organic solvents include propylene glycol and 2-(2-ethoxyethoxy)ethanol. In some embodiments, the one or more organic solvents are a mixture of propylene glycol and 2-(2-ethoxyethoxy)ethanol.

In some embodiments of aqueous gel formulation (AG-3), ethanol, when present, is in an amount of from about 5% to about 20% by weight. In some embodiments, ethanol is present in an amount of from about 5% to about 15% by weight. In some embodiments, ethanol is present in an amount of about 11% by weight.

In some embodiments of aqueous gel formulation (AG-3), propylene glycol, when present, is in an amount of from about 5% to about 20% by weight. In some embodiments, propylene glycol is present in an amount of from about 10% to about 20% by weight. In some embodiments, propylene glycol is present in an amount of about 13% by weight.

In some embodiments of aqueous gel formulation (AG-3), 2-(2-ethoxyethoxy)ethanol is present in an amount of from about 10% to about 30% by weight. In some embodiments, 2-(2-ethoxyethoxy)ethanol is present in an amount of from about 20% to about 30% by weight. In some embodiments, 2-(2-ethoxyethoxy)ethanol is present in an amount of about 24%, about 25%, about 27%, or about 28% by weight. In some embodiments, 2-(2-ethoxyethoxy)ethanol is present in an amount of about 24% by weight. In some embodiments, 2-(2-ethoxyethoxy)ethanol is present in an amount of about 25% by weight. In some embodiments, 2-(2-ethoxyethoxy)ethanol is present in an amount of about 27% by weight. In some embodiments, 2-(2-ethoxyethoxy)ethanol is present in an amount of about 28% by weight.

In some embodiments of aqueous gel formulation (AG-3), the one or more surfactants are absent. In some embodiments, the one or more surfactants, when present, are polyoxyl 20 cetostearyl ether. In some embodiments, polyoxyl 20 cetostearyl ether is present in an amount of from about 1% to about 5% by weight. In some embodiments, polyoxyl 20 cetostearyl ether is present in an amount of about 2% by weight.

In some embodiments of any one of aqueous gel formulations, PEG-400 is a super refined PEG-400. In some embodiments, propylene glycol is a super refined propylene glycol. In some embodiments, 2-(2-ethoxyethoxy)ethanol is Transcutol® HP. In some embodiments, 2-(2-ethoxyethoxy) ethanol is Transcutol® HP having a purity of >about 99.90%.

In some embodiments of any one of aqueous gel formulations, the gelling agent is hydroxypropyl cellulose. The hydroxypropyl celluloses include the ones as described above.

In some embodiments of any one of aqueous gel formulations, hydroxypropyl cellulose has an average molecular weight of about 80,000 Da, 95,000 Da, 100,000 Da, 140,000 Da, 180,000 Da, 280,000 Da, 370,000 Da, 700,000 Da, 850,000 Da, 1,000,000 Da, or 1,150,000 Da. In some embodiments, hydroxypropyl cellulose has an average molecular weight of about 140,000 Da, 180,000 Da, 280,000 Da, 370,000 Da, 700,000 Da, 850,000 Da, 1,000,000 Da, or 1,150,000 Da. In some embodiments, hydroxypropyl cellulose has an average molecular weight of about 140,000 Da, 370,000 Da, 850,000 Da, or 1,150,000 Da. In some embodiments, hydroxypropyl cellulose has an average molecular weight of about 140,000 Da. In some embodiments, hydroxypropyl cellulose has an average molecular weight of about 370,000 Da. In some embodiments, hydroxypropyl cellulose has an average molecular weight of about 850,000

Da. In some embodiments, hydroxypropyl cellulose has an average molecular weight of about 1,150,000 Da.

In some embodiments of any one of aqueous gel formulations, the hydroxypropyl cellulose is Klucel™ JF, Klucel™ GF, Klucel™ MF, or Klucel™ HF. In some embodiments, the hydroxypropyl cellulose is Klucel™ JF, Klucel™ MF, or Klucel™ HF. In some embodiments, the hydroxypropyl cellulose is Klucel™ JF. In some embodiments, the hydroxypropyl cellulose is Klucel™ GF. In some embodiments, the hydroxypropyl cellulose is Klucel™ ME. In some embodiments, the hydroxypropyl cellulose is Klucel™ HF.

In some embodiments of any one of aqueous gel formulations, the gelling agent is poly(acrylic acid) (PAA). In some embodiments, the gelling agent is a Carbopol® polymer. See Technical date sheets of Carbopol® polymer products, the entirety of which is incorporated herein by reference for all purposes. In some embodiments, the gelling agent is Carbopol® 80. In some embodiments, the gelling agent is Carbopol® 80 having a viscosity of from 40,000 to 60,000 cps.

In some embodiments of any one of aqueous gel formulations, the gelling agent is present in an amount of from about 0.2% to about 5% by weight. In some embodiments, the gelling agent is present in an amount of from 0.2% to 5% by weight, wherein the viscosity of the gel formulation is from about 1,000 to about 200,000 cps. In some embodiments, the gelling agent is present in an amount of from about 0.2% to about 5% by weight, wherein the viscosity of the gel formulation is from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps. In some embodiments, the gelling agent is present in an amount of from 0.2% to 5% by weight, wherein the viscosity of the gel formulation is from about 15,000 to about 50,000 cps.

In some embodiments, the gelling agent is Klucel™ HF in an amount of from about 0.2% to about 3% by weight. In some embodiments, the gelling agent is Klucel™ HF in an amount of from about 0.5% to about 2% by weight. In some embodiments, the gelling agent is Klucel™ HF in an amount of about 0.5% by weight. In some embodiments, the gelling agent is Klucel™ HF in an amount of about 0.75% by weight. In some embodiments, the gelling agent is Klucel™ HF in an amount of about 1% by weight. In some embodiments, the gelling agent is Klucel™ HF in an amount of about 1.5% by weight.

In some embodiments of any one of aqueous gel formulations, the gelling agent is Carbopol® 80 in an amount of from about 0.2% to about 1% by weight. In some embodiments, the gelling agent is Carbopol® 80 in an amount of about 0.5% by weight.

The aqueous gel formulation includes water, however the formulation includes substantial amounts of other excipients (e.g., PEG-400, one or more organic solvents) and the gelling agent, therefore the pH value of the partially aqueous solutions can be regarded only as an apparent pH value. See USP chapter <791>, the entirety of which is incorporated herein by reference for all purposes.

In some embodiments, the aqueous gel formulation has a pH value of from about 5 to about 7. In some embodiments, the aqueous gel formulation has a pH value of from about 5 to about 6. In some embodiments, the aqueous gel formulation has a pH value of from about 6 to about 7.

In some embodiments of any one of aqueous gel formulations, a pH of the gel formulation is adjusted with an aqueous solution of sodium hydroxide or ammonia. In some embodiments, a pH is adjusted with an aqueous solution of sodium hydroxide. In some embodiments, a pH is adjusted with 0.1 M NaOH in water. In some embodiments, a pH is adjusted with ammonia. In some embodiments, a pH is adjusted with an aqueous solution of ammonia.

In some embodiments of any one of aqueous gel formulations, the compound of formula (I) is present in the formulation in an amount of from about 0.005% to about 5%, from about 0.01% to about 5%, or from about 0.01% to about 3% by weight on a salt-free and anhydrous basis. In some embodiments, the compound of formula (I) is present in an amount of from about 0.01% to about 3% by weight on a salt-free and anhydrous basis. In some embodiments, the compound of formula (I) is present in an amount of from about 0.01% to about 3% by weight on a salt-free and anhydrous basis.

In some embodiments of any one of aqueous gel formulations, the compound of formula (Ib) is present in the formulation in an amount of from about 0.005% to about 5%, from about 0.01% to about 5%, or from about 0.01% to about 3% by weight on a salt-free and anhydrous basis. In some embodiments, the compound of formula (Ib) is present in an amount of from about 0.01% to about 3% by weight on a salt-free and anhydrous basis. In some embodiments, the compound of formula (Ib) is present in an amount of from about 0.01% to about 3% by weight on a salt-free and anhydrous basis.

In some embodiments of any one of aqueous gel formulations, Compound 1.003 is present in the formulation in an amount of from about 0.005% to about 5%, from about 0.01% to about 5%, from about 0.005% to about 3%, from about 0.01% to about 3%, from about 0.005% to about 1%, or from about 0.01% to about 1% by weight on a salt-free and anhydrous basis. In some embodiments, Compound 1.003 is present in an amount of from about 0.005% to about 1% by weight on a salt-free and anhydrous basis. In some embodiments, Compound 1.003 is present in an amount of from about 0.01% to about 1% by weight on a salt-free and anhydrous basis. In some embodiments, Compound 1.003 is present in an amount of about 0.005% by weight on a salt-free and anhydrous basis. In some embodiments, Compound 1.003 is present in an amount of about 0.01% by weight on a salt-free and anhydrous basis. In some embodiments, Compound 1.003 is present in an amount of about 0.1% by weight on a salt-free and anhydrous basis. In some embodiments, Compound 1.003 is present in an amount of about 0.3% by weight on a salt-free and anhydrous basis. In some embodiments, Compound 1.003 is present in an amount of about 0.5% by weight on a salt-free and anhydrous basis. In some embodiments, Compound 1.003 is present in an amount of about 1% by weight on a salt-free and anhydrous basis.

In some embodiments, the present disclosure provides an aqueous gel formulation (AG-1a), including:
a) a compound represented by the formula:

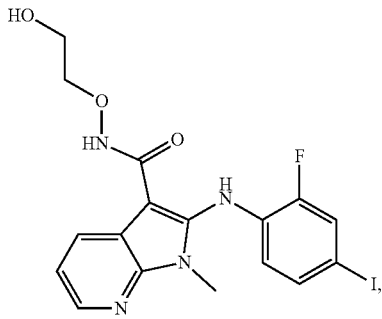

or a pharmaceutically acceptable salt thereof,
b) water, PEG-400, ascorbic acid, a disodium salt of ethylenediaminetetraacetic acid, and phenoxyethanol;
c) a polysorbate and a poloxamer; and
d) a poly(acrylic acid),
wherein the aqueous gel formulation has a pH value of no more than about 7.

In some embodiments of the aqueous gel formulation (AG-1a), water is present in an amount of from about 25% to about 35% by weight. In some embodiments, water is present in an amount of about 30% by weight.

In some embodiments of the aqueous gel formulation (AG-1a), PEG-400 is present in an amount of from about 50% to about 70% by weight. In some embodiments, PEG-400 is present in an amount of about 62% by weight. In some embodiments, PEG-400 is a super refined PEG-400.

In some embodiments of the aqueous gel formulation (AG-1a), ascorbic acid in an amount of from about 0.05% to about 0.2% by weight. In some embodiments, ascorbic acid in an amount of about 0.1% by weight.

In some embodiments of the aqueous gel formulation (AG-1a), the disodium salt of ethylenediaminetetraacetic acid is present in an amount of from about 0.01% to about 0.1% by weight. In some embodiments, the disodium salt of ethylenediaminetetraacetic acid is present in an amount of about 0.05% by weight.

In some embodiments of the aqueous gel formulation (AG-1a), phenoxyethanol is present in an amount of from about 0.5% to about 2% by weight. In some embodiments, phenoxyethanol is present in an amount of about 1% by weight.

In some embodiments of the aqueous gel formulation (AG-1a), the polysorbate is polysorbate 80; and the poloxamer is poloxamer 407. In some embodiments, polysorbate 80 is present in an amount of from about 3% to about 7% by weight. In some embodiments, polysorbate 80 is present in an amount of about 5% by weight. In some embodiments, poloxamer 407 is present in an amount of from about 0.5% to about 2% by weight. In some embodiments, poloxamer 407 is present in an amount of about 1% by weight.

In some embodiments, the aqueous gel formulation (AG-1a) is free of one or more organic solvents. In some embodiments, the aqueous gel formulation (AG-1a) is free of ethanol, propylene glycol, and 2-(2-ethoxyethoxy)ethanol.

In some embodiments of the aqueous gel formulation (AG-1a), the poly(acrylic acid) is Carbopol® 980. In some embodiments, Carbopol® 980 is present in an amount of about 0.5% by weight.

In some embodiments of the aqueous gel formulation (AG-1a), the formulation has a viscosity of from about 10,000 to about 200,000 cps. In some embodiments, the formulation has a viscosity of from about 15,000 to about 50,000 cps. In some embodiments, the formulation has a viscosity of from about 15,000 to about 20,000 cps.

In some embodiments of the aqueous gel formulation (AG-1a), a pH is adjusted with a solution of NaOH in water. In some embodiments, the pH is adjusted with 0.1 M NaOH in water.

In some embodiments of the aqueous gel formulation (AG-1a), the compound (i.e., Compound 1.003) is present in the formulation in an amount of from about 0.005% to about 1% by weight. In some embodiments, the compound is present in an amount of about 0.005% by weight. In some embodiments, the compound is present in an amount of about 0.01% by weight. In some embodiments, the compound is present in an amount of about 0.1% by weight. In some embodiments, the compound is present in an amount of about 0.3% by weight. In some embodiments, the compound is present in an amount of about 0.5% by weight.

In some embodiments, the aqueous gel formulation (AG-1a-1) includes: a) from about 0.005% to about 3% by weight of Compound 1.003 or a hydrate and/or pharmaceutically acceptable salt thereof, on a salt-free and anhydrous basis;
b) from about 25% to about 35% by weight of water;
c) from about 50% to about 70% by weight of PEG-400;
d) from about 0.05% to about 0.2% by weight of ascorbic acid;
e) from about 0.01% to about 0.1% by weight of the disodium salt of ethylenediaminetetraacetic acid;
f) from about 0.5% to about 2% by weight of phenoxyethanol;
g) from about 3% to about 7% by weight of polysorbate 80;
h) from about 0.5% to about 2% by weight of poloxamer 407;
i) from about 0.2% to about 1% by weight of Carbopol® 980; and
j) NaOH,
wherein the total weight of a) to j) is 100%; and NaOH is a solution in water to adjust a pH.

In some embodiments, the gel formulation (AG-1a-1) includes:
a) from about 0.005% to about 1% by weight of Compound 1.003 or a hydrate and/or pharmaceutically acceptable salt thereof, on a salt-free and anhydrous basis;
b) from about 25% to about 35% by weight of water;
c) from about 50% to about 70% by weight of PEG-400;
d) from about 0.05% to about 0.2% by weight of ascorbic acid;
e) from about 0.01% to about 0.1% by weight of the disodium salt of ethylenediaminetetraacetic acid;
f) from about 0.5% to about 2% by weight of phenoxyethanol;
g) from about 3% to about 7% by weight of polysorbate 80;
h) from about 0.5% to about 2% by weight of poloxamer 407;
i) from about 0.2% to about 1% by weight of Carbopol® 980; and
j) NaOH,
wherein the total weight of a) to j) is 100%; and NaOH is a solution in water to adjust a pH.

In some embodiments, the aqueous gel formulation (AG-1a-0.01%) includes:
a) about 0.01% by weight of Compound 1.003 or a hydrate and/or pharmaceutically acceptable salt thereof, on a salt-free and anhydrous basis;
b) about 30% by weight of water;
c) about 62% by weight of PEG-400;
d) about 0.1% by weight of ascorbic acid;
e) about 0.05% by weight of the disodium salt of ethylenediaminetetraacetic acid;
f) about 1% by weight of phenoxyethanol;
g) about 5% by weight of polysorbate 80;
h) about 1% by weight of poloxamer 407;
i) about 0.5% by weight of Carbopol® 980; and
j) NaOH, wherein the total weight of a) to j) is 100%; and NaOH is a solution in water to adjust a pH.

In some embodiments, the aqueous gel formulation (AG-1a-0.1%) includes:
a) about 0.1% by weight of Compound 1.003 or a hydrate and/or pharmaceutically acceptable salt thereof, on a salt-free and anhydrous basis;
b) about 30% by weight of water;
c) about 62% by weight of PEG-400;
d) about 0.1% by weight of ascorbic acid;
e) about 0.05% by weight of the disodium salt of ethylenediaminetetraacetic acid;
f) about 1% by weight of phenoxyethanol;
g) about 5% by weight of polysorbate 80;
h) about 1% by weight of poloxamer 407;
i) about 0.5% by weight of Carbopol® 980; and
j) NaOH, wherein the total weight of a) to j) is 100%; and NaOH is a solution in water to adjust a pH.

In some embodiments, the aqueous gel formulation (AG-1a-0.3%) includes:
a) about 0.3% by weight of Compound 1.003 or a hydrate and/or pharmaceutically acceptable salt thereof, on a salt-free and anhydrous basis;
b) about 30% by weight of water;
c) about 62% by weight of PEG-400;
d) about 0.1% by weight of ascorbic acid;
e) about 0.05% by weight of the disodium salt of ethylenediaminetetraacetic acid;
f) about 1% by weight of phenoxyethanol;
g) about 5% by weight of polysorbate 80;
h) about 1% by weight of poloxamer 407;
i) about 0.5% by weight of Carbopol® 980; and
j) NaOH, wherein the total weight of a) to j) is 100%; and NaOH is a solution in water to adjust a pH.

In some embodiments of any one of aqueous gel formulations (AG-1a-1), (AG-1a-0.01%), (AG-1a-0.1%), and (AG-1a-0.3%), as described herein, the aqueous NaOH solution has a concentration of from about 0.1 M to about 0.5 M. In some embodiment, the aqueous NaOH solution is a 0.1 M NaOH solution.

In some embodiments of any one of aqueous gel formulations (AG-1a-1), (AG-1a-0.01%), (AG-1a-0.1%), and (AG-1a-0.3%), PEG-400 is a super refined PEG-400.

In some embodiments, the aqueous gel formulations as described herein have a visual appearance as clear, transparent, or monophasic. In some embodiments, the visual appearance of the gel formulation is maintained over a period of 4 weeks at a temperature of about 40° C.

The aqueous gel formulations as described herein have stable viscosity for a period of 4 weeks at a temperature of about 40° C.

The compound of formula (I) in the aqueous gel formulations as described herein is stable for a period of 6 months at a temperature of about 25° C. In some embodiments, a relative purity of the compound of formula (I) is maintained from 95% to 100% over a period of 6 months at a temperature of about 25° C. In some embodiments, a relative purity of Compound 1.003 is maintained from 95% to 100% over a period of 6 months at a temperature of about 25° C.

EMBODIMENTS

Embodiment B1: An aqueous gel formulation, comprising:
a) a compound represented by formula (I):

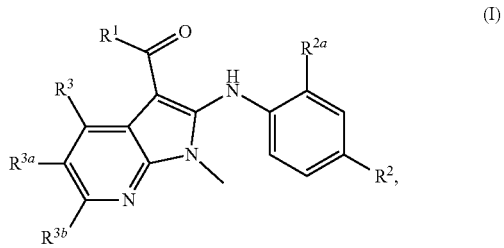

or a stereoisomer, a mixture of stereoisomers, and/or a pharmaceutically acceptable salt thereof,
wherein
$R^1$ is $-OR^4$, $-NR^5R^{5a}$, or $-N(OR^{5b})R^{5a}$;
$R^2$ is halo, $C_1$-$C_6$ alkyl, $-S-C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^3$, $R^{3a}$, and $R^{3b}$ are independently hydrogen, halo, $C_1$-$C_6$ alkyl, or $C_1$-$C_6$ alkoxy;
$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^{5a}$ is hydrogen or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
b) water, a polyethylene glycol, an antioxidant, and a preservative;
c) optionally one or more organic solvents; and
d) a gelling agent,
wherein:
water is present in an amount of at least 10% by weight;
the polyethylene glycol has an average molecular weight of from about 200 Da to 900 Da;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof;
the gelling agent is hydroxypropyl cellulose having an average molecular weight of from about 80,000 Da to about 1,700,000 Da, or the gelling agent is poly(acrylic acid); and
the aqueous gel formulation has a pH value of no more than about 7, provided that an aqueous solution without the gelling agent is miscible.

Embodiment B2: The aqueous gel formulation of embodiment B1, wherein the gel formulation has a viscosity of from about 10,000 to about 200,000 cps.

Embodiment B3: The aqueous gel formulation of embodiment B1 or B2, wherein the compound is represented by formula (Ib):

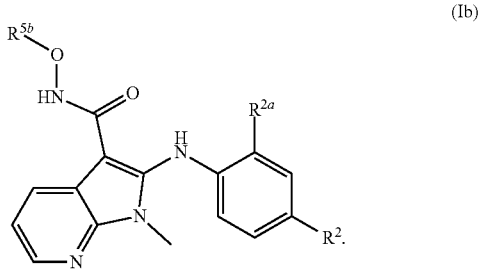

Embodiment B4: The aqueous gel formulation of any one of embodiments B1 to B3, wherein the compound is represented by formula (Ib-1):

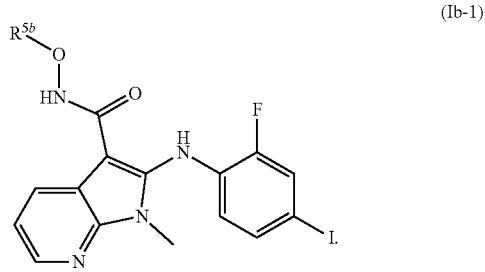

Embodiment B5: The aqueous gel formulation of any one of embodiments B1-B4, wherein the compound is represented by the formula:

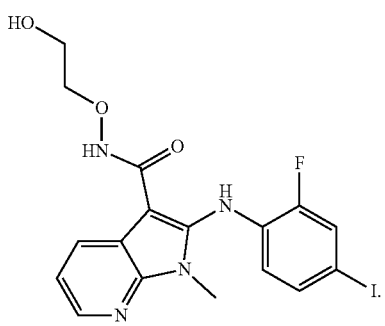 [SMILES: Cn1c(Nc2ccc(I)cc2F)c(C(=O)NOCCO)c2cccnc21]

Embodiment B6: The aqueous gel formulation of any one of embodiments B1-B5, wherein the polyethylene glycol is PEG-400.

Embodiment B7: The aqueous gel formulation of any one of embodiments B1-B6, wherein the antioxidant is butylated hydroxytoluene, butylated hydroxyanisole, ascorbic acid, or combinations thereof.

Embodiment B8: The aqueous gel formulation of any one of embodiments B1-B7, wherein the antioxidant is present in an amount of from about 0.01% to about 0.5% by weight.

Embodiment B9: The aqueous gel formulation of embodiment B7, wherein the antioxidant is butylated hydroxytoluene.

Embodiment B10: The aqueous gel formulation of embodiment B7, wherein the antioxidant is ascorbic acid.

Embodiment Bit: The aqueous gel formulation of embodiment B10, further comprising a stabilizer.

Embodiment B12: The aqueous gel formulation of embodiment Bit, wherein the stabilizer is a disodium salt of ethylenediaminetetraacetic acid.

Embodiment B13: The aqueous gel formulation of any one of embodiments B1 to B12, wherein the preservative is benzyl alcohol or phenoxyethanol.

Embodiment B14: The aqueous gel formulation of embodiment B13, wherein the preservative is phenoxyethanol.

Embodiment B15: The aqueous gel formulation of any one of embodiments B1 to B14, wherein the preservative is present in an amount of from about 0.1% to about 5% by weight.

Embodiment B16: The aqueous gel formulation of any one of embodiments B1 to B15, further comprising one or more surfactants.

Embodiment B17: The aqueous gel formulation of embodiment B16, wherein the one or more surfactants are a polysorbate, a poloxamer, a polyoxyethylene fatty ether, a polyoxyethylene fatty acid ester, or combinations thereof.

Embodiment B18: The aqueous gel formulation of embodiment B17, wherein the one or more surfactants are polysorbate 80, poloxamer 407, polyoxyl 20 cetostearyl ether, or combinations thereof.

Embodiment B19: The aqueous gel formulation of any one of embodiments B1 to B18, wherein the one or more organic solvents are absent.

Embodiment B20: The aqueous gel formulation of embodiment B1 or B2, comprising:
  a) the compound of formula (I);
  b) water, PEG-400, ascorbic acid, a disodium salt of ethylenediaminetetraacetic acid, and phenoxyethanol;
  c) one or more surfactants; and
  d) the gelling agent,
wherein the one or more surfactants comprise the polysorbate and the poloxamer.

Embodiment B21: The aqueous gel formulation of embodiment B20, wherein water is present in an amount of from about 20% to about 40% or from about 25% to about 35% by weight.

Embodiment B22: The aqueous gel formulation of embodiment B21, wherein water is present in an amount of about 30% by weight.

Embodiment B23: The aqueous gel formulation of any one of embodiments B20 to B22, wherein PEG-400 is present in an amount of from about 40% to about 80% or from about 50% to about 70% by weight.

Embodiment B24: The aqueous gel formulation of embodiment B23, wherein PEG-400 is present in an amount of about 62% by weight.

Embodiment B25: The aqueous gel formulation of any one of embodiments B20 to B24, wherein ascorbic acid in an amount of from about 0.05% to about 0.2% by weight.

Embodiment B26: The aqueous gel formulation of embodiment B25, wherein ascorbic acid in an amount of about 0.1% by weight.

Embodiment B27: The aqueous gel formulation of any one of embodiments B20 to B26, wherein the disodium salt of ethylenediaminetetraacetic acid is present in an amount of from about 0.01% to about 0.1% by weight.

Embodiment B28: The aqueous gel formulation of embodiment B27, wherein the disodium salt of ethylenediaminetetraacetic acid is present in an amount of about 0.05% by weight.

Embodiment B29: The aqueous gel formulation of any one of embodiments B20 to B28, wherein phenoxyethanol is present in an amount of from about 0.5% to about 2% by weight.

Embodiment B30: The aqueous gel formulation of embodiment B29, wherein phenoxyethanol is present in an amount of about 1% by weight.

Embodiment B31: The aqueous gel formulation of any one of embodiments B20 to B30, wherein the one or more surfactants are polysorbate 80 and poloxamer 407.

Embodiment B32: The aqueous gel formulation of embodiment B31, wherein polysorbate 80 is present in an amount of about 5% by weight.

Embodiment B33: The aqueous gel formulation of embodiment B31, wherein poloxamer 407 is present in an amount of about 1% by weight.

Embodiment B34: The aqueous gel formulation of embodiment B1 or B2, comprising:
a) the compound of formula (I);
b) water, PEG-400, butylated hydroxytoluene, and phenoxyethanol;
c) one or more organic solvents; and
d) the gelling agent,
wherein the one or more organic solvents are a $C_{2-6}$ alcohol, a $C_{2-6}$ alkylene glycol, $C_{1-3}$ alkyl-$(OCH_2CH_2)_{1-5}$—OH, glycerol, or combinations thereof.

Embodiment B35: The aqueous gel formulation of embodiment B34, wherein water is present in an amount of from about 10% to about 30% or from about 15% to about 25% by weight.

Embodiment B36: The aqueous gel formulation of embodiment B35, wherein water is present in an amount of about 20% by weight.

Embodiment B37: The aqueous gel formulation of any one of embodiments B34 to B36, wherein PEG-400 is present in an amount of from about 20% to about 50%, from about 30% to about 50%, or from about 20% to about 40% by weight.

Embodiment B38: The aqueous gel formulation of embodiment B37, wherein PEG-400 is present in an amount of about 38% or about 29% by weight.

Embodiment B39: The aqueous gel formulation of any one of embodiments B34 to B38, wherein butylated hydroxytoluene is present in an amount of from about 0.01% to about 0.1% by weight.

Embodiment B40: The aqueous gel formulation of embodiment B39, wherein butylated hydroxytoluene is present in an amount of about 0.05% by weight.

Embodiment B41: The aqueous gel formulation of any one of embodiments B34 to B40, wherein phenoxyethanol is present in an amount of from about 0.5% to about 2% by weight.

Embodiment B42: The aqueous gel formulation of embodiment B41, wherein phenoxyethanol is present in an amount of about 1% by weight.

Embodiment B43: The aqueous gel formulation of any one of embodiments B34 to B42, wherein the $C_{2-6}$ alcohol is ethanol.

Embodiment B44: The aqueous gel formulation of embodiment B43, wherein ethanol is present in an amount of from about 2% to about 15% by weight.

Embodiment B45: The aqueous gel formulation of embodiment B44, wherein ethanol is present in an amount of about 5% or about 10% by weight.

Embodiment B46: The aqueous gel formulation of any one of embodiments B34 to 45, wherein the $C_{2-6}$ alkylene glycol is propylene glycol.

Embodiment B47: The aqueous gel formulation of embodiment B46, wherein propylene glycol is present in an amount of from about 5% to about 20% by weight.

Embodiment B48: The aqueous gel formulation of embodiment B47, wherein propylene glycol is present in an amount of about 10% or about 15% by weight.

Embodiment B49: The aqueous gel formulation of any one of embodiments B34 to B48, wherein $C_{1-3}$ alkyl-$(OCH_2CH_2)_{1-5}$—OH is 2-(2-ethoxyethoxy)ethanol.

Embodiment B50: The aqueous gel formulation of embodiment B49, wherein 2-(2-ethoxyethoxy)ethanol is present in an amount of from about 10% to about 30% by weight.

Embodiment B51: The aqueous gel formulation of embodiment B50, wherein 2-(2-ethoxyethoxy)ethanol is present in an amount of about 20% by weight.

Embodiment B52: The aqueous gel formulation of any one of embodiments B34 to B51, wherein glycerol is absent.

Embodiment B53: The aqueous gel formulation of any one of embodiments B34 to B51, wherein glycerol is present in an amount of from about 5% to about 15% by weight.

Embodiment B54: The aqueous gel formulation of embodiment B53, wherein glycerol is present in an amount of about 9% by weight.

Embodiment B55: The aqueous gel formulation of embodiment B1 or B2, comprising:
a) the compound of formula (I);
b) water, PEG-400, ascorbic acid, a disodium salt of ethylenediaminetetraacetic acid, and the preservative;
c) one or more organic solvents, and optionally one or more surfactants; and
d) the gelling agent,
wherein the preservative is phenoxyethanol or benzyl alcohol;
the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof, and
the one or more surfactants comprise the polyoxyethylene fatty ether.

Embodiment B56: The aqueous gel formulation of embodiment B55, wherein water is present in an amount of from about 20% to about 50%, from about 20% to about 40%, from about 30% to about 50%, from about 20% to about 30%, or from about 30% to about 40% by weight.

Embodiment B57: The aqueous gel formulation of embodiment B56, wherein water is present in an amount of from about 20% to about 40% by weight.

Embodiment B58: The aqueous gel formulation of any one of embodiments B55 to B57, wherein PEG-400 is present in an amount of from about 10% to about 50%, from about 20% to about 50%, from about 20% to about 40%, from about 20% to about 30%, from about 30% to about 40%, or from about 10% to about 20% by weight.

Embodiment B59: The aqueous gel formulation of embodiment B58, wherein PEG-400 is present in an amount of about 13%, about 25%, or about 35% by weight.

Embodiment B60: The aqueous gel formulation of any one of embodiments B55 to B59, wherein ascorbic acid in an amount of from about 0.05% to about 0.2% by weight.

Embodiment B61: The aqueous gel formulation of embodiment B60, wherein ascorbic acid in an amount of about 0.1% by weight.

Embodiment B62: The aqueous gel formulation of any one of embodiments B55 to B61, wherein the disodium salt of ethylenediaminetetraacetic acid is present in an amount of from about 0.01% to about 0.1% by weight.

Embodiment B63: The aqueous gel formulation of embodiment B62, wherein the disodium salt of ethylenediaminetetraacetic acid is present in an amount of about 0.02% or about 0.05% by weight.

Embodiment B64: The aqueous gel formulation of any one of embodiments B55 to B63, wherein the preservative is phenoxyethanol in an amount of from about 0.5% to about 2% by weight.

Embodiment B65: The aqueous gel formulation of embodiment B64, wherein phenoxyethanol is present in an amount of about 1% by weight.

Embodiment B66: The aqueous gel formulation of any one of embodiments B55 to B63, wherein the preservative is benzyl alcohol in an amount of from about 1% to about 5% by weight.

Embodiment B67: The aqueous gel formulation of embodiment B66, wherein benzyl alcohol is present in an amount of about 2% by weight.

Embodiment B68: The aqueous gel formulation of any one of embodiments B55 to B67, wherein the $C_{2-6}$ alcohol is absent.

Embodiment B69: The aqueous gel formulation of any one of embodiments B55 to B67, wherein the $C_{2-6}$ alcohol is ethanol.

Embodiment B70: The aqueous gel formulation of embodiment B69, wherein ethanol is present in an amount of from about 5% to about 20% by weight.

Embodiment B71: The aqueous gel formulation of embodiment B70, wherein ethanol is present in an amount of about 11% by weight.

Embodiment B72: The aqueous gel formulation of any one of embodiments B55 to B71, wherein the $C_{2-6}$ alkylene glycol is absent.

Embodiment B73: The aqueous gel formulation of any one of embodiments B55 to B71, wherein the $C_{2-6}$ alkylene glycol is propylene glycol.

Embodiment B74: The aqueous gel formulation of embodiment B73, wherein propylene glycol is present in an amount of from about 5% to about 20% by weight.

Embodiment B75: The aqueous gel formulation of embodiment B74, wherein propylene glycol is present in an amount of about 13% by weight.

Embodiment B76: The aqueous gel formulation of any one of embodiments B55 to B75, wherein $C_{1-3}$ alkyl-$(OCH_2CH_2)_{1-5}$—OH is 2-(2-ethoxyethoxy)ethanol.

Embodiment B77: The aqueous gel formulation of embodiment B76, wherein 2-(2-ethoxyethoxy)ethanol is present in an amount of from about 10% to about 30% by weight.

Embodiment B78: The aqueous gel formulation of embodiment B77, wherein 2-(2-ethoxyethoxy)ethanol is present in an amount of from about 23% to about 28% by weight.

Embodiment B79: The aqueous gel formulation of any one of embodiments B55 to B78, wherein the one or more surfactants are absent.

Embodiment B80: The aqueous gel formulation of embodiment B79, wherein the one or more surfactants, when present, are polyoxyl 20 cetostearyl ether in an amount of about 2% by weight.

Embodiment B81: The aqueous gel formulation of any one of embodiments B1 to B80, wherein PEG-400 is a super refined PEG-400.

Embodiment B82: The aqueous gel formulation of any one of embodiments B1 to B81, wherein propylene glycol is a super refined propylene glycol.

Embodiment B83: The aqueous gel formulation of any one of embodiments B1 to B82, wherein 2-(2-ethoxyethoxy)ethanol is Transcutol® HP having a purity of >about 99.90%.

Embodiment B84: The aqueous gel formulation of any one of embodiments B1 to B83, wherein the gelling agent is hydroxypropyl cellulose.

Embodiment B85: The aqueous gel formulation of embodiment B84, wherein the hydroxypropyl cellulose has an average molecular weight selected from the group consisting of about 140,000 Da, about 370,000 Da, about 850,000 Da, and about 1,150,000 Da.

Embodiment B86: The aqueous gel formulation of embodiment B84, wherein the hydroxypropyl cellulose is Klucel™ JF, Klucel™ GF, Klucel™ MF, or Klucel™ HF.

Embodiment B87: The aqueous gel formulation of embodiment B86, wherein the hydroxypropyl cellulose is Klucel™ HF.

Embodiment B88: The aqueous gel formulation of embodiment B87, wherein Klucel™ HF is present in an amount of about 0.5% by weight.

Embodiment B89: The aqueous gel formulation of any one of embodiments B1 to B83, wherein the gelling agent is poly(acrylic acid).

Embodiment B90: The aqueous gel formulation of embodiment B89, wherein poly(acrylic acid) is Carbopol® 980.

Embodiment B91: The aqueous gel formulation of embodiment B90, wherein Carbopol® 980 is present in an amount of about 0.5% by weight.

Embodiment B92: The aqueous gel formulation of any one of embodiments B1 to B91, wherein a pH is adjusted with an aqueous solution of sodium hydroxide or ammonia.

Embodiment B93: The aqueous gel formulation of any one of embodiments B1 to B92, wherein the viscosity is from about 10,000 to about 25,000 cps.

Embodiment B94: The aqueous gel formulation of any one of embodiments B1 to B92, wherein the viscosity is from about 25,000 to about 200,000 cps.

Embodiment B95: The aqueous gel formulation of any one of embodiments B1 to B94, wherein the compound of formula (I) is present in an amount of from about 0.005% to about 3% or from about 0.005% to about 1% by weight.

Embodiment B96: The aqueous gel formulation of embodiment B95, wherein the compound of formula (I) is present in an amount of from about 0.005% to about 1% by weight.

Embodiment B97: The aqueous gel formulation of any one of embodiments B1 to B96, having a visual appearance as clear, transparent, or monophasic.

Embodiment B98: The aqueous gel formulation of embodiment B97, wherein the visual appearance is maintained over a period of 4 weeks at a temperature of about 40° C.

Embodiment B99: The aqueous gel formulation of embodiment B1, wherein the formulation has a stable viscosity for a period of 4 weeks at a temperature of about 40° C.

Embodiment B100: The aqueous gel formulation of any one of embodiments B1 to B99, wherein a relative purity of the compound of formula (I) is maintained from 95% to 100% over a period of 6 months at a temperature of about 25° C.

III-C. Emulsion-Based Formulation Including a Compound of Formula (I)

In a third aspect, the present disclosure provides an emulsion-based formulation useful for the treatment of skin disorders. The emulsion-based formulation includes:

a) a compound represented by formula (I):

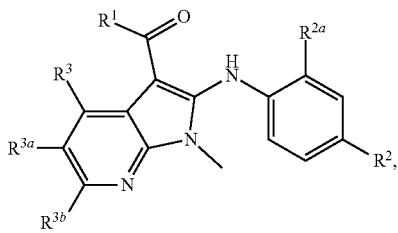

(I)

or a stereoisomer, a mixture of stereoisomers, and/or a pharmaceutically acceptable salt thereof,
wherein
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^3$, $R^{3a}$, and $R^{3b}$ are independently hydrogen, halo, $C_1$-$C_6$ alkyl, or $C_1$-$C_6$ alkoxy;
$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^{5a}$ is hydrogen or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

b) water, a polyethylene glycol, an antioxidant, a preservative, and optionally a stabilizer;
c) one or more organic solvents;
d) an oil-based mixture; and
e) one or more additional excipients,
wherein:
water is present in an amount of at least 10% by weight;
the polyethylene glycol has an average molecular weight of from about 200 Da to about 900 Da;
the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof;
a total amount of a) to c) is from 70% to 85% by weight;
the oil-based mixture comprises one or more pharmaceutical excipients selected from the group consisting of an oil, liquid paraffin, medium chain triglycerides, a cyclomethicone, a dimethicone, a fatty acid, and a fatty alcohol;
the one or more additional excipients are one or more emulsifiers, surfactants, thickening agents, or combinations thereof; and
the emulsion-based formulation has a pH value of no more than about 7.

In some embodiments, the compound of formula (I) is represented by formula (Ia):

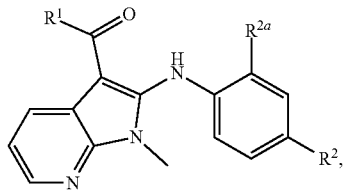

(Ia)

wherein $R^1$, $R^2$, and $R^{2a}$ are as defined and described herein.

In some embodiments, the compound is represented by formula (Ib):

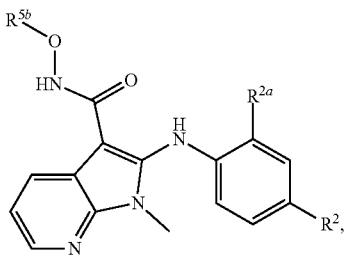

(Ib)

wherein $R^2$, $R^{2a}$, and $R^{5b}$ are defined and described herein.

In some embodiments, $R^2$ and $R^{2a}$ are each halo. In some embodiments, $R^{5b}$ is $C_3$-$C_8$ cycloalkyl-$C_1$-$C_6$ alkyl or $C_1$-$C_6$ hydroxyalkyl. In some embodiments, $R^{5b}$ is $C_1$-$C_6$ hydroxyalkyl. In some embodiments, $R^{5b}$ is unbranched $C_1$-$C_6$ hydroxyalkyl. In some embodiments, $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy. In some embodiments, $R^2$ and $R^{2a}$ are each halo; and $R^{5b}$ is $C_1$-$C_6$ hydroxyalkyl. In some embodiments, $R^2$ and $R^{2a}$ are each halo; and $R^{5b}$ is unbranched $C_1$-$C_6$ hydroxyalkyl. In some embodiments, $R^2$ and $R^{2a}$ are each halo; and $R^{5b}$ is unbranched $C_1$-$C_6$ hydroxyalkyl, wherein the $C_1$-$C_6$ alkyl in the $C_1$-$C_6$ hydroxyalkyl is substituted with one hydroxy.

In some embodiments, the compound is represented by formula (Ib-1):

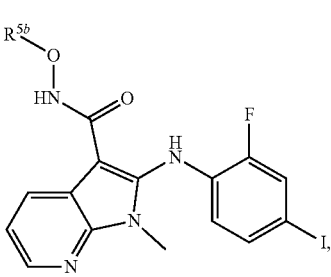

(Ib-1)

wherein $R^{5b}$ is defined and described herein.

In some embodiments, the compound is represented by the formula:

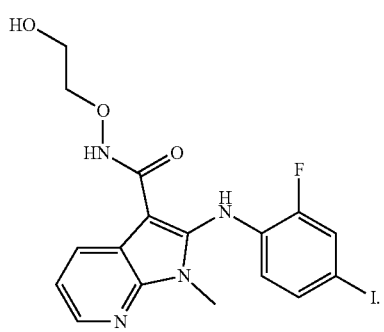 [SMILES: Cn1c(Nc2ccc(I)cc2F)c(C(=O)NOCCO)c2cccnc21]

(Compound 1.003)

In some embodiments, the emulsion-based formulation has a viscosity of at least about 25,000 cps, about 50,000 cps, about 100,000 cps, or about 200,000 cps. In some embodiments, the viscosity is from about 50,000 to about 2,000,000 cps.

In some embodiments, water is present in an amount of at least about 20% or about 25% by weight. In some embodiments, water is present in an amount of at least about 20% by weight. In some embodiments, water is present in an amount of at least about 25% by weight. In some embodiments, water is present in an amount of from about 15% to about 40% by weight.

In some embodiments, the polyethylene glycol is PEG-200, PEG-300, PEG-400, PEG-600, or PEG-900. In some embodiments, the polyethylene glycol is PEG-400. In some embodiments, PEG-400 is a super refined PEG-400.

In some embodiments, the antioxidant is butylated hydroxytoluene, butylated hydroxyanisole, ascorbic acid, or combinations thereof. In some embodiments, the antioxidant is ascorbic acid.

In some embodiments, the antioxidant is present in an amount of from about 0.01% to about 1% by weight. In some embodiments, the antioxidant is present in an amount of from about 0.01% to about 0.5% by weight. In some embodiments, the antioxidant is present in an amount of from about 0.01% to about 0.1% by weight. In some embodiments, the antioxidant is present in an amount of from about 0.1% to about 0.5% by weight.

In some embodiments, when the antioxidant is ascorbic acid, the emulsion-based formulation includes a stabilizer. In some embodiments, the stabilizer is a disodium salt of ethylenediaminetetraacetic acid. In some embodiments, the stabilizer is present in an amount of from about 0.01% to about 0.5% by weight.

In some embodiments, the preservative is benzyl alcohol, phenoxyethanol, or a combination thereof. In some embodiments, the preservative is benzyl alcohol. In some embodiments, the preservative is phenoxyethanol. In some embodiments, the preservative is a mixture of benzyl alcohol and phenoxyethanol.

In some embodiments, the preservative is present in an amount of from about 0.1% to about 5% by weight. In some embodiments, the preservative is present in an amount of from about 0.5% to about 3% by weight.

In some embodiments, one or more organic solvents include $C_{1-3}$ alkyl-$(OCH_2CH_2)_{1-5}$—OH. In some embodiments, $C_{1-3}$ alkyl-$(OCH_2CH_2)_{1-5}$—OH is absent. In some embodiments, one or more organic solvents include a $C_{2-6}$ alcohol and $C_{1-3}$ alkyl-$(OCH_2CH_2)_{1-5}$—OH. In some embodiments, one or more organic solvents are a $C_{2-6}$ alcohol, a $C_{2-6}$ alkylene glycol, and $C_{1-3}$ alkyl-$(OCH_2CH_2)_{1-5}$—OH. In some embodiments, the $C_{2-6}$ alcohol is ethanol. In some embodiments, the $C_{2-6}$ alkylene glycol is propylene glycol. In some embodiments, $C_{1-3}$ alkyl-$(OCH_2CH_2)_{1-5}$—OH is 2-(2-ethoxyethoxy)ethanol.

In some embodiments, the one or more organic solvents are ethanol, isopropyl alcohol, propylene glycol, 2-(2-ethoxyethoxy)ethanol, or combinations thereof. In some embodiments, the one or more organic solvents are ethanol, propylene glycol, 2-(2-ethoxyethoxy)ethanol, or combinations thereof. In some embodiments, the one or more organic solvents include 2-(2-ethoxyethoxy)ethanol. In some embodiments, the one or more organic solvents are 2-(2-ethoxyethoxy)ethanol. In some embodiments, the one or more organic solvents include propylene glycol and 2-(2-ethoxyethoxy)ethanol. In some embodiments, the one or more organic solvents are a mixture of propylene glycol and 2-(2-ethoxyethoxy)ethanol. In some embodiments, the one or more organic solvents include ethanol and 2-(2-ethoxyethoxy)ethanol. In some embodiments, the one or more organic solvents are a mixture of ethanol and 2-(2-ethoxyethoxy)ethanol. In some embodiments, the one or more organic solvents include ethanol, propylene glycol, and 2-(2-ethoxyethoxy)ethanol. In some embodiments, the one or more organic solvents are a mixture of ethanol, propylene glycol, and 2-(2-ethoxyethoxy)ethanol. In some embodiments, the one or more organic solvents include isopropyl alcohol. In some embodiments, the one or more organic solvents are isopropyl alcohol.

In some embodiments, the one or more organic solvents are in an amount of from 5% to 50% by weight. In some embodiments, the one or more organic solvents include 2-(2-ethoxyethoxy)ethanol in an amount of from about 5% to about 25% by weight.

In some embodiments, propylene glycol is a super refined propylene glycol.

In some embodiments, 2-(2-ethoxyethoxy)ethanol is Transcutol® HP. In some embodiments, 2-(2-ethoxyethoxy)ethanol is Transcutol® HP having a purity of >about 99.90%.

In some embodiments, the oil-based mixture includes one or more pharmaceutical excipients selected from the group consisting of a castor oil, a liquid paraffin, caprylic/capric triglyceride, decamethylcyclopentasiloxane ($D_5$), dimethicone 350, stearic acid, cetostearyl alcohol, and cetyl alcohol. In some embodiments, the oil-based mixture includes a castor oil, a liquid paraffin, caprylic/capric triglyceride, dimethicone 350, cetyl alcohol, or combinations thereof. In some embodiments, caprylic/capric triglyceride is Crodamol™ GTCC. In some embodiments, decamethylcyclopentasiloxane ($D_5$) is Cyclomethicone 5NF.

In some embodiments, the one or more additional excipients are one or more emulsifiers or thickening agents. In some embodiments, the one or more additional excipients are a monoglyceride, a diglyceride, a sorbitan mono-ester, a polysorbate, a polyoxyethylene fatty ether, a polyoxyethylene fatty acid ester, or combinations thereof. In some embodiments, the one or more additional excipients are a blend of glyceryl monostearate and PEG-75 stearate (Gelot™ 64), sorbitan monostearate (Span™ 60), polysorbate 60 (Tween® 60), steareth-20 (Brij™ S20), mono and diglycerides (Geleol™ mono and diglycerides), polyoxy 20 cetostearyl ether, Sepineo™ P600, or combinations thereof.

The emulsion-based formulation used to deliver the compound of formula (I) is a lotion, a cream, or an emulsified gel.

In some embodiments, the emulsion-based formulation is a lotion.

In some embodiments, the emulsion-based formulation is a lotion and the lotion includes:
 a) the compound of any one of formulae (I), (Ia), (Ib), (Ib-1), and Compound 1.003;
 b) water, PEG-400, ascorbic acid, a disodium salt of ethylenediaminetetraacetic acid, and phenoxyethanol;
 c) 2-(2-ethoxyethoxy)ethanol; and
 d) the oil-based mixture; and
 e) the one or more additional excipients,
wherein a total amount of a) to c) is from about 75% to about 85% by weight.

In some embodiments of the lotion, water is present in the lotion in an amount of from about 20% to about 40% or from about 25% to about 35% by weight. In some embodiments, water is present in an amount of about 30% by weight.

In some embodiments of the lotion, PEG-400 is present in the lotion in an amount of from about 20% to about 50%, from about 20% to about 40%, or from about 30% to about 50% by weight. In some embodiments, PEG-400 is present in an amount of from about 20% to about 40% by weight. In some embodiments, PEG-400 is present in an amount of from about 30% to about 50% by weight. In some embodiments, PEG-400 is present in an amount of about 31% by weight. In some embodiments, PEG-400 is present in an amount of about 39 by weight.

In some embodiments of the lotion, 2-(2-ethoxyethoxy)ethanol is present in the lotion in an amount of from about 5% to about 25%, from about 5% to about 20%, or from about 5% to about 15% by weight. In some embodiments, 2-(2-ethoxyethoxy)ethanol is present in an amount of from about 10% to about 20% by weight. In some embodiments, 2-(2-ethoxyethoxy)ethanol is present in an amount of from about 5% to about 15% by weight. In some embodiments, 2-(2-ethoxyethoxy)ethanol is present in an amount of about 16% by weight. In some embodiments, 2-(2-ethoxyethoxy)ethanol is present in an amount of about 10% by weight.

In some embodiments of the lotion, the oil-based mixture includes a castor oil and caprylic/capric triglyceride (e.g., Crodamol™ GTCC). In some embodiments, the oil-based mixture is a mixture of a castor oil and caprylic/capric triglyceride (e.g., Crodamol™ GTCC). In some embodiments, the castor oil is present in an amount of from about 5% to about 15% by weight. In some embodiments, the castor oil is present in the lotion in an amount of about 10% by weight. In some embodiments, caprylic/capric triglyceride is present in the lotion in an amount of from about 5% to about 15% by weight. In some embodiments, caprylic/capric triglyceride is present in an amount of about 8% by weight. In some embodiments, caprylic/capric triglyceride is Crodamol™ GTCC.

In some embodiments of the lotion, the oil-based mixture includes caprylic/capric triglyceride, dimethicone 350, steric acid, and cetostearyl alcohol. In some embodiments, the oil-based mixture are a mixture of caprylic/capric triglyceride, dimethicone 350, steric acid, and cetostearyl alcohol. In some embodiments, caprylic/capric triglyceride is present in the lotion in an amount of from about 5% to about 10% by weight. In some embodiments, caprylic/capric triglyceride is present in an amount of about 6.5% by weight. In some embodiments, caprylic/capric triglyceride is Crodamol™ GTCC. In some embodiments, dimethicone 350 is present in the lotion in an amount of from about 0.5% to about 2% by weight. In some embodiments, dimethicone 350 is present in an amount of about 1% by weight. In some embodiments, steric acid is present in the lotion in an amount of from about 2% to about 10% by weight. In some embodiments, steric acid is present in an amount of about 4.5% by weight. In some embodiments, cetostearyl alcohol is present in the lotion in an amount of from about 1% to about 5% by weight. In some embodiments, cetostearyl alcohol is present in an amount of about 2% by weight.

In some embodiments of the lotion, ascorbic acid is present in the lotion in an amount of from about 0.05 to about 0.5% by weight. In some embodiments, ascorbic acid is present in an amount of from about 0.05% to about 0.2% by weight. In some embodiments, ascorbic acid is present in an amount of about 0.1% by weight. In some embodiments, the disodium salt of ethylenediaminetetraacetic acid is present in the lotion in an amount of from about 0.01% to about 0.5% by weight. In some embodiments, the disodium salt of ethylenediaminetetraacetic acid is present in an amount of from about 0.01% to about 0.1% by weight. In some embodiments, the disodium salt of ethylenediaminetetraacetic acid is present in an amount of about 0.05% by weight.

In some embodiments of the lotion, phenoxyethanol is present in the lotion in an amount of from about 0.5% to about 3% by weight. In some embodiments, phenoxyethanol is present in an amount of from about 0.5% to about 2% by weight. In some embodiments, phenoxyethanol is present in an amount of about 1% by weight.

In some embodiments of the lotion, the one or more additional excipients include a blend of glyceryl monostearate and PEG-75 stearate (Gelot™ 64), steareth-20 (Brij™ S20), and mono and diglycerides (Geleol™ mono and diglycerides). In some embodiments, the one or more additional excipients are a mixture of a blend of glyceryl monostearate and PEG-75 stearate (Gelot™ 64), steareth-20 (Brij™ S20), and glycerol monostearate (Geleol™ mono and diglycerides). In some embodiments, Gelot™ 64 is present in the lotion in an amount of from about 0.5% to about 2% by weight. In some embodiments, Gelot™ 64 is present in an amount of about 1% by weight. In some embodiments, steareth-20 is present in the lotion in an amount of from about 1% to about 5% by weight. In some embodiments, steareth-20 is present in an amount of about 3% by weight. In some embodiments, Geleol™ mono and diglycerides is present in the lotion in an amount of from about 1% to about 5% by weight. In some embodiments, Geleol™ mono and diglycerides is present in an amount of about 1.8% by weight.

In some embodiments of the lotion, the one or more additional excipients are a thickening agent. In some embodiments, the one or more additional excipients include Sepineo™ P600. In some embodiments, the one or more additional excipients are Sepineo™ P600. In some embodiments, Sepineo™ P600 is present in the lotion in an amount of from about 0.5% to about 5% by weight. In some embodiments, Sepineo™ P600 is present in an amount of from about 1% to about 3% by weight. In some embodiments, Sepineo™ P600 is present in an amount of about 2% by weight.

In some embodiments, the present disclosure provides a lotion (LO-2a), including:
a) a compound represented by the formula:

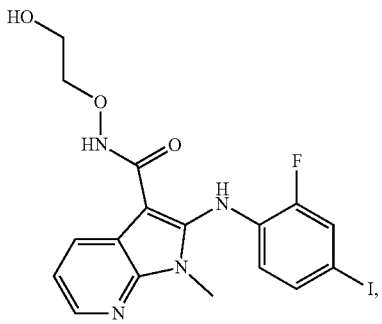

or a pharmaceutically acceptable salt thereof,
b) water, PEG-400, ascorbic acid, a disodium salt of ethylenediaminetetraacetic acid, and phenoxyethanol;
c) 2-(2-ethoxyethoxy)ethanol; and
d) a castor oil and a caprylic/capric triglyceride; and
e) Sepineo™ P600,
wherein a total amount of a) to c) is from 75% to 85% by weight.

In some embodiments of the lotion (LO-2a), water is present in the lotion in an amount of from about 20% to about 40% by weight. In some embodiments, water is present in an amount of about 30% by weight.

In some embodiments of the lotion (LO-2a), In some embodiments, PEG-400 is present in the lotion in an amount of from about 30% to about 50% by weight. In some embodiments, PEG-400 is present in an amount of about 39% by weight.

In some embodiments of the lotion (LO-2a), 2-(2-ethoxyethoxy)ethanol is present in the lotion in an amount of from about 10% to about 20% by weight. In some embodiments, 2-(2-ethoxyethoxy)ethanol is present in an amount of about 10% by weight.

In some embodiments of the lotion (LO-2a), the castor oil is present in the lotion in an amount of from about 5% to about 15% by weight. In some embodiments, the castor oil is present in an amount of about 10% by weight. In some embodiments, caprylic/capric triglyceride is present in the lotion in an amount of from about 5% to about 15% by weight. In some embodiments, caprylic/capric triglyceride is present in an amount of about 8% by weight. In some embodiments, caprylic/capric triglyceride is Crodamol™ GTCC.

In some embodiments of the lotion (LO-2a), ascorbic acid is present in the lotion in an amount of about 0.1% by weight; the disodium salt of ethylenediaminetetraacetic acid is present in the lotion in an amount of about 0.05% by weight; and phenoxyethanol is present in an amount of about 1% by weight.

In some embodiments of the lotion (LO-2a), Sepineo™ P600 is present in the lotion in an amount of from about 1% to about 3% by weight. In some embodiments, Sepineo™ P600 is present in an amount of about 2% by weight.

In some embodiments, the emulsion-based formulation is a cream.

In some embodiments, the emulsion-based formulation is a cream and the cream includes:
a) the compound of any one of formulae (I), (Ia), (Ib), (Ib-1), and Compound 1.003;
b) water, PEG-400, ascorbic acid, a disodium salt of ethylenediaminetetraacetic acid, and phenoxyethanol;
c) 2-(2-ethoxyethoxy)ethanol; and
d) the oil-based mixture; and
e) the one or more additional excipients,
wherein a total amount of a) to c) is from about 75% to about 85% by weight.

In some embodiments of the cream, water is present in the cream in an amount of from 20% to 40% or from about 25% to about 35% by weight. In some embodiments, water is present in an amount of about 32% by weight.

In some embodiments of the cream, PEG-400 is present in the cream in an amount of from about 20% to about 40% or from about 25% to about 35% by weight. In some embodiments, PEG-400 is present in an amount of from about 20% to about 40% by weight. In some embodiments, PEG-400 is present in an amount of about 31% by weight.

In some embodiments of the cream, 2-(2-ethoxyethoxy)ethanol is present in the cream in an amount of from about 10% to about 25% or from about 10% to about 20% by weight. In some embodiments, 2-(2-ethoxyethoxy)ethanol is present in an amount of from about 10% to about 20% by weight. In some embodiments, 2-(2-ethoxyethoxy)ethanol is present in an amount of about 16% by weight.

In some embodiments of the cream, the oil-based mixture includes a liquid paraffin, caprylic/capric triglyceride, dimethicone 350, and cetyl alcohol. In some embodiments, the oil-based mixture is a mixture of a liquid paraffin, caprylic/capric triglyceride, dimethicone 350, and cetyl alcohol. In some embodiments, the liquid paraffin is present in the cream in an amount of from about 1% to about 10% by weight. In some embodiments, the liquid paraffin is present in an amount of from about 3% to about 5% by weight. In some embodiments, the liquid paraffin is present in an amount of about 4% by weight. In some embodiments, caprylic/capric triglyceride is present in the cream in an amount of from about 2% to about 10% by weight. In some embodiments, caprylic/capric triglyceride is present in an amount of about 6% by weight. In some embodiments, caprylic/capric triglyceride is Crodamol™ GTCC. In some embodiments, dimethicone 350 is present in the cream in an amount of from about 0.5% to about 5% by weight. In some embodiments, dimethicone 350 is present in an amount of from about 0.5% to about 2% by weight. In some embodiments, dimethicone 350 is present in an amount of about 1% by weight. In some embodiments, cetyl alcohol is present in the cream in an amount of from about 1% to about 10% by weight. In some embodiments, cetyl alcohol is present in an amount of from about 3% to about 5% by weight. In some embodiments, cetyl alcohol is present in an amount of about 4% by weight.

In some embodiments of the cream, ascorbic acid is present in the cream in an amount of from about 0.05 to about 0.5% by weight. In some embodiments, ascorbic acid is present in an amount of from about 0.05% to about 0.2% by weight. In some embodiments, ascorbic acid is present in an amount of about 0.1% by weight. In some embodiments, the disodium salt of ethylenediaminetetraacetic acid is present in an amount of from about 0.01% to about 0.5% by weight. In some embodiments, the disodium salt of ethylenediaminetetraacetic acid is present in an amount of from about 0.01% to about 0.1% by weight. In some embodiments, the disodium salt of ethylenediaminetetraacetic acid is present in an amount of about 0.05% by weight.

In some embodiments of the cream, phenoxyethanol is present in an amount of from about 0.5% to about 3% by weight. In some embodiments, phenoxyethanol is present in an amount of from about 0.5% to about 2% by weight. In some embodiments, phenoxyethanol is present in an amount of about 1% by weight.

In some embodiments of the cream, the one or more additional excipients include sorbitan monostearate (Span™ 60) and polysorbate 60 (Tween® 60). In some embodiments, the one or more additional excipients are a mixture of sorbitan monostearate (Span™ 60) and polysorbate 60 (Tween® 60). In some embodiments, sorbitan monostearate (Span™ 60) is present in an amount of from 0.5% to 5% by weight. In some embodiments, sorbitan monostearate (Span™ 60) is present in an amount of about 1.8% by weight. In some embodiments, polysorbate 60 (Tween® 60) is present in an amount of from 1% to 5% by weight. In some embodiments, polysorbate 60 (Tween® 60) is present in an amount of about 3.2% by weight.

In some embodiments, the present disclosure provides a cream (CR-1a), including:
a) a compound represented by the formula:

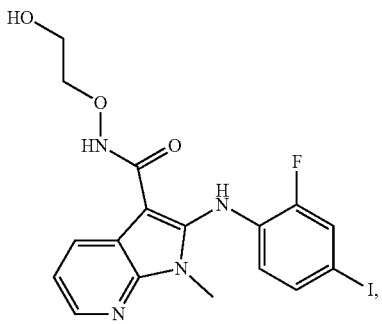 [SMILES: Cn1c(Nc2ccc(I)cc2F)c(C(=O)NOCCO)c2cccnc21]

or a pharmaceutically acceptable salt thereof,
b) water, PEG-400, ascorbic acid, a disodium salt of ethylenediaminetetraacetic acid, and phenoxyethanol;
c) 2-(2-ethoxyethoxy)ethanol; and
d) a liquid paraffin, a caprylic/capric triglyceride, dimethicone 350, and cetyl alcohol; and
e) sorbitan monostearate and polysorbate 60,
wherein a total amount of a) to c) is from about 75% to about 85% by weight.

In some embodiments of the cream (CR-1a), water is present in an amount of about 32% by weight.

In some embodiments of the cream (CR-1a), PEG-400 is present in an amount of about 31% by weight.

In some embodiments of the cream (CR-1a), 2-(2-ethoxyethoxy)ethanol is present in an amount of about 16% by weight.

In some embodiments of the lotion (CR-1a), ascorbic acid is present in an amount of about 0.1% by weight; the disodium salt of ethylenediaminetetraacetic acid is present in an amount of about 0.05% by weight; and phenoxyethanol is present in an amount of about 1% by weight.

In some embodiments of the cream (CR-1a), the liquid paraffin is present in an amount of about 4% by weight; caprylic/capric triglyceride is present in an amount of about 6% by weight; dimethicone 350 is present in an amount of about 1% by weight; and cetyl alcohol is present in an amount of about 4% by weight. In some embodiments, caprylic/capric triglyceride is Crodamol™ GTCC.

In some embodiments of the cream (CR-1a), sorbitan monostearate is present in an amount of about 1.8% by weight; and polysorbate 60 is present in an amount of 3.2% by weight. In some embodiments, sorbitan monostearate is Span™ 60; and polysorbate 60 is Tween® 60.

In some embodiments, the emulsion-based formulation is an emulsified gel and the emulsified gel includes:
a) the compound of any one of formulae (I), (Ia), (Ib), (Ib-1), and Compound 1.003;
b) water, PEG-400, ascorbic acid, a disodium salt of ethylenediaminetetraacetic acid, and phenoxyethanol;
c) 2-(2-ethoxyethoxy)ethanol, ethanol, and optionally propylene glycol; and
d) the oil-based mixture; and
e) the one or more additional excipients,
wherein a total amount of a) to c) is from about 70% to about 75% by weight.

In some embodiments of the emulsified gel, water is present in an amount of from about 15% to about 35% or from about 20% to about 30% by weight. In some embodiments, water is present in an amount of from about 20% to about 30% by weight. In some embodiments, water is present in an amount of about 23.5% by weight.

In some embodiments of the emulsified gel, PEG-400 is present in an amount of from about 5% to about 30%, from about 10% to about 30%, or from about 15% to about 25% by weight. In some embodiments, PEG-400 is present in an amount of from about 10% to about 30% by weight. In some embodiments, PEG-400 is present in an amount of from about 2% to about 15% by weight. In some embodiments, PEG-400 is present in an amount of about 10% by weight. In some embodiments, PEG-400 is present in an amount of about 19.5% by weight.

In some embodiments of the emulsified gel, ascorbic acid is present in an amount of from about 0.05 to about 0.5% by weight. In some embodiments, ascorbic acid is present in an amount of from about 0.05% to about 0.2% by weight. In some embodiments, ascorbic acid is present in an amount of about 0.1% by weight. In some embodiments, the disodium salt of ethylenediaminetetraacetic acid is present in an amount of from about 0.01% to about 0.1% by weight. In some embodiments, the disodium salt of ethylenediaminetetraacetic acid is present in an amount of about 0.02% by weight.

In some embodiments of the emulsified gel, phenoxyethanol is present in an amount of from about 0.5% to about 3% by weight. In some embodiments, phenoxyethanol is present in an amount of from about 0.5% to about 2% by weight. In some embodiments, phenoxyethanol is present in an amount of about 1% by weight.

In some embodiments of the emulsified gel, propylene glycol is absent. In some embodiment, propylene glycol is present.

In some embodiments of the emulsified gel, ethanol is present in an amount of from about 5% to about 15% or from about 5% to about 10% by weight. In some embodiments, ethanol is present in an amount of from about 5% to about 10% by weight. In some embodiments, ethanol is present in an amount of about 8.5% by weight.

In some embodiments of the emulsified gel, 2-(2-ethoxyethoxy)ethanol is present in an amount of from about 10% to about 30% or from about 15% to about 25% by weight. In some embodiments, 2-(2-ethoxyethoxy)ethanol is present in an amount of from about 15% to about 25% by weight. In some embodiments, 2-(2-ethoxyethoxy)ethanol is present in an amount of about 20% by weight.

In some embodiments of the emulsified gel, the oil-based mixture includes a castor oil and caprylic/capric triglyceride. In some embodiments, the oil-based mixture is a mixture of a castor oil and caprylic/capric triglyceride. In some embodiments, the castor oil is present in an amount of from about 10% to about 20% by weight. In some embodiments, the castor oil is present in an amount of about 12.5% by weight. In some embodiments, caprylic/capric triglyceride is present in an amount of from about 5% to about 15% by weight. In some embodiments, caprylic/capric triglyceride is present in an amount of about 10% by weight. In some embodiments, caprylic/capric triglyceride is Crodamol™ GTCC.

In some embodiments of the emulsified gel, the one or more additional excipients include polyoxy 20 cetostearyl ether and Sepineo™ P600. In some embodiments, the one or more additional excipients are a mixture of polyoxy 20 cetostearyl ether and Sepineo™ P600. In some embodiments, the one or more additional excipients include Sepineo™ P600. In some embodiments, the one or more additional excipients are Sepineo™ P600. In some embodiments, polyoxy 20 cetostearyl ether, when present, is in an amount of from about 1% to about 5% by weight. In some embodiments, polyoxy 20 cetostearyl ether, when present, is in an amount of about 2% by weight. In some embodiments, Sepineo™ P600 is present in an amount of from about 1% to about 5% by weight. In some embodiments, Sepineo™ P600 is present in an amount of about 2.5% by weight.

In some embodiments, the present disclosure provides a emulsified gel (EG-2a), including:

a) a compound represented by the formula:

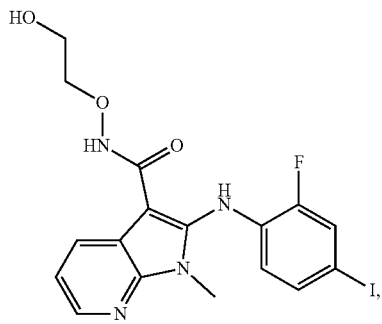 [SMILES: Cn1c(Nc2ccc(I)cc2F)c(C(=O)NOCCO)c2cccnc21]

or a pharmaceutically acceptable salt thereof,
b) water, PEG-400, ascorbic acid, a disodium salt of ethylenediaminetetraacetic acid, and phenoxyethanol;
c) ethanol and 2-(2-ethoxyethoxy)ethanol; and
d) a castor oil and caprylic/capric triglyceride; and
e) polyoxy 20 cetostearyl ether and Sepineo™ P600,
wherein a total amount of a) to c) is from about 75% to about 85% by weight.

In some embodiments of the emulsified gel (EG-2a), water is present in an amount of from about 20% to about 30% by weight. In some embodiments, water is present in an amount of about 23.5% by weight.

In some embodiments of the emulsified gel (EG-2a), PEG-400 is present in an amount of from about 15% to about 25% by weight. In some embodiments, PEG-400 is present in an amount of about 19.5% by weight.

In some embodiments of the emulsified gel (EG-2a), ascorbic acid is present in an amount of about 0.1% by weight; the disodium salt of ethylenediaminetetraacetic acid is present in an amount of about 0.05% by weight; and phenoxyethanol is present in an amount of about 1% by weight.

In some embodiments of the emulsified gel (EG-2a), ethanol is present in an amount of from about 5% to about 10% by weight. In some embodiments, 2-(2-ethoxyethoxy)ethanol is present in an amount of about 8.5% by weight.

In some embodiments of the emulsified gel (EG-2a), 2-(2-ethoxyethoxy)ethanol is present in an amount of from about 15% to about 25% by weight. In some embodiments, 2-(2-ethoxyethoxy)ethanol is present in an amount of about 20% by weight.

In some embodiments of the emulsified gel (EG-2a), the castor oil is present in an amount of from about 5% to about 15% by weight. In some embodiments, the castor oil is present in an amount of about 12.5% by weight. In some embodiments, caprylic/capric triglyceride is present in an amount of from about 5% to about 15% by weight. In some embodiments, caprylic/capric triglyceride is present in an amount of about 10% by weight. In some embodiments, caprylic/capric triglyceride is Crodamol™ GTCC.

In some embodiments of the emulsified gel (EG-2a), polyoxy 20 cetostearyl ether is present in an amount of from about 1% to about 3% by weight. In some embodiments, polyoxy 20 cetostearyl ether is present in an amount of about 2% by weight. In some embodiments, Sepineo™ P600 is present in an amount of from about 1% to about 3% by weight. In some embodiments, Sepineo™ P600 is present in an amount of about 2.5% by weight.

In some embodiments of any one of emulsion-based formulations, PEG-400 is a super refined PEG-400. In some embodiments, propylene glycol is a super refined propylene glycol. In some embodiments, 2-(2-ethoxyethoxy)ethanol is Transcutol® HP. In some embodiments, 2-(2-ethoxyethoxy)ethanol is Transcutol® HP having a purity of >about 99.90%.

The emulsion-based formulation includes water, however the formulation includes substantial amounts of other excipients (e.g., PEG-400, one or more organic solvents) and one or more additional excipients, therefore the pH value of the partially aqueous solutions can be regarded only as an apparent pH value. See USP chapter <791>, the entirety of which is incorporated herein by reference for all purposes.

In some embodiments, the emulsion-based formulation has a pH value of from about 5 to about 7. In some embodiments, the emulsion-based formulation has a pH value of from about 5 to about 6. In some embodiments, the emulsion-based formulation has a pH value of from about 6 to about 7.

In some embodiments of any one of emulsion-based formulations, a pH of the emulsion-based formulation is adjusted with an aqueous solution of sodium hydroxide. In some embodiments, a pH is adjusted with an aqueous solution of citric acid. In some embodiments, a pH is adjusted with 0.1 M NaOH in water. In some embodiments, a pH is adjusted with 0.1 M citric acid in water.

In some embodiments of any one of emulsion-based formulations, the compound of formula (I) is present in the formulation in an amount of from about 0.005% to about 1%, from about 0.005% to about 0.5%, or from about 0.01% to about 0.5% by weight on a salt-free and anhydrous basis. In some embodiments, when in the lotion or cream, the compound of formula (I) is present in an amount of from about 0.005% to about 0.3% by weight on a salt-free and anhydrous basis. In some embodiments, when in the emulsified gel, the compound of formula (I) is present in an amount of from about 0.005% to about 0.6% by weight on a salt-free and anhydrous basis.

In some embodiments of any one of emulsion-based formulations, Compound 1.003 is present in the formulation in an amount of from about 0.005% to about 1%, from about 0.01% to about 1%, from about 0.005% to about 0.5%, or from about 0.01% to about 0.5% by weight on a salt-free and anhydrous basis. In some embodiments, when in the lotion or cream, Compound 1.003 is present in an amount of from about 0.005% to about 0.3% by weight on a salt-free and anhydrous basis. In some embodiments, when in the emulsified gel, Compound 1.003 is present in an amount of from about 0.005% to about 0.6% by weight on a salt-free and anhydrous basis. In some embodiments, Compound 1.003 is present in an amount of about 0.005% by weight on a salt-free and anhydrous basis. In some embodiments, Compound 1.003 is present in an amount of about 0.01% by weight on a salt-free and anhydrous basis. In some embodiments, Compound 1.003 is present in an amount of about 0.1% by weight on a salt-free and anhydrous basis. In some embodiments, Compound 1.003 is present in an amount of about 0.2% by weight on a salt-free and anhydrous basis. In some embodiments, Compound 1.003 is present in an amount of about 0.3% by weight on a salt-free and anhydrous basis. In some embodiments, Compound 1.003 is present in an amount of about 0.5% by weight on a salt-free and anhydrous basis.

In some embodiments, the emulsion-based formulations as described herein have a visual appearance as white, opaque, smooth, or monophasic. In some embodiments, the visual appearance of the emulsion-based formulation is maintained over a period of 4 weeks at a temperature of about 40° C.

The emulsion-based formulations as described herein have stable viscosity for a period of 4 weeks at a temperature of about 40° C.

The compound of formula (I) in the emulsion-based formulations as described herein is stable for a period of 6 months at a temperature of about 25° C. In some embodiments, a relative purity of the compound of formula (I) is maintained from 95% to 100% over a period of 6 months at a temperature of about 25° C. In some embodiments, a relative purity of Compound 1.003 is maintained from 95% to 100% over a period of 6 months at a temperature of about 25° C.

EMBODIMENTS

Embodiment C1: An emulsion-based formulation, comprising:
a) a compound represented by formula (I):

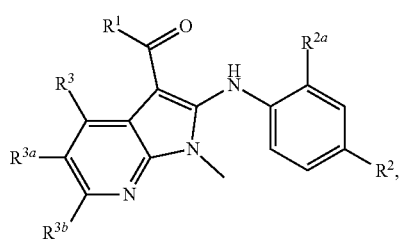

or a stereoisomer, a mixture of stereoisomers, and/or a pharmaceutically acceptable salt thereof,
wherein
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^3$, $R^{3a}$, and $R^{3b}$ are independently hydrogen, halo, $C_1$-$C_6$ alkyl, or $C_1$-$C_6$ alkoxy;

$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
$R^{5a}$ is hydrogen or $C_1$-$C_6$ alkyl; and
$R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;
b) water, a polyethylene glycol, an antioxidant, a preservative, and optionally a stabilizer;
c) one or more organic solvents;
d) an oil-based mixture; and
e) one or more additional excipients,
wherein:
water is present in an amount of at least 10% by weight;
the polyethylene glycol has an average molecular weight of from about 200 Da to about 900 Da;
the one or more organic solvents are a $C_{2-6}$ alcohol, a $C_{2-6}$ alkylene glycol, $C_{1-3}$ alkyl-$(OCH_2CH_2)_{1-5}$—OH, or combinations thereof;
a total amount of a) to c) is from 70% to 85% by weight;
the oil-based mixture comprises one or more pharmaceutical excipients selected from the group consisting of an oil, liquid paraffin, medium chain triglycerides, a cyclomethicone, a dimethicone, a fatty acid, and a fatty alcohol;
the one or more additional excipients are one or more emulsifiers, surfactants, thickening agents, or combinations thereof; and
the emulsion-based formulation has a pH value of no more than about 7.

Embodiment C2: The emulsion-based formulation of embodiment C1, wherein the compound is represented by formula (Ib):

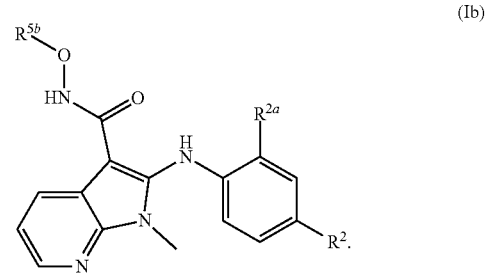

Embodiment C3: The emulsion-based formulation of embodiment C1 or C2, wherein the compound is represented by formula (Ib-1):

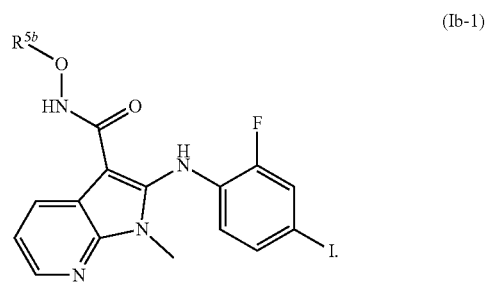

Embodiment C4: The emulsion-based formulation of any one of embodiments C1 to C3, wherein the compound is represented by the formula:

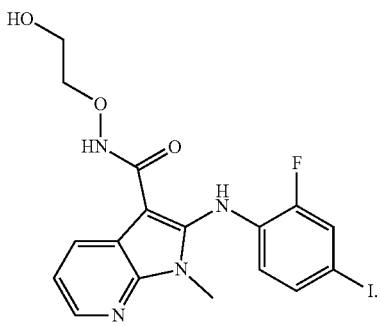 [SMILES: Cn1c(Nc2ccc(I)cc2F)c(C(=O)NOCCO)c2cccnc21]

Embodiment C5: The emulsion-based formulation of any one of embodiments C1 to C4, wherein the polyethylene glycol is PEG-400.

Embodiment C6: The emulsion-based formulation of any one of embodiments C1 to C5, wherein the antioxidant is butylated hydroxytoluene, butylated hydroxyanisole, ascorbic acid, or combinations thereof.

Embodiments C7: The emulsion-based formulation of any one of embodiments C1 to C6, wherein the antioxidant is ascorbic acid.

Embodiment C8: The emulsion-based formulation of embodiment C7, wherein the stabilizer is a disodium salt of ethylenediaminetetraacetic acid.

Embodiment C9: The emulsion-based formulation of any one of embodiments C1 to C8, wherein the preservative is benzyl alcohol or phenoxyethanol.

Embodiment C10: The emulsion-based formulation of embodiment C9, wherein the preservative is phenoxyethanol.

Embodiment C11: The emulsion-based formulation of any one of embodiments C1 to C10, wherein the one or more organic solvents include $C_{1-3}$ alkyl-$(OCH_2CH_2)_{1-5}$—OH.

Embodiment C12: The emulsion-based formulation of embodiment C11, wherein $C_{1-3}$ alkyl-$(OCH_2CH_2)_{1-5}$—OH is 2-(2-ethoxyethoxy)ethanol.

Embodiment C13: The emulsion-based formulation of any one of embodiments C1 to C11, wherein the oil-based mixture comprises one or more pharmaceutical excipients selected from the group consisting of a castor oil, a liquid paraffin, caprylic/capric triglyceride, decamethylcyclopentasiloxane ($D_5$), dimethicone 350, stearic acid, cetostearyl alcohol, and cetyl alcohol.

Embodiment C14: The emulsion-based formulation of embodiment C13, wherein the oil-based mixture comprises a castor oil, a liquid paraffin, caprylic/capric triglyceride, dimethicone 350, cetyl alcohol, or combinations thereof.

Embodiment C15: The emulsion-based formulation of any one of embodiments C1 to C14, wherein the one or more additional excipients are a monoglyceride, a diglyceride, a sorbitan mono-ester, a polysorbate, a polyoxyethylene fatty ether, a polyoxyethylene fatty acid ester, or combinations thereof.

Embodiment C16: The emulsion-based formulation of any one of embodiments C1 to C14, wherein the one or more additional excipients are a blend of glyceryl monostearate and PEG-75 stearate (Gelot™ 64), sorbitan monostearate (Span™ 60), polysorbate 60 (Tween® 60), steareth-20 (Brij™ S20), mono and diglycerides (Geleol™ mono and diglycerides), polyoxy 20 cetostearyl ether, Sepineo™ P600, or combinations thereof.

Embodiment C17: The emulsion-based formulation of any one of embodiments C1 to C16, in a lotion.

Embodiment C18: The emulsion-based formulation of embodiment C17, wherein the lotion comprises:
a) the compound of formula (I);
b) water, PEG-400, ascorbic acid, a disodium salt of ethylenediaminetetraacetic acid, and phenoxyethanol;
c) 2-(2-ethoxyethoxy)ethanol; and
d) the oil-based mixture; and
e) the one or more additional excipients,
wherein a total amount of a) to c) is from about 75% to about 85% by weight.

Embodiment C19: The emulsion-based formulation of embodiment C18, wherein water is present in an amount of from about 20% to about 40% or from about 25% to about 35% by weight.

Embodiment C20: The emulsion-based formulation of embodiment C19, wherein water is present in an amount of about 30% by weight.

Embodiment C21: The emulsion-based formulation of any one of embodiments C18 to C20, wherein PEG-400 is present in an amount of from about 20% to about 50%, from about 20% to about 40%, or from about 30% to about 50% by weight.

Embodiment C22: The emulsion-based formulation of embodiment C21, wherein PEG-400 is present in an amount of about 39% by weight.

Embodiment C23: The emulsion-based formulation of any one of embodiments C18 to C22, wherein 2-(2-ethoxyethoxy)ethanol is present in an amount of from about 5% to about 25%, from about 5% to about 20%, or from about 5% to about 15% by weight.

Embodiment C24: The emulsion-based formulation of embodiment C23, wherein 2-(2-ethoxyethoxy)ethanol is present in an amount of about 10% by weight.

Embodiment C25: The emulsion-based formulation of any one of embodiments C18 to C24, wherein the oil-based mixture comprises a castor oil and caprylic/capric triglyceride.

Embodiment C26: The emulsion-based formulation of embodiment C25, wherein the castor oil is present in an amount of about 10% by weight.

Embodiment C27: The emulsion-based formulation of embodiment C25, wherein caprylic/capric triglyceride is present in an amount of about 8% by weight.

Embodiment C28: The emulsion-based formulation of any one of embodiments C18 to C27, the one or more additional excipients are Sepineo™ P600.

Embodiment C29: The emulsion-based formulation of embodiment C28, wherein Sepineo™ P600 is present in an amount of about 2% by weight.

Embodiments C30: The emulsion-based formulation of any one of embodiments C1 to C16, in a cream.

Embodiment C31: The emulsion-based formulation of embodiment C30, wherein the cream comprises:
a) the compound of formula (I);
b) water, PEG-400, ascorbic acid, a disodium salt of ethylenediaminetetraacetic acid, and phenoxyethanol;
c) 2-(2-ethoxyethoxy)ethanol; and
d) the oil-based mixture; and
e) the one or more additional excipients,
wherein a total amount of a) to c) is from about 75% to about 85% by weight.

Embodiment C32: The emulsion-based formulation of embodiment C31, wherein water is present in an amount of from about 20% to about 40% or from about 25% to about 35% by weight.

Embodiment C33: The emulsion-based formulation of embodiment C32, wherein water is present in an amount of about 32% by weight.

Embodiment C34: The emulsion-based formulation of any one of embodiments C31 to C33, wherein PEG-400 is present in an amount of from about 20% to about 50% or from about 20% to about 40% by weight.

Embodiment C35: The emulsion-based formulation of embodiment C34, wherein PEG-400 is present in an amount of about 31% by weight.

Embodiment C36: The emulsion-based formulation of any one of embodiments C31 to C35, wherein 2-(2-ethoxyethoxy)ethanol is present in an amount of from about 10% to about 25% or from about 10% to about 20% by weight.

Embodiment C37: The emulsion-based formulation of embodiment C36, wherein 2-(2-ethoxyethoxy)ethanol is present in an amount of about 16% by weight.

Embodiment C38: The emulsion-based formulation of any one of embodiments C31 to C37, wherein the oil-based mixture comprises a liquid paraffin, caprylic/capric triglyceride, dimethicone 350, and cetyl alcohol.

Embodiment C39: The emulsion-based formulation of embodiment C38, wherein the liquid paraffin is present in an amount of about 4% by weight.

Embodiment C40: The emulsion-based formulation of embodiment C38, wherein caprylic/capric triglyceride is present in an amount of about 6% by weight.

Embodiment C41: The emulsion-based formulation of embodiment C38, wherein dimethicone 350 is present in an amount of about 1% by weight.

Embodiment C42: The emulsion-based formulation of embodiment C38, wherein cetyl alcohol is present in an amount of about 4% by weight.

Embodiment C43: The emulsion-based formulation of any one of embodiments C31 to C42, wherein the one or more additional excipients are sorbitan monostearate (Span™ 60) and polysorbate 60 (Tween® 60).

Embodiment C44: The emulsion-based formulation of embodiment C43, wherein sorbitan monostearate (Span™ 60) is present in an amount of about 1.8% by weight.

Embodiment C45: The emulsion-based formulation of embodiment C43, wherein polysorbate 60 (Tween® 60) is present in an amount of about 3.2% by weight.

Embodiment C46: The emulsion-based formulation of any one of embodiments C17 to C45, wherein ascorbic acid is present in an amount of from about 0.05% to about 0.2% by weight.

Embodiment C47: The emulsion-based formulation of embodiment C46, wherein ascorbic acid is present in an amount of about 0.10% by weight.

Embodiment C48: The emulsion-based formulation of any one of embodiments C17 to C47, wherein the disodium salt of ethylenediaminetetraacetic acid is present in an amount of from about 0.01% to about 0.1% by weight.

Embodiment C49: The emulsion-based formulation of embodiment C48, wherein the disodium salt of ethylenediaminetetraacetic acid is present in an amount of about 0.05% by weight.

Embodiment C50: The emulsion-based formulation of any one of embodiments C1 to C16, in an emulsified gel.

Embodiment C51: The emulsion-based formulation of embodiment C50, wherein the emulsified gel comprises:
a) the compound of formula (I);
b) water, PEG-400, ascorbic acid, a disodium salt of ethylenediaminetetraacetic acid, and phenoxyethanol;
c) 2-(2-ethoxyethoxy)ethanol, ethanol, and optionally propylene glycol; and
d) the oil-based mixture; and
e) the one or more additional excipients,
wherein a total amount of a) to c) is from about 70% to about 75% by weight.

Embodiment C52: The emulsion-based formulation of embodiment C51, wherein water is present in an amount of from about 15% to about 35% or from about 20% to about 30% by weight.

Embodiment C53: The emulsion-based formulation of embodiment C52, wherein water is present in an amount of about 23.5% by weight.

Embodiment C54: The emulsion-based formulation of any one of embodiments C51 to C53, wherein PEG-400 is present in an amount of from about 5% to about 30%, from about 10% to about 30%, or from about 15% to about 25% by weight.

Embodiment C55: The emulsion-based formulation of embodiment C54, wherein PEG-400 is present in an amount of about 19.5% by weight.

Embodiment C56: The emulsion-based formulation of any one of embodiments C51 to C55, wherein ascorbic acid is present in an amount of from about 0.05% to about 0.2% by weight.

Embodiment C57: The emulsion-based formulation of embodiment C56, wherein ascorbic acid is present in an amount of about 0.10% by weight.

Embodiment C58: The emulsion-based formulation of any one of embodiments C51 to C57, wherein the disodium salt of ethylenediaminetetraacetic acid is present in an amount of from about 0.01% to about 0.1% by weight.

Embodiment C59: The emulsion-based formulation of embodiment C58, wherein the disodium salt of ethylenediaminetetraacetic acid is present in an amount of about 0.02% by weight.

Embodiment C60: The emulsion-based gel formulation of any one of embodiments C51 to C59, wherein propylene glycol is absent.

Embodiment C61: The emulsion-based gel formulation of any one of embodiments C51 to C60, wherein ethanol is present in an amount of from about 5% to about 15% or from about 5% to about 10% by weight.

Embodiment C62: The emulsion-based gel formulation of embodiment C61, wherein ethanol is present in an amount of about 8.5% by weight.

Embodiment C63: The emulsion-based formulation of any one of embodiments C51 to C62, wherein 2-(2-ethoxyethoxy)ethanol is present in an amount of from about 10% to about 30% or from about 15% to about 25% by weight.

Embodiment C64: The emulsion-based formulation of embodiment C63, wherein 2-(2-ethoxyethoxy)ethanol is present in an amount of about 20% by weight.

Embodiment C65: The emulsion-based formulation of any one of embodiments C51 to C64, wherein the oil-based mixture comprises a castor oil and caprylic/capric triglyceride.

Embodiment C66: The emulsion-based formulation of embodiment C65, wherein the castor oil is present in an amount of about 12.5% by weight.

Embodiment C67: The emulsion-based formulation of embodiment C65, wherein caprylic/capric triglyceride is present in an amount of about 10% by weight.

Embodiment C68: The emulsion-based formulation of any one of embodiments C51 to C67, wherein the one or more additional excipients are polyoxy 20 cetostearyl ether, Sepineo™ P600, or a combination thereof.

Embodiment C69: The emulsion-based formulation of embodiment C68, wherein polyoxy 20 cetostearyl ether, when present, is in an amount of about 2% by weight.

Embodiment C70: The emulsion-based formulation of embodiment C68, wherein Sepineo™ P600 is present in an amount of about 2.5% by weight.

Embodiment C71: The emulsion-based formulation of any one of embodiments C1 to C70, wherein phenoxyethanol is present in an amount of from about 0.5% to about 2% by weight.

Embodiment C72: The emulsion-based formulation of embodiment C71, wherein phenoxyethanol is present in an amount of about 1.05% by weight.

Embodiment C73: The emulsion-based formulation of any one of embodiments C1 to C72, wherein PEG-400 is a super refined PEG-400.

Embodiment C74: The emulsion-based formulation of any one of embodiments C1 to C73, wherein 2-(2-ethoxyethoxy)ethanol is Transcutol® HP having a purity of >about 99.90%.

Embodiment C75: The emulsion-based formulation of any one of embodiments C1 to C74, wherein propylene glycol is a super refined propylene glycol.

Embodiment C76: The emulsion-based formulation of any one of embodiments C1 to C75, wherein a pH is adjusted with aqueous sodium hydroxide or citric acid.

Embodiment C77: The emulsion-based formulation of any one of embodiments C1 to C76, wherein the compound of formula (I) is present in an amount of from about 0.005% to about 1% or from about 0.005% to about 0.5% by weight.

Embodiment C78: The emulsion-based formulation of embodiment C77, wherein, when in the lotion or cream, the compound of formula (I) is present in an amount of from about 0.005% to about 0.3% by weight.

Embodiment C79: The emulsion-based formulation of embodiment C77, wherein, when in the emulsified gel, the compound of formula (I) is present in an amount of from about 0.005% to about 0.6% by weight.

Embodiment C80: The emulsion-based formulation of any one of embodiments C1 to C79, having a visual appearance as white, opaque, smooth, or monophasic.

Embodiment C81: The emulsion-based formulation of embodiment C80, wherein the visual appearance is maintained over a period of 4 weeks at a temperature of about 40° C.

Embodiment C82: The emulsion-based formulation of any one of embodiments C1 to C81, wherein the formulation has a stable viscosity over a period of 4 weeks at a temperature of about 40° C.

Embodiment C83: The emulsion-based formulation of any one of embodiments C1 to C82, wherein a relative purity of the compound of formula (I) is maintained from 95% to 100% over a period of 6 months at a temperature of about 25° C.

III-D. Gel Formulations (Non-Aqueous) Including a Compound of Formula (II)

In a fourth aspect, the present disclosure provides a gel formulation useful for the treatment of skin disorders. The gel formulation includes:

a) a compound represented by formula (II):

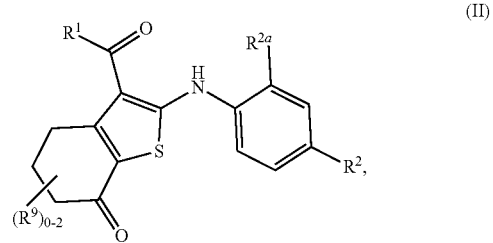

or a stereoisomer, a mixture of stereoisomers, and/or a pharmaceutically acceptable salt thereof,
wherein:
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^4$, $R^5$, and $R^{5b}$ are each independently hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl;
$R^{5a}$ is hydrogen or $C_1$-$C_6$ alkyl; and
each $R^9$ is independently $C_1$-$C_6$ alkyl;

b) a polyethylene glycol, an antioxidant, and optionally a preservative;
c) one or more organic solvents; and
d) a gelling agent,
wherein:
the polyethylene glycol has an average molecular weight of from about 200 Da to about 900 Da and is present in an amount of at least about 30% by weight;
the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof,
the gelling agent is hydroxypropyl cellulose or polyvinylpyrrolidone, each of which has an average molecular weight of from about 80,000 Da to about 1,700,000 Da;
the gel formulation has a pH value of no more than about 7; and
water, when present, is no more than about 5% by weight.

Compounds of formula (II) are described herein according to Section IV.

Compounds.

In some embodiments, the compound of formula (II) is represented by formula (IIa):

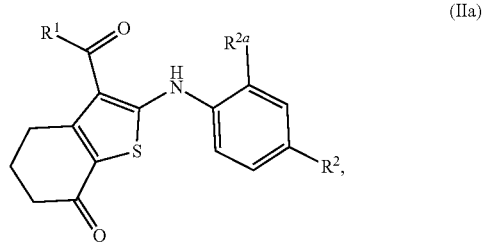

wherein $R^1$, $R^2$, and $R^{2a}$ are as defined and described herein.

In some embodiments, the compound is represented by formula (IIb):

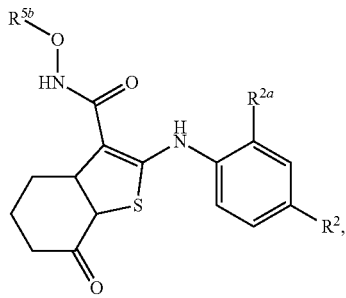

(IIb)

wherein:

R$^2$ is halo, C$_1$-C$_6$ alkyl, —S—C$_1$-C$_6$ alkyl, C$_3$-C$_5$ cycloalkyl, C$_2$-C$_6$ alkenyl, or C$_2$-C$_6$ alkynyl;

R$^{2a}$ is halo or C$_1$-C$_6$ alkyl; and

R$^{5b}$ is hydrogen, C$_1$-C$_6$ alkyl, C$_3$-C$_8$ cycloalkyl, C$_3$-C$_8$ cycloalkyl-C$_1$-C$_6$ alkyl, or C$_1$-C$_6$ hydroxyalkyl.

In some embodiments, R$^2$ and R$^{2a}$ are each halo. In some embodiments, R$^{5b}$ is C$_3$-C$_8$ cycloalkyl-C$_1$-C$_6$ alkyl or C$_1$-C$_6$ hydroxyalkyl. In some embodiments, R$^{5b}$ is C$_1$-C$_6$ hydroxyalkyl. In some embodiments, R$^{5b}$ is unbranched C$_1$-C$_6$ hydroxyalkyl. In some embodiments, R$^{5b}$ is unbranched C$_1$-C$_6$ hydroxyalkyl, wherein the C$_1$-C$_6$ alkyl in the C$_1$-C$_6$ hydroxyalkyl is substituted with one hydroxy. In some embodiments, R$^2$ and R$^{2a}$ are each halo; and R$^{5b}$ is C$_1$-C$_6$ hydroxyalkyl. In some embodiments, R$^2$ and R$^{2a}$ are each halo; and R$^{5b}$ is unbranched C$_1$-C$_6$ hydroxyalkyl. In some embodiments, R$^2$ and R$^{2a}$ are each halo; and R$^{5b}$ is unbranched C$_1$-C$_6$ hydroxyalkyl, wherein the C$_1$-C$_6$ alkyl in the C$_1$-C$_6$ hydroxyalkyl is substituted with one hydroxy.

In some embodiments, the compound is represented by formula (IIb-1):

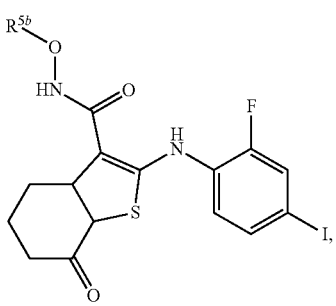

(IIb-1)

wherein R$^{5b}$ is defined and described herein.

In some embodiments, the compound is represented by the formula:

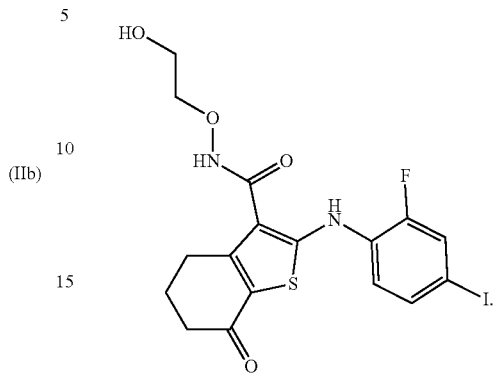

(Compound 2.003)

With reference to the gel formulation including any one of formulae (II), (IIa), (IIb), (IIb-1), and Compound 2.003, the viscosity of the gel formulation is described according to Section III-A. In some embodiments, the viscosity of the gel formulation is any one of embodiments as described in Section III-A. In some embodiments, the viscosity is from about 15,000 to about 50,000 cps.

With reference to the gel formulation including any one of formulae (II), (IIa), (IIb), (IIb-1), and Compound 2.003, the polyethylene glycol, antioxidant, preservative, one or more organic solvents, and gelling agent are each described according to Section III-A. In some embodiments, each of the polyethylene glycol, antioxidant, preservative, one or more organic solvents, and gelling agent is any one of embodiments as described in Section III-A.

With reference to the gel formulation including any one of formulae (II), (IIa), (IIb), (IIb-1), and Compound 2.003, the pH of the gel formulation, water content, and stability of the gel formulation are each described according to Section III-A. In some embodiments, each of the pH of the gel formulation, water content, and stability of the gel formulation is any one of embodiments as described in Section III-A.

In some embodiments of any one of gel formulations, the compound of formula (II) is present in the gel formulation in an amount of from about 0.005% to about 3%, from about 0.005% to about 2%, from about 0.01% to about 2%, from about 0.01% to about 1%, or from about 0.1% to about 1% by weight on a salt-free and anhydrous basis. In some embodiments, the compound of formula (II) is present in an amount of from about 0.01% to about 2% by weight on a salt-free and anhydrous basis. In some embodiments, the compound of formula (II) is present in an amount of from about 0.1% to about 1% by weight on a salt-free and anhydrous basis.

In some embodiments of any one of gel formulations, the compound of formula (IIb) is present in the gel formulation in an amount of from about 0.005% to about 3%, f from about 0.005% to about 2%, from about 0.01% to about 2%, from about 0.01% to about 1%, or from about 0.1% to about 1% by weight on a salt-free and anhydrous basis. In some embodiments, the compound of formula (IIb) is present in an amount of from about 0.01% to about 2% by weight on a salt-free and anhydrous basis. In some embodiments, the compound of formula (IIb) is present in an amount of from about 0.1% to about 1% by weight on a salt-free and anhydrous basis.

In some embodiments of any one of gel formulations, Compound 2.003 is present in the gel formulation in an amount of from about 0.005% to about 3%, from about 0.005% to about 2%, from about 0.01% to about 2%, from about 0.01% to about 1%, or from about 0.1% to about 1% by weight on a salt-free and anhydrous basis. In some embodiments, Compound 2.003 is present in an amount of from about 0.005% to about 2% by weight on a salt-free and anhydrous basis. In some embodiments, Compound 2.003 is present in an amount of from about 0.01% to about 2% by weight on a salt-free and anhydrous basis. In some embodiments, Compound 2.003 is present in an amount of from about 0.01% to about 1% by weight on a salt free and anhydrous basis. I In some embodiments, Compound 2.003 is present in an amount of from about 0.1% to about 1% by weight on a salt free and anhydrous basis. In some embodiments, Compound 2.003 is present in an amount of about 0.05% by weight on a salt-free and anhydrous basis. In some embodiments, Compound 2.003 is present in an amount of about 0.1% by weight on a salt-free and anhydrous basis. In some embodiments, Compound 2.003 is present in an amount of about 0.15% by weight on a salt-free and anhydrous basis. In some embodiments, Compound 2.003 is present in an amount of about 0.25% by weight on a salt-free and anhydrous basis. In some embodiments, Compound 2.003 is present in an amount of about 0.5% by weight on a salt-free and anhydrous basis. In some embodiments, Compound 2.003 is present in an amount of about 1% by weight on a salt-free and anhydrous basis.

In some embodiments, the gel formulation (NA-II) includes:
  a) the compound of any one of formulae (II), (IIa), (IIb), (IIb-1), and Compound 2.003;
  b) PEG-400, the antioxidant, optionally the preservative, and optionally a stabilizer;
  c) $C_{1-3}$ alkyl-$(OCH_2CH_2)_{1-5}$—OH; and
  d) the gelling agent.

With reference to the gel formulation (NA-II), the PEG-400, the antioxidant, the preservative, and the stabilizer are each described according to the gel formulation (NA-1) in Section III-A. In some embodiments, each of the PEG-400, the antioxidant, the preservative, and the stabilizer is any one of embodiments as described according to the gel formulation (NA-1) in Section III-A.

In some embodiments, the present disclosure provides a gel formulation (NA-IIa), including:
  a) a compound represented by the formula:

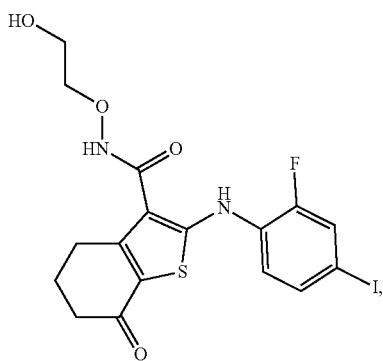 [SMILES: O=C1CCCc2c1sc(Nc1ccc(I)cc1F)c2C(=O)NOCCO]

or a pharmaceutically acceptable salt thereof, b) PEG-400, 2-(2-ethoxyethoxy)ethanol, ascorbyl palmitate, and alpha tocopherol or alpha tocopherol acetate; and
  c) a hydroxypropyl cellulose having an average molecular weight of from about 140,000 Da to about 1,150,000 Da, wherein the gel formulation has a pH value of no more than about 7.

With reference to the gel formulations (NA-IIa), the PEG-400, 2-(2-ethoxyethoxy)ethanol, ascorbyl palmitate, alpha tocopherol or alpha tocopherol acetate, hydroxypropyl cellulose, pH, and viscosity are each described according to the gel formulation (NA-1a) in Section III-A. In some embodiments, each of the PEG-400, 2-(2-ethoxyethoxy) ethanol, ascorbyl palmitate, alpha tocopherol or alpha tocopherol acetate, hydroxypropyl cellulose, pH, and viscosity is any one of embodiments as described according to the gel formulation (NA-Ia) in Section III-A.

In some embodiments, the present disclosure provides a gel formulation (NA-IIb), comprising:
  a) a compound represented by the formula:

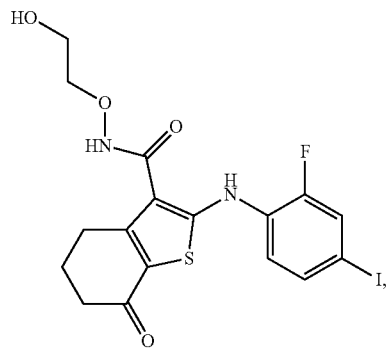 [SMILES: O=C1CCCc2c1sc(Nc1ccc(I)cc1F)c2C(=O)NOCCO]

or a pharmaceutically acceptable salt thereof, b) PEG-400, 2-(2-ethoxyethoxy)ethanol, butylated hydroxytoluene, and potassium sorbate; and
  c) a hydroxypropyl cellulose having an average molecular weight of from about 850,000 Da to about 1,150,000 Da, wherein the gel formulation has a pH value of no more than about 7.

With reference to the gel formulation (NA-IIb), the PEG-400, 2-(2-ethoxyethoxy)ethanol, butylated hydroxytoluene, potassium sorbate, hydroxypropyl cellulose, pH, and viscosity are each described according to the gel formulation (NA-1b) in Section III-A. In some embodiments, each of the PEG-400, 2-(2-ethoxyethoxy)ethanol, butylated hydroxytoluene, potassium sorbate, hydroxypropyl cellulose, pH, and viscosity is any one of embodiments as described according to the gel formulation (NA-1b) in Section III-A.

87

In some embodiments, the present disclosure provides a gel formulation (NA-IIc), comprising:
a) a compound represented by the formula:

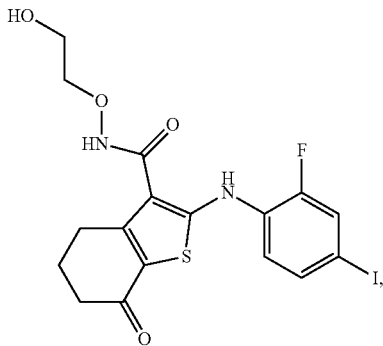

or a pharmaceutically acceptable salt thereof,
b) PEG-400, 2-(2-ethoxyethoxy)ethanol, butylated hydroxytoluene, and phenoxyethanol; and
c) a hydroxypropyl cellulose having an average molecular weight of from about 850,000 Da to about 1,150,000 Da, wherein the gel formulation has a pH value of no more than about 7.

With reference to the gel formulation (NA-IIc), the PEG-400, 2-(2-ethoxyethoxy)ethanol, butylated hydroxytoluene, phenoxyethanol, hydroxypropyl cellulose, pH, and viscosity are each described according to the gel formulation (NA-1c) in Section III-A. In some embodiments, each of the PEG-400, 2-(2-ethoxyethoxy)ethanol, butylated hydroxytoluene, phenoxyethanol, hydroxypropyl cellulose, pH, and viscosity is any one of embodiments as described according to the gel formulation (NA-1c) in Section III-A.

In some embodiments, the gel formulation (NA-IIc) includes:
a) from about 0.005% to about 2% by weight of Compound 2.003 or a hydrate and/or pharmaceutically acceptable salt thereof, on a salt-free and anhydrous basis;
b) from about 50% to about 55% by weight of PEG-400;
c) from about 40% to about 50% by weight of 2-(2-ethoxyethoxy)ethanol;
d) from about 0.1% to about 0.3% by weight of butylated hydroxytoluene;
e) from about 0.5% to about 2% by weight of phenoxyethanol;
f) optionally from about 1% to about 3% PEG-1500;
g) from about 0.5% to about 2% by weight of the hydroxypropyl cellulose having an average molecular weight of about 1,150,000 Da;
h) citric acid; and
i) optionally from about 0.001% to about 0.05% by weight of one or more dyes, wherein the total weight of a) to i) is 100%; and citric acid is a solution in PEG-400 or 2-(2-ethoxyethoxy)ethanol to adjust a pH.

In some embodiments, the gel formulation (NA-IIc-0.1%) includes:
a) about 0.1% by weight of Compound 2.003 or a hydrate and/or pharmaceutically acceptable salt thereof, on a salt-free and anhydrous basis;
b) about 52% by weight of PEG-400;
c) about 45% by weight of 2-(2-ethoxyethoxy)ethanol;

88 d) about 0.2% by weight of butylated hydroxytoluene;
e) about 1% by weight of phenoxyethanol;
f) about 1% by weight of the hydroxypropyl cellulose having an average molecular weight of about 1,150,000 Da;
g) citric acid; and
h) optionally about 0.02% by weight of one or more dyes, wherein the total weight of a) to h) is 100%; and citric acid is a solution in PEG-400 or 2-(2-ethoxyethoxy)ethanol to adjust a pH.

In some embodiments, the gel formulation (NA-IIc-0.5%) includes:
a) about 0.5% by weight of Compound 2.003 or a hydrate and/or pharmaceutically acceptable salt thereof, on a salt-free and anhydrous basis;
b) about 52% by weight of PEG-400;
c) about 45% by weight of 2-(2-ethoxyethoxy)ethanol;
d) about 0.2% by weight of butylated hydroxytoluene;
e) about 1% by weight of phenoxyethanol;
f) about 1% by weight of the hydroxypropyl cellulose having an average molecular weight of about 1,150,000 Da;
g) citric acid; and
h) optionally about 0.02% by weight of one or more dyes, wherein the total weight of a) to h) is 100%; and citric acid is a solution in PEG-400 or 2-(2-ethoxyethoxy)ethanol to adjust a pH.

In some embodiments of any one of gel formulations (e.g., NA-IIa, NA-IIb, and NA-IIc) as described herein, the solution of citric acid or sodium hydroxide in PEG-400 or 2-(2-ethoxyethoxy)ethanol has a concentration of from about 0.1 M to about 0.5 M. In some embodiments, the solution of citric acid or sodium hydroxide in PEG-400 or 2-(2-ethoxyethoxy)ethanol has a concentration of about 0.1 M. In some embodiments, the solution of citric acid or sodium hydroxide in PEG-400 or 2-(2-ethoxyethoxy)ethanol has a concentration of about 0.5 M. In some embodiments, the solution of citric acid in 2-(2-ethoxyethoxy)ethanol has a concentration of about 0.5 M.

EMBODIMENTS

Embodiment D1. A gel formulation, comprising:
a) a compound represented by formula (II):

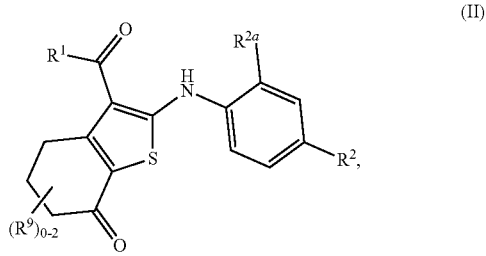

or a stereoisomer, a mixture of stereoisomers, and/or a pharmaceutically acceptable salt thereof,
wherein:
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^4$, $R^5$, and $R^{5b}$ are each independently hydrogen, $C_1$-$C_6$ alkyl, $C_3$-$C_8$ cycloalkyl, $C_3$-$C_8$ cycloalkyl-$C_1$-

$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl;

$R^{5a}$ is hydrogen or $C_1$-$C_6$ alkyl; and each $R^9$ is independently $C_1$-$C_6$ alkyl;

b) a polyethylene glycol, an antioxidant, and optionally a preservative;

c) one or more organic solvents; and d) a gelling agent, wherein:

the polyethylene glycol has an average molecular weight of from about 200 to about 900 Da and is present in an amount of at least about 30% by weight;

the one or more organic solvents are a $C_{2-6}$ alcohol, a $C_{2-6}$ alkylene glycol, $C_{1-3}$ alkyl-$(OCH_2CH_2)_{1-5}$—OH, a fatty alcohol, glycerol, or combinations thereof, the gelling agent is hydroxypropyl cellulose or polyvinylpyrrolidone, each of which has an average molecular weight of from about 80,000 Da to about 1,700,000 Da;

the gel formulation has a pH value of no more than about 7; and water, when present, is no more than about 5% by weight.

Embodiment D2. The gel formulation of Embodiment D1, wherein the gel formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

Embodiment D3. The gel formulation of Embodiment D1 or D2, wherein the gel formulation has a viscosity of from about 15,000 to about 50,000 cps.

Embodiment D4. The gel formulation of any one of Embodiments D1 to D3, wherein the compound is represented by formula (Ib):

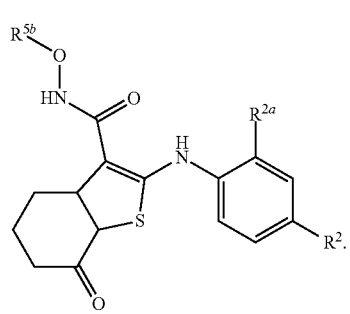

(Ib)

Embodiment D5. The gel formulation of any one of Embodiments D1 to D4, wherein the compound is represented by the formula:

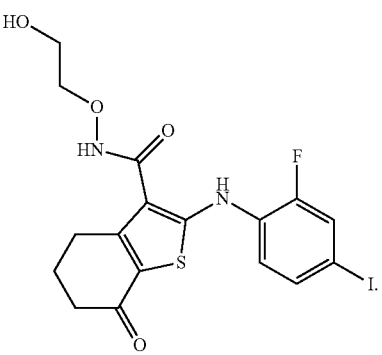 [SMILES: O=C1CCCc2c1sc(Nc1ccc(I)cc1F)c2C(=O)NOCCO]

Embodiment D6. The gel formulation of any one of Embodiments D1 to D5, wherein the polyethylene glycol is PEG-400.

Embodiment D7. The gel formulation of Embodiment D6, wherein PEG-400 is present in an amount of from about 50% to about 60% by weight.

Embodiment D8. The gel formulation of any one of Embodiments D1 to D7, wherein the one or more organic solvents are $C_{1-3}$ alkyl-$(OCH_2CH_2)_{1-5}$—OH; and $C_{1-3}$ alkyl-$(OCH_2CH_2)_{1-5}$—OH is 2-(2-ethoxyethoxy)ethanol.

Embodiment D9. The gel formulation of Embodiment D8, wherein 2-(2-ethoxyethoxy)ethanol is present in an amount of from about 40% to about 50% by weight.

Embodiment D10. The gel formulation of any one of Embodiments D1 to D9, wherein the antioxidant is butylated hydroxytoluene, butylated hydroxyanisole, an ascorbyl ester, or combinations thereof.

Embodiment D11. The gel formulation of any one of Embodiments D1 to D10, wherein the antioxidant is butylated hydroxytoluene in an amount of from about 0.1% to about 0.5%, from about 0.1% to about 0.4%, or from about 0.1% to about 0.3% by weight.

Embodiment D12. The gel formulation of Embodiment D11, wherein butylated hydroxytoluene is present in an amount of about 0.2% by weight.

Embodiment D13. The gel formulation of any one of Embodiments D1 to D10, wherein the antioxidant is an ascorbyl ester comprising ascorbyl palmitate.

Embodiment D14. The gel formulation of Embodiment D13, wherein ascorbyl palmitate is present in an amount of from about 0.01% to about 0.1% by weight.

Embodiment D15. The gel formulation of Embodiment D14, wherein ascorbyl palmitate is present in an amount of about 0.05% by weight.

Embodiment D16. The gel formulation of any one of Embodiments D13 to D15, further comprising a stabilizer, wherein the stabilizer is alpha tocopherol or alpha tocopherol acetate.

Embodiment D17. The gel formulation of Embodiment D16, wherein alpha tocopherol or alpha tocopherol acetate is present in an amount of about 0.002% by weight.

Embodiment D18. The gel formulation of any one of Embodiments D1 to D17, wherein the preservative, when present, is benzyl alcohol, phenoxyethanol, potassium sorbate, or combinations thereof.

Embodiment D19. The gel formulation of any one of Embodiments D1 to D18, wherein the preservative, when present, is phenoxyethanol in an amount of from about 0.5% to about 5%, from about 0.5% to about 4%, from about 0.5% to about 3%, or from about 0.5% to about 2% by weight.

Embodiment D20. The gel formulation of Embodiment D19, wherein phenoxyethanol is present in an amount of about 1% by weight.

Embodiment D21. The gel formulation of any one of Embodiments D1 to D18, wherein the preservative, when present, is potassium sorbate in an amount of from about 0.05% to about 0.5%, from about 0.05% to about 0.4%, from about 0.05% to about 0.3%, or from about 0.05% to about 0.2% by weight.

Embodiment D22. The gel formulation of Embodiment D21, wherein potassium sorbate is present in an amount of about 0.1% by weight.

Embodiment D23. The gel formulation of any one of Embodiments D1 to D22, further comprising a thickening agent, wherein the thickening agent is a polyethylene glycol having an average molecular weight of from about 1000 to about 3000 Da.

Embodiment D24. The gel formulation of any one of Embodiments D6 to D23, wherein PEG-400 is a super refined PEG-400.

Embodiment D25. The gel formulation of any one of Embodiments D8 to D24, wherein 2-(2-ethoxyethoxy)ethanol is Transcutol® HP having a purity of >about 99.90%.

Embodiment D26. The gel formulation of any one of Embodiments D1 to D25, wherein the gelling agent is hydroxypropyl cellulose.

Embodiment D27. The gel formulation of Embodiment D26, wherein the hydroxypropyl cellulose has an average molecular weight of from about 850,000 Da to about 1,150,000 Da.

Embodiment D28. The gel formulation of Embodiment D26, wherein the hydroxypropyl cellulose is Klucel™ MF or Klucel™ HF.

Embodiment D29. The gel formulation of Embodiment D28, wherein the hydroxypropyl cellulose is Klucel™ HF in an amount of from about 0.5% to about 2% by weight.

Embodiment D30. The gel formulation of any one of Embodiments D1 to D29, wherein the compound of formula (II) is present in an amount of from about 0.1% to about 1% by weight.

Embodiment D31. A gel formulation, comprising:
a) a compound represented by the formula:

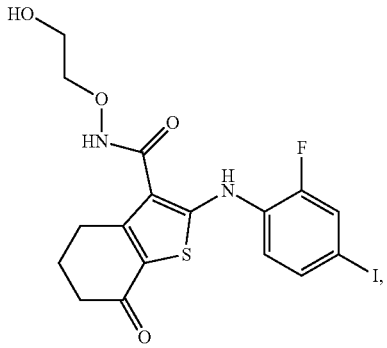

or a pharmaceutically acceptable salt thereof,
b) PEG-400, 2-(2-ethoxyethoxy)ethanol, butylated hydroxytoluene, and potassium sorbate; and
c) a hydroxypropyl cellulose having an average molecular weight of from about 850,000 Da to about 1,150,000 Da, wherein the gel formulation has a pH value of no more than about 7.

Embodiment D32. A gel formulation, comprising:
a) a compound represented by the formula:

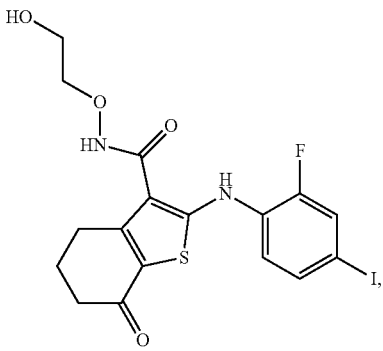 [SMILES: O=C1CCCc2c1sc(Nc1ccc(I)cc1F)c2C(=O)NOCCO]

or a pharmaceutically acceptable salt thereof,
b) PEG-400, 2-(2-ethoxyethoxy)ethanol, butylated hydroxytoluene, and phenoxyethanol; and
c) a hydroxypropyl cellulose having an average molecular weight of from about 850,000 Da to about 1,150,000 Da, wherein the gel formulation has a pH value of no more than about 7.

Embodiment D33. The gel formulation of Embodiment D31 or D32, wherein the gel formulation has a viscosity of from about 15,000 to about 50,000 cps.

Embodiment D34. A method of treating a skin disorder comprising administering a gel formulation of any one of Embodiments D1 to D33, wherein the skin disorder is a MEK-inhibitor responsive dermal disorder or a MEK-mediated dermal disorder, a birthmark, or a skin cancer.

Embodiment D35. The method of Embodiment D34, wherein the MEK-inhibitor responsive dermal disorder or MEK-mediated dermal disorder is selected from the group consisting of neurofibromatosis type 1, dermal neurofibroma, subdermal neurofibroma, superficial plexiform neurofibroma, and dermal rasopathy.

Embodiment D36. The method of Embodiment D35, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

Embodiment D37. The method of Embodiment D34, wherein the birthmark is selected from the group consisting of port-wine stains/capillary malformations, nevus cellular nevus, displastic nevi, capillary angioma, epidermal nevi, nevus sebaceous, nevus spilus, arterio-venous malformations, lymphatic malformations, and congenital melanocytic nevus.

Embodiment D38. The method of Embodiment D34 or D37, wherein the birthmark is associated with activation of p-ERK.

Embodiment D39. The method of Embodiment D38, wherein the birthmark associated with activation of p-ERK is selected from the group consisting of epidermal nevi, nevus sebaceous, nevus spilus, arterio-venous malformations, capillary malformations/port-wine stain, congenital melanocytic nevus, and lymphatic malformations.

Embodiment D40. The method of Embodiment D34, wherein the skin cancer is a cutaneous squamous-cell carcinoma.

Embodiment D41. The method of Embodiment D34, wherein the skin cancer is a MEK-inhibitor responsive or MEK-mediated cutaneous squamous-cell carcinoma.

Embodiment D42. The method of Embodiment D40 or D41, wherein the cutaneous squamous-cell carcinoma is associated with activation of p-ERK.

Embodiment D43. The method of any one of Embodiments D34 to D42, wherein the gel formulation is administered topically.

Embodiment D44. The method of any one of Embodiments D34 to D43, wherein the gel formulation is administered as a paint, a lotion, an ointment, a cream, a gel, or a patch.

III-E. Forms of Topical Formulations

The topical formulations (e.g., non-aqueous gel, aqueous gel, and/or emulsion-based formulations) as described herein used to deliver the compound of formula (I) or (II) is a lotion, an ointment, a cream, a gel, a paste, or a patch.

In some embodiments, the topical formulation used to deliver the compound of formula (I) or (II) is a gel, as described herein. In some embodiments, the topical formulation used to deliver the compound of formula (I) is a gel, as described herein. In some embodiments, the topical formulation used to deliver the compound of formula (II) is a gel, as described herein.

In some embodiments, the topical formulation used to deliver the compound of formula (I) or (II) is a lotion or a cream as described herein. In some embodiments, the topical formulation used to deliver the compound of formula (I) is a lotion or a cream as described herein. In some embodiments, the topical formulation used to deliver the compound of formula (II) is a lotion or a cream as described herein.

In some embodiments, the topical formulation used to deliver the compound of formula (I) or (II) is an ointment. In some embodiments, the topical formulation used to deliver the compound of formula (I) is an ointment. In some embodiments, the topical formulation used to deliver the compound of formula (II) is an ointment. Ointments are oleaginous semisolids that contain little if any water. In some instances, the ointment is hydrocarbon based, such as a wax, petrolatum, or gelled mineral oil. Suitable ointments for use in the disclosure are well known in the art and are disclosed in REMINGTON: THE SCIENCE AND PRACTICE OF PHARMACY 1585-1591 (Alfonso R. Gennaro ed. 19$^{th}$ ed. 1995), hereby incorporated herein by reference.

In some embodiments, the topical administration may be achieved in the form of patches comprising the topical formulation as described herein, where the patch is in contact with the affected area on the skin.

IV. Compounds

Compounds of Formula (I)

The present disclosure provides a compound for use in the topical formulations (e.g., non-aqueous gel, aqueous gel, and/or emulsion-based formulations) for the treatment of skin disorders as defined and described herein, wherein the compound is represented by formula (I):

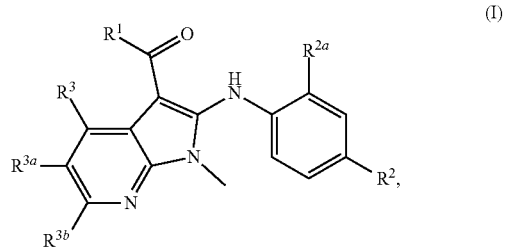

or a stereoisomer, a mixture of stereoisomers, and/or a pharmaceutically acceptable salt thereof, wherein:

$R^1$ is —$OR^4$, —$NR^5R^{5a}$, or —$N(OR^{5b})R^{5a}$;

$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;

$R^{2a}$ is halo or $C_1$-$C_6$ alkyl;

$R^3$, $R^{3a}$, and $R^{3b}$ are independently hydrogen, halo, $C_1$-$C_6$ alkyl, or $C_1$-$C_6$ alkoxy;

$R^4$ is $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

$R^5$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl;

$R^{5a}$ is hydrogen or $C_1$-$C_6$ alkyl; and $R^{5b}$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, or $C_1$-$C_6$ alkoxy-$C_1$-$C_6$ alkyl.

In some embodiments, the cycloalkyl group provided in formula (I) is a saturated monocyclic $C_3$-$C_8$ cycloalkyl. In some embodiments, the $C_3$-$C_8$ cycloalkyl group, as alone or as part of $C_3$-$C_8$ cycloalkyl-$C_1$-$C_6$ alkyl is cyclopropyl or cyclobutyl. In some embodiments, the $C_3$-$C_8$ cycloalkyl group, as alone or as part of $C_3$-$C_8$ cycloalkyl-$C_1$-$C_6$ alkyl, is unsubstituted.

In some embodiments, $R^3$, $R^{3a}$, and $R^{3b}$ are each independently hydrogen, halo, or $C_1$-$C_6$ alkoxy. In some embodiments, $R^3$, $R^{3a}$, and $R^{3b}$ are each independently hydrogen or $C_1$-$C_6$ alkoxy. In some embodiments, $R^3$, $R^{3a}$, and $R^{3b}$ are each independently hydrogen, fluoro, or methoxy.

In some embodiments, $R^3$ is hydrogen.

In some embodiments, $R^{3a}$ is hydrogen, halo, or $C_1$-$C_6$ alkoxy. In some embodiments, $R^{3a}$ is hydrogen. In some embodiments, $R^{3a}$ is halo. In some embodiments, $R^{3a}$ is fluoro, chloro, bromo, or iodo. In some embodiments, $R^{3a}$ is fluoro. In some embodiments, $R^{3a}$ is $C_1$-$C_6$ alkoxy. In some embodiments, $R^{3a}$ is methoxy, ethoxy, propoxy, iso-propoxy, butoxy, 2-butoxy, iso-butoxy, sec-butoxy, tert-butoxy, pentoxy, or hexoxy. In some embodiments, $R^{3a}$ is methoxy.

In some embodiments, $R^{3b}$ is hydrogen.

In some embodiments, $R^3$, $R^{3a}$, and $R^{3b}$ are each hydrogen. In some embodiments, $R^3$ and $R^{3b}$ are each hydrogen and $R^{3a}$ is halo or $C_1$-$C_6$ alkoxy. In some embodiments, $R^3$ and $R^{3b}$ are each hydrogen and $R^{3a}$ is fluoro or methoxy. In some embodiments, $R^3$ and $R^{3b}$ are each hydrogen and $R^{3a}$ is fluoro. In some embodiments, $R^3$ and $R^{3b}$ are each hydrogen and $R^{3a}$ is methoxy.

In some embodiments, the compound is represented by formula (Ia):

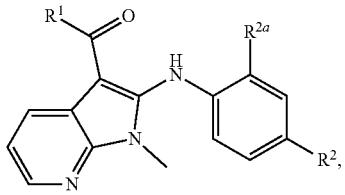

(Ia)

wherein $R^1$, $R^2$, and $R^{2a}$ are as defined and described herein.

In some embodiments of formula (I) or (Ia), $R^1$ is $-OR^4$. In some embodiments, $R^4$ is $C_1$-$C_6$ alkyl. In some embodiments, $R^4$ is $C_1$-$C_3$ alkyl. In some embodiments, $R^4$ is $C_3$-$C_8$ cycloalkyl. In some embodiments, $R^4$ is $C_3$-$C_6$ cycloalkyl. In some embodiments, $R^4$ is $C_3$-$C_8$ cycloalkyl-$C_1$-$C_6$ alkyl. In some embodiments, $R^4$ is $C_3$-$C_6$ cycloalkyl-$C_1$-$C_6$ alkyl. In some embodiments, $R^4$ is cyclopropyl, cyclobutyl, cyclopropyl-$C_1$-$C_3$ alkyl, or cyclobutyl-$C_1$-$C_3$ alkyl. In some embodiments, $R^4$ is cyclopropylmethyl. In some embodiments, $R^4$ is $C_1$-$C_6$ hydroxyalkyl. In some embodiments, $R^4$ is $C_1$-$C_6$ monohydroxyalkyl. In some embodiments, $R^4$ is $C_1$-$C_6$ dihydroxyalkyl. In some embodiments, $R^4$ is $HOCH_2$—$C_1$-$C_5$ alkyl. In some embodiments, $R^4$ is $C_1$-$C_3$ hydroxyalkyl. In some embodiments, $R^4$ is $C_1$-$C_3$ monohydroxyalkyl. In some embodiments, $R^4$ is $C_1$-$C_3$ dihydroxyalkyl. In some embodiments, $R^4$ is $HOCH_2$—$C_1$-$C_2$ alkyl. In some embodiments, $R^4$ is $CH_2CH_2OH$. In some embodiments, $R^4$ is $CH_2CH(OH)CH_2OH$.

In some embodiments of formula (I) or (Ia), $R^1$ is selected from the group consisting of:

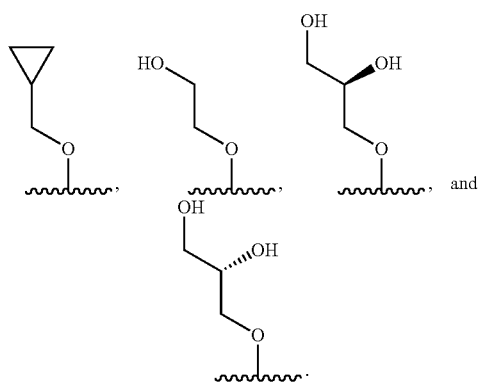

In some embodiments of formula (I) or (Ia), $R^1$ is $-NR^5R^{5a}$. In some embodiments, $R^5$ is hydrogen. In some embodiments, $R^5$ is $C_1$-$C_6$ alkyl. In some embodiments, $R^5$ is $C_1$-$C_3$ alkyl. In some embodiments, $R^5$ is $C_3$-$C_8$ cycloalkyl. In some embodiments, $R^5$ is $C_3$-$C_6$ cycloalkyl. In some embodiments, $R^5$ is $C_3$-$C_8$ cycloalkyl-$C_1$-$C_6$ alkyl. In some embodiments, $R^5$ is $C_3$-$C_6$ cycloalkyl-$C_1$-$C_6$ alkyl. In some embodiments, $R^5$ is cyclopropyl, cyclobutyl, cyclopropyl-$C_1$-$C_3$ alkyl, or cyclobutyl-$C_1$-$C_3$ alkyl. In some embodiments, $R^5$ is cyclopropylmethyl. In some embodiments, $R^5$ is $C_1$-$C_6$ hydroxyalkyl. In some embodiments, $R^5$ is $C_1$-$C_6$ monohydroxyalkyl. In some embodiments, $R^5$ is $C_1$-$C_6$ dihydroxyalkyl. In some embodiments, $R^5$ is $HOCH_2$—$C_1$-$C_5$ alkyl. In some embodiments, $R^5$ is $C_1$-$C_3$ hydroxyalkyl. In some embodiments, $R^5$ is $C_1$-$C_3$ monohydroxyalkyl. In some embodiments, $R^5$ is $C_1$-$C_3$ dihydroxyalkyl. In some embodiments, $R^5$ is $HOCH_2$—$C_1$-$C_2$ alkyl. In some embodiments, $R^5$ is $CH_2CH_2OH$. In some embodiments, $R^5$ is $CH_2CH(OH)CH_2OH$.

In some embodiments of formula (I) or (Ia), $R^1$ is $-NR^5R^{5a}$; $R^{5a}$ is hydrogen; and $R^5$ is as defined and described herein. In some embodiments, $R^1$ is $-NR^5R^{5a}$; $R^{5a}$ is $C_1$-$C_6$ alkyl; and $R^5$ is as defined and described herein. In some embodiments, $R^1$ is $-NR^5R^{5a}$; $R^{5a}$ is $C_1$-$C_3$ alkyl; and $R^5$ is as defined and described herein.

In some embodiments of formula (I) or (Ia), $R^1$ is selected from the group consisting of:

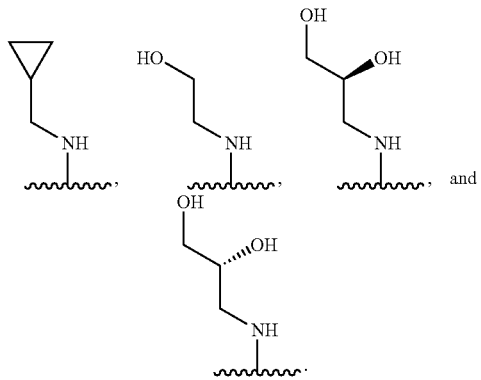

In some embodiments of formula (I) or (Ia), $R^1$ is $-N(OR^{5b})R^{5a}$. In some embodiments, $R^{5b}$ is hydrogen. In some embodiments, $R^{5b}$ is $C_1$-$C_6$ alkyl. In some embodiments, $R^{5b}$ is $C_1$-$C_3$ alkyl. In some embodiments, $R^{5b}$ is $C_3$-$C_8$ cycloalkyl. In some embodiments, $R^{5b}$ is $C_3$-$C_6$ cycloalkyl. In some embodiments, $R^{5b}$ is $C_3$-$C_8$ cycloalkyl-$C_1$-$C_6$ alkyl. In some embodiments, $R^{5b}$ is $C_3$-$C_6$ cycloalkyl-$C_1$-$C_6$ alkyl. In some embodiments, $R^{5b}$ is cyclopropyl, cyclobutyl, cyclopropyl-$C_1$-$C_3$ alkyl, or cyclobutyl-$C_1$-$C_3$ alkyl. In some embodiments, $R^{5b}$ is cyclopropylmethyl. In some embodiments, $R^{5b}$ is $C_1$-$C_6$ hydroxyalkyl. In some embodiments, $R^{5b}$ is $C_1$-$C_6$ monohydroxyalkyl. In some embodiments, $R^{5b}$ is $C_1$-$C_6$ dihydroxyalkyl. In some embodiments, $R^{5b}$ is $HOCH_2$—$C_1$-$C_5$ alkyl. In some embodiments, $R^{5b}$ is $C_1$-$C_3$ hydroxyalkyl. In some embodiments, $R^{5b}$ is $C_1$-$C_3$ monohydroxyalkyl. In some embodiments, $R^{5b}$ is $C_1$-$C_3$ dihydroxyalkyl. In some embodiments, $R^{5b}$ is $HOCH_2$—$C_1$-$C_2$ alkyl. In some embodiments, $R^{5b}$ is $CH_2CH_2OH$. In some embodiments, $R^{5b}$ is $CH_2CH(OH)CH_2OH$.

In some embodiments of formula (I) or (Ia), $R^1$ is $-N(OR^{5b})R^{5a}$; $R^{5a}$ is hydrogen; and $R^{5b}$ is as defined and described herein. In some embodiments, $R^1$ is $-N(OR^{5b})R^{5a}$; $R^{5a}$ is $C_1$-$C_6$ alkyl; and $R^{5b}$ is as defined and described herein. In some embodiments, $R^1$ is $-N(OR^{5b})R^{5a}$; $R^{5a}$ is $C_1$-$C_3$ alkyl; and $R^{5b}$ is as defined and described herein.

In some embodiments of formula (I) or (Ia), $R^1$ is selected from the group consisting of:

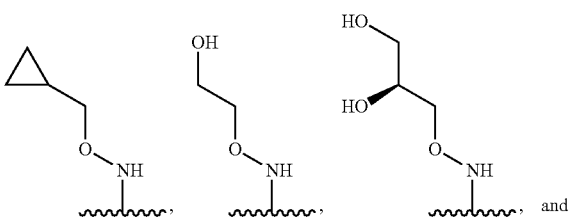

-continued

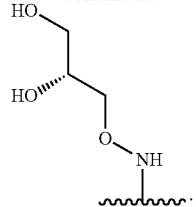

In some embodiments of formula (I) or (Ia), $R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl. In some embodiments, $R^2$ is halo or $C_1$-$C_6$ alkyl. In some embodiments, $R^2$ is halo, —$CH_3$, —$SCH_3$, $C_2$-$C_3$ alkenyl, or $C_2$-$C_3$ alkynyl.

In some embodiments of formula (I) or (Ia), $R^2$ is halo. In some embodiments, $R^2$ is fluoro. In some embodiments, $R^2$ is iodo. In some embodiments, $R^2$ is chloro. In some embodiments, $R^2$ is bromo.

In some embodiments of formula (I) or (Ia), $R^2$ is $C_1$-$C_6$ alkyl. In some embodiments, $R^2$ is $C_1$-$C_3$ alkyl. In some embodiments, $R^2$ is methyl.

In some embodiments of formula (I) or (Ia), $R^2$ is —S—$C_1$-$C_6$ alkyl. In some embodiments, $R^2$ is —S—$C_1$-$C_3$ alkyl. In some embodiments, $R^2$ is —$SCH_3$.

In some embodiments of formula (I) or (Ia), $R^2$ is $C_3$-$C_8$ cycloalkyl. In some embodiments, $R^2$ is cyclopropyl.

In some embodiments of formula (I) or (Ia), $R^2$ is $C_2$-$C_6$ alkenyl. In some embodiments, $R^2$ is $C_2$-$C_4$ alkenyl. In some embodiments, $R^2$ is vinyl (ethenyl), propenyl, isopropenyl, 1-butenyl, 2-butenyl, isobutenyl, or butadienyl. In some embodiments, $R^2$ is vinyl.

In some embodiments of formula (I) or (Ia), $R^2$ is $C_2$-$C_6$ alkynyl. In some embodiments, $R^2$ is $C_2$-$C_3$ alkynyl. In some embodiments, $R^2$ is acetylenyl or propynyl. In some embodiments, $R^2$ is acetylenyl.

In some embodiments of formula (I) or (Ia), $R^{2a}$ is halo or $C_1$-$C_3$ alkyl. In some embodiments, $R^{2a}$ is halo or $CH_3$. In some embodiments, $R^{2a}$ is fluoro or $CH_3$. In some embodiments, $R^{2a}$ is iodo or $CH_3$. In some embodiments, $R^{2a}$ is chloro or $CH_3$. In some embodiments, $R^{2a}$ is bromo or $CH_3$.

In some embodiments of formula (I) or (Ia), $R^{2a}$ is halo. In some embodiments, $R^{2a}$ is fluoro. In some embodiments, $R^{2a}$ is iodo. In some embodiments, $R^{2a}$ is chloro. In some embodiments, $R^{2a}$ is bromo.

In some embodiments of formula (I) or (Ia), $R^{2a}$ is $C_1$-$C_6$ alkyl. In some embodiments, $R^{2a}$ is $C_1$-$C_3$ alkyl. In some embodiments, $R^{2a}$ is $CH_3$.

In some embodiments of formula (I) or (Ia), $R^2$ and $R^{2a}$ are each halo. In some embodiments, $R^2$ is halo and $R^{2a}$ is $C_1$-$C_6$ alkyl. In some embodiments, $R^2$ is $C_1$-$C_6$ alkyl and $R^{2a}$ is halo. In some embodiments, $R^2$ is —S—$C_1$-$C_6$ alkyl and $R^{2a}$ is halo. In some embodiments, $R^2$ is —$SCH_3$ and $R^{2a}$ is halo. In some embodiments, $R^2$ is $C_3$-$C_8$ cycloalkyl and $R^{2a}$ is halo. In some embodiments, $R^2$ is cyclopropyl and $R^{2a}$ is halo. In some embodiments, $R^2$ is $C_2$-$C_6$ alkenyl and $R^{2a}$ is halo. In some embodiments, $R^2$ is $C_2$-$C_6$ alkynyl and $R^{2a}$ is halo. In some embodiments, $R^2$ is acetylenyl and $R^{2a}$ is halo. In some embodiments, $R^2$ and $R^{2a}$ are each independently fluoro, chloro, bromo, or iodo. In some embodiments, $R^2$ is iodo and $R^{2a}$ is fluoro. In some embodiments, $R^2$ is halo and $R^{2a}$ is —$CH_3$. In some embodiments, $R^2$ is bromo and $R^{2a}$ is —$CH_3$. In some embodiments, $R^2$ is iodo and $R^{2a}$ is —$CH_3$. In some embodiments, $R^2$ is —$SCH_3$ and $R^{2a}$ is fluoro. In some embodiments, $R^2$ is acetylenyl and $R^{2a}$ is fluoro.

In some embodiments of formula (I) or (Ia), the compound is represented by formula (Ib):

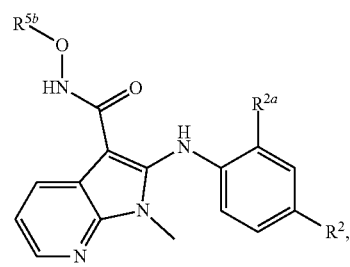

(Ib)

wherein $R^2$, $R^{2a}$, and $R^{5b}$ are defined and described herein.

In some embodiments of formula (Ib), $R^2$ is iodo and $R^{2a}$ is fluoro. In some embodiments, $R^2$ is iodo and $R^{2a}$ is methyl. In some embodiments, $R^2$ is acetylenyl and $R^{2a}$ is fluoro. In some embodiments, $R^2$ is —$SCH_3$ and $R^{2a}$ is fluoro. In some embodiments of the above structures, $R^2$ is —$SCH_3$ and $R^{2a}$ is methyl.

In some embodiments, the compound is represented by formula (Ib-1):

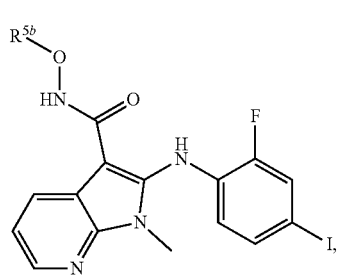

(Ib-1)

wherein $R^{5b}$ is defined and described herein.

In some embodiments of formula (Ib) or (Ib-1), $R^{5b}$ is cyclopropylmethyl. In some embodiments, $R^{5b}$ is $C_1$-$C_3$ monohydroxyalkyl. In some embodiments, $R^{5b}$ is $C_1$-$C_3$ dihydroxyalkyl. In some embodiments, $R^{5b}$ is $HOCH_2$—$C_1$-$C_2$ alkyl. In some embodiments, $R^{5b}$ is $CH_2CH_2OH$. In some embodiments, $R^{5b}$ is $CH_2CH(OH)CH_2OH$.

In some embodiments of formula (Ib) or (Ib-1), $R^{5b}$ is selected from the group consisting of:

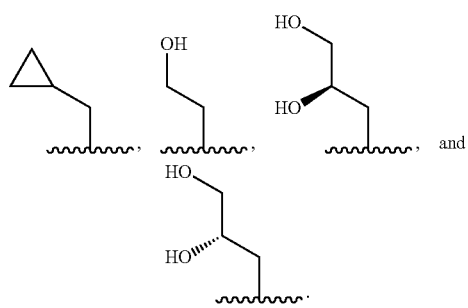

In some embodiments, the compound is represented by the formula:
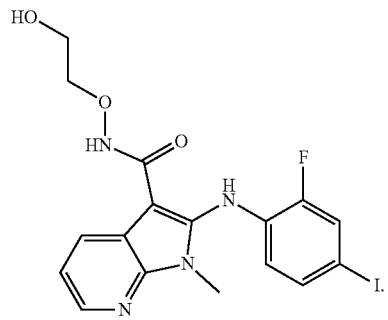
(Compound 1.003)
Exemplified compounds of formula (I) are listed in Table 1.
TABLE 1
Compounds of formula (I)
| No. | Structure |
|---|---|
| 1.001 | 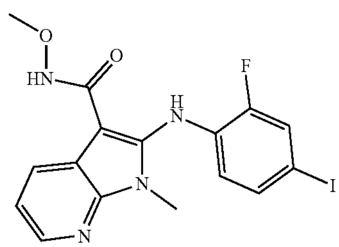 [SMILES: CONC(=O)c1c(Nc2ccc(I)cc2F)n(C)c2ncccc12] |
| 1.002 | 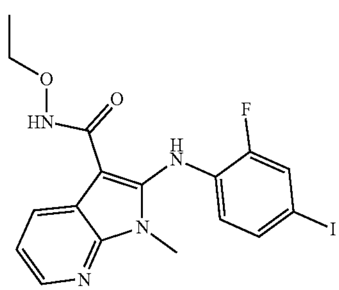 [SMILES: CCONC(=O)c1c(Nc2ccc(I)cc2F)n(C)c2ncccc12] |
| 1.003 | 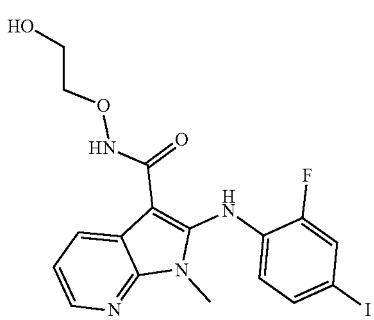 [SMILES: Cn1c(Nc2ccc(I)cc2F)c(C(=O)NOCCO)c2cccnc21] |
TABLE 1-continued
Compounds of formula (I)
| No. | Structure |
|---|---|
| 1.004 | 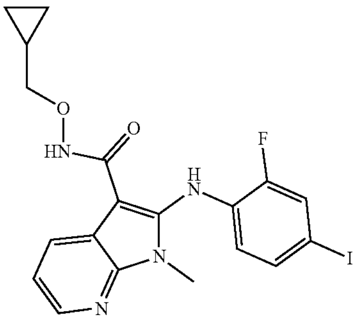 [SMILES: Cn1c(Nc2ccc(I)cc2F)c(C(=O)NOCC2CC2)c2cccnc21] |
| 1.005 | 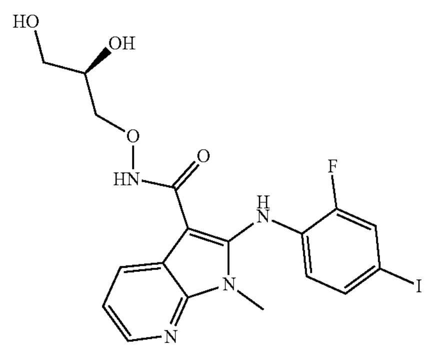 [SMILES: Cn1c(Nc2ccc(I)cc2F)c(C(=O)NOC[C@H](O)CO)c2cccnc21] |
| 1.006 | 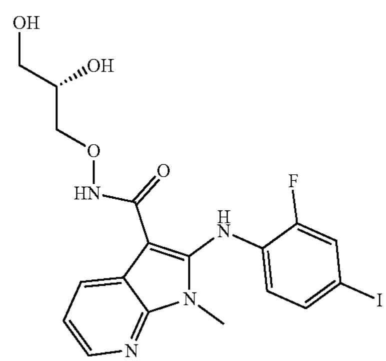 [SMILES: Cn1c(Nc2ccc(I)cc2F)c(C(=O)NOC[C@@H](O)CO)c2cccnc21] |
| 1.007 | 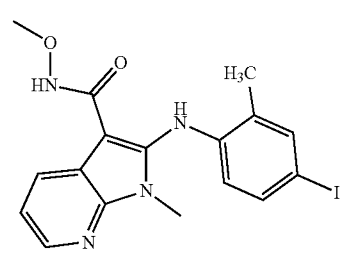 [SMILES: CONC(=O)c1c(Nc2ccc(I)cc2C)n(C)c2ncccc12] |
| 1.008 | 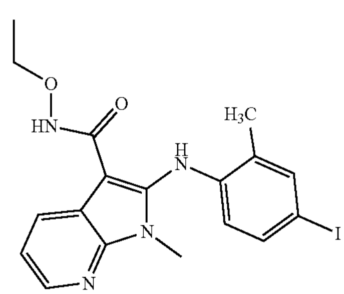 [SMILES: CCONC(=O)c1c(Nc2ccc(I)cc2C)n(C)c2ncccc12] |

TABLE 1-continued

Compounds of formula (I)

| No. | Structure |
|---|---|
| 1.009 | (structure) |
| 1.010 | (structure) |
| 1.011 | (structure) |
| 1.012 | (structure) |
| 1.013 | (structure) |
| 1.014 | (structure) |
| 1.015 | (structure) |
| 1.016 | (structure) |
| 1.017 | (structure) |

TABLE 1-continued
Compounds of formula (I)
| No. | Structure |
| --- | --- |
| 1.018 | 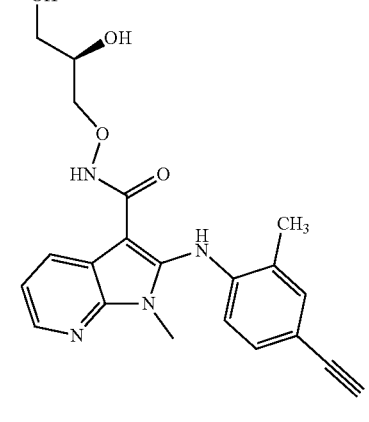 |
| 1.019 | 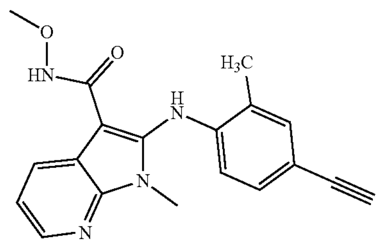 [SMILES: C#Cc1ccc(Nc2c(C(=O)NOC)c3cccnc3n2C)c(C)c1] |
| 1.020 | 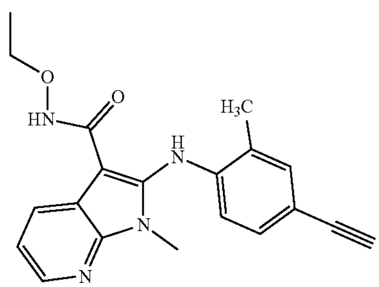 [SMILES: C#Cc1ccc(Nc2c(C(=O)NOCC)c3cccnc3n2C)c(C)c1] |
| 1.021 | 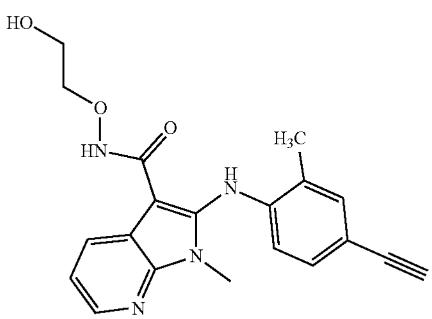 [SMILES: C#Cc1ccc(Nc2c(C(=O)NOCCO)c3cccnc3n2C)c(C)c1] |
| 1.022 | 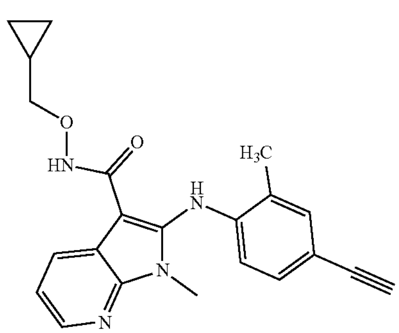 [SMILES: C#Cc1ccc(Nc2c(C(=O)NOCC3CC3)c3cccnc3n2C)c(C)c1] |
TABLE 1-continued
Compounds of formula (I)
| No. | Structure |
| --- | --- |
| 1.023 | 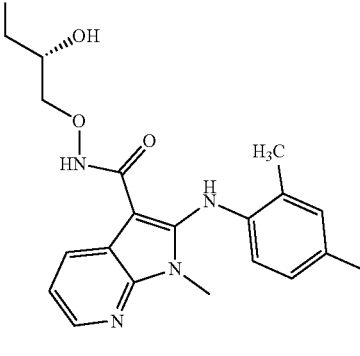 |
| 1.024 | 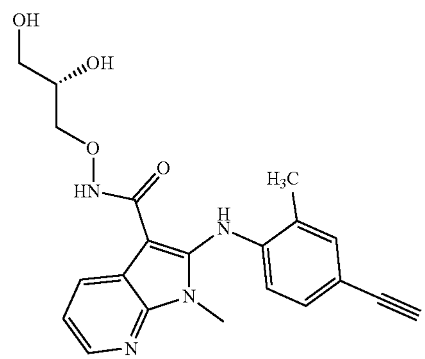 [SMILES: C#Cc1ccc(Nc2c(C(=O)NOC[C@@H](O)CO)c3cccnc3n2C)c(C)c1] |
| 1.025 | 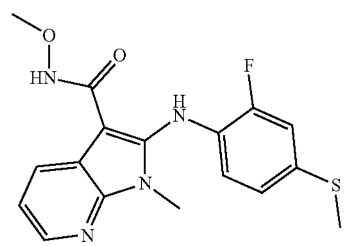 |
| 1.026 | 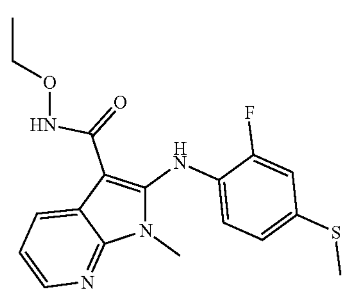 [SMILES: CCONC(=O)c1c(Nc2ccc(SC)cc2F)n(C)c2ncccc12] |

TABLE 1-continued

Compounds of formula (I)

| No. | Structure |
|---|---|
| 1.027 | (structure) |
| 1.028 | (structure) |
| 1.029 | (structure) |
| 1.030 | (structure) |
| 1.031 | (structure) |
| 1.032 | (structure) |
| 1.033 | (structure) |
| 1.034 | (structure) |

TABLE 1-continued

Compounds of formula (I)

| No. | Structure |
|---|---|
| 1.035 | (structure) |
| 1.036 | (structure) |
| 1.037 | (structure) |
| 1.040 | (structure) |
| 1.042 | (structure) |
| 1.043 | (structure) |
| 1.044 | (structure) |
| 1.045 | (structure) |

The compounds of formula (I) can be prepared according to International Application No. PCT/US2018/033547, the entirety of which is incorporated herein by reference for all purposes.

Compounds of Formula (II)

The present disclosure provides a compound for use in the topical formulations (e.g., non-aqueous gel) for the treatment of skin disorders as defined and described herein, wherein the compound is represented by formula (II):

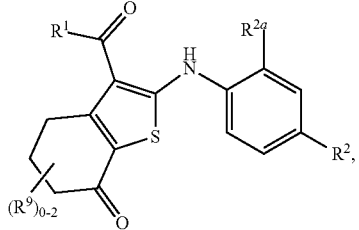

(II)

or a stereoisomer, a mixture of stereoisomers, and/or a pharmaceutically acceptable salt thereof, wherein:
$R^1$ is —$OR^4$, —$NR^5R^{5a}$, or —$N(OR^{5b})R^{5a}$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
$R^4$, $R^5$, and $R^{5b}$ are each independently hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl;
$R^{5a}$ is hydrogen or $C_1$-$C_6$ alkyl; and
each $R^9$ is independently $C_1$-$C_6$ alkyl.

In some embodiments, the cycloalkyl groups recited in $R^2$, $R^4$, $R^5$, and $R^{5a}$, $R^6$, $R^7$ are each a saturated monocyclic $C_3$-$C_8$ cycloalkyl. In some embodiments, the $C_3$-$C_8$ cycloalkyl group, as alone or as part of $C_3$-$C_8$ cycloalkyl-$C_1$-$C_6$ alkyl is cyclopropyl or cyclobutyl. In some embodiments, the $C_3$-$C_8$ cycloalkyl group, as alone or as part of $C_3$-$C_8$ cycloalkyl-$C_1$-$C_6$ alkyl, is unsubstituted.

In some embodiments, each $R^9$ is independently $C_1$-$C_6$ alkyl. In some embodiments, $R^9$ is absent.

In some embodiments, the compound of formula (II) is represented by formula (IIa):

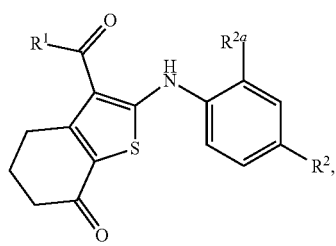

(IIa)

wherein $R^1$, $R^2$, and $R^{2a}$ are as defined and described herein.

In some embodiments of formula (II) or (IIa), $R^1$ is —$OR^4$. In some embodiments, $R^4$ is hydrogen. In some embodiments, $R^4$ is $C_1$-$C_6$ alkyl. In some embodiments, $R^4$ is $C_1$-$C_3$ alkyl. In some embodiments, $R^4$ is $C_3$-$C_8$ cycloalkyl. In some embodiments, $R^4$ is $C_3$-$C_6$ cycloalkyl. In some embodiments, $R^4$ is $C_3$-$C_8$ cycloalkyl-$C_1$-$C_6$ alkyl. In some embodiments, $R^4$ is $C_3$-$C_6$ cycloalkyl-$C_1$-$C_6$ alkyl. In some embodiments, $R^4$ is cyclopropyl, cyclobutyl, cyclopropyl-$C_1$-$C_3$ alkyl, or cyclobutyl-$C_1$-$C_3$ alkyl. In some embodiments, $R^4$ is cyclopropylmethyl. In some embodiments, $R^4$ is $C_1$-$C_6$ hydroxyalkyl. In some embodiments, $R^4$ is $C_1$-$C_6$ monohydroxyalkyl. In some embodiments, $R^4$ is $C_1$-$C_6$ dihydroxyalkyl. In some embodiments, $R^4$ is $HOCH_2$—$C_1$-$C_5$ alkyl. In some embodiments, $R^4$ is $C_1$-$C_3$ hydroxyalkyl. In some embodiments, $R^4$ is $C_1$-$C_3$ monohydroxyalkyl. In some embodiments, $R^4$ is $C_1$-$C_3$ dihydroxyalkyl. In some embodiments, $R^4$ is $HOCH_2$—$C_1$-$C_2$ alkyl. In some embodiments, $R^4$ is $CH_2CH_2OH$. In some embodiments, $R^4$ is $CH_2CH(OH)CH_2OH$.

In some embodiments of formula (II) or (IIa), $R^1$ is selected from the group consisting of:

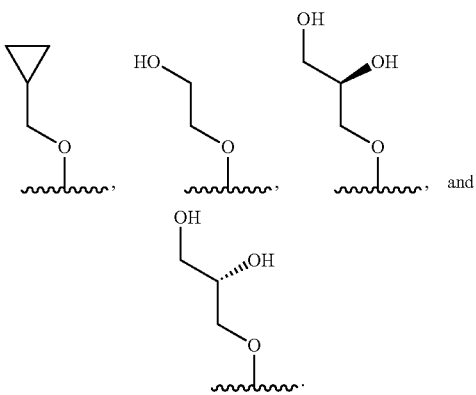

In some embodiments of formula (II) or (IIa), $R^1$ is —$NR^5R^{5a}$. In some embodiments, $R^5$ is hydrogen. In some embodiments, $R^5$ is $C_1$-$C_6$ alkyl. In some embodiments, $R^5$ is $C_1$-$C_3$ alkyl. In some embodiments, $R^5$ is $C_3$-$C_8$ cycloalkyl. In some embodiments, $R^5$ is $C_3$-$C_6$ cycloalkyl. In some embodiments, $R^5$ is $C_3$-$C_8$ cycloalkyl-$C_1$-$C_6$ alkyl. In some embodiments, $R^5$ is $C_3$-$C_6$ cycloalkyl-$C_1$-$C_6$ alkyl. In some embodiments, $R^5$ is cyclopropyl, cyclobutyl, cyclopropyl-$C_1$-$C_3$ alkyl, or cyclobutyl-$C_1$-$C_3$ alkyl. In some embodiments, $R^5$ is cyclopropylmethyl. In some embodiments, $R^5$ is $C_1$-$C_6$ hydroxyalkyl. In some embodiments, $R^5$ is $C_1$-$C_6$ monohydroxyalkyl. In some embodiments, $R^5$ is $C_1$-$C_6$ dihydroxyalkyl. In some embodiments, $R^5$ is $HOCH_2$—$C_1$-$C_5$ alkyl. In some embodiments, $R^5$ is $C_1$-$C_3$ hydroxyalkyl. In some embodiments, $R^5$ is $C_1$-$C_3$ monohydroxyalkyl. In some embodiments, $R^5$ is $C_1$-$C_3$ dihydroxyalkyl. In some embodiments, $R^5$ is $HOCH_2$—$C_1$-$C_2$ alkyl. In some embodiments, $R^5$ is $CH_2CH_2OH$. In some embodiments, $R^5$ is $CH_2CH(OH)CH_2OH$.

In some embodiments of formula (II) or (IIa), $R^1$ is —$NR^5R^{5a}$; $R^{5a}$ is hydrogen; and $R^5$ is as defined and described herein. In some embodiments, $R^1$ is —$NR^5R^{5a}$; $R^{5a}$ is $C_1$-$C_6$ alkyl; and $R^5$ is as defined and described herein. In some embodiments, $R^1$ is —$NR^5R^{5a}$; $R^{5a}$ is $C_1$-$C_3$ alkyl; and $R^5$ is as defined and described herein.

In some embodiments of formula (II) or (IIa), $R^1$ is selected from the group consisting of:

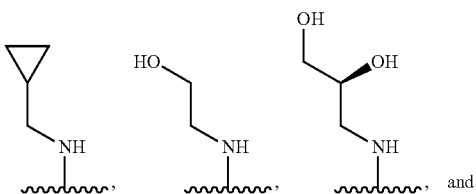

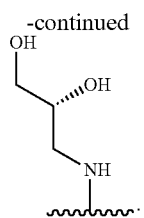

In some embodiments of formula (II) or (IIa), $R^1$ is $-N(OR^{5b})R^{5a}$. In some embodiments, $R^{5b}$ is hydrogen. In some embodiments, $R^{5b}$ is $C_1$-$C_6$ alkyl. In some embodiments, $R^{5b}$ is $C_1$-$C_3$ alkyl. In some embodiments, $R^{5b}$ is $C_3$-$C_8$ cycloalkyl. In some embodiments, $R^{5b}$ is $C_3$-$C_6$ cycloalkyl. In some embodiments, $R^{5b}$ is $C_3$-$C_8$ cycloalkyl-$C_1$-$C_6$ alkyl. In some embodiments, $R^{5b}$ is $C_3$-$C_6$ cycloalkyl-$C_1$-$C_6$ alkyl. In some embodiments, $R^{5b}$ is cyclopropyl, cyclobutyl, cyclopropyl-$C_1$-$C_3$ alkyl, or cyclobutyl-$C_1$-$C_3$ alkyl. In some embodiments, $R^{5b}$ is cyclopropylmethyl. In some embodiments, $R^{5b}$ is $C_1$-$C_6$ hydroxyalkyl. In some embodiments, $R^{5b}$ is $C_1$-$C_6$ monohydroxyalkyl. In some embodiments, $R^{5b}$ is $C_1$-$C_6$ dihydroxyalkyl. In some embodiments, $R^{5b}$ is $HOCH_2$—$C_1$-$C_5$ alkyl. In some embodiments, $R^{5b}$ is $C_1$-$C_3$ hydroxyalkyl. In some embodiments, $R^{5b}$ is $C_1$-$C_3$ monohydroxyalkyl. In some embodiments, $R^{5b}$ is $C_1$-$C_3$ dihydroxyalkyl. In some embodiments, $R^{5b}$ is $HOCH_2$—$C_1$-$C_2$ alkyl. In some embodiments, $R^{5b}$ is $CH_2CH_2OH$. In some embodiments, $R^{5b}$ is $CH_2CH(OH)CH_2OH$.

In some embodiments of formula (II) or (IIa), $R^1$ is $-N(OR^{5b})R^{5a}$; $R^{5a}$ is hydrogen; and $R^{5b}$ is as defined and described herein. In some embodiments, $R^1$ is $-N(OR^{5b})R^{5a}$; $R^{5a}$ is $C_1$-$C_6$ alkyl; and $R^{5b}$ is as defined and described herein. In some embodiments, $R^1$ is $-N(OR^{5b})R^{5a}$; $R^{5a}$ is $C_1$-$C_3$ alkyl; and $R^{5b}$ is as defined and described herein.

In some embodiments of formula (II) or (IIa), $R^1$ is selected from the group consisting of:

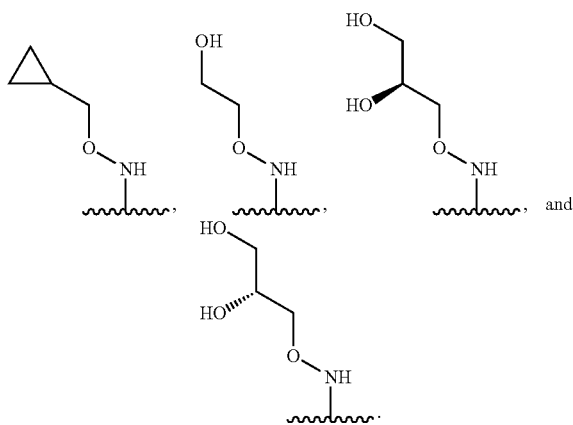

In some embodiments of formula (II) or (IIa), $R^2$ is halo, $C_1$-$C_6$ alkyl, $-S-C_1$-$C_6$ alkyl, $C_3$-$C_8$ cycloalkyl, $C_2$-$C_6$ alkenyl, or $C_2$-$C_6$ alkynyl. In some embodiments, $R^2$ is halo or $C_1$-$C_6$ alkyl. In some embodiments, $R^2$ is halo, $-CH_3$, $-SCH_3$, $C_2$-$C_3$ alkenyl, or $C_2$-$C_3$ alkynyl.

In some embodiments of formula (II) or (IIa), $R^2$ is halo. In some embodiments, $R^2$ is fluoro. In some embodiments, $R^2$ is iodo. In some embodiments, $R^2$ is chloro. In some embodiments, $R^2$ is bromo.

In some embodiments of formula (II) or (IIa), $R^2$ is $C_1$-$C_6$ alkyl. In some embodiments, $R^2$ is $C_1$-$C_3$ alkyl. In some embodiments, $R^2$ is methyl.

In some embodiments of formula (II) or (IIa), $R^2$ is $-S-C_1$-$C_6$ alkyl. In some embodiments, $R^2$ is $-S-C_1$-$C_3$ alkyl. In some embodiments, $R^2$ is $-SCH_3$.

In some embodiments of formula (II) or (IIa), $R^2$ is $C_3$-$C_8$ cycloalkyl. In some embodiments, $R^2$ is cyclopropyl.

In some embodiments of formula (II) or (IIa), $R^2$ is $C_2$-$C_6$ alkenyl. In some embodiments, $R^2$ is $C_2$-$C_4$ alkenyl. In some embodiments, $R^2$ is vinyl (ethenyl), propenyl, isopropenyl, 1-butenyl, 2-butenyl, isobutenyl, or butadienyl. In some embodiments, $R^2$ is vinyl.

In some embodiments of formula (II) or (IIa), $R^2$ is $C_2$-$C_6$ alkynyl. In some embodiments, $R^2$ is $C_2$-$C_3$ alkynyl. In some embodiments, $R^2$ is acetylenyl or propynyl. In some embodiments, $R^2$ is acetylenyl.

In some embodiments of formula (II) or (IIa), $R^{2a}$ is halo or $C_1$-$C_3$ alkyl. In some embodiments, $R^{2a}$ is halo or $CH_3$. In some embodiments, $R^{2a}$ is fluoro or $CH_3$. In some embodiments, $R^{2a}$ is iodo or $CH_3$. In some embodiments, $R^{2a}$ is chloro or $CH_3$. In some embodiments, $R^{2a}$ is bromo or $CH_3$.

In some embodiments of formula (II) or (IIa), $R^{2a}$ is halo. In some embodiments, $R^{2a}$ is fluoro. In some embodiments, $R^{2a}$ is iodo. In some embodiments, $R^{2a}$ is chloro. In some embodiments, $R^{2a}$ is bromo.

In some embodiments of formula (II) or (IIa), $R^{2a}$ is $C_1$-$C_6$ alkyl. In some embodiments, $R^{2a}$ is $C_1$-$C_3$ alkyl. In some embodiments, $R^{2a}$ is $CH_3$.

In some embodiments of formula (II) or (IIa), $R^2$ and $R^{2a}$ are each halo. In some embodiments, $R^2$ is halo and $R^{2a}$ is $C_1$-$C_6$ alkyl. In some embodiments, $R^2$ is $C_1$-$C_6$ alkyl and $R^{2a}$ is halo. In some embodiments, $R^2$ is $-S-C_1$-$C_6$ alkyl and $R^{2a}$ is halo. In some embodiments, $R^2$ is $-SCH_3$ and $R^{2a}$ is halo. In some embodiments, $R^2$ is $C_3$-$C_8$ cycloalkyl and $R^{2a}$ is halo. In some embodiments, $R^2$ is cyclopropyl and $R^{2a}$ is halo. In some embodiments, $R^2$ is $C_2$-$C_6$ alkenyl and $R^{2a}$ is halo. In some embodiments, $R^2$ is $C_2$-$C_6$ alkynyl and $R^{2a}$ is halo. In some embodiments, $R^2$ is acetylenyl and $R^{2a}$ is halo. In some embodiments, $R^2$ and $R^{2a}$ are each independently fluoro, chloro, bromo, or iodo. In some embodiments, $R^2$ is iodo and $R^{2a}$ is fluoro. In some embodiments, $R^2$ is halo and $R^{2a}$ is $-CH_3$. In some embodiments, $R^2$ is bromo and $R^{2a}$ is $-CH_3$. In some embodiments, $R^2$ is iodo and $R^{2a}$ is $-CH_3$. In some embodiments, $R^2$ is $-SCH_3$ and $R^{2a}$ is fluoro. In some embodiments, $R^2$ is acetylenyl and $R^{2a}$ is fluoro.

In some embodiments of formula (II) or (IIa), the compound is represented by formula (IIb):

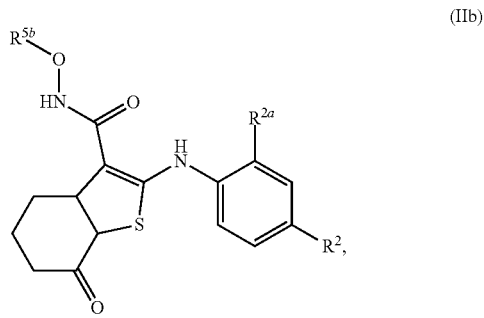

(IIb)

wherein $R^2$, $R^{2a}$, and $R^{5b}$ are defined and described herein.

In some embodiments of formula (IIb), $R^2$ is iodo and $R^{2a}$ is fluoro. In some embodiments, $R^2$ is iodo and $R^{2a}$ is methyl. In some embodiments, $R^2$ is acetylenyl and $R^{2a}$ is fluoro. In some embodiments, $R^2$ is —SCH$_3$ and $R^{2a}$ is fluoro. In some embodiments of the above structures, $R^2$ is —SCH$_3$ and $R^{2a}$ is methyl.

In some embodiments, the compound is represented by formula (IIb-1):

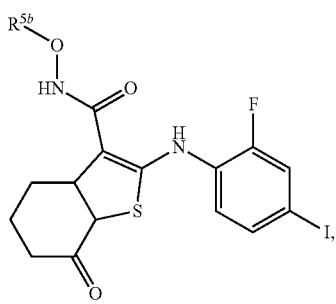

(IIb-1)

wherein $R^{5b}$ is defined and described herein.

In some embodiments of formula (IIb) or (IIb-1), $R^{5b}$ is cyclopropylmethyl. In some embodiments, $R^{5b}$ is $C_1$-$C_3$ monohydroxyalkyl. In some embodiments, $R^{5b}$ is $C_1$-$C_3$ dihydroxyalkyl. In some embodiments, $R^{5b}$ is HOCH$_2$—$C_1$-$C_2$ alkyl. In some embodiments, $R^{5b}$ is CH$_2$CH$_2$OH. In some embodiments, $R^{5b}$ is CH$_2$CH(OH)CH$_2$OH.

In some embodiments of formula (IIb) or (IIb-1), $R^{5b}$ is selected from the group consisting of:

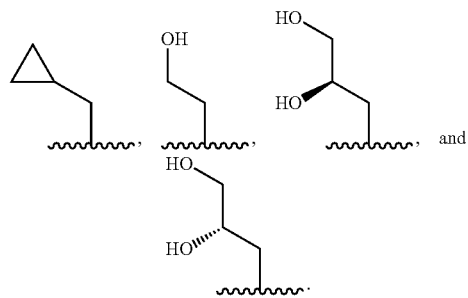

In some embodiments, the compound is represented by the formula:

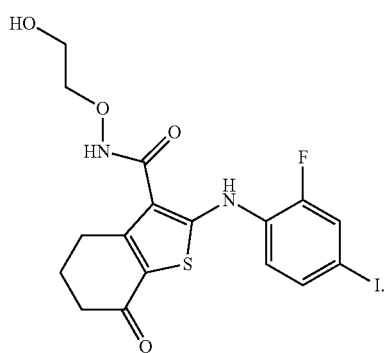

(Compound 2.003)

Exemplified compounds of formula (II) are listed in Table 2.

TABLE 2

Compounds of formula (II)

| No. | Structure |
|---|---|
| 2.001 | ethyl ester, 2-(2-fluoro-4-iodoanilino), tetrahydrobenzothiophene ketone |
| 2.002 | carboxylic acid, 2-(2-fluoro-4-iodoanilino), tetrahydrobenzothiophene ketone |
| 2.003 | N-(2-hydroxyethoxy)amide, 2-(2-fluoro-4-iodoanilino), tetrahydrobenzothiophene ketone |
| 2.004 | N-((R)-2,3-dihydroxypropoxy)amide, 2-(2-fluoro-4-iodoanilino), tetrahydrobenzothiophene ketone |

TABLE 2-continued

Compounds of formula (II)

| No. | Structure |
|---|---|
| 2.005 | 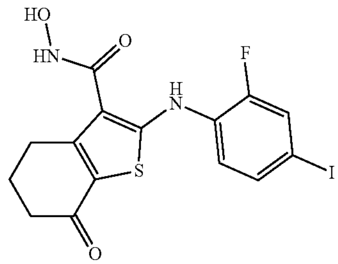 [SMILES: O=C1CCCc2c1sc(Nc1ccc(I)cc1F)c2C(=O)NO] |
| 2.006 | 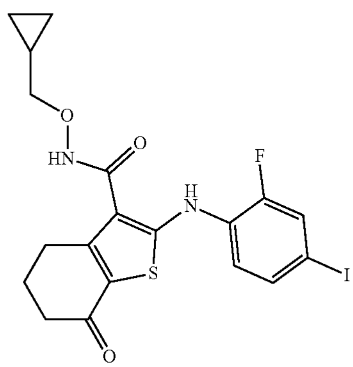 [SMILES: O=C1CCCc2c1sc(Nc1ccc(I)cc1F)c2C(=O)NOCC1CC1] |
| 2.007 | 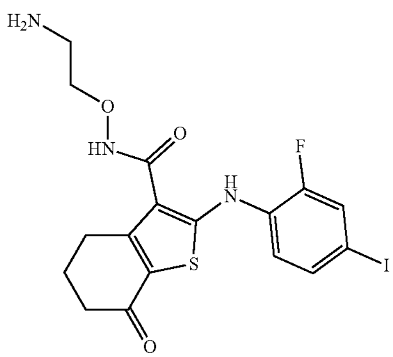 [SMILES: NCCONC(=O)c1c(Nc2ccc(I)cc2F)sc2c1CCCC2=O] |
| 2.008 | 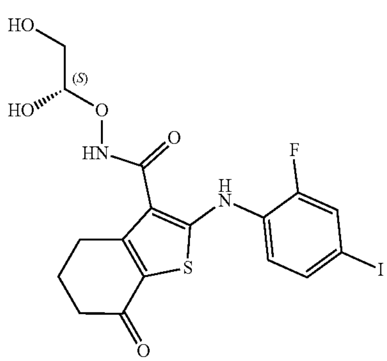 |
| 2.009 | 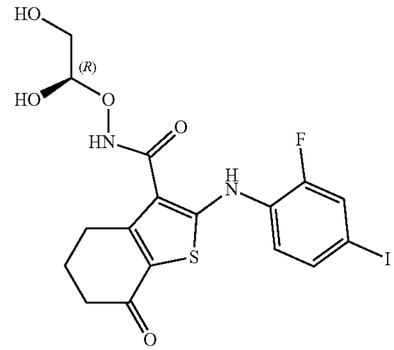 |

The compounds of formula (II) can be prepared according to International Application No. PCT/US2019/000067, the entirety of which is incorporated herein by reference for all purposes.

Compounds in Other Forms

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

Other salts include acid or base salts of the compounds used in the methods of the present disclosure. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17$^{th}$ ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the enantiomers, racemates, diastereomers, tautomers, geometric isomers, stereoisometric forms that may be defined, in terms of absolute stereochemistry, as I- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active I- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this disclosure may exist in tautomeric forms, all such tautomeric forms of the compounds being within the scope of the disclosure. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, the compounds of the present disclosure may also contain unnatural proportions of atomic isotopes at one or more of the atoms that constitute such compounds. For example, the compounds of the present disclosure may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present disclosure, whether radioactive or not, are encompassed within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The compounds of the present application are designed for topical, subcutaneous, intradermal, or intralesional application, resulting in inhibition of MEK activity in the dermal and epidermal layers for treatment of skin disorders as described herein. After acting to treat the skin disorders, in some embodiments, the compound is designed to be metabolically labile in order to limit systemic toxicity after topical, subcutaneous, transdermal, intradermal, of intralesional application by limiting the amount of time the compound remains in the peripheral circulation. The present application provides a solution for the treatment of skin disorders with compounds which demonstrate the ability to penetrate the skin and suppress p-ERK.

V. Methods

In one aspect, the present disclosure provides a method of treating a skin disorder. The method includes administering a topical formulation (e.g., a non-aqueous gel, an aqueous gel, or an emulsion-based formulation) including a compound of formula (I), thereby treating the skin disease, wherein the topical formulation and the compound of formula (I) are as defined and described herein.

In another aspect, the present disclosure provides a method of treating a skin disorder. The method includes administering a topical formulation (e.g., a non-aqueous gel) including a compound of formula (II), thereby treating the skin disease, wherein the topical formulation and the compound of formula (II) are as defined and described herein.

In some embodiments, provided herein is a method for treating a skin disorder where the subject is in need thereof and the skin disorder is a MEK-inhibitor responsive dermal disorder or disease or a MEK-mediated dermal disorder or disease in a subject. The method includes administering the subject with a therapeutically or prophylactically effective amount of a topical formulation including a compound of formula (I) or (II), wherein the topical formulation and the compound of formula (I) or (II) are as defined and described herein. In some embodiments, the method includes administering the subject with a therapeutically effective amount of a topical formulation including a compound of formula (I), wherein the topical formulation and the compound of formula (I) are as defined and described herein. In some embodiments, the method includes administering the subject with a therapeutically effective amount of a topical formulation including a compound of formula (II), wherein the topical formulation and the compound of formula (II) are as defined and described herein.

In some embodiments, the MEK-inhibitor responsive dermal disorder or MEK-mediated dermal disorder is selected from the group consisting of dermal rasopathy, neurofibromatosis type 1, dermal neurofibroma, subdermal neurofibroma, and superficial plexiform neurofibroma.

In some embodiments, the MEK-inhibitor responsive dermal disorder or MEK-mediated dermal disorder is neurofibromatosis type 1.

In some embodiments, administering includes contacting the topical formulation including the compound of formula (I) or (II) with the skin, mucous membranes, vagina, penis, larynx, vulva, cervix, or anus of the subject, by local or non-systemic application, e.g., topical application.

In some embodiments, the tumor associated with neurofibromatosis type 1 (NF1), e.g., a dermal neurofibroma, a subdermal neurofibroma, or a superficial plexiform neurofibroma, is reduced, e.g., the size or the total tumor volume is reduced, by at least about 15% relative to the reference standard (e.g., from about 15% to about 60%), thereby treating the subject. In some embodiments, the reference standard is the size or the total tumor volume in an untreated control, e.g., from the same subject or a different subject.

In some embodiments, the size or total tumor volume of the tumor associated with neurofibromatosis type 1 (NF1), e.g., a dermal neurofibroma, a subdermal neurofibroma, or a superficial plexiform neurofibroma, is reduced by at least about 15%, by at least about 20%, by at least about 25%, by at least about 30%, by at least about 35%, by at least about 40%, by at least about 45%, by at least about 50%, by at least about 55%, by at least about 60% relative to the reference standard. In some embodiments, the reference standard is the size or the total tumor volume in an untreated control, e.g., from the same subject or a different subject.

In some embodiments, the method includes evaluating the subject with magnetic resonance imaging (MRI), or optical imaging, e.g., evaluating the volume of tumors obtained from the subject, e.g., prior to, during and/or after treatment.

Neurofibromatosis type 1 (NF1): In some embodiments, the dermal disorder is associated with NF1. NF1, also known as von Recklinghausen Neurofibromatosis or Peripheral Neurofibromatosis, occurs in approximately 1:3,000 births, and is one of the most prevalent genetic disorders and the most common neurocutaneous disorders. NF1 is caused by a deficiency in neurofibromin, which leads to hyperactivation of various cell-signaling pathways, e.g., Ras and Rho, is associated with several dermal disorders, including dermal neurofibromas (DFs); subdermal neurofibromas; superficial plexiform neurofibromas (PFs); cutaneous neurofibromas (CFs); café au lait spots; and axillary and inguinal freckling. DFs occur in over 95% of NF1 patients. DFs can appear anywhere on the body, with 88% of NF1 patients over 40 years of age having over 100 DFs. DFs can cause both severe physical pain, disfigurement, as well as social anxiety. Facial DFs can create significant social anxiety issues and pain among affected individuals. DFs (also known as cutaneous neurofibromas or discrete neurofibromas) grow from small nerves in the skin or just under the skin and appear as small bumps typically beginning around the time of puberty. Current treatment options for DF are limited to surgical excisin and $CO_2$ laser removal, both of which cause scarring and neither of which is preventative.

Other Dermal Rasopathies: In some embodiments, the dermal disorder is associated with enhanced activation of Ras. In some embodiments, the dermal disorder is selected from: psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots and Multiple lentigines syndrome (formerly called Leopard syndrome).

In some or any embodiments, the disease to be reduced, ameliorated, treated, or prevented is not cancer (e.g. melanoma).

In some embodiments, the disease to be reduced, ameliorated, treated, or prevented is cancer, a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the disease to be reduced, ameliorated, treated, or prevented is cancer. In some embodiments, the disease to be reduced, ameliorated, treated, or prevented is selected from the group consisting of basal cell carcinoma, squamous cell carcinoma, actinic keratosis, Kaposi's sarcoma, dermal lymphoma, cervical cancer, HPV-related squamous cell carcinoma, and melanoma.

In some embodiments, the disease to be reduced, ameliorated, treated, or prevented is a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the topical formulations described herein are used for the reduction of a MEK-inhibitor responsive dermal disorder or disease or a MEK-mediated dermal disorder or disease where the subject is in need thereof.

In some embodiments, the topical formulations described herein are used for the amelioration of a MEK-inhibitor responsive dermal disorder or disease or a MEK-mediated dermal disorder or disease where the subject is in need thereof.

In some embodiments, the topical formulations described herein are used for prevention of a MEK-inhibitor responsive dermal disorder or disease or a MEK-mediated dermal disorder or disease where the subject is in need thereof.

In some embodiments, the topical formulations described herein are used for treatment of a MEK-inhibitor responsive dermal disorder or disease or a MEK-mediated dermal disorder or disease where the subject is in need thereof.

In some embodiments, provided herein is a method for treating a skin disorder where the subject is in need thereof and the skin disorder is a birthmark in a subject. The method includes administering the subject with a therapeutically or prophylactically effective amount of a topical formulation including a compound of formula (I) or (II), wherein the topical formulation and the compound of formula (I) or (II) are as defined and described herein. In some embodiments, the method includes administering the subject with a therapeutically effective amount of a topical formulation including a compound of formula (I), wherein the topical formulation and the compound of formula (I) are as defined and described herein. In some embodiments, the method includes administering the subject with a therapeutically effective amount of a topical formulation including a compound of formula (II), wherein the topical formulation and the compound of formula (II) are as defined and described herein.

In some embodiments, the birthmark is a port-wine stain (capillary malformation). Port-wine stains may be present at birth. Port-wine stains may be present at birth. Port-wine stains can occur anywhere on the body and the area of affected skin grows in proportion to general growth. Thickening of the lesion or the development of small lumps may occur in adulthood and can interfere with normal function (e.g., where the port-wine stain is near the eye or mouth). Port-wine stains may, in some cases, be part of a syndrome such as Sturge-Weber syndrome or Klippel-Trénaunay-Weber syndrome.

In some embodiments, provided herein is a method of treating a port-wine stain (capillary malformation) birthmark to reduce the cosmetic disfigurement or progression of the birthmark. In some embodiments, provided herein is a method of prophylactically treating a port-wine stain (capillary malformation) birthmark to prevent the progression of the birthmark, delaying the onset of the birthmark, or delaying the progression of the birthmark.

In some embodiments, the birthmark is epidermal nevi. Epidermal nevus is a benign skin growth with localized epidermal thickening that is often present at birth or within the first year of life. It typically appears as one or more oblong or linear growths that are skin colored, brown or gray in color. The surface can be wart-like or velvety with sharp borders. Malignant transformation can occur in some cases in middle aged or elderly subjects. Epidermal nevi are subdivided into keratinocytic and organoid nevi. Organoid nevi include nevus sebaceous (NS). In some embodiments, the birthmark is nevus sebaceous. Non-organoid keratinocytic epidermal nevus (KEN) is characterized by benign congenital hyperpigmented skin lesions. Contemplated within the scope of embodiments presented herein are other types of epidermal nevi, including nevus comedonicus. Nevus comedonicus (NC) is a hamartoma of the pilosebaceous unit that, like other epidermal nevi, typically presents at birth or during childhood. Clinically, NC lesions consist of linear arrays or clusters of dilated, keratin-plugged follicular orifices resembling comedones.

In some embodiments, provided herein is a method of treating epidermal nevi to reduce the cosmetic disfigurement or progression of the birthmark. In some embodiments, provided herein is a method of prophylactically treating epidermal nevi to prevent the progression of the birthmark, delaying the onset of the birthmark, or delaying the progression of the birthmark.

In some embodiments, the birthmark is nevus sebaceous. In some embodiments, provided herein is a method of treating a nevus sebaceous birthmark to reduce the cosmetic disfigurement or progression of the birthmark. In some embodiments, provided herein is a method of prophylactically treating a nevus sebaceous birthmark to prevent the progression of the birthmark, delaying the onset of the birthmark, or delaying the progression of the birthmark.

In some embodiments the birthmark is melanocytic nevus, including congenital nevi, blue nevi, and acquired melanocytic nevi. Malignant melanoma occasionally develops from the melanocytic nevus (also known as nevocytic nevus, nevus-cell nevus and commonly as a mole). Reasons for treatment of pigmented nevi (i.e., nevus cellular nevus) include prevention of malignant change, limiting malignant progression, cosmetic improvement, or prevention of other functional or anatomical changes.

In some embodiments, provided herein is a method of treating a melanocytic nevus to reduce the risk of cosmetic disfigurement or progression of the birthmark. In some embodiments, provided herein is a method of prophylactically treating a melanocytic nevus to prevent the progression of the birthmark, delaying the onset of the birthmark, or delaying the progression of the birthmark.

In some embodiments, the birthmark is dysplastic nevi. Dysplastic nevi (or atypical moles) are unusual-looking benign moles and may resemble melanoma. People who have atypical moles are at increased risk of developing melanoma in a mole or elsewhere on the body.

In some embodiments, provided herein is a method of treating dysplastic nevi to reduce the cosmetic disfigurement or progression of the birthmark. In some embodiments, provided herein is a method of prophylactically treating dysplastic nevi to prevent the progression of the birthmark, delaying the onset of the birthmark, or delaying the progression of the birthmark.

In some embodiments, the birthmark is a nevus spilus. Nevus spilus (also known as speckled lentiginous nevus and zosteriform lentiginous nevus) is a skin lesion that presents as a light brown patch of pigmentation, and within this patch, are multiple tiny dark brown spots.

In some embodiments, provided herein is a method of treating a nevus spilus birthmark to reduce the cosmetic disfigurement or progression of the birthmark. In some embodiments, provided herein is a method of prophylactically treating a nevus spilus birthmark to prevent the progression of the birthmark, delaying the onset of the birthmark, or delaying the progression of the birthmark.

In some embodiments, the birthmark is an arterio-venous malformation in the skin (e.g., blue rubber bleb nevus syndrome) which may present as skin lesions comprised of compressible blue subcutaneous nodules.

In some embodiments, provided herein is a method of treating an arterio-venous malformation to reduce the cosmetic disfigurement or progression of the birthmark. In some embodiments, provided herein is a method of prophylactically treating an arterio-venous malformation to prevent the progression of the birthmark, delaying the onset of the birthmark, or delaying the progression of the birthmark.

In some embodiments, the birthmark is a lymphatic malformation. A lymphatic malformation is a type of vascular nevus or birthmark due to malformed and dilated lymphatic vessels. The cystic hygroma (also called 'cystic lymphangioma' and 'lymphangioma cysticum') is a 'macrocytic' lymphatic malformation, and is composed of large fluid-filled spaces. It appears as a skin colored, red or bluish, somewhat transparent, swelling under the skin. Cavernous lymphangioma can affect any site on the body, including the tongue. Lymphangioma circumscriptum is a 'microcytic' lymphatic malformation. It appears as a cluster of small firm blisters filled with lymph fluid, resembling frogspawn.

In some embodiments, provided herein is a method of treating a lymphatic malformation to reduce the risk of the cosmetic disfigurement or progression of the birthmark. In some embodiments, provided herein is a method of prophylactically treating a lymphatic malformation to prevent the progression of the birthmark, delaying the onset of the birthmark, or delaying the progression of the birthmark.

In some embodiments, the birthmark is a congenital melanocytic nevus. The congenital melanocytic nevus appears as a circumscribed, light brown to black patch or plaque, heterogeneous in consistency, covering any size surface area and any part of the body. Congenital melanocytic nevus poses a risk for malignancy degeneration.

In some embodiments, provided herein is a method of treating a congenital melanocytic nevus to reduce the risk of cosmetic disfigurement or progression of the birthmark. In some embodiments, provided herein is a method of prophylactically treating a congenital melanocytic nevus to prevent the progression of the birthmark, delaying the onset of the birthmark, or delaying the progression of the birthmark.

In some embodiments, the topical formulations described herein are used for the reduction of a birthmark in a subject in need thereof.

In some embodiments, the topical formulations described herein are used for the amelioration of a birthmark in a subject in need thereof In some embodiments, the topical formulations described herein are used for prevention of a birthmark (e.g., MEK-inhibitor responsive or MEK-mediated birthmarks) and/or prevention of worsening of a birthmark (e.g., where the birthmark may progress to a proliferative disease) in a subject in need thereof.

In some embodiments, the subject in need thereof is a human.

The birthmark is not cafe au lait spots.

In some embodiments, administering includes contacting the topical formulation including the compound of formula (I) with the skin of the subject, e.g., an affected region of the skin, e.g., a region of the skin having a birthmark.

In some embodiments, the appearance of a birthmark is reduced, e.g., the size, volume, or the total surface area is reduced, by at least about 15% relative to the reference standard (e.g., the size of the birthmark prior to start of treatment), thereby treating the subject. In some embodiments, the size, volume, or the total surface area on skin is reduced, by at least about 15%, by at least about 20%, by at least about 25%, by at least about 30%, by at least about 35%, by at least about 40%, by at least about 45%, by at least about 50%, by at least about 55%, by at least about 60% relative to the reference standard. In one embodiment, the reference standard is the size of the birthmark prior to start of treatment.

In some embodiments, provided herein is a method for treating a skin disorder where the subject is in need thereof and the skin disorder is a skin cancer in a subject. The method includes administering the subject with a therapeutically or prophylactically effective amount of a topical formulation including a compound of formula (I) or (II), wherein the topical formulation and the compound of formula (I) or (II) are as defined and described herein. In some embodiments, the method includes administering the subject with a therapeutically or prophylactically effective amount of a topical formulation including a compound of formula (I), wherein the topical formulation and the compound of formula (I) are as defined and described herein. In some embodiments, the method includes administering the subject with a therapeutically or prophylactically effective amount of a topical formulation including a compound of formula (II), wherein the topical formulation and the compound of formula (II) are as defined and described herein.

In some embodiments, the skin cancer is a MEK-inhibitor responsive or MEK-mediated skin cancer.

In some embodiments, the skin cancer is a cutaneous squamous-cell carcinoma (cSCC).

In some embodiments, the cutaneous squamous-cell carcinoma is associate with exposure to ultraviolet radiation or immunosuppression in solid organ transplantation recipients (SOTRs). In some embodiments, the cutaneous squamous-cell carcinoma is associate with immunosuppression in solid organ transplantation recipients.

In some embodiments, the cutaneous squamous-cell carcinoma in solid organ transplantation recipients is a MEK-inhibitor responsive or MEK-mediated cutaneous squamous-cell carcinoma.

In some embodiments, administering includes contacting the topical formulation including the compound of formula (I) or (II) with the skin, mucous membranes, vagina, penis, larynx, vulva, cervix, or anus of the subject, by local or non-systemic application, e.g., topical, intradermal, or intralesional application or application by suppository, of the soft MEK inhibitor.

In some embodiments, the tumor associated with cutaneous squamous-cell carcinoma (cSCC), e.g., a dermal carcinoma, is reduced, e.g., the size or the total tumor volume is reduced, by at least about 15% relative to the reference standard (e.g., from about 15% to about 60%), thereby treating the subject. In some embodiments, the reference standard is the size or the total tumor volume in an untreated control, e.g., from the same subject or a different subject.

In the SOTR population, these include patients who currently have SCC, who have had cSCC previously, or who have pre-cancers including squamous cell carcinoma in Situ (also known as Bowen's disease), or Actinic Keratoses, both of which are known to progress to SCC.

In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of treating a cutaneous squamous-cell carcinoma in solid organ transplantation recipients to reduce the progression of the cutaneous squamous-cell carcinoma (cSCC). In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients have had cutaneous squamous-cell carcinoma (cSCC) previously. In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of treating a cutaneous squamous-cell carcinoma in solid organ transplantation recipients to reduce the progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC). In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to reduce the risk of tumor progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to delay the progression of the cutaneous squamous-cell carcinoma (cSCC). In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to delay the progression of the cutaneous squamous-cell carcinoma (cSCC), wherein solid organ transplantation recipients currently have Actinic Keratoses.

In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients currently have cutaneous squamous-cell carcinoma (cSCC), have had cutaneous squamous-cell carcinoma (cSCC) previously, have pre-cancers including squamous cell carcinoma in Situ (also known as Bowen's disease), or have Actinic Keratoses. In some embodiments, provided herein is a method of prophylactically treating or preventing a cutaneous squamous-cell carcinoma in solid organ transplantation recipients to prevent the progression of the cutaneous squamous-cell carcinoma (cSCC). In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients have had cutaneous squamous-cell carcinoma (cSCC) previously. In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients have pre-cancers including squamous cell carcinoma in Situ (also known as Bowen's disease). In some embodiments, provided herein is a method of prophylactically treating or preventing a cutaneous squamous-cell carcinoma in solid organ transplantation recipients to prevent the progression of the cutaneous squamous-cell carcinoma (cSCC), wherein solid organ transplantation recipients currently have Actinic Keratoses.

In some embodiments, provided herein is a method of treating a cutaneous squamous-cell carcinoma in patients to reduce the progression of the cutaneous squamous-cell carcinoma (cSCC), wherein the patients have chronic lymphocytic leukemia (CLL) and are also immunocompromised and susceptible to significantly elevated rates of cSCC. In some embodiments, provided herein is a method of prophylactically treating or preventing a cutaneous squamous-cell carcinoma in patients to reduce the risk of tumor progression of the cutaneous squamous-cell carcinoma (cSCC), wherein the patients have chronic lymphocytic leukemia (CLL) and are also immunocompromised and susceptible to significantly elevated rates of cSCC. In some embodiments, provided herein is a method of prophylactically treating or preventing a cutaneous squamous-cell carcinoma in patients to delay or prevent the progression of the cutaneous squamous-cell carcinoma (cSCC), wherein the patients have chronic lymphocytic leukemia (CLL) and are also immunocompromised and susceptible to significantly elevated rates of cSCC.

In some embodiments, provided herein is a method of treating a cutaneous squamous-cell carcinoma in patients to reduce the progression of the cSCC, wherein the patients have inoperable cSCC. In some embodiments, provided herein is a method of prophylactically treating or preventing a cutaneous squamous-cell carcinoma in patients to reduce the risk of tumor progression of the cSCC, wherein the patients have inoperable cSCC. In some embodiments, provided herein is a method of prophylactically treating or preventing a cutaneous squamous-cell carcinoma in patients to delay or prevent the progression of the cSCC, wherein the patients have inoperable cSCC.

In some embodiments, provided herein is a method of treating a cutaneous squamous-cell carcinoma in patients to reduce the progression of the cSCC, wherein the patients have cSCC previously removed surgically. In some embodiments, provided herein is a method of prophylactically treating or preventing a cutaneous squamous-cell carcinoma in patients to reduce the risk of tumor progression of the cSCC, wherein the patients have cSCC previously removed surgically. In some embodiments, provided herein is a method of prophylactically treating or preventing a cutaneous squamous-cell carcinoma in patients to delay or prevent the progression of the cSCC, wherein the patients have cSCC previously removed surgically.

In some or any embodiments, the tumor or skin cancer associated with cutaneous squamous-cell carcinoma to be reduced, prophylactically treated, or prevented, using the methods described herein is carcinoma.

In some embodiments, the disease to be reduced, ameliorated, treated, or prevented is a skin cancer. In some embodiments, the disease to be reduced, ameliorated, treated, or prevented is selected from the group consisting of basal cell carcinoma, squamous cell carcinoma, squamous cell carcinoma in Situ (also known as Bowen's disease), actinic keratosis, and HPV-related squamous cell carcinoma. In some embodiments, the disease to be reduced, ameliorated, treated, or prevented is a dermal disorder associated with squamous cell carcinoma. In some embodiments, the disease to be reduced, ameliorated, treated, or prevented is a dermal disorder associated with squamous cell carcinoma in solid organ transplantation recipients. In some embodiments, the disease to be reduced, ameliorated, treated, or prevented is a dermal disorder associated with squamous cell carcinoma in patients with chronic lymphocytic leukemia (CLL).

In some embodiments, the topical formulations described herein are used for the reduction of a MEK-inhibitor responsive skin cancer or MEK-mediated skin cancer where the subject is in need thereof.

In some embodiments, the topical formulations described herein are used for the amelioration of a MEK-inhibitor responsive skin cancer or MEK-mediated skin cancer where the subject is in need thereof.

In some embodiments, the topical formulations described herein are used for prevention of a MEK-inhibitor responsive skin cancer or MEK-mediated skin cancer where the subject is in need thereof.

In some embodiments, the topical formulations described herein are used for treatment of a MEK-inhibitor responsive squamous cell carcinoma or MEK-mediated squamous cell carcinoma where the subject is in need thereof.

In some embodiments, the topical formulations described herein are used for the reduction of a MEK-inhibitor responsive squamous cell carcinoma or MEK-mediated squamous cell carcinoma where the subject is in need thereof.

In some embodiments, the topical formulations described herein are used for the amelioration of a MEK-inhibitor responsive squamous cell carcinoma or MEK-mediated squamous cell carcinoma where the subject is in need thereof.

In some embodiments, the topical formulations described herein are used for prevention of a MEK-inhibitor responsive squamous cell carcinoma or MEK-mediated squamous cell carcinoma where the subject is in need thereof.

In some embodiments, the topical formulations described herein are used for treatment of a cutaneous squamous-cell carcinoma in a subject in need thereof.

In some embodiments, the topical formulations described herein are used for the reduction of a cutaneous squamous-cell carcinoma in a subject in need thereof.

In some embodiments, the topical formulations described herein are used for the amelioration of a cutaneous squamous-cell carcinoma in a subject in need thereof In some embodiments, the topical formulations described herein are used for prevention of a cutaneous squamous-cell carcinoma in a subject in need thereof.

In some embodiments, the subject in need thereof is a human.

VI. Combination Therapies

In some embodiments, the topical formulation (e.g., a non-aqueous gel, an aqueous gel, or an emulsion-based formulation) including the compound of formula (I) or (II) provided herein are useful in methods of treatment of a skin disorder where the subject is in need thereof, that comprise further administration of a second agent effective for the treatment of a skin disorder. The second agent can be any agent known to those of skill in the art to be effective for the treatment of dermal disorders or diseases, including those currently approved by the United States Food and Drug Administration, or other similar body of a country foreign to the United States.

In some embodiments, a topical formulation including a compound of formula (I) or (II) provided herein is administered in combination with one second agent. In further embodiments, a topical formulation including a compound of formula (I) or (II) provided herein is administered in combination with two second agents. In still further embodiments, a topical formulation including a compound of formula (I) or (II) provided herein is administered in combination with two or more second agents.

In some embodiments, the methods encompass the step of administering (e.g., topically) to the subject in need thereof an amount of a topical formulation including a compound of formula (I) or (II) provided herein in combination with a second agent effective for the treatment or prevention of skin disorders (e.g., MEK-inhibitor responsive or MEK-mediated skin disorders). The topical formulation can be any topical formulation as described herein; the compound of formula (I) or (II) can be any compound as described herein, and the second agent can be any second agent described in the art or herein.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce one or more adverse or unwanted side effects associated with the use of either therapy alone.

The topical formulations including active compounds provided herein can be administered in combination or alternation with another therapeutic agent, in particular an agent effective in the treatment of a skin disorder (e.g., MEK-inhibitor responsive or MEK-mediated skin disorders) where the subject is in need thereof. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the birthmark to be alleviated. It is to be further understood that for any particular subject, specific dosage regimens and schedules should be adjusted over time according to the individual need and the professional judgment of the person administering or supervising the administration of the compositions.

In some embodiments, dosages of the second agents to be used in a combination therapy are provided herein. In some embodiments, dosages lower than those which have been or are currently being used to treat MEK-inhibitor responsive or MEK-mediated skin conditions are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics 9$^{th}$ Ed, McGraw-Hill, New York; Physician's Desk Reference (PDR) 57$^{th}$ Ed., 2003, Medical Economics Co., Inc., Montvale, NJ; which are incorporated herein by reference in their entirety.

The disclosure provides combination treatments by administration of a topical formulation including a compound of formula (I) or (II) described herein with one or more additional agent(s) or a composition thereof. In some embodiments, the one or more additional agent(s) is selected from:

agents that treat acne (e.g., Accutane, Azelaic acid, Benzoyl Peroxide, Salicylic acid); analgesics (e.g., Acetaminophen, Capsaicin), e.g., a Cox2 Inhibitor, e.g. Celecoxib);

anesthetics (e.g., Benzocaine, Benzocaine/Menthol, Dibucaine, Diperodon, Lidocaine, Lidocaine/Prilocaine, Pramoxine);

anti-infectives (e.g., Crotamiton);

anti-pruritus (e.g., Ammonium lactate, Benzocaine, an ascomycin macrolactam, e.g., Pimecrolimus);

anti-pruritus/5HT3 receptor antagonists (e.g., Ondansetron);

antibiotics (e.g., clindamycin, doxycycline, erythromycin, tetracycline);

anticholinergic antiemetics (e.g., diphenhydramine);

antifibrotics (e.g., Collagenase, Pirfenidone);

antihistamines (e.g., Triprolidine (Actifed®), Fexofenadine (Allergra®, Allegra® D-12, Allegra®-24), Astepro/Astelin Nasal Spray (Azalastine) (Dymista®), Hydroxyzine hydrochloride (Atarax®), Diphenhydramine Hydrochloride (Benadryl®), Brompheniramine (Dimetapp® Cold and Allergy Elixir), Zyrtec® (Cetirizine), Chlor-Trimeton® (Chlorpheniramine), Descoratadine (Clarinex®, Clarinex® D-12, and Clarinex® D-24), Loratadine (Claritin®, Claritin® D-12, Claritin® D-24, and Alavert®), Dimenhydrinate (Dramamine®), Diphenhydramine (Benadryl® Allergy, Nytol®, Sominex®), Doxylamine (Vicks® NyQuil®, Alka-Seltzer® Plus Night-Time Cold Medicine), Cyproheptadine (Periactin®), Promethazine (Phenergan®), Acrivastine (Semprex®, Semprex®-D), Clemastine (Tavist®), doxylamine (Unisom®), Levocetirizine (Xyzal®);

mast cell stabalizers (e.g. Beta2-adrenergic agonists, Cromoglicic acid, cromolyn sodium, Gastrocrom®, Ketotifen, Methylxanthines, Omalizumab, Pemirolast, Quercetin, Ketotifen (Zaditen®));

anti-inflammatory agents (e.g., NSAID (e.g. Aspirin, Choline and magnesium salicylates, Diclofenac potassium (Cataflam®), Diclofenac sodium (Voltaren®, Voltaren® XR), Diclofenac sodium with misoprostol (Arthrotec®), Diflunisal (Dolobid®), Etodolac (Lodine®, Lodine® XL), Fenoprofen calcium (Nalfon®), Flurbiprofen (Ansaid®), Ibuprofen (Advil®, Motrin®, Motrin® IB, Nuprin®), Indomethacin (Indocin®, Indocin® SR), Ketoprofen (Actron®, Orudis®, Orudis® KT, Oruvail®), Magnesium salicylate (Arthritab, Bayer® Select, Doan's Pills, Magan, Mobidin, Mobogesic) Meclofenamate sodium (Meclomen®), Mefenamic acid (Ponstel®), Meloxicam (Mobic®), Nabumetone (Relafen®), Naproxen (Naprosyn®, Naprelan®), Naproxen sodium (Aleve®, Anaprox®), Oxaprozin (Daypro®), Piroxicam (Feldene®), Rofecoxib (Vioxx®), Salsalate (Amigesic, Anaflex 750, Disalcid, Marthritic, Mono-Gesic, Salflex, Salsitab), Sodium salicylate, Sulindac (Clinoril®), Tolmetin sodium (Tolectin®), Valdecoxib (Bextra®));

Receptor Tyrosine Kinase Inhibitor (e.g. Sunitinib);

Alkylating Agents (e.g., Dacarbazine, Carboplatin);

CDK 4/6 Inhibitors (e.g., LEE011);

PKC Inhibitors (e.g., AEB071);

MAPK inhibitors (e.g., RAS Inhibitors/Farnesyltransferase inhibitor (e.g. Tipifarnib), Raf Kinase Inhibitor (e.g. Sorafenib (BAY 43-9006, Nexavar), Vemurafenib, Dabrafenib, LGX818, TAK-632, MLN2480, PLX-4720), ERK Inhibitors (e.g., SCH772984, VTX11e);

BRAF inhibitors (e.g., vemurafenib, dabrafenib)

PI3K Inhibitor (e.g., LY294002);

AKT Inhibitor (e.g., MK 2206);

PI3K/AKT Inhibitor (e.g. buparlisib, Cixutumumab);

mTOR Inhibitors (e.g. Topical Rapamycin, RAD001 (Everolimus/Rapamycin), Temsirolimus, Sirolimus);

Tyrosine Kinase Inhibitors (e.g. Imatinib (Gleevec®), Cabozantinib (inhibitor of tyrosine kinases c-Met and VEGFR2), Nilotinib (Tasigna®);

VEGF Inhibitor (e.g. Ranibizumab (Lucentis®), Cediranib);

Immune Response Modifier (e.g. Topical Imiquimod, Interferon, PEG Interferon);

Calcium Channel Blocker (e.g. Avocil (Mederma)/15% Verapamil, vitamin D separately, Doxycyline Injections);

Statin (e.g. Lovastatin, Methotrexate, Vinblastine, Pregabalin, Temozolomide, PLX3397);

HDAC Inhibitor (e.g. AR-42);

HSP-90 Inhibitors (e.g. Ganetespib);

retinoids (e.g. adapalene, Isotretinoin, tazarotene, tretinoin);

steroids (e.g. Alclometasone, Amcinonide, Betamethasone, Betamethasone dipropionate, Betamethasone dipropionate, augmented, Budesonide, Clobetasol propionate, Cortisone, Desonide, Dexamethasone, Diflorasone diacetate, Fluocinolone acetonide, Fluocinonide, Flurandrenolide, Fluticasone propionate, Halobetasol propionate, Halocinonide, Hydrocortisone, Hydrocortisone butyrate, Hydrocortisone valerate, Methylprednisolone, Mometasone, Mometasone furoate, Prednicarbate, Prednisolone, Prednisone, Triamcinolone, Triamcinolone acetonide);

topical calcineurin inhibitors (e.g., pimecrolimus (Elidel® Cream 1%, Novartis, tacrolimus (Protopic® Ointment, Astellas)); and Non-pharmaceutical Interventions (e.g. photodynamic Therapy (Levulan Kerastick Topical+light), Electrodesication (ED), YAG Laser).

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In some embodiments, two or more therapies are administered within the same patient visit. In some embodiments, the compound provided herein and the second agent are administered concurrently.

In some embodiments, the compound provided herein and the second agent are administered at about 2 to 4 days apart, at about 4 to 6 days apart, at about 1 week part, at about 1 to 2 weeks apart, or more than 2 weeks apart.

In some embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In some embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In some embodiments, a compound provided herein and a second agent are administered to a patient, in some embodiments, a mammal, such as a human, in a sequence and within a time interval such that the compound provided herein can act together with the other agent to provide an increased benefit than if they were administered otherwise. In some embodiments, the second active agent can be administered at the same time or sequentially in any order at different points in time; however, if not administered at the same time, they should be administered sufficiently close in time so as to provide the desired therapeutic or prophylactic effect. In some embodiments, the compound provided herein and the second active agent exert their effect at times which overlap. Each second active agent can be administered separately, in any appropriate form and by any suitable route. In some embodiments, the compound provided herein is administered before, concurrently or after administration of the second active agent.

In some embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce one or more of the side effects of one of the therapies, and/or improve the efficacy of the treatment.

In some embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In some embodiments, courses of treatment are administered concurrently to a patient, i.e., individual doses of the second agent are administered separately yet within a time interval such that the compound provided herein can work together with the second active agent. In some embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In some embodiments, the compound provided herein is administered concurrently with one or more second agents in the same pharmaceutical composition, such as the topical formulation as described herein. In some embodiments, a compound provided herein is administered concurrently with one or more second agents in separate pharmaceutical compositions. In some embodiments, a compound provided herein is administered prior to or subsequent to administration of a second agent. Also contemplated are administration of a compound provided herein and a second agent by the same or different routes of administration, e.g., oral and parenteral. In some embodiments, when the compound provided herein is administered concurrently with a second agent that potentially produces one or more adverse side effects including, but not limited to, toxicity, the second active agent can advantageously be administered at a dose that falls below the threshold that the adverse side effect is elicited.

VII. Kits

Also provided are kits for use in methods of treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof; or a MEK-inhibitor responsive disorder or disease, a MEK-inhibitor responsive dermal disorder or disease, a MEK-mediated disorder or disease, or a MEK-mediated dermal disorder or disease. The kits can include a topical formulation (e.g., a non-aqueous gel, an aqueous gel, or an emulsion-based formulation) including a compound of formula (I) or (II) provided herein, a second agent or composition, and instructions providing information to a health care provider regarding usage for treating a MEK-inhibitor responsive disorder or disease, a MEK-inhibitor responsive dermal disorder or disease, a MEK-mediated disorder or disease, or a MEK-mediated dermal disorder or disease. Instructions may be provided in printed form or in the form of an electronic medium such as a floppy disc, CD, or DVD, or in the form of a website address where such instructions may be obtained. A unit dose of a compound or a topical formulation provided herein, or a second agent or composition, can include a dosage such that when administered to a subject, a therapeutically or prophylactically effective plasma level of the compound or the topical formulation can be maintained in the subject for at least 1 day.

Also provided are kits for use in methods of treatment of a birthmark (e.g., a MEK-inhibitor responsive or MEK-mediated birthmark), where the subject is in need thereof. The kits can include a topical formulation including a compound of formula (I) or (II) provided herein, a second agent or composition, and instructions providing information to a health care provider regarding usage for treating a birthmark (e.g., a MEK-inhibitor responsive or MEK-mediated birthmark). Instructions may be provided in printed form or in the form of an electronic medium such as a floppy disc, CD, or DVD, or in the form of a website address where such instructions may be obtained. A unit dose of a compound or a topical formulation provided herein, or a second agent or composition, can include a dosage such that when administered to a subject, a therapeutically effective plasma level of the compound or the topical formulation can be maintained in the subject for at least 1 day.

Also provided are kits for use in methods of treatment of a skin cancer (e.g., a MEK-inhibitor responsive or MEK-mediated skin cancer), where the subject is in need thereof. The kits can include a topical formulation including a compound of formula (I) or (II) provided herein, a second agent or composition, and instructions providing information to a health care provider regarding usage for treating a skin cancer (e.g., a MEK-inhibitor responsive or MEK-mediated skin cancer). Instructions may be provided in printed form or in the form of an electronic medium such as a floppy disc, CD, or DVD, or in the form of a website address where such instructions may be obtained. A unit dose of a compound or a topical formulation provided herein, or a second agent or composition, can include a dosage such that when administered to a subject, a therapeutically effective plasma level of the compound or the topical formulation can be maintained in the subject for at least 1 day.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

VIII. EXAMPLES

Example 1: Preparation of Gel Formulations

The gel formulations of the present disclosure can be prepared according to the procedure provided below. Reaction conditions, steps and reactants not provided in the procedure below would be apparent to, and known by, those skilled in the art.

Excipients (i.e., organic solvents, the antioxidant/stabilizer, antioxidants, and/or the preservative) were aliquoted or weighted into individual vials to form a mixture. The compound of formula (I) (e.g., Compound 1.003) was added to the mixture to achieve a desired concentration or saturation. Then the gelling agent (e.g., HPC) were added accordingly. The pH was adjusted with 0.1 M citric acid in PEG-400 to about 6-7. Finally, a second addition of PEG-400 was used to titrate the formulation to 100% by weight. The vials were vortexed to mix and spin overnight. Afterwards, a viscosity and a visual inspection were immediately recorded, then stored at ambient conditions for 7 days.

The gel formulations (NA-1a) were prepared according to the general procedure using the excipients of Table 3.

TABLE 3

| Gel Formulation (NA-1a) | | | |
|---|---|---|---|
| | | Compositions (wt/wt %) | |
| Function | Components | NA-1a-2% | NA-1a-0.01% |
| API | Compound 1.003* | 2.340 | 0.01 |
| Organic solvents | S.R. PEG-400** | 47.11 | 48.31 |
| | Transcutol ® HP | 45.00 | 46.13 |
| Antioxidant/ stabilizer | Ascorbyl palmitate | 0.05 | 0.05 |
| | Alpha tocopherol | 0.002 | 0.002 |
| Gelling agent | HPC HF | 0.50 | 0.50 |
| pH adjuster | 0.1M citric acid in S.R. PEG-400 | To pH 6-7 | |
| Organic solvents | $2^{nd}$ addition of S.R. PEG-400 | Q.S. 100 | |
| | Total | 100 | 100 |

*The amount of Compound 1.003 added may be adjusted based on API purity/potency;
**Part of PEG-400 was adjusted to compensate the addition of the pH adjusting solution and final Q.S. 100; and Abbreviations: S.R.—super refined; HP—high purity; and Q.S.—quantum satis The gel formulations (NA-2) were prepared according to the general procedure using the excipients of Table 4.

TABLE 4

Gel Formulation (NA-2)

| Function | Components | Compositions (wt/wt %) | |
|---|---|---|---|
| | | NA-2a | NA-2b |
| API | Compound 1.003* | 0.96 | 0.94 |
| Organic solvents | Ethanol | 10.00 | 10.00 |
| | S.R. PEG-400** | 62.09 | 62.11 |
| | S.R. propylene glycol | 20.00 | 10.00 |
| | Transcutol ® HP | — | 10.00 |
| Preservative | Phenoxyethanol | 1.05 | 1.05 |
| Antioxidant | Butylated hydroxytoluene | 0.20 | 0.20 |
| | Butylated hydroxyanisole | 0.20 | 0.20 |
| Gelling agent | HPC HF | 0.50 | 0.50 |
| pH adjuster | 0.1M citric acid in S.R. PEG-400 | To pH 6-7 | |
| Organic solvent | $2^{nd}$ addition of S.R. PEG-400 | Q.S. 100 | |
| | Total | 100 | 100 |

*The amount of Compound 1.003 added may be adjusted based on API purity/potency;
**Part of PEG-400 was adjusted to compensate the addition of the pH adjusting solution and final Q.S. 100; and Abbreviations: S.R.—super refined; HP—high purity; and Q.S.—quantum satis

Example 2: Preparation of Aqueous Gel Formulations

The aqueous gel formulations of the present disclosure can be prepared according to the procedure provided below. Reaction conditions, steps and reactants not provided in the procedure below would be apparent to, and known by, those skilled in the art.

Excipients (i.e., solvents, the antioxidant/stabilizer, the antioxidant, the preservative, and/or surfactants) were aliquoted or weighted into individual vials to form a mixture. The compound of formula (I) (e.g., Compound 1.003) was added to the mixture to achieve a desired concentration or saturation. Then the gelling agent (e.g., HPC or poly(acrylic acid)) were added accordingly. The pH was adjusted with 0.1 M NaOH in water or ammonia to about 6-7. Finally, a second addition of water was used to titrate the formulation to 100% by weight. The vials were vortexed to mix and spin overnight. Afterwards, a viscosity and a visual inspection were immediately recorded, then stored at ambient conditions for 7 days.

The aqueous gel formulations (AG-1a) were prepared according to the general procedure using the excipients of Table 5.

TABLE 5

| | Aqueous Gel Formulation (AG-1a) | | |
|---|---|---|---|
| | | Compositions (wt/wt %) | |
| Function | Components | AG-1a | AG-1a-0.01% |
| API | Compound 1.003* | 0.30 | 0.01 |
| Solvents | Water** | 25.00 | 25.00 |
| | S.R. PEG-400 | 62.00 | 62.00 |
| Preservative | Phenoxyethanol | 1.05 | 1.05 |
| Antioxidant/ stabilizer | Ascorbic acid | 0.10 | 0.10 |
| | EDTA, disodium salt | 0.05 | 0.05 |
| Surfactant | Polysorbate 80 (Tween ® 80) | 5.00 | 5.00 |
| | Poloxamer 407 | 1.00 | 1.00 |
| Gelling agent | Carbopol ® 980 | 0.50 | 0.50 |
| pH adjuster | 0.1M NaOH in water | To pH 6-7 | |
| Solvent | $2^{nd}$ addition of water | Q.S. 100 | |

*The amount of Compound 1.003 added may be adjusted based on API purity/potency;
**Part of water was adjusted to compensate the addition of the pH adjusting solution and final Q.S. 100; and Abbreviations: S.R.—super refined; HP—high purity; and Q.S.—quantum satis The aqueous gel formulations (AG-2a) and (AG-2b) were prepared according to the general procedure using the excipients of Table 6.

TABLE 6

| | Aqueous Gel Formulations (AG-2a) and (AG-2b) | | | | |
|---|---|---|---|---|---|
| | | Compositions (wt/wt %) | | | |
| Function | Components | AG-2a | AG-2a-0.01% | AG-2b | AG-2b-0.01% |
| API | Compound 1.003* | 0.70 | 0.01 | 0.52 | 0.01 |
| Solvents | Water** | 15.00 | 15.12 | 15.00 | 15.09 |
| | Ethanol | 10.00 | 10.07 | 5.00 | 5.03 |
| | S.R. PEG-400 | 37.70 | 37.96 | 28.98 | 29.14 |
| | S.R. propylene glycol | 10.00 | 10.07 | 15.00 | 15.08 |
| | Transcutol ® HP | 20.00 | 20.15 | 20.00 | 20.11 |
| | Glycerol | — | — | 8.90 | 8.95 |
| Preservative | Phenoxyethanol | 1.05 | 1.05 | 1.05 | 1.05 |
| Antioxidant | Butylated hydroxytoluene | 0.05 | 0.05 | 0.05 | 0.05 |
| Gelling agent | Carbopol ® 980 | 0.50 | 0.50 | 0.50 | 0.50 |
| pH adjuster | 0.1M NaOH in water | To pH 6-7 | | | |
| Solvent | $2^{nd}$ addition of water | Q.S. 100 | | | |
| | Total | 100 | 100 | 100 | 100 |

*The amount of Compound 1.003 added may be adjusted based on API purity/potency;
**Part of water was adjusted to compensate the addition of the pH adjusting solution and final Q.S. 100; and Abbreviations: S.R.—super refined; HP—high purity; and Q.S.—quantum satis The aqueous gel formulations (AG-3a) to (AG-3d) were prepared according to the general procedure using the excipients of Table 7.

TABLE 7

Aqueous Gel Formulations (AG-3a) to (AG-3d)

| Function | Components | AG-3a | AG-3b | AG-3c | AG-3c-0.01% | AG-3d |
|---|---|---|---|---|---|---|
| API | Compound 1.003* | 0.14 | 0.14 | 0.45 | 0.01 | 0.35 |
| Solvents | Water** | 32.50 | 28.31 | 26.00 | 26.11 | 20.03 |
|  | Ethanol | — | 11.33 | 11.67 | 11.72 | — |
|  | S.R. PEG-400 | 35.90 | 13.17 | 25.19 | 25.31 | 35.45 |
|  | S.R. propylene glycol | — | 13.33 | — | — | 12.50 |
|  | Transcutol ® HP | 23.81 | 27.02 | 28.02 | 28.15 | 25.00 |
| Preservative | Phenoxyethanol | — | 1.05 | 1.05 | 1.05 | 1.05 |
|  | Benzyl alcohol | 2.00 | — | — | — | — |
| Antioxidant/stabilizer | EDTA, disodium salt | 0.05 | 0.05 | 0.02 | 0.02 | 0.02 |
|  | Ascorbic acid | 0.10 | 0.10 | 0.10 | 0.10 | 0.10 |
| Surfactant | Polyoxyl 20 cetostearyl ether (Kolliphor ® CS20) | — | — | 2.00 | 2.00 | — |
| Gelling agent | HPC HF | — | 0.50 | — | — | — |
|  | Carbopol ® 980 | 0.50 | — | 0.50 | 0.50 | 0.50 |
| pH adjuster | 0.1M NaOH in water | To pH 6-7 | | | — | |
|  | Ammonia | | — | | To pH 6-7 | |
| Solvent | 2$^{nd}$ addition of water | | | Q.S. 100 | | |
|  | Total | 100 | 100 | 100 | 100 | 100 |

*The amount of Compound 1.003 added may be adjusted based on API purity/potency;
**Part of water was adjusted to compensate the addition of the pH adjusting solution and final Q.S. 100; and
Abbreviations: S.R.—super refined; HP—high purity; and Q.S.—quantum satis

Example 3: Preparation of Emulsion-Based Formulations

Excipients (i.e., solvents, the antioxidant/stabilizer, and/or the preservative) were aliquoted or weighted into individual vials to form a non-oil mixture. The oil-based mixture was prepared accordingly and mixed with the non-oil mixture. The compound of formula (I) (e.g., Compound 1.003) was added to the resulted mixture to achieve a desired concentration or saturation. Then the one or more additional excipients (e.g., emulsifiers, surfactants, and/or thickening agents), whenever applicable, were added accordingly. The pH was adjusted with 0.1 M NaOH in water or ammonia to about 6-7. Finally, a second addition of water was used to titrate the formulation to 100% by weight. The vials were vortexed to mix and spin overnight. Afterwards, a visual inspection were immediately recorded, then stored at ambient conditions for 7 days.

The lotion formulations were prepared according to the general procedure using the excipients of Table 8.

TABLE 8

Lotion Formulations

| Function | Components | LO-1a | LO-2a |
|---|---|---|---|
| API | Compound 1.003* | 0.13 | 0.13 |
| Solvents | Water** | 26.87 | 24.87 |
|  | S.R. PEG-400 | 30.95 | 38.80 |
|  | Transcutol ® HP | 15.85 | 10.00 |
| Preservative | Phenoxyethanol | 1.05 | 1.05 |
| Oxidant/stabilizer | Ascorbic acid | 0.10 | 0.10 |
|  | EDTA, disodium salt | 0.05 | 0.05 |
| Oil-based mixture | Crodamol ™ GTCC | 6.50 | 8.00 |
|  | Stearic acid | 4.50 | — |
|  | Liquid paraffin | — | — |
|  | Castor oil | — | 10.00 |
|  | Dimethicone 350 | 1.00 | — |
|  | Cetostearyl alcohol | 2.00 | — |
| Additional excipients | Gelot ™ 64 | 1.00 | — |
|  | Steareth 20 | 3.18 | — |
|  | Geleol ™ Mono and diglycerides | 1.82 | — |
|  | Sepineo ™ P600 | — | 2.00 |
| pH adjuster | 0.1M NaOH/0.1M citric acid in water | To pH 6-7 | |
| Solvent | 2$^{nd}$ addition of water | Q.S. 100 | |
|  | Total | 100 | 100 |

*The amount of Compound 1.003 added may be adjusted based on API purity/potency;
**Part of water was adjusted to compensate the addition of the pH adjusting solution and final Q.S. 100; and
Abbreviations:
S.R.—super refined;
HP—high purity; and
Q.S.—quantum satis The cream formulations were prepared according to the general procedure using the excipients of Table 9.

TABLE 9

Cream Formulations

| Function | Components | Compositions (wt/wt %) | | |
|---|---|---|---|---|
| | | CR-1a | CR-1a-0.01% | CR-2a |
| API | Compound 1.003* | 0.13 | 0.01 | 0.14 |
| Solvents | Water** | 26.87 | 26.99 | 29.21 |
| | S.R. PEG-400 | 30.95 | 30.95 | 35.88 |
| | Transcutol ® HP | 15.85 | 15.85 | — |
| | Isopropyl alcohol | — | — | 8.57 |
| Preservative | Phenoxyethanol | 1.05 | 1.05 | 1.05 |
| Antioxidant/ | Ascorbic acid | 0.10 | 0.10 | 0.10 |
| stabilizer | EDTA, disodium salt | 0.05 | 0.05 | 0.05 |
| Oil-based | Cyclomethicone 5NF | — | — | 6.50 |
| mixture | Crodamol ™ GTCC | 6.00 | 6.00 | — |
| | Stearic acid | — | — | 4.50 |
| | Liquid paraffin | 4.00 | 4.00 | — |
| | Dimethicone 350 | 1.00 | 1.00 | 1.00 |
| | Cetostearyl alcohol | — | — | 2.00 |
| | Cetyl alcohol | 4.00 | 4.00 | — |
| Additional | Gelot ™ 64 | — | — | 1.00 |
| excipients | Span ™ 60 | 1.81 | 1.81 | — |
| | Tween ® 60 | 3.19 | 3.19 | — |
| | Steareth 20 | — | — | 3.18 |
| | Geleol ™ Mono and diglycerides | — | — | 1.82 |
| pH adjuster | 0.1M NaOH/0.1M citric acid in water | To pH 6-7 | | |
| Solvent | 2$^{nd}$ addition of water | Q.S. 100 | | |
| | Total | 100 | 100 | 100 |

*The amount of Compound 1.003 added may be adjusted based on API purity/potency;
**Part of water was adjusted to compensate the addition of the pH adjusting solution and final Q.S. 100; and
Abbreviations:
S.R.—super refined;
HP—high purity; and
Q.S.—quantum satis The emulsified gel formulations were prepared according to the general procedure using the excipients of Table 10.

TABLE 10

Emulsified Gel Formulations

| Function | Components | Compositions (wt/wt %) | | |
|---|---|---|---|---|
| | | EG-1a | EG-2a | EG-2a-0.01% |
| API | Compound 1.003* | 0.21 | 0.34 | 0.01 |
| Solvents | Water** | 19.98 | 18.48 | 18.81 |
| | S.R. PEG-400 | 10.14 | 19.51 | 19.51 |
| | S.R. propylene glycol | 10.00 | — | — |
| | Transcutol ® HP | 20.00 | 20.00 | 20.00 |
| | Ethanol | 8.50 | 8.50 | 8.50 |
| Preservative | Phenoxyethanol | 1.05 | 1.05 | 1.05 |
| Antioxidant/ | Ascorbic acid | 0.10 | 0.10 | 0.10 |
| stabilizer | EDTA, disodium salt | 0.02 | 0.02 | 0.02 |
| Oil-based | Crodamol ™ GTCC | 10.00 | 10.00 | 10.00 |
| mixture | Castor oil | 12.50 | 12.50 | 12.50 |
| Additional | Polyoxyl 20 cetostearyl ether | — | 2.00 | 2.00 |
| excipients | Sepineo ™ P600 | 2.50 | 2.50 | 2.50 |
| pH adjuster | 0.1M NaOH/0.1M citric acid in water | To pH 6-7 | | |
| Solvent | 2$^{nd}$ addition of water | Q.S. 100 | | |
| | Total | 100 | 100 | 100 |

*The amount of Compound 1.003 added may be adjusted based on API purity/potency;
**Part of water was adjusted to compensate the addition of the pH adjusting solution and final Q.S. 100; and
Abbreviations:
S.R.—super refined;
HP—high purity; and
Q.S.—quantum satis Example 4: Stability Study of Topical Formulations Selected topical formulations of the present disclosure were studied for their stability under storage of 12 weeks at 25° C. or 40° C.

A. Content and Purity of Compound 1.003

The content and purity of Compound 1.003) was determined by a HPLC method. Purity and recovery of Compound 1.003 were measured at 2, 4, 6, 8, and 12 weeks stored at 25° C. or 40° C. It is noted that only data at 4 and 8 weeks were shown in Table 11 and Table 12.

TABLE 11

Purity of Compound 1.003 under storage of 8 weeks at 25° C. or 40° C.

| Formulation ID | T = 0 (%) | T = 4 weeks (%) | | T = 8 weeks (%) | |
|---|---|---|---|---|---|
| | | 25° C. | 40° C. | 25° C. | 40° C. |
| NA-1a | 98.76 (98.75-98.77) | 98.65 (98.63-98.66) | 97.81 (97.76-97.84) | 98.33 (98.33-98.33) | 98.17 (98.17-98.17) |
| NA-2a | 98.18 (98.16-98.20) | 98.60 (98.59-98.62) | 97.93 (97.88-97.98) | 98.30 (98.30-98.31) | 97.60 (97.56-97.62) |
| AG-1a | 96.68 (96.62-96.71) | 98.73 (98.72-98.74) | 98.11 (98.10-98.12) | 97.69 (97.64-97.73) | 97.28 (97.23-97.34) |
| AG-2a | 98.44 (98.44-98.45) | 98.67 (98.66-98.68) | 97.92 (97.90-97.95) | 98.35 (98.34-98.36) | 97.77 (97.62-97.88) |
| AG-2b | 98.43 (98.42-98.44) | 98.64 (98.63-98.66) | 97.84 (97.79-97.91) | 98.28 (98.26-98.29) | 97.70 (97.65-97.73) |
| AG-3a | 98.58 (98.51-98.63) | 98.30 (98.27-98.32) | 97.48 (97.44-97.50) | 98.33 (98.31-98.35) | 97.82 (97.79-97.84) |
| AG-3b | 98.65 (98.64-98.66) | 98.44 (98.42-98.44) | 97.84 (97.79-97.93) | 98.27 (98.25-98.29) | 97.85 (97.82-97.88) |
| AG-3c | 98.50 (98.49-98.51) | 98.62 (98.60-98.66) | 98.13 (98.12-98.13) | 91.40 (91.28-91.53) | 97.92 (97.89-97.96) |
| AG-3d | 98.53 (98.50-98.55) | 98.64 (98.61-98.66) | 97.92 (97.91-97.94) | 98.32 (98.31-98.32) | 97.94 (97.92-97.98) |
| LO-1a | 98.55 (98.54-98.56) | 98.58 (98.57-98.59) | 97.96 (97.89-98.01) | 98.19 (98.18-98.21) | 96.99 (96.93-97.09) |
| LO-2a | 98.46 (98.46-98.46) | 98.63 (98.62-98.64) | 97.73 (97.71-97.76) | 77.20 (77.20-77.20) | 75.02 (74.31-75.54) |

TABLE 11-continued

Purity of Compound 1.003 under storage of 8 weeks at 25° C. or 40° C.

| Formulation ID | T = 0 (%) | T = 4 weeks (%) | | T = 8 weeks (%) | |
|---|---|---|---|---|---|
| | | 25° C. | 40° C. | 25° C. | 40° C. |
| CR-1a | 98.58 (98.55-98.61) | 98.59 (98.58-98.59) | 98.52 (98.48-98.55) | 98.03 (98.01-98.04) | 96.22 (96.08-96.35) |
| CR-2a | 98.41 (98.40-98.42) | 98.61 (98.58-98.65) | 98.64 (98.63-98.65) | 97.89 (97.49-98.10) | 97.16 (96.87-97.34) |
| EG-1a | 98.45 (98.42-98.47) | 98.11 (97.67-98.34) | 97.57 (97.54-97.61) | 98.09 (98.05-98.13) | 97.30 (97.29-97.31) |
| EG-2a | 98.55 (98.50-98.59) | 98.35 (98.32-98.38) | 97.65 (97.64-97.66) | 88.82 (88.65-88.98) | 97.72 (97.69-97.75) |

TABLE 12

Recovery of Compound 1.003 under storage of 8 weeks at 25° C. or 40° C.

| Formulation ID | T = 0 (%) | T = 4 weeks (%) | | T = 8 weeks (%) | |
|---|---|---|---|---|---|
| | | 25° C. | 40° C. | 25° C. | 40° C. |
| NA-1a | 97.58 (95.39-99.56) | 98.91 (97.07-99.92) | 95.99 (94.27-96.90) | 93.42 (91.33-95.32) | 96.33 (95.45-97.00) |
| NA-2a | 100.60 (99.67-101.72) | 99.78 (98.54-101.73) | 98.19 (97.26-98.84) | 98.81 (98.30-99.60) | 98.76 (98.19-99.11) |
| AG-1a | 102.18 (101.27-102.82) | 99.27 (98.42-100.09) | 96.24 (95.97-96.43) | 98.37 (97.92-98.93) | 98.17 (97.38-99.34) |
| AG-2a | 101.17 (99.14-102.29) | 100.52 (100.01-100.83) | 97.75 (97.66-97.90) | 97.27 (96.69-97.82) | 99.65 (99.18-99.94) |
| AG-2b | 99.17 (98.40-99.91) | 100.49 (99.85-100.87) | 94.36 (93.45-95.00) | 96.69 (96.48-96.94) | 94.28 (92.58-95.87) |
| AG-3a | 103.34 (103.13-103.45) | 96.97 (95.84-98.56) | 97.04 (96.35-97.50) | 94.98 (91.65-97.08) | 97.06 (96.41-98.11) |
| AG-3b | 98.35 (97.76-99.05) | 96.09 (95.03-97.84) | 96.35 (95.99-96.78) | 85.44 (78.19-97.97) | 97.19 (90.02-105.04) |
| AG-3c | 101.69 (101.54-101.85) | 96.46 (95.45-98.27) | 97.75 (97.65-97.85) | 97.85 (96.95-98.75) | 100.34 (99.08-101.37) |
| AG-3d | 101.88 (100.84-103.63) | 99.13 (97.37-100.07) | 95.52 (92.90-97.12) | 97.85 (96.95-98.75) | 94.81 (94.64-95.01) |
| LO-1a | 107.08 (105.58-109.11) | 104.45 (103.83-105.08) | 102.07 (100.59-104.31) | 99.75 (98.95-100.37) | 93.75 (92.73-95.38) |
| LO-2a | 102.79 (97.98-106.86) | 91.97 (90.79-92.93) | 95.40 (94.63-96.63) | 103.02 (103.02-103.02) | 98.77 (96.70-100.59) |
| CR-1a | 99.74 (99.09-100.39) | 102.18 (101.92-102.52) | 96.36 (94.02-97.71) | 98.70 (98.46-99.12) | 100.35 (99.19-101.68) |
| CR-2a | 105.39 (102.59-106.87) | 101.68 (101.09-102.30) | 93.57 (92.74-93.99) | 96.43 (95.25-97.16) | 105.51 (102.06-110.33) |
| EG-1a | 105.06 (103.06-107.06) | 93.46 (92.95-93.89) | 94.23 (93.19-96.22) | 106.42 (99.57-113.27) | 105.55 (104.55-106.55) |
| EG-2a | 103.55 (97.45-107.00) | 94.55 (93.05-95.75) | 96.61 (92.21-99.42) | 97.58 (93.44-99.94) | 99.47 (99.15-99.79) |

The purity of the drug at t=0 was >9800 area (with the exception of AG-1a in which drug purity was ca. 9600 at t=0). Following 4 weeks of storage at 25° C., the purity of Compound 1.003 in the formulations was consistent with t=0, with purity of from 98.11% (EG-1a) to 98.73% (AG-1a). At 40° C., decreases of between 0.06% (CR-1a)-1.1% (AG-3a) in the purity of the drug were observed in the majority of formulations, with formulation (AG-3a) exhibiting a decrease of 1.1% (97.48% at t=4 weeks and 98.58 at t=0).

At the final 12 week time point, the purity of formulation (NA-1a) remained stable at 25° C., with purity of 98.31% when compared to 98.76% at t=0. Additionally, following storage at 40° C., the peak purity of the drug in this formulation was 98.05%. While a slight downward trend is evident over 12 weeks, it remains within 1% of the purity observed at t=0 and is therefore considered to be stable.

Formulation (CR-1a) remained consistent with t=0 at the 25° C. storage condition, however this was shown to decrease slightly at 40° C.

At t=0, the recoveries were between 95%-105% for all formulations with the exception of formulations (LO-1a), (CR-2a), and (EG-1a) which were 107.08, 105.39 and 103.55% respectively. After 4 weeks, the recovery of Compound 1.003 from emulsion-based formulations ranged from 91.97% (LO-2a)-104.45% (LO-1a) at 25° C., and 93.57% (CR-2a)-102.07% (LO-1a) at 40° C.

After 12 weeks of storage, the recovery of Compound 1.003 remained variable and no clear trends were apparent. Further optimization of the method may minimize the noted variability.

The above data suggest that drug chemical stability is achieved at 25° C. in a number of the formulations, in particular formulations (NA-1a), (AG-1a), and (CR-1a). At 40° C., formulation (NA-1a) exhibited purity broadly consistent with t=0 (98.05%).

B. Apparent pH of Formulations

The apparent pH of the formulations was measured at t=0 and at 2, 4, 6. 8. And 12 weeks of storage. It is noted that only data at 4 and 8 weeks were shown in Table 13. It should be noted that the formulations are not entirely aqueous, and therefore the pH is considered an apparent pH (USP <721>).

TABLE 13

Apparent pH under storage of 8 weeks at 25° C. or 40° C.

| Formulation ID | T = 0 | T = 4 weeks | | T = 8 weeks | |
|---|---|---|---|---|---|
| | | 25° C. | 40° C. | 25° C. | 40° C. |
| NA-1a ACT | 4.93 | 4.98 | 4.40 | 4.97 | 5.13 |
| NA-1a PLB | 5.72 | 5.24 | 5.04 | 6.58 | 3.96 |
| NA-2a ACT | 6.80 | 7.35 | 6.94 | 7.94 | 8.28 |
| NA-2a PLB | 6.95 | 7.15 | 6.86 | 8.31 | 7.20 |
| AG-1a ACT | 5.65 | 5.42 | 5.16 | 5.32 | 4.47 |
| AG-1a PLB | 6.10 | 6.17 | 5.93 | 5.92 | 5.41 |
| AG-2a ACT | 6.23 | 6.42 | 6.12 | 6.17 | 6.19 |
| AG-2a PLB | 6.55 | 6.64 | 6.06 | 5.72 | 6.33 |
| AG-2b ACT | 6.35 | 6.22 | 6.08 | 6.14 | 6.15 |
| AG-2b PLB | 6.40 | 6.32 | 6.34 | 6.36 | 6.10 |
| AG-3a ACT | 5.60 | 5.42 | 5.53 | 4.87 | 4.17 |
| AG-3a PLB | 5.51 | 5.38 | 5.10 | 5.09 | 4.98 |
| AG-3b ACT | 5.80 | 4.65 | 4.75 | 4.77 | 4.52 |
| AG-3b PLB | 5.52 | 5.08 | 4.62 | 4.79 | 3.61 |
| AG-3c ACT | 5.48 | 4.73 | 4.46 | 4.62 | 4.56 |
| AG-3c PLB | 5.58 | 5.19 | 4.76 | 4.71 | 4.99 |
| AG-3d ACT | 5.50 | 5.02 | 4.27 | 4.61 | 4.41 |
| AG-3d PLB | 5.85 | 5.58 | 5.16 | 5.08 | 3.65 |
| LO-1a ACT | 6.01 | 5.74 | 5.48 | 5.19 | 4.89 |
| LO-1a PLB | 6.25 | 6.03 | 4.76 | 6.23 | 5.88 |
| LO-2a ACT | 6.73 | 5.94 | 5.59 | 6.24 | 5.69 |
| LO-2a PLB | 7.45 | 7.22 | 6.13 | 6.39 | 5.50 |
| CR-1a ACT | 6.61 | 5.67 | 6.33 | 6.18 | — |
| CR-1a PLB | 6.74 | 6.95 | 6.20 | 6.68 | 5.92 |
| CR-2a ACT | 5.98 | 5.47 | 5.31 | 5.59 | — |
| CR-2a PLB | 5.96 | 5.84 | 5.46 | 5.62 | 5.36 |
| EG-1a ACT | 6.97 | 6.27 | 5.96 | 5.76 | 5.47 |
| EG-1a PLB | 6.73 | 6.23 | 5.55 | 5.39 | 5.43 |
| EG-2a ACT | 5.65 | 4.76 | 4.73 | 5.33 | 5.11 |
| EG-2a PLB | 5.76 | 5.32 | 5.13 | 4.88 | 4.80 |

ACT: active formulation containing API; and
PLB: placebo formulation; and
—: No pH determined due to phase separation.

After 12 weeks of storage, the active gel formulation (NA-1a) had an apparent pH consistent to t=0, with no obvious downward trend, while the pH of the placebo formulation at both 25° C. and 40° C. was greater than +0.5 pH units from that observed at t=0.

At the t=12 week time point at both temperatures, formulation (AG-1a) exhibited a downward trend in pH (>0.5 pH units from t=0) from 5.65 at t=0 to 4.98 at 25° C. and 5.02 at 40° C. following 12 weeks.

The emulsion based formulations exhibited no clear trend in apparent pH, however decreases from t=0, particularly at the 40° C. were observed where it was possible to evaluate pH (i.e. when formulation had no phase separation).

No obvious trend in apparent pH was observed with formulation (NA-1a) following 12 weeks of storage, while a slight downward trend in formulation (AG-1a) was observed.

C. Macroscopic Observations

The macroscopic observations (i.e. color, clarity, application and visual viscosity) of the formulations were recorded at 2, 4, 6, 8, and 12 weeks (data are not shown here in the present application). The test results are summarized below:

Following 12 weeks of storage, formulation (NA-1a) remained similar to t=0 but slight color change was observed (faint yellow to faint beige at 25° C. and faint yellow to light yellow at 40° C.). The formulation appeared stringy, however this does not appear to have an impact on any other product attribute (e.g. drug content/purity, microscopic appearance) and is typical of formulations which include this gelling agent.

Aqueous gel formulation (AG-3b) active formulation did not exhibit any change from t=0 over the stability program, however all other active gels exhibited small changes in either color, clarity or viscosity. Notably, formulation (AG-1a) appeared to be turbid at t=12 weeks after storage at 25° C., and may be due to decreasing apparent pH and Carbopol becoming less solvated following pH. This was not observed at the 40° C. condition, perhaps that the temperature is aiding in keeping the polymer solvated.

Formulation (CR-1a) active and placebo appeared to change in color and viscosity across time, and was notably phase separated at the 40° C. across the stability experiment. The phase separation is thought to be due to the partial melt of the excipients (cetyl alcohol in CR-1a has a melting point of ca. 49° C.). However, as no major signs of coalescence were observed in the microscopic characterization at the 25° C. temperature, the formulations appear physically stable. Over time formulation (CR-2a) exhibited a similar trend (active and placebo), however at the t=8 and 12 week time point it was phase separated at both conditions.

The emulsified gel formulations (EG-1a) and (EG-2a) did not appear to change from t=0 at the 12 week time point, however the placebo was noted to be slightly yellow or beige.

In summary, following 12 weeks of storage, slight color changes and differences in the physical characteristics of the majority of the formulations were observed. However in formulation (NA-1a), such changes were minimum (e.g., color change from faint yellow to faint beige at 8 weeks).

Example 5: Stability Study of Low-Strength Topical Formulations

Selected topical formulations containing Compound 1.003 in an amount of 0.01% by weight were studied for their stability under storage of 12 weeks at 25° C. or 40° C.

A. Content and Purity of Compound 1.003

The content and purity of Compound 1.003) was determined by a HPLC method. Purity and recovery of Compound 1.003 were measured at 2, 4, 6, and 8 weeks stored at 25° C. or 40° C. It is noted that only data at 4 and 8 weeks are shown in Table 14 and Table 15.

TABLE 14

Purity of Compound 1.003 under storage of 8 weeks at 25° C. or 40° C.

| Formulation | | T = 4 weeks (%) | | T = 8 weeks (%) | |
|---|---|---|---|---|---|
| ID | T = 0 (%) | 25° C. | 40° C. | 25° C. | 40° C. |
| NA-1a-0.01% | 97.69 | 97.85 | 97.34 | 97.20 | 96.67 |
| | (97.68-97.72) | (97.85-97.86) | (97.27-97.44) | (97.13-97.25) | (96.64-95.74) |
| AG-2a-0.01% | 98.12 | 99.30 | 98.63 | 99.03 | 98.87 |
| | (98.08-98.16) | (99.29-99.31) | (98.52-98.79) | (99.00-99.05) | (98.84-98.89) |
| AG-2b-0.01% | 98.31 | 99.24 | 98.53 | 98.57 | 98.97 |
| | (98.26-98.34) | (99.23-99.26) | (98.46-98.60) | (98.55-98.60) | (98.85-98.98) |
| AG-3c-0.01% | 97.72 | 98.70 | 98.37 | 97.31 | 93.62 |
| | (97.56-97.83) | (98.54-98.79) | (98.27-98.48) | (97.06-97.51) | (93.44-93.79) |
| CR-1a-0.01% | 96.59 | 98.73 | 98.26 | 98.56 | 98.08 |
| | (96.53-96.62) | (98.68-98.76) | (98.08-98.42) | (98.48-98.60) | (98.03-98.15) |
| EG-2a-0.01% | 95.33 | 87.02 | 76.36 | 96.55 | 96.07 |
| | (95.25-95.46) | (86.87-87.17) | (75.10-77.61) | (96.37-96.72) | (95.81-96.21) |

TABLE 15

Recovery of Compound 1.003 under storage of 8 weeks at 25° C. or 40° C.

| Formulation | | T = 4 weeks (%) | | T = 8 weeks (%) | |
|---|---|---|---|---|---|
| ID | T = 0 (%) | 25° C. | 40° C. | 25° C. | 40° C. |
| NA-1a-0.01% | 98.08 | 104.58 | 97.97 | 100.29 | 99.29 |
| | (97.08-98.61) | (104.29-104.96) | (96.85-99.87) | (98.99-101.11) | (94.38-103.18) |
| AG-2a-0.01% | 103.86 | 104.58 | 105.51 | 102.44 | 101.69 |
| | (102.81-104.91) | (104.29-104.96) | (104.91-106.12) | (101.44-102.47) | (99.95-103.10) |
| AG-2b-0.01% | 101.52 | 105.88 | 105.02 | 101.77 | 100.60 |
| | (98.30-104.72) | (105.43-106.18) | (104.79-105.24) | (101.09-102.20) | (100.59-100.63) |
| AG-3c-0.01% | 103.81 | 105.63 | 106.25 | 101.22 | 104.91 |
| | (103.12-105.02) | (100.69-109.23) | (105.61-106.83) | (99.76-102.04) | (101.10-108.64) |
| CR-1a-0.01% | 105.84 | 101.70 | 104.03 | 104.83 | 103.41 |
| | (105.02-106.53) | (98.42-105.49) | (103.33-104.86) | (101.63-106.96) | (100.92-105.98) |
| EG-2a-0.01% | 101.56 | 99.80 | 103.79 | 102.70 | 108.48 |
| | (99.92-103.57) | (98.42-101.18) | (101.61-105.97) | (101.91-103.59) | (106.66-109.95) |

After 8 weeks of storage, the drug content was observed to be similar to t=0 (ca.±5% of the theoretical amount of Compound 1.003 in the formulations) at 25° C. and 40° C., with the exception of formulation (EG-2a-0.01%) which exhibited phase separation. The recovery of drug from formulation (NA-1a) appeared to be consistent to t=0 up to 8 weeks.

The purity of the drug from the 0.0100 formulations was shown to be within 2% area of the T=0 purity at both temperatures after 8 weeks, with the exception of formulation (AG-3c-0.01%) at 40° C. (which appeared turbid following storage). Purity of the drug in formulation (CR-1a-0.01%) appeared to be variable from t=0, but was broadly consistent from t=2 weeks onwards at both temperatures.

A slight downward trend in purity was observed in formulation (NA-1a-0.01%) over 8 weeks of storage, and in this formulation drug purity was observed to decrease 1.02% at 40° C. following 8 weeks of storage following analysis with a UPLC method or 0.27% when analyzed using a HPLC method. It was noted that the higher strength formulation (NA-1a) was more stable than the low strength formulation (NA-1a-0.01%).

Regarding the other gel formulations, despite turning turbid at 40° C., formulations (AG-2a-0.01%) and (AG-2b-0.01%) exhibited drug purity that was consistent with previous time points.

The above data suggest that drug chemical stability is achieved at 25° C. and 40° C. for the 0.01% formulations.

B. Apparent pH of Formulations

The apparent pH of the formulations was measured at t=0 and at 2, 4, 6. 8. And 12 weeks of storage. It is noted that only data at 4 and 8 weeks are shown in Table 16. It should be noted that the formulations are not entirely aqueous, and therefore the pH is considered an apparent pH (USP <721>).

TABLE 16

Apparent pH under storage of 8 weeks at 25° C. or 40° C.

| Formulation | | T = 4 weeks | | T = 8 weeks | |
|---|---|---|---|---|---|
| ID | T = 0 | 25° C. | 40° C. | 25° C. | 40° C. |
| NA-1a-0.01% | 5.49 | 4.74 | 4.50 | 4.88 | 5.13 |
| AG-2a-0.01% | 6.20 | 6.19 | 6.18 | 6.10 | 5.45 |
| AG-2b-0.01% | 5.78 | 5.88 | 5.87 | 5.73 | 5.34 |
| AG-3c-0.01% | 5.78 | 5.63 | 5.51 | 5.57 | 5.49 |
| CR-1a-0.01% | 6.80 | 6.97 | 6.35 | 6.82 | 6.04 |
| EG-2a-0.01% | 6.41 | 6.47 | 6.53 | 6.17 | 6.17 |

Formulation apparent pH remained within 0.5 pH units of t=0 at both 25° C. and 40° C. for formulations containing water (e.g., AG-2a-0.01% to EG-2a-0.01%). The apparent pH of non-aqueous formulation (NA-1a-0.01%) has a decrease of 0.57 and 0.79 units observed, respectively. This trend for formulation (NA-1a-0.01%) continued at the 4 week time point, but no substantial change from the t=4 week time point was noted following 6 or 8 weeks of storage. No notable change in the pH was observed for the other formulations when compared to t=0.

It should be noted that formulation (NA-1a-0.01%) is the only entirely non-aqueous formulation and thus, the pH is apparent and therefore variability is anticipated (up to approximately 1 pH unit as referenced in USP chapter <791>).

C. Macroscopic Observations

The macroscopic observations (i.e. color, clarity, application and visual viscosity) of the formulations were recorded at 2, 4, 6, and 8 weeks (data are not shown here in the present application). The test results are summarized below:

Following 8 weeks of storage at 25° C. and 40° C., no obvious change from t=0 was observed from NA-1a-0.01%. A slight color change from t=0 was observed in formulations (AG-3c-0.01%) (colorless to faint yellow at both temperatures) and (CR-1a-0.01%) (off-white to faint beige). Formulation (EG-2a-0.01%) appeared to also increase in viscosity from t=0, making it more in line with what was previously observed with the high strength EG-2a variant.

Additionally, after 4 weeks of storage at 40° C., CR-1a-0.01% was observed to phase separate but this is likely due to the partial melting of excipients in the formulation (also observed for CR-1a at the higher strength of drug).

Formulation (NA-1a-0.01%) containing 0.01% drug did not appear to change in appearance from t=0 over 8 weeks, suggesting drug and polymer are physically stable in the formulation Following 8 weeks, formulation (AG-3c-0.01%) was observed to turn slightly yellow and became turbid at both temperatures, while turbidity was observed in formulations (AG-2a-0.01%) and (AG-2b-0.01%) following 8 weeks of storage at 40° C. only. Formulation (EG-2a-0.01%) was also reported to phase separated but only following 8 weeks of storage at both temperatures. Turbidity was noted in formulations (AG-2a-0.01%) and (AG-2b-0.01%) following 8 weeks of storage at 40° C., and in formulation (AG-3c-0.01%) following the same time at both temperatures, however no particulates were observed in the microscopy.

In summary, no obvious change from t=0 was observed in formulation (NA-1a-0.01%). While slight changes in the other formulations were observed, these were in line with some of the changes reported in the formulations containing higher levels of Compound 1.003. It should also be noted that the results suggest that Compound 1.003 is physically stable in the formulations.

Example 6: In Vitro Skin Permeation

Human skin from a single donor was mounted between the donor and receptor compartment of the flow through diffusion cell (with an exposed dosing surface area of about 1 cm$^2$). The skin was dosed with ca. 10 mg of Compound 1.003 (i.e., 10 mg/cm$^2$). A blank diffusion cell (no skin nor formulation) and skin mounted in a diffusion cell (skin without formulation) were included as controls. The pump was adjusted to maintain a continuous flow rate of approximately 6 μL/min (360 μL/hr) directly under the skin. Receptor solution was automatically collected into a 96 well plate at 3 hour intervals over the course of 24 h (8 time points) and analysed using a LC MS/MS method. Following 24 h, the residual formulation was removed from the surface of the skin and then the skin surface was tape stripped up to 5 times to remove residual formulation and the top of the skin surface layers (Stratum Corneum). The epidermis was then heat separated from the dermis by placing the skin into an incubator at 60° C. for 2 min, followed by manual separation using gloved hands. The amount of Compound 1.003 delivered to epidermis and dermis was quantified by the LC MS/MS method.

Table 17 summarizes the loading of Compound 1.003 in various formulations and corresponding compositions.

TABLE 17

Loading of Compound 1.003 in Various Formulations

| Formulation ID | Compound 1.003 (wt/wt %) | Composition |
|---|---|---|
| NA-1a-2.34% | 2.34 | Table 3 of Example 1 |
| NA-2a-0.96% | 0.96 | Table 4 of Example 1 |
| NA-2b-0.95% | 0.94 | |
| AG-1a-0.30% | 0.30 | Table 5 of Example 2 |
| AG-2a-0.70% | 0.70 | Table 6 of Example 2 |
| AG-2b-0.52% | 0.52 | |
| AG-3b-0.14% | 0.14 | Table 7 of Example 2 |
| AG-3c-0.45% | 0.45 | |
| LO-2a-0.13% | 0.13 | Table 8 of Example 3 |
| CR-1a-0.13% | 0.13 | Table 9 of Example 3 |
| EG-2a-0.34% | 0.34 | Table 10 of Example 3 |

A. Receptor Solution

Table 18 shows mean cumulative amount of Compound 1.003 (ng/cm$^2$) delivered to the receptor solution at 24 h and peak flux of Compound 1.003 (ng/cm$^2$/hr) following application of multiple formulations.

TABLE 18

Cumulative Amount and Flux Data in Receptor Solution

| Formulation ID | replicates | Cumulative Amount of Compound 1.003 (ng/cm$^2$) Mean Value | Peak Flux of Compound 1.003 (ng/cm$^2$/hr) Mean Value |
|---|---|---|---|
| NA-2a-0.96% | 4 | 41.02 | 5.36 |
| NA-1a-2.34% | 4 | 38.45 | 4.25 |
| NA-2b-0.95% | 4 | 31.27 | 2.19 |
| CR-1a-0.13% | 5 | 19.34 | 1.15 |
| AG-2b-0.52% | 5 | 17.47 | 1.45 |
| EG-2a-0.34% | 4 | 11.30 | 1.08 |
| AG-3c-0.45% | 5 | 10.33 | 0.75 |
| AG-1a-0.30% | 5 | 8.34 | 0.64 |
| AG-3b-0.14% | 4 | 7.95 | 0.52 |
| AG-2a-0.70% | 5 | 5.93 | 0.51 |
| LO-2a-0.13% | 5 | 0.06 | 0.02 |
| Blank | 2 | 0.07 | 0.01 |
| Flow through | 2 | 0.04 | 0.01 |

Table 19 shows mean cumulative amount of Compound 1.003 (ng/cm$^2$) delivered to the receptor solution at 24 h and peak flux of Compound 1.003 (ng/cm$^2$/hr) following application of multiple formulations in low strength formulations as compared to the corresponding formulations.

TABLE 19

Cumulative Amount and Flux Data in Receptor Solution

| Formulation ID | Cumulative Amount of Compound 1.003 (ng/cm$^2$) | | Peak Flux of Compound 1.003 (ng/cm$^2$/hr) | |
|---|---|---|---|---|
| | replicates | Mean Value | replicates | Mean Value |
| NA-1a-2.34% | 4 | 38.45 | 5 | 9.53 |
| CR-1a-0.13% | 5 | 19.34 | 5 | 1.15 |
| AG-2b-0.52% | 5 | 17.47 | 5 | 1.45 |
| EG-2a-0.34% | 4 | 11.30 | 5 | 1.76 |
| AG-3c-0.45% | 5 | 10.33 | 5 | 0.75 |
| AG-2a-0.70% | 5 | 5.93 | 5 | 0.51 |

TABLE 19-continued

Cumulative Amount and Flux Data in Receptor Solution

| Formulation ID | Cumulative Amount of Compound 1.003 (ng/cm$^2$) | | Peak Flux of Compound 1.003 (ng/cm$^2$/hr) | |
|---|---|---|---|---|
| | replicates | Mean Value | replicates | Mean Value |
| AG-2a-0.01% | 5 | 1.57 | 5 | 0.14 |
| AG-2b-0.01% | 5 | 1.26 | 5 | 0.11 |
| NA-1a-0.01% | 5 | 1.07 | 5 | 0.09 |
| AG-3c-0.01% | 4 | 0.73 | 5 | 0.11 |
| CR-1a-0.01% | 5 | 0.53 | 5 | 0.05 |
| EG-2a-0.01% | 4 | 0.32 | 5 | 0.07 |

B. Epidermis and Dermis

Table 20 summarizes mean cumulative amount of Compound 1.003 (expressed as percent applied dose) recovered from epidermis and dermis following application of 19 formulations.

TABLE 20

Cumulative Amount Data in Epidermis and Dermis

| Formulation ID | Epidermis (% Applied Dose) | | Dermis (% Applied Dose) | |
|---|---|---|---|---|
| | replicates | Mean Value | replicates | Mean Value |
| NA-1a-2.34% | 5 | 0.33 | 4 | 1.67 |
| AG-3c-0.45% | 5 | 0.71 | 5 | 5.27 |
| NA-2a-0.96% | 5 | 0.44 | 5 | 1.89 |
| NA-2b-0.95% | 5 | 0.48 | 4 | 1.94 |
| AG-1a-0.30% | 5 | 0.54 | 5 | 5.84 |
| CR-1a-0.13% | 4 | 1.68 | 5 | 11.76 |
| AG-3b-0.14% | 5 | 1.59 | 5 | 7.87 |
| AG-2a-0.70% | 5 | 0.48 | 5 | 1.38 |
| AG-2b-0.52% | 5 | 2.07 | 4 | 1.29 |
| EG-2a-0.34% | 5 | 7.79 | 5 | 1.47 |
| LO-2a-0.13% | 4 | 0.00 | 5 | 0.78 |
| AG-3c-0.01% | 5 | 1.91 | 5 | 7.85 |
| NA-1a-0.01% | 4 | 1.29 | 5 | 7.80 |
| AG-2b-0.01% | 5 | 3.48 | 5 | 5.85 |
| EG-2a-0.01% | 5 | 2.39 | 5 | 5.23 |
| AG-2a-0.01% | 5 | 1.19 | 5 | 3.48 |
| CR-1a-0.01% | 5 | 2.49 | 5 | 2.91 |

The summary of the above studies is provided below. For epidermis: EG-2a-0.34%, AG-2b-0.52%$_0$, and NA-1a-2.34% delivered similar amounts of Compound 1.003 to the epidermis (~800 to 2700 ng). For dermis: All formulations (with exclusion of AG-2b-0.52%, EG-2a-0.34%, and LO-2a-0.13%) delivered similar amounts of Compound 1.003 to the epidermis (~1000 to 4000 ng). For receptor solution: 1) NA-2a-0.95% and NA-1a-2.34% showed a trend for higher delivery of Compound 1.003 to the receptor solution compared to the remaining formulations, possibly due to the inclusion of the excipients Transcutol® and propylene glycol; 2) Only a single replicate of LO-2a-0.13% had detectable levels of Compound 1.003 (0.06 ng/cm$^2$) in the receptor solution. For low strength formulations: Across the "low strength" formulations, Compound 1.003 was detected in epidermis (12 to 35 ng), dermis (29 to 81 ng), and receptor solution (0.32 to 1.57 ng/cm$^2$).

Example 7: In Vivo Tolerability Study and Skin Permeation

Mouse Model 8 week old 129 mice are obtained from Jackson Laboratories and are shaved prior to the start of the study. 21 mice were used for study. Different doses of topical formulations including Compound 1.003 are applied to the hairless dorsal skin of the mouse. Skin biopsies are obtained prior to treatment and at different time points using 6 mm punches and subjected to Western blotting and immunohistochemistry.

Minipig Model

Non-GLP 28-Day Dermal Tolerability Study: 4 doses of A-D formulations applied to each of 4 pigs (2 females, 2 males), where A: vehicle (NA-1a without Compound 1.003) at 30 uL/cm$^2$; B: NA-1a-0.01% at 10 uL/cm$^2$; C: NA-1a-0.1% at 30 uL/cm$^2$; and D: NA-1a-0.1% at 10 uL/cm$^2$. Minipigs were treated QD (twice daily) for 28 days. Biopsy obtained 4 hours after last dose on Day 28. FIG. 1 shows dose dependent suppression of p-ERK by Compound 1.003 in gel formulation (NA-1a) in minipig skin.

Table 21 shows the correlation of p-ERK to concentrations of Compound 1.003 applied to skin in the 28-day tolerability study in the minipig.

TABLE 21

Correlation of p-ERK to Concentrations of Compound 1.003 Applied to skin

| | | Skin concentrations (ng/g) (p-ERK suppression (+/−)) | | |
|---|---|---|---|---|
| Animal # | A: Vehicle | B: NA-1a-0.01% at 10 uL/cm$^2$ | C: NA-1a-0.1% at 30 uL/cm$^2$ | D: NA-1a-0.1% at 10 uL/cm$^2$ |
| 194 | BQL (−) | 859 (−) | 4660 (−) | 7980 (+) |
| 195 | BQL (−) | 404 (−) | 3950 (−) | 4650 (+) |
| 196 | 534 (−) | 1640 (−) | 12600 (+) | 25700 (+) |
| 197 | 728 (−) | 1170 (+) | 5130 (+) | 7510 (+) |

(−) no p-ERK suppression; and
(+) p-ERK Suppression

GLP toxicology/TK study: The dermal toxic kinetics of Compound 1.003 in the NA-1a formulation was evaluated following daily dermal applications for 28 days in Gottingen minipigs in a GLP toxicology/TK study. Male and female minipigs (n=4 or 6/sex/group) received a single daily administration of Compound 1.003 for 28 days at 0.005%, 0.1%, 0.25%, or 0.5% w/w (0.06, 1.2, 3.0, and 6.0 mg/kg/dose, respectively) administered at 1.2 mL/kg/dose over 10% of BSA (400 cm$^2$). A dose density of 30 μL/cm$^2$ was previously shown to form a uniform layer of gel on minipig skin and was the maximum feasible amount that could be applied without excess. Therefore, for animals receiving formulations containing test item during this study, a fixed dose volume of 12 mL was applied to an area of 400 cm$^2$, giving a coverage of approximately 30 μL/cm$^2$.

Samples from each area of treated skin were taken at necropsy from all animals. The skin was trimmed and the stratum corneum was removed from the epidermis using a tape to give a sample consisting of the dermis and epidermis only. The skin was weighed and then homogenized with 1% formic acid in acetonitrile in a ratio of 1:9 (w/v), e.g., 1 g of sample into 9000 μL of 1% formic acid in acetonitrile. Samples were then stored frozen (<−70° C.) until analysis for the level of Compound 1.003 by LC-MS/MS.

The results for the concentration of Compound 1.003 in skin are shown in Table 22.

TABLE 22

Skin Concentration of Compound 1.003

| Dose Group | Concentration of Compound 1.003 (ng/g) | |
|---|---|---|
| | Male | Female |
| Vehicle (NA-1a) | 230* | 117* |
| NA-1a-0.005% | 856 | 1062 |
| NA-1a-0.1% | 17780 | 18453 |
| NA-1a-0.25% | 53967 | 22533 |
| NA-1a-0.5% | 22667 | 94333 |

*One pig per sex showed Compound 1.003 levels and remaining pigs were BQL; and all remaining data presented were mean of 3 pigs per group.

Figure 2:
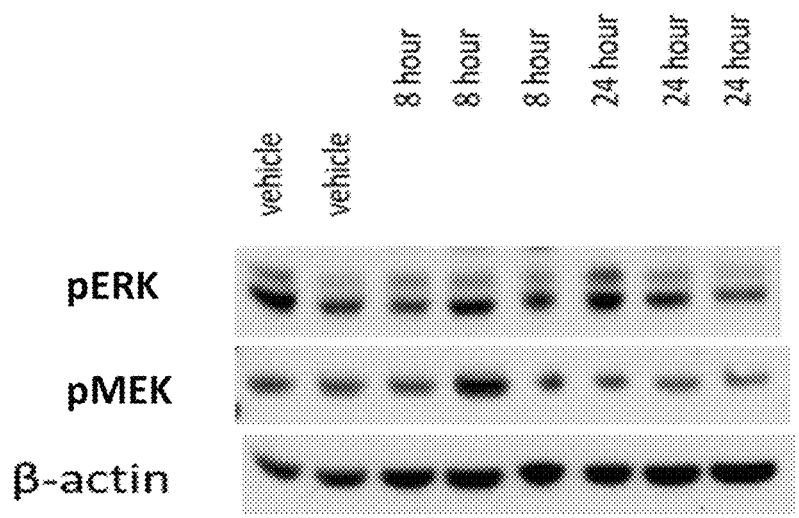
FIG. 2 shows no change of p-ERK after oral administration of Compound 1.003 at various doses.

Example 8: Evaluation of p-ERK Suppression by Oral Administration p-ERK suppression in rat skin was evaluated by oral administration of Compound 1.003. After 21-days of oral administration of Compound 1.003 at 300 mg/kg/day (Cmax ~1360 ng/mL), suppression of p-ERK was not observed in the skin. FIG. 2 shows no change of p-ERK after oral administration of Compound 1.003 at various doses.

It is believed to obtain levels of Compound 1.003 in the skin at a concentration sufficient to inhibit p-ERK, Compound 1.003 must be delivered topically in a cosmetically elegant, highly permeable, non-irritating formulation.

Example 9: Human cSCC Explant Protocol

Ex-Vivo Investigation of RAS/MAPK Pathway Suppression with a MEK Inhibitor Exposure in Human Explant Models of Squamous Cell Cancer (cSCC)

Study Objective: Ex-vivo investigation of RAS/MAPK pathway suppression exposure in human explant models of squamous cell cancer (cSCC).

Study Procedure: Three cSCC specimens were taken from patients undergoing excision of cSCC for clinical purposes. The specimen was cut into cuboids containing both epidermis and dermis which were then partially submerged in DMEM/F-12 medium supplemented with 2.5 ug/ml of Amphotericin B, and 50 units/ml of Penicillin-50 µg/ml of Streptomycin in a 384-square well plate with the epidermis exposed to the air. 0.1% Compound 1.003 in NA-1a gel formulation or vehicle gel was applied to the epidermal surface of the tumor for 4 hours. After drug treatment, the tissue was collected and fixed in formalin for immunohistochemistry analysis for phosphorylated-ERK1/2 (pERK), a downstream biomarker of the Ras/MAPK signaling pathway.

Figure 3:
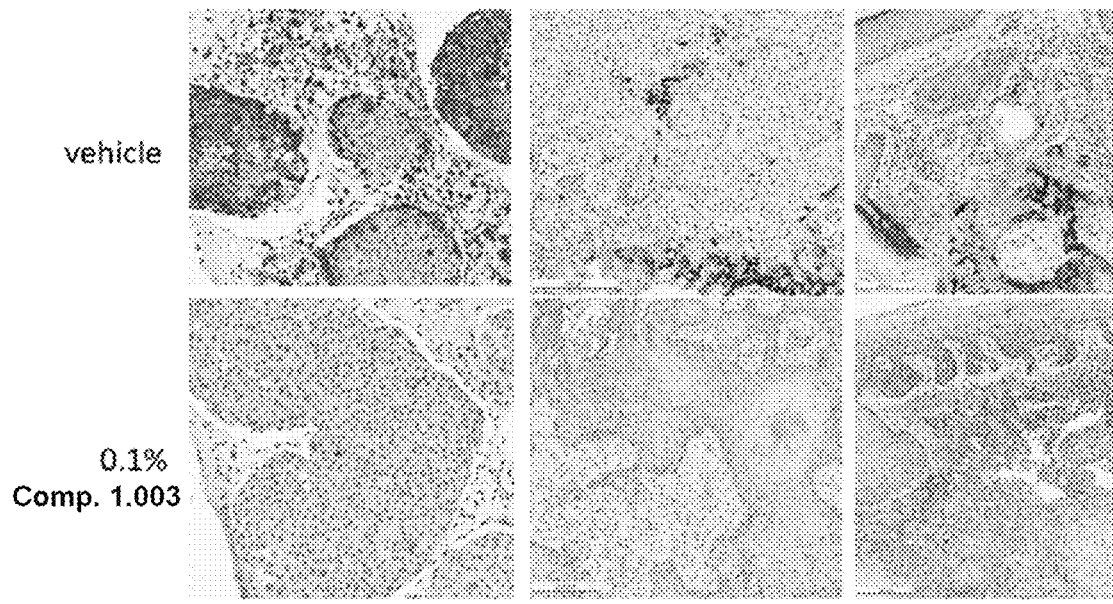
FIG. 3 shows robust suppression of p-ERK in the human cSCC specimens treated with Compound 1.003 in gel formulation (NA-1a) as compared with vehicle alone in human explant models of squamous cell cancer (cSCC).

FIG. 3: Immunohistochemistry of p-ERK (brown) showing SCC tumor cells with retained p-ERK expression in vehicle treated cSCC tumors but absent from cSCC tumors treated with 0.1% Compound 1.003. Immunohistochemistry for phosphorylated ERK demonstrated robust suppression of p-ERK in the drug treated specimens as compared with vehicle alone.

This demonstrates that topical application of Compound 1.003 can penetrate human skin and suppress the Ras/MAPK pathway in cSCC tissue.

Figure 4:
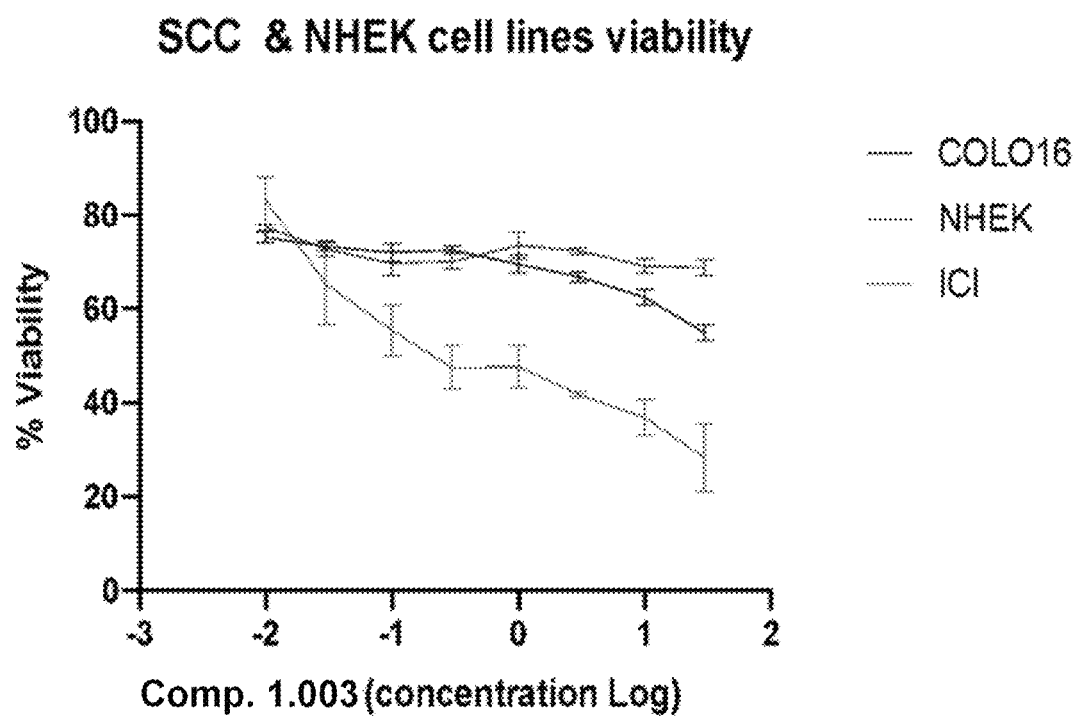
FIG. 4 shows cell viability in human SCC cell lines treated with Compound 1.003.

Assessment of Cellular-Viability after Application of a MEK Inhibitor in Keratinocytes Derived from Normal Skin and Squamous Cell Cancer Primary human keratinocytes (NHEK) and SCC cells (COLO 16 and ICI) were cultured in KGM-Gold basal medium supplemented with (hydrocortisone, transferrin, epinephrine, GA-1000, BPE, rhEGF, insulin) or DMEM/F-12 supplemented with Cholera toxin, Human Insulin, Hydrocortisone, Liothyronin, H-EGF and apotransferin respectively. The cell were plated in 96-well plates and treated for 72 hours with Compound 1.003 at 30, 10, 3, 1, 0.3, 0.1, 0.03, 0.01 µM concentrations along with the control (DMSO only) in triplicates. Cell viability measured using the CellTiter-Glo Luminescent Cell Viability Assay (Promega). DMSO served as the negative control and doxorubicin (30 µM) as the positive control. Cell viability assay demonstrated dose dependent reduction in cell viability of both SCC cell lines (COLO 16 and ICI) as compared to normal human keratinocytes (NHEK). The results are shown in FIG. 4.

Example 10: In Vivo Model of cSCC—Chemoprevention Study

Mouse Model: The UV-driven cuSCC model used here has been described extensively, for example *Journal of Investigative Dermatology*, vol. 136, no. 9, 2016, pp. 1920-1924 by Adelmann, C. H., et al., the entirety of which is incorporated herein by reference for all purposes. UV radiation was administered using a solar simulator (Oriel) metered at 12.5 kJ/m$^2$ UVB weekly, 3.4 SED for three months on Hairless SKH-1E mice. Papillomas typically develop within the following 1-2 months, approximately 10% of which become invasive cSCC.

Samples: The gel formulation (NA-1a) including Compound 1.003 in an amount of 0.1%, 0.5%, 1.0%, and 2.3% by weight of the formulation was used in the study.

Topical Application of Compound 1.003 Prevents the Formation of cSCC in a UV-Driven Mouse Model without Systemic Toxicity.

A UV-driven mouse model was used to test if a topical formulation including Compound 1.003 could be used to reduce tumor burden in vivo. Four doses of Compound 1.003 (n=10 per group) were administered to mice that had been chronically irradiated using low-dose UV light (12.5 kJ/m$^2$ UVB weekly) for three months. Once a mouse developed one tumor that measured 3 mm in diameter, they were randomly assigned to receive Vehicle, 0.1% Compound 1.003, 0.5% Compound 1.003, 1.0% Compound 1.003, or 2.3% Compound 1.003. Once enrolled, mice were treated with 200 uL of vehicle or the gel formulation of Compound 1.003. Drug was evenly applied to the back skin of the mouse and allowed to dry. Mice were treated for 30 days (5 d/week). Mice that were treated with vehicle showed an increased number of tumors (n=60 tumors) at the end of treatment compared to those treated with the MEK inhibitor (e.g., Compound 1.003) (2.3% n=16 tumors, 1.0% n=13 tumors, 0.5% n=23 tumors, 0.1% n=31) (see FIG. 5). The highest doses of Compound 1.003 resulted in an approximately 4-fold decrease in the total number of tumors that were present at the end of treatment. No skin peeling or erosions were observed. Biweekly weight measurement revealed no weight loss. Skin biopsies were obtained 4 hours after drug treatment at end of study. Nano-immunoassay for p-ERK1/2 and total ERK1/2 demonstrated suppression of p-ERK levels in skin biopsies of mice treated with Compound 1.003 at 0.1% and greater as compared with mice treated with vehicle (0.1% vs vehicle, p=0.02; 0.5% vs vehicle, p=0.04; 1% vs vehicle, p=0.02, 2.3% vs vehicle, p=0.01 by t-test). Results are shown in FIG. 5.

Figure 5:
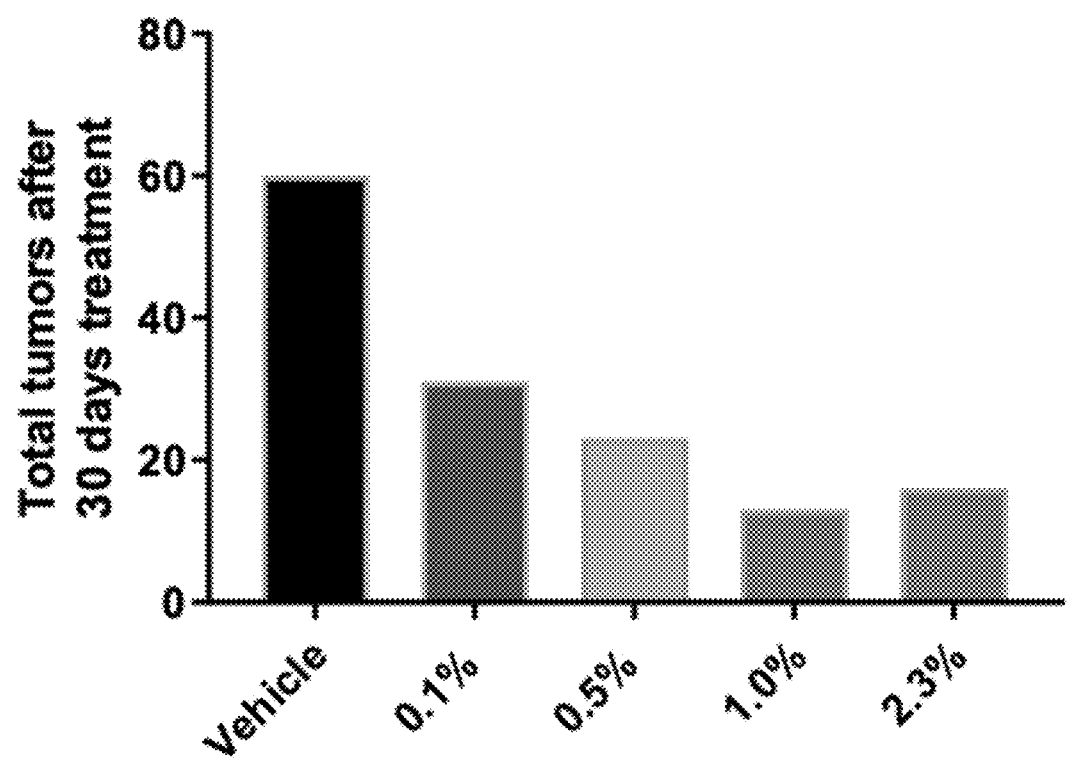
FIG. 5 shows suppression of total tumors in the UV-drive mouse model of cSCC after the treatment with Compound 1.003 in gel formulation (NA-1a).
Figure 6A:
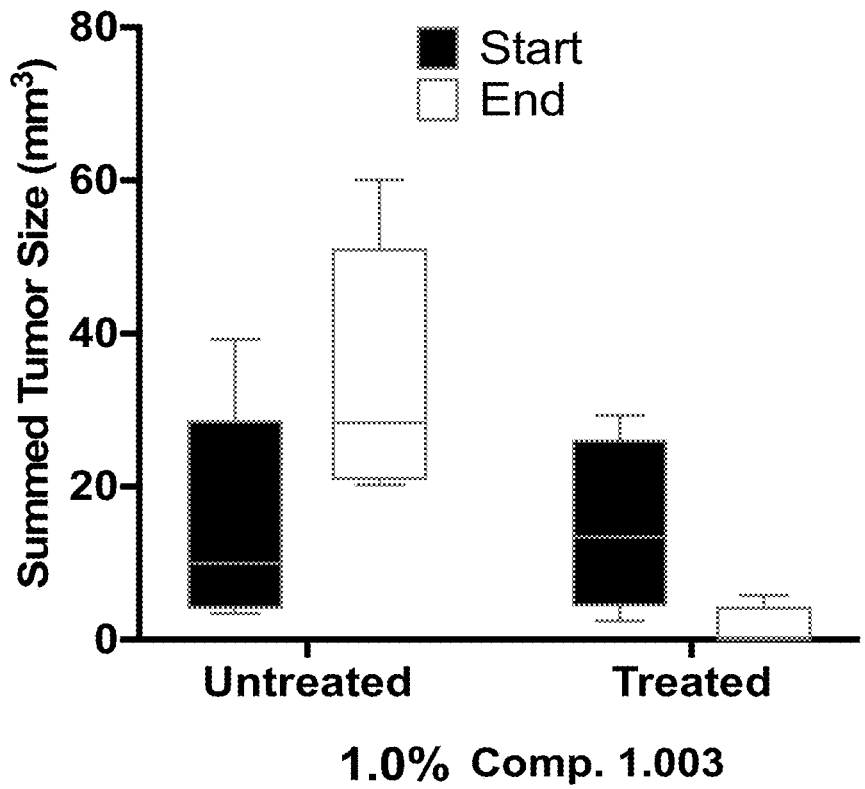
FIGS. 6A-6B show a local and targeted suppression of cSCC in only areas treated with Compound 1.003 in gel formulation (NA-1a).

FIG. 5: Compound 1.003 dramatically suppresses new tumor formation in UV-drive mouse model of cuSCC. Total tumors remaining after 30 days of treatment with the indicated concentrations of Compound 1.003 are shown in FIG. 5 with near complete suppression of new tumors at 1.0% dose and above (n=10 per group). To internally control for potential systemic exposure, 5 mice were treated in split-control fashion with one side getting vehicle only and the other side of the same mouse receiving topical 1.0% Compound 1.003. Total tumor burden (summed volume) is quantified in untreated vs. treated sides at the beginning (black) as compared to the end of treatment 30 days later (n=5). Substantial tumor regression and tumor suppression is noted only on the treated side (FIG. 6A).

Compound 1.003 Demonstrates a Local and Targeted Suppression of cSCC in Only Drug-Treated Areas in a Split-Mouse Study To definitively address the possibility of systemic exposure and non-local effects of topically applied Compound 1.003, 5 mice was treated in split-control fashion with one side with vehicle only and the other side with 1.0% Compound 1.003. Total tumor volume decreased to nearly undetectable levels on the treated side (FIG. 6A), in contrast to the untreated side, in which total tumor burden increased by about 3-fold over the same time period.

Figure 6B:
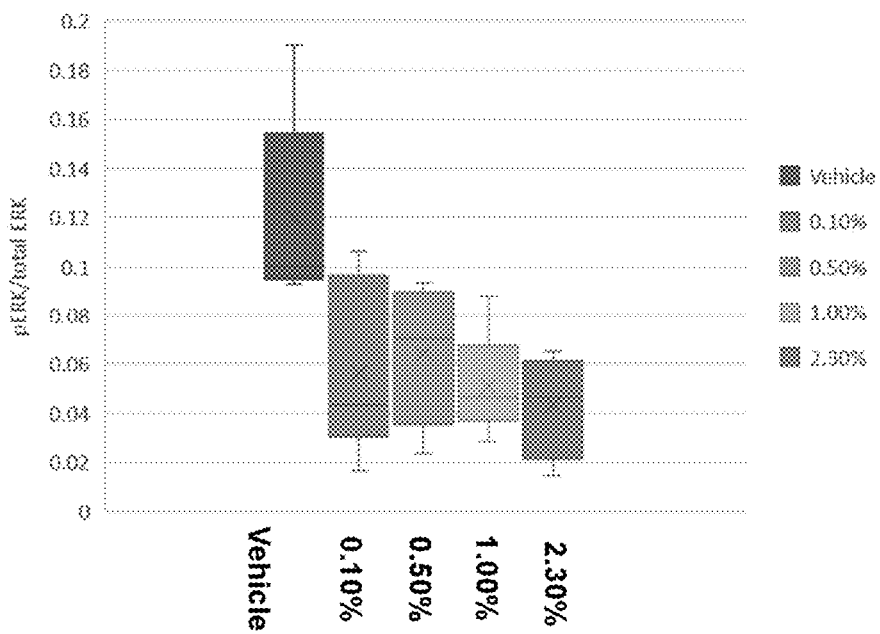

With respect to p-ERK/total-ERK levels, FIG. 6B demonstrates 65 or greater suppression of p-ERK levels in mouse skin treated with Compound 1.003 at concentrations 0.6 or greater.

This demonstrates that the effect of cSCC in SCC chemoprevention is localized only to the area of application.

Example 11: Optimization of Gel Formulations (NA-1) (First Round)

The gel formulations were further optimized with addition of a preservative and modification of the antioxidant levels/system, according to Table 23A and Table 23B.

TABLE 23A

Modified Gel Formulations (about 2.3% of Compound 1.003 by Weight)

| Function | Components | Compositions (wt/wt %) | | |
|---|---|---|---|---|
| | | NA-1aa | NA-1b | NA-1c |
| API | Compound 1.003* | 2.36 | 2.36 | 2.36 |
| Organic solvents | S.R. PEG-400* | 51.09 | 51.84 | 50.94 |
| | Transcutol ® HP** | 42.50 | 42.50 | 42.50 |
| Antioxidant/stabilizer | Ascorbyl palmitate | 0.03 | — | — |
| | Alpha tocopherol acetate | 0.02 | — | — |
| Antioxidant | Butylated hydroxytoluene | — | 0.20 | 0.20 |
| Preservative | Potassium sorbate | — | 0.10 | — |
| | Phenoxyethanol | 1.00 | — | 1.00 |
| Gelling agent | HPC HF | 0.50 | 0.50 | 0.50 |
| pH adjuster | 0.1M citric acid in Transcutol ® HP | To pH 5-6 | | |
| Organic solvents | 2$^{nd}$ addition of Transcutol ® HP | Q.S. 100 | | |
| | Total | 100 | 100 | 100 |

*The amount of Compound 1.003 and S.R. PEG-400 added may be adjusted based on API purity/potency;

**Part of Transcutol ® was adjusted to compensate the addition of the pH adjusting solution and final Q.S. 100; and Abbreviations: S.R. - super refined; HP - high purity; and Q.S. - quantum satis

TABLE 22B

Modified Gel Formulations (about 0.1% of Compound 1.003 by Weight)

| Function | Components | Compositions (wt/wt %) | | |
|---|---|---|---|---|
| | | NA-1aa | NA-1b | NA-1c |
| API | Compound 1.003* | 0.10 | 0.10 | 0.10 |
| Organic solvents | S.R. PEG-400* | 53.35 | 54.10 | 53.20 |
| | Transcutol ® HP** | 42.50 | 42.50 | 42.50 |
| Antioxidant/stabilizer | Ascorbyl palmitate | 0.03 | — | — |
| | Alpha tocopherol acetate | 0.02 | — | — |
| Antioxidant | Butylated hydroxytoluene | — | 0.20 | 0.20 |
| Preservative | Potassium sorbate | — | 0.10 | — |
| | Phenoxyethanol | 1.00 | — | 1.00 |
| Gelling agent | HPC HF | 0.50 | 0.50 | 0.50 |
| pH adjuster | 0.1M citric acid in Transcutol ® HP | To pH 5-6 | | |
| Organic solvents | 2$^{nd}$ addition of Transcutol ® HP | Q.S. 100 | | |
| | Total | 100 | 100 | 100 |

*The amount of Compound 1.003 and S.R. PEG-400 added may be adjusted based on API purity/potency;

**Part of Transcutol ® was adjusted to compensate the addition of the pH adjusting solution and final Q.S. 100; and Abbreviations: S.R. - super refined; HP - high purity; and Q.S. - quantum satis Example 12: Short-Term Stability of First-Round Modified Gel Formulations (NA-1)

The gel formulations of Table 23A and Table 23B were manufactured and filled into 30 g coated HDPE tubes (Montebello) and assessed for their short-term stability under storage of 12 weeks at 25° C. or 40° C. The following tests were performed: A) Compound 1.003 content and impurity (n=3 for content and n=1 for impurity); B) Apparent pH (n=1); C) Macroscopic appearance (n=1); D) Microscopic appearance (n=1); E) Microbial Quality Testing (MQT; n=1); and F) Preservative Efficacy Testing (PET; n=1).

A. Content and Purity of Compound 1.003

The content and purity of Compound 1.003 was determined by a HPLC method. Purity and recovery of Compound 1.003 were measured at 2, 4, 6, 8, and 12 weeks stored at 25° C. or 40° C. It is noted that only data at 4 and 12 weeks were shown in Table 24 and Table 25.

TABLE 24

Purity of Compound 1.003 under storage of 12 weeks at 25° C. or 40° C.

| Formulation ID | T = 0 (%) | T = 4 weeks (%) | | T = 12 weeks (%) | |
|---|---|---|---|---|---|
| | | 25° C. | 40° C. | 25° C. | 40° C. |
| NA-1aa-0.1% | 97.36 | 97.48 | 97.51 | 97.31 | 97.05 |
| NA-1aa-2.3% | 97.31 | 97.58 | 97.46 | 97.25 | 97.42 |
| NA-1b-0.1% | 97.06 | 97.11 | 96.90 | 96.95 | 96.39 |
| NA-1b-2.3% | 97.66 | 97.49 | 97.70 | 97.60 | 97.55 |
| NA-1c-0.1% | 97.27 | 97.31 | 96.88 | 97.03 | 95.49 |
| Na-1c-2.3% | 97.63 | 97.69 | 97.67 | 97.46 | 97.52 |

TABLE 25

Recovery of Compound 1.003 under storage of 12 weeks at 25° C. or 40° C.

| Formulation ID | T = 0 (%) | T = 4 weeks (%) | | T = 12 weeks (%) | |
|---|---|---|---|---|---|
| | | 25° C. | 40° C. | 25° C. | 40° C. |
| NA-1aa-0.1% | 107.19 (106.21-108.10) | 105.65 (105.24-106.43) | 103.90 (103.01-105.37) | 106.71 (105.93-107.17) | 104.18 (100.81-106.46) |
| NA-1aa-2.3% | 97.68 (95.82-98.68) | 98.91 (96.88-100.71) | 100.43 (99.73-101.43) | 96.80 (96.71-96.91) | 98.54 (98.30-98.72) |
| NA-1b-0.1% | 100.42 (100.12-100.78) | 100.06 (99.55-100.47) | 99.71 (99.01-100.45) | 102.01 (101.36-103.11) | 99.70 (98.52-101.86) |
| NA-1b-2.3% | 97.77 (96.70-98.32) | 95.89 (94.05-96.87) | 98.33 (96.62-100.17) | 95.63 (95.53-95.71) | 97.38 (96.44-97.90) |
| NA-1c-0.1% | 109.61 (109.19-110.12) | 113.94 (113.83-114.10) | 108.57 (106.35-109.93) | 115.72 (114.73-116.72) | 112.64 (112.29-112.99) |
| Na-1c-2.3% | 96.50 (95.09-97.86) | 94.64 (94.10-95.49) | 99.00 (97.20-102.39) | 94.37 (93.92-94.79) | 97.76 (96.47-98.93) |

At t=0, the recovery of Compound 1.003 was slightly variable (96.5-109.61%) which may have been as a result of the gelling agent not being fully solvated and therefore not homogenous in the batch. The variation in the recovery data continued over the duration of the stability experiments at 2 weeks (91.78-114.70%) and 4 weeks (91.78-108.57%) continuing into the 12 week time point (94.37-115.72%) with no overall trend for increase or decrease in recovery. Although there are no obvious issues with drug recovery, Applicant notes that the peak purity result gives a more accurate indication of batch stability.

The peak purity of Compound 1.003 following storage for 12 weeks at 25° C. was consistent with that observed at t=0. Over the duration of the experiment, the peak purity of Compound 1.003 was between 97.03-97.60% area at 12 weeks, which was in line with t=0 (97.06-97.66% area) for all formulations with exception of a trend of slightly decreasing peak purity was observed for formulations (NA-1b-0.1%) and (NA-1c-0.1%). All formulations, other than NA-1c-0.1% (95.49% area) and NA-1b-0.1% (96.39% area), were also observed to have comparable peak purity values to t=0 following storage at 40° C. for 12 weeks (97.05-97.55% area). This trend in the slightly decreasing peak purity for formulation (NA-1b-0.1%) and (NA-1c-0.1%) continued from the t=4 weeks storage result (96.90 and 96.88% area, respectively). The major degradants (RRT 1.01; 1.05; 1.28; 1.33) do not show much growth over the stability period and were largely in-line with the values observed at t=0 with the exception of NA-1b-0.1% and NA-1c-0.1% at 40° C. Nevertheless, all formulations under the study maintained the desired stability of Compound 1.003 with a peak purity of >95% area by the HPLC method.

The above short-term stability study demonstrates that the modification of the antioxidant and inclusion of the preservative has no negative impact on the purity of Compound 1.003 overtime.

B. Apparent pH of Formulations

The apparent pH of the formulations was measured at t=0 and at 2, 4, 6. 8. And 12 weeks of storage. It is noted that only data at 4 and 12 weeks were shown in Table 26. It should be noted that the formulations are not entirely aqueous, and therefore the pH is considered an apparent pH (USP <721>).

TABLE 26

Apparent pH under storage of 12 weeks at 25° C. or 40° C.

| Formulation ID | T = 0 | T = 4 weeks | | T = 12 weeks | |
|---|---|---|---|---|---|
| | | 25° C. | 40° C. | 25° C. | 40° C. |
| NA-1aa-0.1% | 5.35 | 5.09 | 4.87 | 4.84 | 5.05 |
| NA-1aa-2.3% | 5.35 | 4.99 | 4.93 | 4.96 | 4.86 |
| NA-1aa PLB | 5.12 | 4.56 | 4.79 | 4.96 | 4.86 |
| NA-1b-0.1% | 5.90 | 6.24 | 6.18 | 5.91 | 6.19 |
| NA-1b-2.3% | 5.66 | 5.89 | 5.81 | 5.78 | 6.27 |
| NA-1b PLB | 5.85 | 5.98 | 6.16 | 6.08 | 6.40 |

TABLE 26-continued

Apparent pH under storage of 12 weeks at 25° C. or 40° C.

| Formulation | | T = 4 weeks | | T = 12 weeks | |
|---|---|---|---|---|---|
| ID | T = 0 | 25° C. | 40° C. | 25° C. | 40° C. |
| NA-1c-0.1% | 7.01 | 6.89 | 7.07 | 7.19 | 6.83 |
| Na-1c-2.3% | 5.63 | 5.66 | 5.66 | 5.74 | 5.90 |
| NA-1c PLB | 6.78 | 6.66 | 6.98 | 7.06 | 7.03 |

At t=0, the apparent pH of the active formulations ranged from 5.35-7.01. Although the initial adjustment of formulation (NA-1c-0.1%) was below pH 7, it was suspected that further solvation of the gelling agent may have led to a slight increase in the pH.

Over 12 weeks storage at 25° C. and 40° C., the apparent pH was remained consistent with the values observed at t=0 (within 1 pH unit of the t=0 values). As the pH of non-aqueous gel formulations is apparent, the noted variability is anticipated (up to approximately 1 pH unit as referenced in USP chapter <791>).

Overall, the modification to the formulation (inclusion of a preservative and modification of the antioxidant type/level) has no impact on the stability of the formulation with respect to apparent pH change overtime. A closely monitoring the process to ensure the initial pH closer to pH 5 is recommended, as these modifications may impact the initial pH of the formulations.

C. Macroscopic Observations

The macroscopic observations (i.e. color, clarity, application and visual viscosity) of the formulations were recorded at 2, 4, 6, 8, and 12 weeks (data are not shown here in the present application). The test results are summarized below:

At t=0, all placebo and formulations having 0.1% w/w Compound 1.003 were colorless, clear, low viscosity and had smooth application. The formulations prepared at 2.3 w/w % API were light brown due to the increased concentration of Compound 1.003. Following 12 weeks storage at 25° C. and 40° C., there was no change in the macroscopic observations for the formulations. It appears that the changes in antioxidant content/type and inclusion of a preservative have no impact on the macroscopic properties of the formulation.

C. Microscopic Observations

The microscopic appearance of formulations were recorded at 2, 4, 6, 8, and 12 weeks (data are not shown here in the present application). The test results are summarized below:

At t=0, all formulations were monophasic and free of API crystals. However, gelling agent which had not fully solvated was observed in a number of the formulations (NA-1aa (2.3%, 0.1% and placebo) and NA-1c (placebo only)), suggesting that the formulations may require a slightly longer period of stirring following addition of gelling agent during manufacture. Following 2 weeks storage at 25° C. and 40° C., there was no change in the microscopic appearance, except that the gelling agent was fully solvated in the formulations. Following 12 weeks storage at 25° C. and 40° C., the microscopic appearance was consistent with the t=2 and 4 week time points (i.e. no gelling agent observed). The inclusion of a preservative and modification of the antioxidant type/level appear to have no impact on the microscopic properties of the formulation.

E. Microbial Quality Testing

MQT was performed on the formulations at t=0 and at 12 weeks. At t=0 and t=12 weeks, all samples assessed passed the microbial quality testing (MQT) specifications (e.g., passed EP, USP and JP requirements), which were as follows: Total Aerobic Microbial Count; NMT 100 CFU/g; Total Combined Yeast/Moulds; NMT 10 CFU/g; *P. aeruginosa*: absent in 1 g; and *S. aureus*: absent in 1 g.

F. Preservative Efficacy Testing

PET was performed on the formulations at t=0 and 12 weeks. The PET results confirm that the NA-1aa (0.1%, 2.3% and PLB) and NA-1b (0.1%, 2.3% and PLB) and NA-1c (2.3%) formulations have the ability to prevent microbial growth in the case of ingress.

Example 13: Optimization of Gel Formulations (NA-1) (Second Round)

The gel formulations were further studied to optimize viscosity. The optimization included the amount of HPC HF, an alternative grade of HPC (e.g., MF), and an additional thickening agent (e.g., PEG-1500), for example according to Table 27A and Table 27B

TABLE 27A

Modification of Gel Formulations (NA-1b)

| Excipient | Composition of NA-1b variant formulations (% w/w) | | | | |
|---|---|---|---|---|---|
| | NA-1b-V1 | NA-1b-V2 | NA-1b-V3 | NA-1b-V4 | NA-1b-V5 |
| S.R. PEG-400* | 53.95 | 53.70 | 53.20 | 50.70 | 52.20 |
| Transcutol ® HP** | 42.50 | 42.50 | 42.50 | 42.50 | 42.50 |
| PEG-1500 | — | — | — | — | 2.00 |
| BHT | 0.20 | 0.20 | 0.20 | 0.20 | 0.20 |
| Potassium Sorbate | 0.10 | 0.10 | 0.10 | 0.10 | 0.10 |
| HPC HF | 0.75 | 1.00 | 1.50 | | 0.50 |
| HPC MF | | | | 4.00 | |
| 0.1M citric acid in Transcutol ® HP | | | to pH 5-6 | | |
| 2nd addition of Transcutol ® HP | | | Q.S. 100 | | |

*The amount of Compound 1.003 and S.R. PEG-400 added may be adjusted based on strength (e.g., 2.3% or 0.1% by weight) and API purity/potency;
**Part of Transcutol ® was adjusted to compensate the addition of the pH adjusting solution and final Q.S. 100; and
Abbreviations: S.R. - super refined; HP - high purity; Q.S. - quantum satis; and BHT - Butylated hydroxytoluene

TABLE 26B

Modification of Gel Formulations (NA-1c)

Composition of NA-1b variant formulations (% w/w)

| Excipient | NA-1c-V1 | NA-1c-V2 | NA-1c-V3 | NA-1c-V4 | NA-1c-V5 |
|---|---|---|---|---|---|
| S.R. PEG-400* | 53.05 | 52.80 | 52.3 | 49.80 | 51.30 |
| Transcutol ® HP** | 42.50 | 42.50 | 42.50 | 42.50 | 42.50 |
| PEG-1500 | — | — | — | — | 2.00 |
| BHT | 0.20 | 0.20 | 0.20 | 0.20 | 0.20 |
| Phenoxyethanol | 1.00 | 1.00 | 1.00 | 1.00 | 1.00 |
| HPC HF | 0.75 | 1.00 | 1.50 | | 0.50 |
| HPC MF | | | | 4.00 | |
| 0.1M citric acid in Transcutol ® HP | | | to pH 5-6 | | |
| 2nd addition of Transcutol ® HP | | | Q.S. 100 | | |

*The amount of Compound 1.003 and S.R. PEG-400 added may be adjusted based on strength (e.g., 2.3% or 0.1% by weight) and API purity/potency;
**Part of Transcutol ® HP was adjusted to compensate the addition of the pH adjusting solution and final Q.S. 100; and
Abbreviations: S.R. - super refined; HP - high purity; Q.S. - quantum satis; and BHT - Butylated hydroxytoluene In summary, modifications to formulation (NA-1) were made including a preservative and a change in the antioxidant type/level. These changes appear to have no impact on the macroscopic, microscopic, or pH stability of the formulations over time. The chemical stability of formulations was observed to be consistent with gel formulations (NA-1a). In fact, most modified gel formulations showed improvement in chemical stability of Compound 1.003.

Example 14: Manufacturing Process for Preparing Gel Formulations

The manufacturing process for preparing gel formulations includes steps as follows: making the PH adjustment solutions in side vessels; dissolving the excipients in the main vessel; adjusting the pH of the mixture; dissolving the Active Pharmaceutical Ingredient (API) (e.g., Compound 1.003) in the mixture; adjusting the pH of the solution; adding the remainder of the Transcutol® HP; adding the Klucel™ HF gelling agent; and mixing until gelled. Visual observation of the formed formulations as well as pH checks were performed to meet the requirements.

Figure 7:
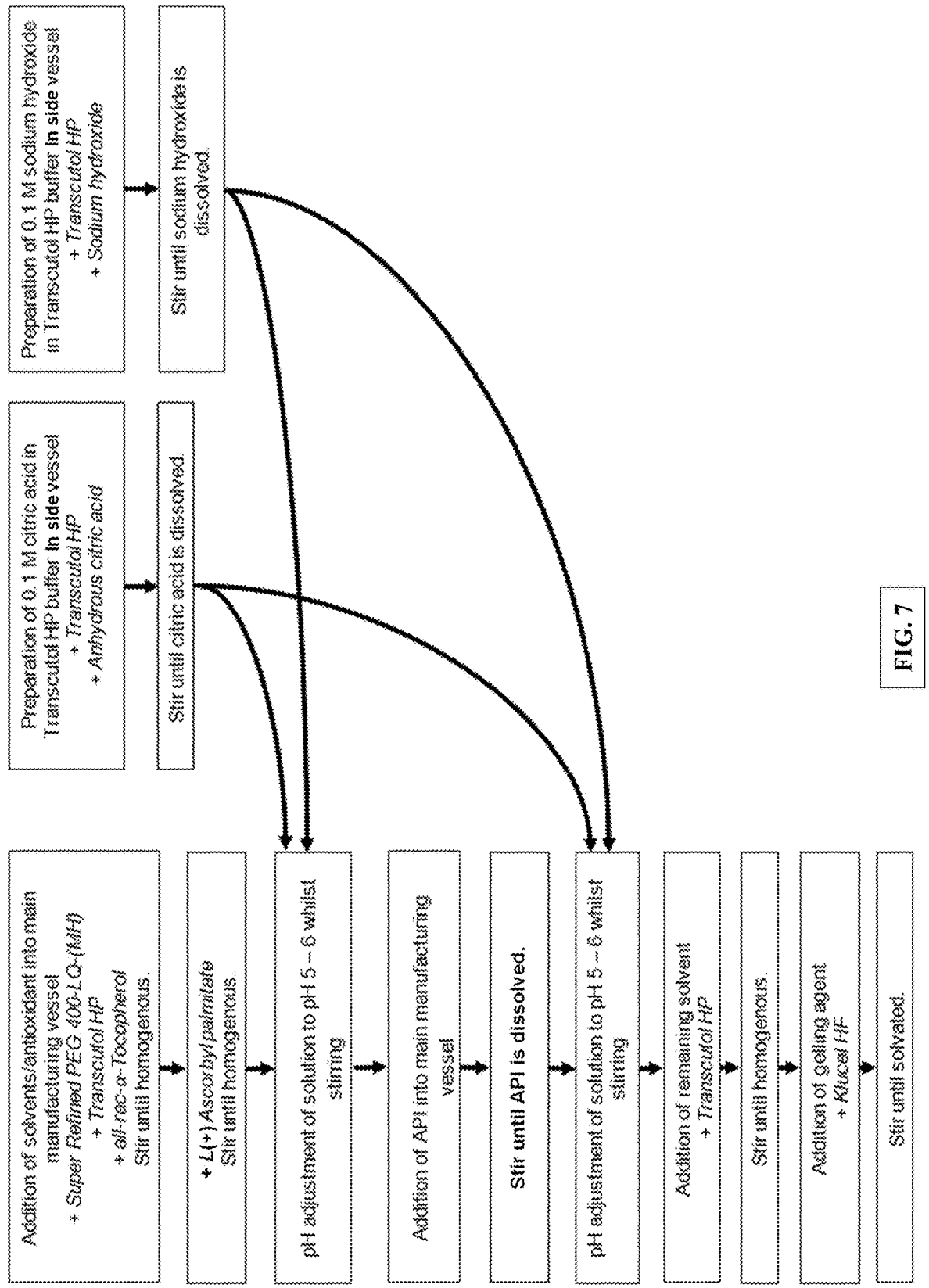
FIG. 7 shows the manufacturing process flow diagram for preparing gel formulation (NA-1a) including Compound 1.003.

The manufacturing process flow diagram for gel formulation (NA-1a) including Compound 1.003 is illustrated in FIG. 7.

The gel formulations (NA-1a) were prepared according to the manufacturing process using the excipients of Table 28.

TABLE 28

Gel Formulation (NA-1a)

| | | Compositions (wt/wt %) | | |
|---|---|---|---|---|
| Function | Components | NA-1a-0.05% | NA-1a-0.15% | NA-1a-0.5% |
| API | [1]Compound 1.003 | 0.05 | 0.15 | 0.5 |
| Organic solvents | [1]S.R. PEG-400 | 54.398 | 54.298 | 53.948 |
| | [2]Transcutol ® HP | 45.000 | 45.000 | 45.000 |
| Antioxidant/ stabilizer | Ascorbyl palmitate | 0.050 | 0.050 | 0.050 |
| | Vitamin E acetate (all-rac-α-tocopherol acetate) | 0.002 | 0.002 | 0.002 |
| pH adjuster | 0.1M citric acid in Transcutol ® HP | | q.s. to pH 5-6 | |
| | 0.1M sodium hydroxide in Transcutol ® HP | | q.s. to pH 5-6 | |
| Gelling agent | HPC (Klucel ™ HF) | 0.500 | 0.500 | 0.500 |
| | Total | 100.0 | 100.0 | 100.0 |

Figure 8:
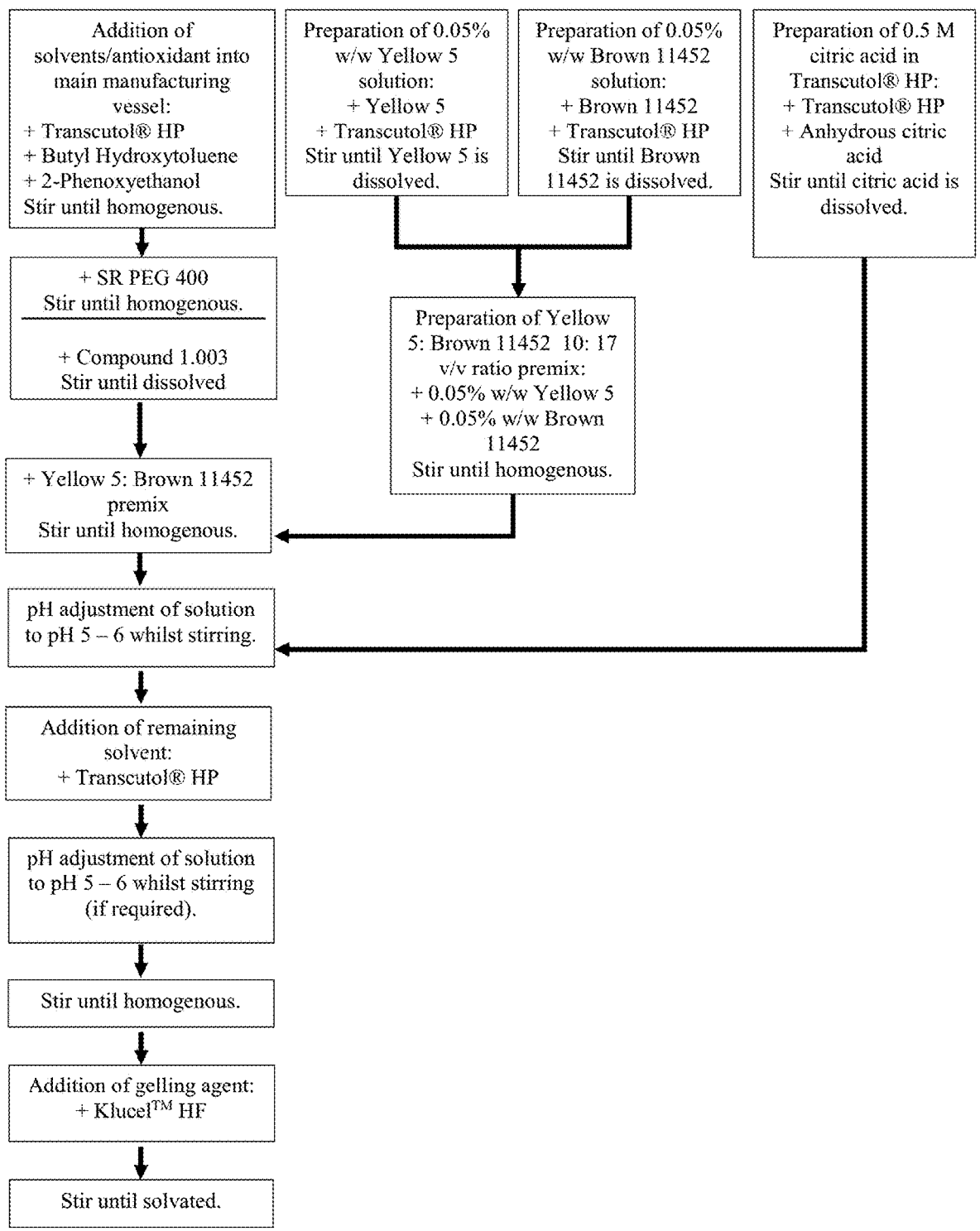
FIG. 8 shows the manufacturing process flow diagrams for preparing gel formulation (NA-1c-V2-0.5%) including Compound 1.003 in 0.5% by weight.
Figure 9:
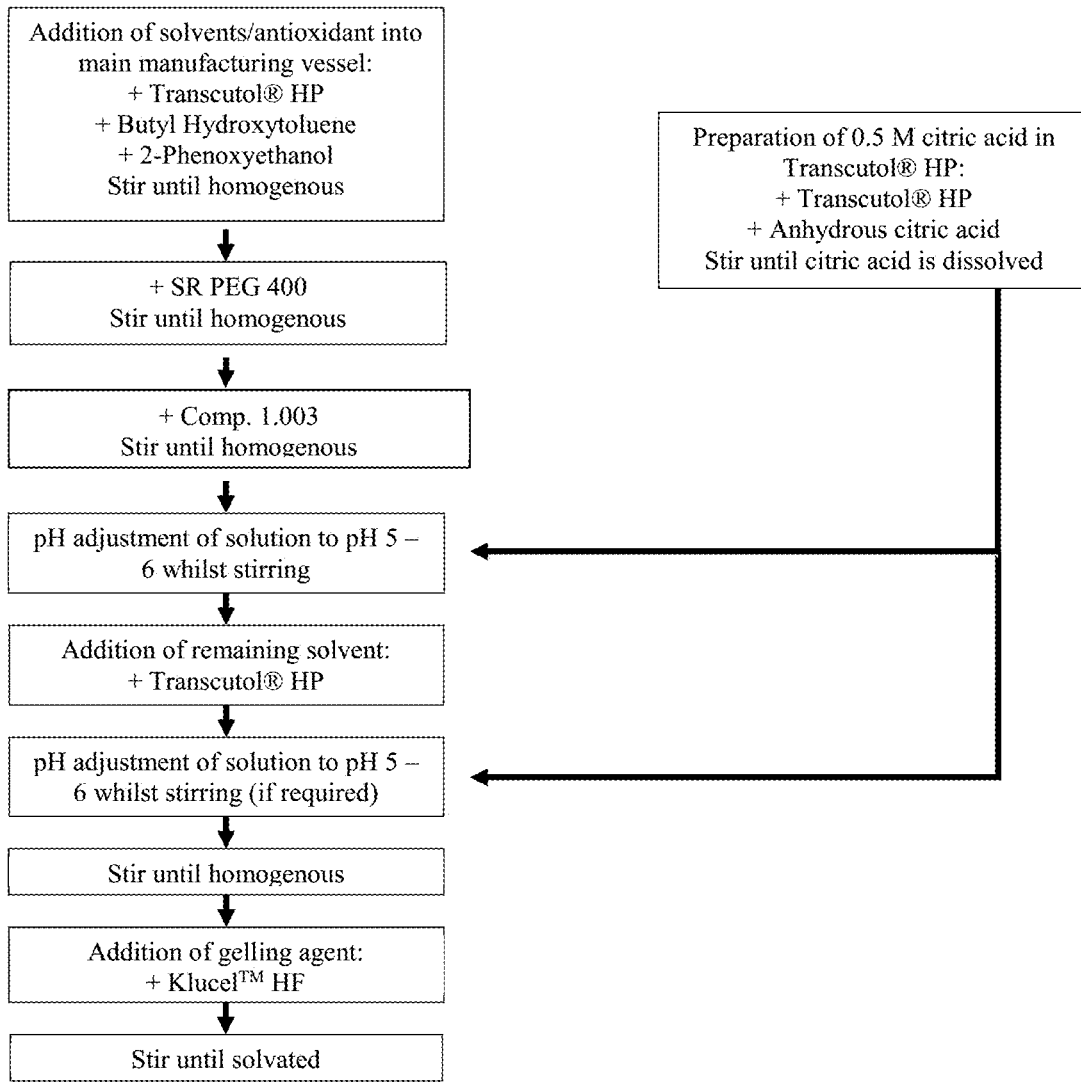
FIG. 9 shows the manufacturing process flow diagrams for preparing gel formulation (NA-1c-V2-1.5%) including Compound 1.003 in 1.5% by weight.

[1]The amount of Compound 1.003 and S.R. PEG-400 added may be adjusted based on API purity/potency;
[2]Part of Transcutol ® HP was adjusted to compensate the addition of the pH adjusting solution; and
Abbreviations: S.R. - super refined; HP - high purity; and Q.S. - quantum satis The manufacturing process flow diagram for gel formulation (NA-1c-V2-0.5%) including Compound 1.003 (in 0.50 by weight) is illustrated in FIG. 8. The manufacturing process flow diagram for gel formulation (NA-1c-V2-1.5%) including Compound 1.003 (in 1.5% by weight) is illustrated in FIG. 9.

The gel formulations (NA-1c-V2-0.5%) and (NA-1c-V2-1.5%) were prepared according to the manufacturing process using the excipients of Table 29.

TABLE 29

Gel Formulations (NA-1c-V2-0.5%) and (NA-1c-V2-1.5%)

| Function | Components | Compositions (wt/wt %) | |
| --- | --- | --- | --- |
| API | [1]Compound 1.003 | 0.5 | 1.5 |
| Organic solvents | [1]S.R. PEG-400 | 52.30 | 51.30 |
| | [2]Transcutol ® HP | 44.9833 | 45.00 |
| Antioxidant | Butylated hydroxytoluene | 0.20 | 0.20 |
| Preservative | Phenoxyethanol | 1.00 | 1.00 |
| Color dyes | [3]Neelicert FD&C Yellow #5 (Prepared as a 0.05% w/w in Transcutol ® HP) | 0.0062 | — |
| Color dyes | [3]Neelicert FD&C Brown 11452 (prepared as a 0.05% w/w in Transcutol ® HP) | 0.0105 | — |
| pH adjuster | 0.5M citric acid in Transcutol ® HP | q.s. to pH 5-6 | |
| Gelling agent | HPC (Klucel ™ HF) | 1.00 | 1.00 |
| | Total | 100.0 | 100.0 |

[1]The unit of quantity of Compound 1.003 was adjusted for water, residual solvents and assay (anhydrous basis). The values for water, residual solvents, and assay from the certificate of analysis of the API batch in use were used. Any adjustment to the amount of Compound 1.003 added was subtracted from the amount of polyethylene glycol 400;
[2]Part of the Transcutol ® HP was adjusted to compensate for the addition of the pH adjusting solution (0.5M citric acid in Transcutol ® HP) and/or the yellow #5 (0.05% w/w in Transcutol ® HP) and Brown 11452 (0.05% in Transcutol ® HP) colorant solutions. The amount of the Transcutol ® HP also includes the second addition of Transcutol ® HP (e.g., 40.50% + 4.50% by weight);
[3]The color dyes were added to the formulation during manufacture as a premixed solution, yellow #5 (0.05% w/w in Transcutol ® HP) and Brown 11452 (0.05% in Transcutol ® HP); and
Abbreviations: S.R. - super refined; HP - high purity; and Q.S. - quantum satis With reference to gel formulation (NA-1c-V2-0.5%), the content of Compound 1.003 was determined to be 0.5% by weight (with about 99.9% of label claim); microbial quality was met according to USP <61> and <062>; apparent pH was measured as about 7.05 according to USP <791>.

With reference to gel formulation (NA-1c-V2-1.5%), the content of Compound 1.003 was determined to be 1.5% by weight (with about 100.0% of label claim); microbial quality was met according to USP <61> and <062>; apparent pH was measured as about 6.55 according to USP <791>.

Separate batches of gel formulations (NA-1c-V2-0%, as a Placebo) and (NA-1c-V2-1.5%) were prepared according to the manufacturing process (FIG. 9) using the excipients of Table 30.

TABLE 30

Gel Formulations (NA-1c-V2-0%, as a Placebo) and (NA-1c-V2-1.5%)

| Function | Components | Compositions (wt/wt %) | |
| --- | --- | --- | --- |
| API | [1]Compound 1.003 | 0 (none) | 1.5 |
| Organic solvents | [1]S.R. PEG-400 | 52.80 | 51.30 |
| | [2]Transcutol ® HP | 45.00 | 45.00 |
| Antioxidant | Butylated hydroxytoluene | 0.20 | 0.20 |
| Preservative | Phenoxyethanol | 1.00 | 1.00 |
| pH adjuster | 0.5M citric acid in Transcutol ® HP | q.s. to pH 5-6 | |
| Gelling agent | HPC (Klucel ™ HF) | 1.00 | 1.00 |
| | Total | 100.0 | 100.0 |

[1]The unit of quantity of Compound 1.003 was adjusted for water, residual solvents and assay (anhydrous basis). The values for water, residual solvents, and assay from the certificate of analysis of the API batch in use were used. Any adjustment to the amount of Compound 1.003 added was subtracted from the amount of polyethylene glycol 400;
[2]Part of the Transcutol ® HP was adjusted to compensate for the addition of the pH adjusting solution (0.5M citric acid in Transcutol ® HP) and/or the yellow #5 (0.05% w/w in Transcutol ® HP) and Brown 11452 (0.05% in Transcutol ® HP) colorant solutions. The amount of the Transcutol ® HP also includes the second addition of Transcutol ® HP (e.g., 40.50% + 4.50% by weight); and
Abbreviations: S.R. - super refined; HP - high purity; and Q.S. - quantum satis With reference to gel formulation (NA-1c-V2-1.5%), the content of Compound 1.003 was determined to be 1.5% by weight (with about 98.6% of label claim); microbial quality was met according to USP <61> and <062>; apparent pH was measured as about 6.7 according to USP <791>.

Viscosity of several samples of gel formulations was measured, as shown in Table 31.

TABLE 31

Viscosity of Gel Formulations (NA-1c-V2-0%, as a Placebo) and (NA-1c-V2-1.5%)

| NA-1c-V2-0%, as a Placebo | | | NA-1c-V2-1.5%, as an active gel | | |
|---|---|---|---|---|---|
| Sample ID | Viscosity (cP) | Average (cP) | Sample ID | Viscosity | Average (cP) |
| Placebo-1-1 | 33024 | 33024 | Active-1-1 | 31744 | 31829 |
| Placebo-1-2 | 33024 | | Active-1-2 | 31744 | |
| Placebo-1-3 | 33024 | | Active-1-3 | 32000 | |
| Placebo-2-1 | 38144 | 38059 | Active-2-1 | 37120 | 37205 |
| Placebo-2-2 | 38144 | | Active-2-2 | 37120 | |
| Placebo-3-3 | 37888 | | Active-2-3 | 37376 | |
| Placebo-3-1 | 34304 | 34133 | Active-3-1 | 26880 | 26965 |
| Placebo-3-2 | 34048 | | Active-3-2 | 26880 | |
| Placebo-3-3 | 34048 | | Active-3-3 | 27136 | |
| Placebo-4-1 | 34048 | 34048 | Active-4-1 | 35328 | 35328 |
| Placebo-4-2 | 34048 | | Active-4-2 | 35328 | |
| Placebo-4-3 | 34048 | | Active-4-3 | 35328 | |
| Placebo-5-1 | 34304 | 34389 | Active-5-1 | 32768 | 32768 |
| Placebo-5-2 | 34304 | | Active-5-2 | 32768 | |
| Placebo-5-3 | 34560 | | Active-5-3 | 32768 | |
| Placebo-6-1 | 34816 | 34816 | Active-6-1 | 28672 | 28843 |
| Placebo-6-2 | 34816 | | Active-6-2 | 28928 | |
| Placebo-6-3 | 34816 | | Active-6-3 | 28928 | |
| Placebo-0% | | 34744 | Active-1.5 wt % | | 32156 |

Example 15: In Vitro Skin Permeation of Various Gel Formulations (NA-1)

The in vitro permeation and penetration was performed using 6 formulations of Table 32.

TABLE 32

Gel Formulations

| | Composition of Variant (NA-1) formulations (% w/w) | | | | | |
|---|---|---|---|---|---|---|
| Excipient | NA-1a-0.5% | NA-1a-1.5% | NA-1b-V2-0.5% | NA-1b-V2-1.5% | NA-1c-V2-0.5% | NA-1c-V2-1.5% |
| Compound 1.003 | 0.5 | 1.5 | 0.5 | 1.5 | 0.5 | 1.5 |
| S.R. PEG-400 | 53.95 | 52.95 | 53.20 | 52.20 | 52.30 | 51.30 |
| Transcutol ® HP | 45.00 | 45.00 | 45.00 | 45.00 | 45.00 | 45.00 |
| BHT | — | — | 0.20 | 0.20 | 0.20 | 0.20 |
| Potassium Sorbate | — | — | 0.10 | 0.10 | — | — |
| Phenoxyethanol | — | — | — | — | 1.00 | 1.00 |
| Ascorbyl palmitate | 0.05 | 0.05 | — | — | — | — |
| Alpha tocopherol acetate | 0.002 | 0.002 | — | — | — | — |
| HPC HF | 0.50 | 0.50 | 1.00 | 1.00 | 1.00 | 1.00 |
| 0.1M citric acid in Transcutol ® HP | | | to pH 5-6 | | | |
| Total | 100.00 | 100.00 | 100.00 | 100.00 | 100.00 | 100.00 |

In Vitro Skin Permeation and Penetration Experiment

Figure 10:
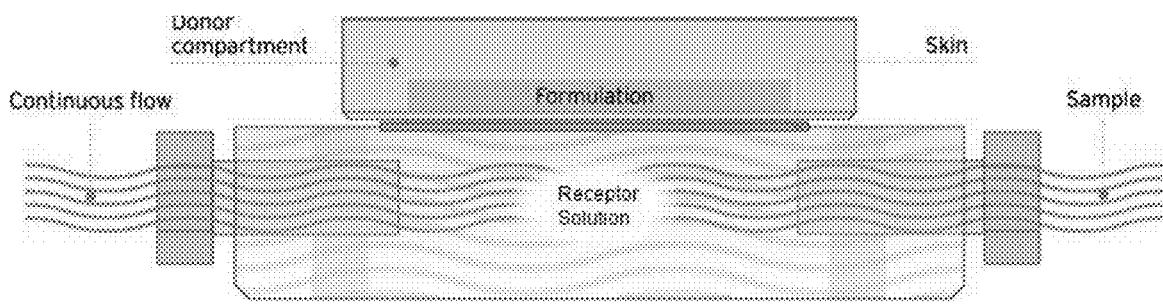
FIG. 10 shows schematic representation of flow-through cell for in vitro skin permeation and penetration experiments.

In vitro skin permeation and penetration experiments involve the use of a diffusion cell designed to mimic the physiological and anatomical conditions of skin in situ. The model used in this experiment was the flow-through cell, as described in FIG. 10, where ex vivo human skin was placed between the donor and receptor compartments.

Experimental conditions for the in vitro permeation and penetration experiments are described in Table 33. Skin tissue procedures: extraction fluid—90/10 v/v acetonitrile/water; residual drug—discarded; stratum corneum—discarded; dermis and epidermis—separated; epidermis and dermis extraction—per protocol.

TABLE 33

Experimental conditions for the in vitro permeation and penetration experiments

Figure 11A:
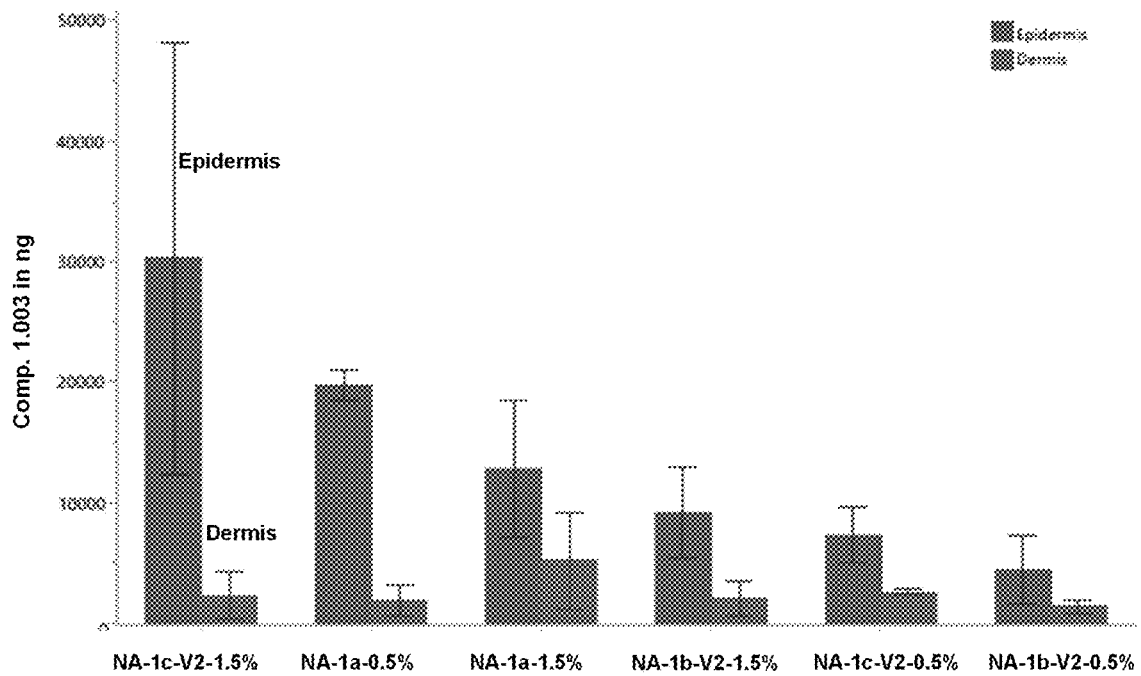
FIG. 11A-FIG. 11B show mean amounts of Compound 1.003 recovered from epidermis and dermis 24 hours following application of Six (6) formulations of Example 15. A: mean amounts of Compound 1.003 (in ng); and B: mean amounts of Compound 1.003 (in % applied dose).
Figure 11B:
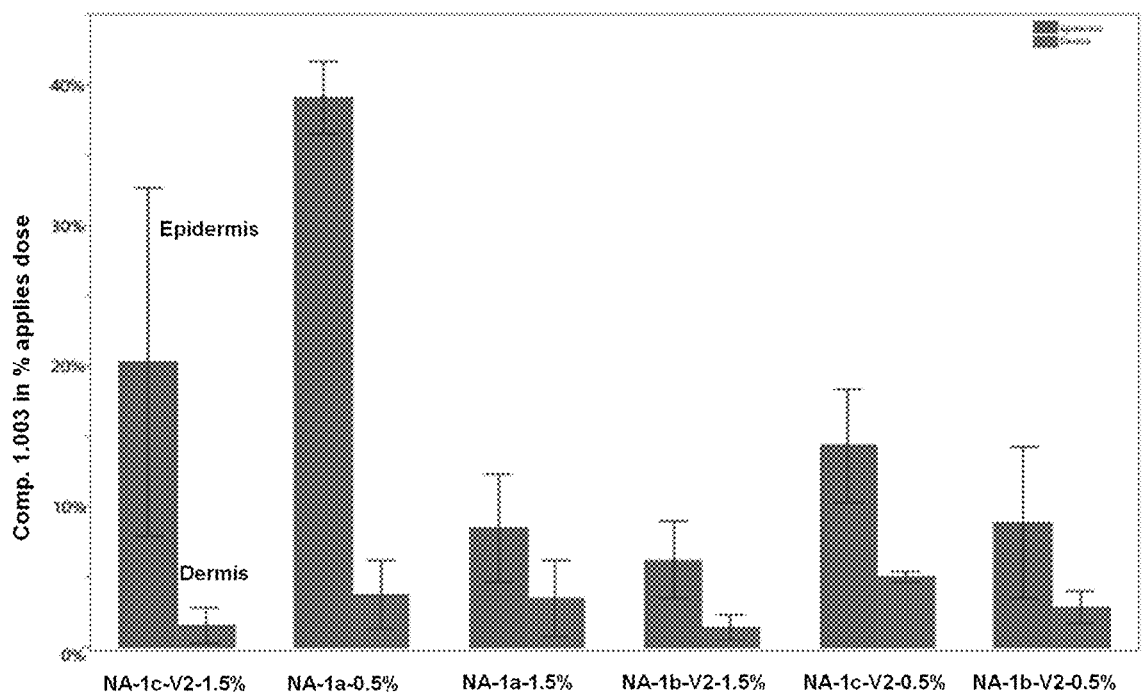

| Skin type | Human abdominal skin from elective surgery |
|---|---|
| Thickness (μm) | 500 ± 50 μm |
| No. skin donors | 1 |
| Receptor solution | Phosphate/citrate buffer pH 5.6 with 0.01% Brij ™ |
| No. formulations | 6 |
| No. replicates | n = 5 |
| No. skin blanks | 1 |
| Dose amount | 10 mg/cm$^2$ |
| MedFlux Cell Type/Flow Rate | Low velocity/6 μL/min |
| RS collection times | Every 3 hours for 24 hours | results in Table 34A. In addition, the mean percent applied dose of Compound 1.003 recovered from the epidermis and dermis is presented in FIG. 11B with corresponding results in Table 34B. Formulations are listed in rank order according to the epidermal values. Outliers removed by Dixon outlier test.

TABLE 34A

Mean amount of Compound 1.003 (ng) recovered from epidermis and dermis 24 hours following application.

| | Epidermis (ng) | | | Dermis (ng) | | |
|---|---|---|---|---|---|---|
| Formulation | n | Mean | Std Dev | n | Mean | Std Dev |
| NA-1c-V2-1.5% | 5 | 30280 | 17867 | 5 | 2314 | 1961 |
| NA-1a-0.5% | 4 | 19700 | 1268 | 5 | 1885 | 1250 |
| NA-1a-1.5% | 5 | 12784 | 5689 | 5 | 5180 | 3992 |
| NA-1b-V2-1.5% | 5 | 9178 | 3725 | 5 | 2072 | 1397 |
| NA-1c-V2-0.5% | 5 | 7358 | 2242 | 4 | 2565 | 243 |
| NA-1b-V2-0.5% | 5 | 4488 | 2838 | 5 | 1426 | 558 |

TABLE 33B

Mean amount of Compound 1.003 (% applied dose) recovered from epidermis and dermis 24 hours following application.

| | Epidermis (% applied dose) | | | Dermis (% applied dose) | | |
|---|---|---|---|---|---|---|
| Formulation | n | Mean | Std Dev | n | Mean | Std Dev |
| NA-1c-V2-1.5% | 5 | 20.3% | 12.4% | 5 | 1.5% | 1.3% |
| NA-1a-0.5% | 4 | 39.0% | 2.6% | 5 | 3.7% | 2.4% |
| NA-1a-1.5% | 5 | 8.5% | 3.9% | 5 | 3.4% | 2.7% |
| NA-1b-V2-1.5% | 5 | 6.2% | 2.7% | 5 | 1.4% | 0.9% |
| NA-1c-V2-0.5% | 5 | 14.3% | 4.0% | 4 | 5.0% | 0.4% |
| NA-1b-V2-0.5% | 5 | 8.9% | 5.4% | 5 | 2.9% | 1.2% |

Data Analysis

The concentration of Compound 1.003 detected in the receptor solution and skin layers was quantified using a calibration range optimized for the analysis of the samples generated during the ex vivo skin permeation and penetration experiments. The following parameters were calculated, where possible, for each replicate, as follows:

AUC: Cumulative amount of API permeated into the receptor solution over the duration of the experiment (ng/cm$^2$);

PF: The maximal rate of absorption, or peak flux (ng/cm$^2$/hr);

Epidermis: Total API recovered from the epidermis (ng; percent applied dose); and Dermis: Total API recovered from the dermis (in ng; percent applied dose).

Results

Penetration: The mean amount (ng) of Compound 1.003 recovered from the epidermis and dermis from the 6 formulations is presented in FIG. 11A with corresponding Epidermis: The delivery of Compound 1.003 to the epidermis was ranked as follows: NA-1c-V2-1.5%>NA-1a-0.5%>NA-1a-1.5%>NA-1b-V2-1.5%>NA-1c-V2 0.5%>NA-1b-V2-0.5%.

As expected, generally more Compound 1.003 was delivered from the 1.50% strength formulations than the 0.5% strength formulations, the exception being formulation (NA-1a-0.5%) which was second ranked overall.

Formulation (NA-1a-0.5%) delivered ca. 2.6 and 4.3 fold more Compound 1.003 to the epidermis than formulations (NA-1c-V2-0.5%) and (NA-1b-V2-0.5%) respectively ($p<0.05$). Surprisingly, formulation (NA-1a-0.5%) delivered slightly more (1.5 and 2.1 fold respectively) Compound 1.003 to the epidermis than formulations (NA-1a-1.5%) and (NA-1b-V2-1.5%) though there was no statistically significant difference ($p>0.05$). Formulation (NA-1c-V2-1.5%) delivered more Compound 1.003 to the epidermis that formulation (NA-1a-0.5%) (ca. 30,000 ng vs 20,000 ng) although this difference was not statistically significant ($p<0.05$).

When ranking by percent applied dose, formulation (NA-1a-0.5%) delivered the most Compound 1.003 to the epidermis (ca. 40%), which was significantly more than all formulations except for formulation (NA-1c-V2-1.5%) (ca. 20% of applied dose).

Dermis: There were no statistical differences noted between any of the tested formulations in delivery of Compound 1.003 to the dermis. The general trend for delivery to the dermis is ranked as follows: NA-1a-1.5%>NA-1c-V2-0.5%>NA-1c-V2-1.5%>NA-1b-V2-1.5%>NA-1a-0.5%>NA-1b-V2-0.5%. However, by percent applied dose, formulation (NA-1c-V2-0.5%) delivered more Compound 1.003 to the dermis (ca. 3-fold; $p<0.05$) compared to both formulations (NA-1b-V2-1.5%) and (NA-1c-V2-1.5%).

Permeation: The amount of Compound 1.003 which permeated across the skin into the receptor solution over 24 hours, following the application of the 6 test formulations is shown in. Formulations listed in rank order by cumulative amount. Technical outliers removed.

TABLE 35

Mean cumulative amount of Compound 1.003 ($ng/cm^2$ and % applied dose) delivered to the receptor solution after 24 hours and mean peak flux ($ng/cm^2/hr$) following application of the 6 formulations

| Formulation | Cumulative Amount Comp. 1.003 ($ng/cm^2$) | | | Peak Flux Comp. 1.003 ($ng/cm^2/hr$) | | | Comp. 1.003 (% Applied Dose) | | |
| --- | --- | --- | --- | --- | --- | --- | --- | --- | --- |
| | n | Mean | Std Dev | n | Mean | Std Dev | n | Mean | Std Dev |
| NA-1a-1.5% | 5 | 788.88 | 140.87 | 5 | 67.18 | 17.27 | 5 | 0.52% | 0.10% |
| NA-1c-V2-1.5% | 4 | 494.51 | 269.13 | 4 | 34.74 | 17.30 | 4 | 0.33% | 0.19% |
| NA-1c-V2-0.5% | 5 | 470.83 | 356.65 | 5 | 43.87 | 27.41 | 5 | 0.91% | 0.66% |
| NA-1a-0.5% | 4 | 451.12 | 285.94 | 4 | 37.69 | 12.96 | 4 | 0.89% | 0.54% |
| NA-1b-V2-0.5% | 5 | 416.15 | 194.57 | 5 | 42.47 | 15.78 | 5 | 0.83% | 0.38% |
| NA-1b-V2-1.5% | 5 | 307.43 | 201.03 | 5 | 28.86 | 20.34 | 5 | 0.21% | 0.13% |

The ranking of the formulations for delivery of Compound 1.003 to the receptor solution was as follows: NA-1a-1.5%>NA-1c-V2-1.5%>NA-1c-V2-0.5%>NA-1a-0.5%>NA-1b-V2-0.5%>NA-1b-V2-1.5%. Formulation (NA-1a-1.5%) delivered more (ca. 2.5-fold; $p<0.05$) compound 1.003 to the receptor solution after 24 hours compared to formulation (NA-1b-V2-1.5%). Similarly, formulation (NA-1a-1.5%) also had a greater peak flux (ca. 2.3-fold; $p<0.05$) compared to formulation (NA-1b-V2-1.5%). No other statistical differences were noted in either cumulative amount of Compound 1.003 delivered to the receptor solution after 24 hours nor peak flux.

Example 16: Ex Vivo Evaluation in Human Dermal Neurofibroma or Cutaneous Neurofibroma Explants Study Objectives: To determine the ability of Compound 1.003 in 0.5% and 1.5% by weight in three gel formulations (see Table 36) to penetrate human skin and suppress the MAPK pathway as measured by p-ERK suppression ex-vivo in human neurofibroma explants.

TABLE 36

Composition of Gel Formulations

| | Composition of Variant (NA-1) formulations (% w/w) | | | | | | | | |
| --- | --- | --- | --- | --- | --- | --- | --- | --- | --- |
| Excipient | NA-1a | NA-1a-0.5% | NA-1a-1.5% | NA-1b-V2 | NA-1b-V2-0.5% | NA-1b-V2-1.5% | NA-1c-V2 | NA-1c-V2-0.5% | NA-1c-V2-1.5% |
| Compound 1.003* | — | 0.5 | 1.5 | — | 0.5 | 1.5 | — | 0.5 | 1.5 |
| S.R. PEG-400 | 54.45 | 53.95 | 52.95 | 53.70 | 53.20 | 52.20 | 52.80 | 52.30 | 51.30 |
| Transcutol ® HP** | 45.00 | 45.00 | 45.00 | 45.00 | 45.00 | 45.00 | 45.00 | 45.00 | 45.00 |

TABLE 36-continued

Composition of Gel Formulations

| Excipient | Composition of Variant (NA-1) formulations (% w/w) | | | | | | | | |
|---|---|---|---|---|---|---|---|---|---|
| | NA-1a | NA-1a-0.5% | NA-1a-1.5% | NA-1b-V2 | NA-1b-V2-0.5% | NA-1b-V2-1.5% | NA-1c-V2 | NA-1c-V2-0.5% | NA-1c-V2-1.5% |
| BHT | — | — | — | 0.20 | 0.20 | 0.20 | 0.20 | 0.20 | 0.20 |
| Potassium Sorbate | — | — | — | 0.10 | 0.10 | 0.10 | — | — | — |
| Phenoxyethanol | — | — | — | — | — | — | 1.00 | 1.00 | 1.00 |
| Ascorbyl palmitate | 0.05 | 0.05 | 0.05 | — | — | — | — | — | — |
| Alpha tocopherol acetate | 0.002 | 0.002 | 0.002 | — | — | — | — | — | — |
| HPC HF | 0.50 | 0.50 | 0.50 | 1.00 | 1.00 | 1.00 | 1.00 | 1.00 | 1.00 |
| Neelicert FD&C Yellow 5 (as a 0.05% w/w solution in Transcutol ® HP) | — | — | — | 0.00815 | 0.0062 | — | 0.00815 | 0.0062 | — |
| Neelicert FD&C Brown 11452 (as a 0.05% w/w solution in Transcutol ® HP) | — | — | — | 0.0138 | 0.0105 | — | 0.0138 | 0.0105 | — |
| 0.1M citric acid in Transcutol ® HP | | | | | to pH 5-6 | | | | |
| 2nd addition of Transcutol ® HP | | | | | Q.S. 100 | | | | |

*the amount of Compound 1.003 and SR PEG 400 added was adjusted based on API purity/potency;
**part of Transcutol ® HP was adjusted to compensate the addition of the pH adjusting solutions; and Formulations (NA-1a), (NA-1b-V2), (NA-1c-V2) are Placebo formulations without compound 1.003.

Experimental Model

Biopsies of cutaneous neurofibroma were taken from patients undergoing excision of neurofibromas for clinical purposes. The ex vivo human explant model was established by incubating sections of biopsies of human cutaneous neurofibroma. Cutaneous Neurofibroma samples were removed from patients, transferred immediately to the lab in 15 ml council tubes containing 5 ml DMEM/F-12 medium (Thermo Fisher, Cat #11320033) supplemented with 1XB27 supplement (Gibco™ B-27™ Supplement (50×) serum free (Cat #17504044), 2.5 µg/ml of Amphotericin B (Thermo Fisher, Cat #15290018), and 50 units/ml of Penicillin-50 µg/ml of Streptomycin (Thermo Fisher, Cat #15070063), and 10% human serum (Gemini 100-110). Skin samples divided to smaller 3-4 mm pieces and placed dermal side down onto membranes (Transwell Permeable Supports, 12 well plate, Corning 12 mm Transwell® with 3.0 µm Pore Polycarbonate Membrane Insert, Sterile Corning #3402). The edges of the samples were sealed with semisoft 3% agarose (Sigma, CAS 9012-36-6) prepared in DMEMF-12 medium, and the apical surface was kept in contact with air to use formulations. The basal surface was in contact with the growth medium DMEMF-12 containing 10% human serum, Amphotericin B, Penicillin-Streptomycin and 1XB27. This set up enables testing of transdermal drug delivery while the tissues remain viable in the medium for the duration of the test. 3 µl of the test Compound 1.003 at 0.5% and 1.5% concentrations along vehicle only in three formulations (NA-1a), (NA-1b). and (NA-1c) (see Table 36) were applied to the surface of the cutaneous neurofibroma for analysis. Four hours after drug application, half of the samples were flash frozen in liquid nitrogen and collected for western blot analysis and half of the samples were fixed in 10% neutral buffered formalin for 24 hours then sent to Histowiz in 70% Ethanol for embedding, sectioning and IHC.

Materials and Equipment

Materials required for tissue culture included DMEM/F-12 (Thermo Fisher, Cat #11320033), Gibco™ B-27™ Supplement (50×), serum free (Thermo Fisher, Gibco Cat #17504044), Amphotericin B (Thermo Fisher, Cat #15290018), Penicillin-Streptomycin 5,000 U/mL (Thermo Fisher, Cat #15070063), Human serum (Gemini 100-110), Agarose (Sigma, CAS 9012-36-6), Transwell Permeable Supports, 12 well plate, Corning 12 mm Transwell® with 3.0 µm Pore Polycarbonate Membrane Insert, Sterile (Corning #3402), agarose (Sigma, CAS 9012-36-6).

Materials required for Western blot included: Thermo Scientific RIPA Lysis Buffer PI89901, Halt protease and phosphatase inhibitor cocktail (Thermo Fisher, PI78442), Thermo Scientific™ Pierce™ BCA Protein Assay Kit (Cat #PI23225), NuPAGE 4-12% Bis-Tris gel (Invitrogen NP0329BOX), NuPAGE MES SDS running buffer (Thermo Fisher, Cat #NP0002), iBlot 2PVDF Mini Stacks (Invitrogen, IB24002), Invitrogen NuPAGE LDS Sample Buffer (4×) 2107346, monoclonal rabbit anti-phospho-p44/42 MAPK (Erk1/2) (Thr202/Tyr204) antibody (Cell Signaling, Cat #4370L), monoclonal rabbit anti-p44/42 MAPK (Erk1/2) antibody (Cell Signaling, Cat #4695S), LI-COR IRDye 680RD Goat anti-Rabbit IgG (H+L), 0.5 mg (LI-COR Part No:926-68071), Intercept Blocking Buffer TBS (LI-COR Part No:927-60001), Intercept Antibody Diluent TBS (LI-COR Part No:927-65001, LI-COR Chameleon® Duo Pre-stained Protein Ladder, 500 µL (LI-COR Part No:928-60000).

Gel Formulations used for study are described in Table 36.

Methods

Study Designs: The ex vivo study was conducted to determine whether Compound 1.003 in the gel formulations (NA-1a), (NA-1b), and (NA-1c) would penetrate a human cutaneous lesion with dysregulation in the RAF/MEK/ERK pathway and successfully suppress elevated p-ERK. Biopsies of human cutaneous neurofibroma, which are driven by dysregulation of RAS upstream and have elevated p-ERK, were collected and immediately prepared for drug treatment as described in the Experimental Model as described above. 2.5 µl of the gel formulation containing Compound 1.003 or the corresponding formulation placebo was applied topically to the partially submerged tissue. After 4 hours incubation at 37° C. and 5% $CO_2$, part of the specimen was fixed for 24 hours in 10% formalin and then transferred to 70% ethanol for immunohistochemistry. The remaining part of the tissue was sectioned as described above and flash frozen in liquid nitrogen for Western Blot analysis.

Study Measurements and Sample Collection

Western Blot analysis: Frozen skin samples were thawed on ice and weighed. 10 volume (10 µl for each mg of tissue) of lysis buffer (RIPA buffer+0.5 mM EDTA+1× Halt protease and phosphatase inhibitor cocktail) was then added to each sample. The samples were cut into smaller pieces and homogenized with a sonicating probe on ice. The homogenized samples were centrifuged at 12,000 rpm 4° C. for 10 minutes. Supernatant was transferred to a new tube and stored at −80° C. until Western Blot analysis. The lysate protein concentration was determined by the BCA protein assay kit using bovine serum albumin (BSA) as standards. All samples were diluted with lysis buffer to reach the same final concentration. 10-20 µg of total protein was loaded to each well and separated on a NuPAGE 4-12% Bis-Tris gel in 1×NuPAGE MES SDS running buffer. Proteins were then transferred to a PVDF membrane using Invitrogen™ iBlot™ 2 Dry Blotting System. The membrane was then blocked for 1 hour in Intercept Blocking Buffer TBS (LI-COR). The following primary antibodies and dilutions were used: monoclonal rabbit anti-phospho-p44/42 MAPK (Erk1/2) (Thr202/Tyr204) antibody at 1:1000, monoclonal rabbit anti-p44/42 MAPK (Erk1/2) antibody at 1:1000. Both diluted in Intercept Antibody Diluent TBS (LI-COR). The membrane was incubated with the primary antibodies overnight at 4° C. followed by three washes with 1×TBST. Secondary antibodies goat anti-rabbit IgG (H+L), LI-COR IRDye 680RD Goat anti-Rabbit IgG (H+L) diluted in Intercept Antibody Diluent TBS (LI-COR) at 1:15000 and incubated for 1-3 hours at room temperature. After three washes with 1×TBST, the blots were developed with LI-COR Oddyssey® CLx infrared imaging system.

Immunohistochemistry: Immunohistochemistry for p-ERK was performed by HistoWiz Inc. (Brooklyn, NY) using standard operating procedures and fully automated workflow. Samples were processed, embedded in paraffin, and sectioned at 4 m. Immunohistochemistry was performed on a Bond Rx autostainer (Leica Biosystems) with enzyme treatment (1:1000) using standard protocols. Antibodies used were rabbit p-ERK (Cell Signaling, 4307S, 1:100). Bond Polymer Refine anti-rabbit HRP Detection (Leica Biosystems) was used according to manufacturer's protocol. Sections were then counterstained with hematoxylin, dehydrated and film coverslipped using a TissueTek-Prisma and Coverslipper (Sakura). Whole slide scanning (40×) was performed on an Aperio AT2 (Leica Biosystems). The images were quantified using Halo image analysis software (Indica Labs) using CytoNuclear module.

Results

Figure 12:
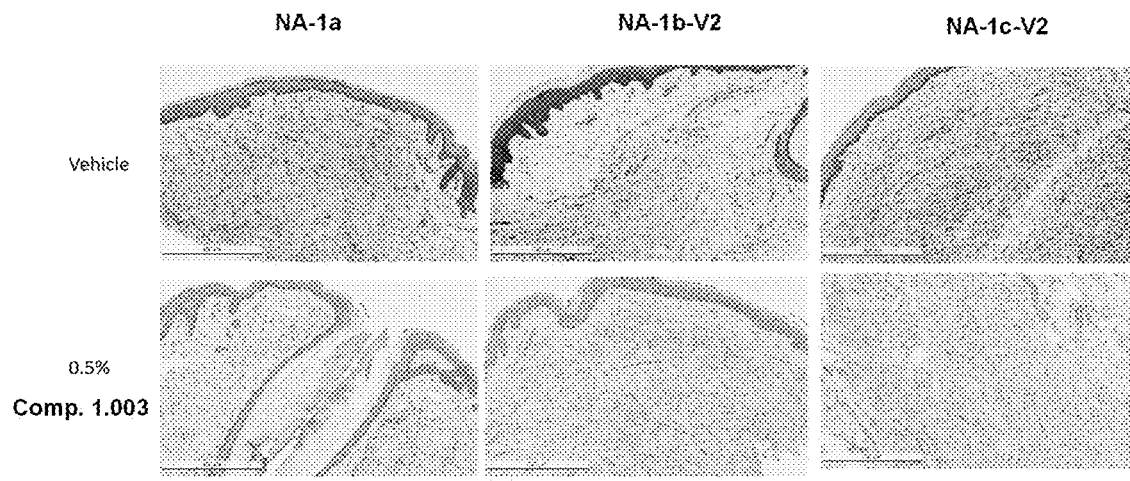
FIG. 12 shows suppression of p-ERK by Compound 1.003 in gel formulations (NA-1a), (NA-1b-V2), and (NA-1c-V2) in human cutaneous neurofibroma explants by immunohistochemistry.

Dose dependent suppression of the shared biomarker, p-ERK, by Compound 1.003 (0.5% or 1.5% by weight) in all three formulations (NA-1a), (NA-1b-V2), and (NA-1c-V2) was observed in human cutaneous neurofibroma explants as shown by immunohistochemistry (FIG. 12). p-ERK suppression was not observed in neurofibroma explants treated with the vehicle only formulations (FIG. 12).

Figure 13:
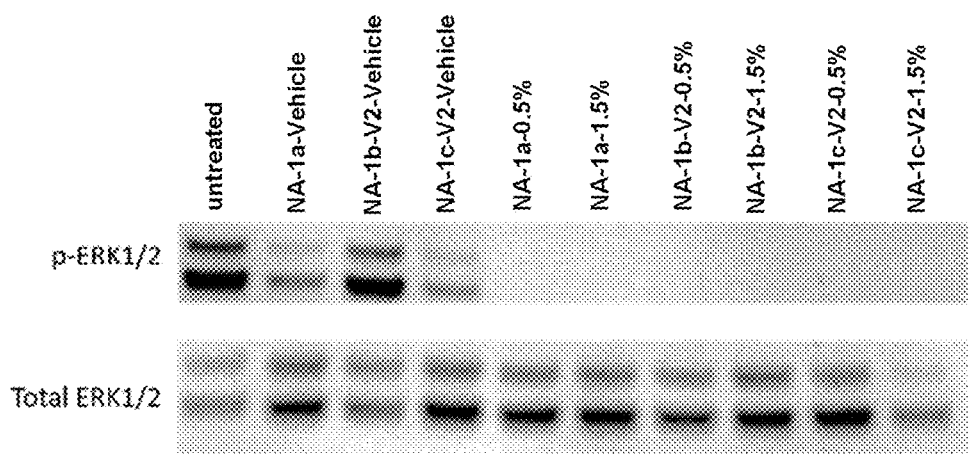
FIG. 13 shows Compound 1.003 in gel formulations (NA-1a), (NA-1b-V2), and (NA-1c-V2) penetrates human epidermis and suppresses p-ERK in human cutaneous neurofibroma explants by Western Blot analysis.

Western Blot analysis of p-ERK level showed complete suppression of p-ERK by all two dosages of Compound 1.003 in all three formulations (FIG. 13). These data clearly demonstrate that gel formulations containing Compound 1.003 (0.5%, 1.5%) (see Table 36) can penetrate human epidermis and suppress p-ERK in human cutaneous neurofibroma explants.

Example 17: Human Birthmark Explant Protocol

This study establishes an in vitro birthmark explant model.

Study Objectives: The primary objective is to assess the efficacy of a topically-formulated compound described herein in suppressing p-ERK, a downstream biomarker of RAS/MAPK signaling in epidermal nevus and nevus sebaceous. The secondary objectives is to assess permeability (where the compound was applied topically) in birthmark explants treated with a compound described herein.

Sample Collection and Eligibility: Discarded human birthmark (epidermal nevus and nevus sebaceous) samples are obtained from the Stanford Surgery Clinic, using an approved human subjects protocol (Stanford IRB #18325). Specimens are identified under the direction of the Principal Investigator and placed in cell proliferation media (DMEM/F12 containing penicillin/streptomycin (0.1%); fungizone (40 µg/mL); B27 (without vitamin A).

Patients had the following data to be enrolled in the study:
Patient must be older than 18 years of age.
Samples must be birthmarks of at least 6 mm in size
Samples will be excised by a shave, punch biopsy or elliptical excision.
Patient cannot be undergoing chemotherapy treatment at time of biopsy.

Study Procedures

Samples are primary, untreated birthmarks of at least 6 mm in size; samples are excised by a shave, punch biopsy or elliptical excision. Specimens are identified under the direction of the Principal Investigator. Specimens are chopped into 2 mm fragments and placed in 24-well plates containing cell proliferation media (DMEM/F12 containing penicillin/streptomycin (0.1%); fungizone (40 µg/mL); B27 (without vitamin A) and submerged in media with drug. For topical gel application, samples are placed in 96 well plates with epidermal surface exposed to air.

The gel gel formulation of Compound No. 1.003 or the gel formulation of vehicle only are topically applied to the surface of a birthmark explant at 4 hours for analysis. Samples are harvested at 4 hours for analysis. Harvested tissue is bisected and with half snap frozen and half fixed in 10% formalin and paraffin embedded for further analysis.

Western Blot analysis: For immunoblotting, total skin biopsies are lysed in lysis buffer and run on Western blots. Antibodies used for immunoblotting include rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 µm paraffin sections. Antigen retrieval with enzyme treatment (1:1000) using standard protocols. Antibodies used are rabbit p-ERK (Cell Signaling, 4307S, 1:100). Bond Polymer Refine anti-rabbit HRP Detection (Leica Biosystems) is used according to manufacturer's protocol. Sections are then counterstained with hematoxylin, dehydrated and film coverslipped using a TissueTek-Prisma and Coverslipper (Sakura).

Data Analysis: Semi-quantative Western blot is used to assess differences in p-ERK in samples treated with a compound described herein compared to vehicle control.

Study Management: The study is conducted with oversight from an IRB with patient informed consent and HIPAA authorization.

Example 18: Human Dermal Neurofibroma Explant Protocol

Dermal neurofibromas (or cutaneous neurofibromas) are benign tumors which develop in individuals affected with Neurofibromatosis-1 (NF1), a rare genetic disease caused by mutations in the NF1 gene, leading to downstream activation of the RAS/MAPK pathway. Recent studies have demonstrated that inhibition of MEK1 using systemic MEK inhibitors can suppress neurofibromas and other NF-1 related tumors in murine models. See, for example, *New Engl J Med* 2016, 375; 26; *J Clin Invest.* 2013, 123(1), 340-347; and *Pediatr Blood Cancer* 2015, 62(10), 1709-1716. This study establishes an in vitro neurofibroma explant model.

Study Objectives: The primary objective is to assess the efficacy of a topically-formulated compound described herein in suppressing p-ERK, a downstream biomarker of RAS/MAPK signaling in neurofibroma explants. The secondary objectives is to assess permeability (where the compound was applied topically) of neurofibroma explants treated with a compound described herein.

Sample Collection and Eligibility:

Primary dermal neurofibromas or cutaneous neurofibromas are obtained from patients with clinical or genetic diagnoses of NF1. Discarded human neurofibromas samples are obtained from the Stanford Surgery Clinic, using an approved human subjects protocol (Stanford IRB #18325). Specimens are identified under the direction of the Principal Investigator and placed in cell proliferation media (DMEM/F12 containing penicillin/streptomycin (0.1%); fungizone (40 μg/mL); B27 (without vitamin A).

Patients have the following data to be enrolled in the study: Patient is older than 18 years of age; patient is not undergoing chemotherapy treatment at time of biopsy; and patients met clinical and/or genetic diagnosis of NF1 based on presence of two of the following:

1. Six or more café-au-lait macules over 5 mm in diameter in prepubertal individuals and over 15 mm in greatest diameter in postpubertal individuals.
2. Two or more neurofibromas of any type or one plexiform neurofibroma.
3. Freckling in the axillary or inguinal regions.
4. Two or more Lisch nodules (iris hamartomas).
5. Optic glioma.
6. A distinctive osseous lesion such as sphenoid dysplasia or thinning of long bone cortex, with or without pseudarthrosis.
7. First-degree relative (parent, sibling, or offspring) with NF-1 by the above criteria.

Study Procedures

Samples are primary, untreated neurofibromas of at least 6 mm in size; samples are excised by a shave, punch biopsy or elliptical excision; samples have a histologic diagnosis of dermal neurofibroma or cutaneous neurofibroma. Specimens are identified under the direction of the Principal Investigator Specimens are chopped into 2 mm fragments and placed in 24-well plates containing cell proliferation media (DMEM/F12 containing penicillin/streptomycin (0.1%); fungizone (40 g/mL); B27 (without vitamin A) and submerged in media with drug. For topical gel application, samples are placed in 96 well plates with epidermal surface exposed to air.

Western Blot analysis: For immunoblotting, total skin biopsies are lysed in lysis buffer and run on Western blots. Antibodies used for immunoblotting include rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 μm paraffin sections. Antigen retrieval is accomplished with enzyme treatment (1:1000) using standard protocols. Antibodies used are rabbit p-ERK (Cell Signaling, 4307S, 1:100). Bond Polymer Refine anti-rabbit HRP Detection (Leica Biosystems) is used according to manufacturer's protocol. Sections are then counterstained with hematoxylin, dehydrated and film cover slipped using a TissueTek-Prisma and Coverslipper (Sakura).

Data Analysis: Semi-quantative Western blot is used to assess differences in p-ERK in samples treated with a compound described herein compared to vehicle control.

Study Management: The study is conducted with oversight from an IRB with patient informed consent and HIPAA authorization.

Example 19: Preparation of Gel Formulations Including Compound 2.003

Gel formulations including Compound 2.003 were prepared using the process similar to the manufacturing process of Example 14 and FIG. 9. Table 37 lists the components of gel formulations.

TABLE 37

Gel Formulations (NA-IIc-0.1%) and (NA-IIc-0.5%)

| Function | Components | Compositions (wt/wt %) | |
|---|---|---|---|
| API | [1]Compound 2.003 | 0.1 | 0.5 |
| Organic solvents | [1]S.R. PEG-400 | 52.70 | 52.30 |
| | [2]Transcutol ® HP | 45.00 | 45.00 |
| Antioxidant | Butylated hydroxytoluene | 0.20 | 0.20 |
| Preservative | Phenoxyethanol | 1.00 | 1.00 |
| pH adjuster | 0.5M citric acid in Transcutol ® HP | q.s. to pH 5-6 | |
| Gelling agent | HPC (Klucel ™ HF) | 1.00 | 1.00 |
| | Total | 100.0 | 100.0 |

[1]The unit of quantity of Compound 2.003 was adjusted for water, residual solvents and assay (anhydrous basis). The values for water, residual solvents, and assay from the certificate of analysis of the API batch in use were used. Any adjustment to the amount of Compound 2.003 added was subtracted from the amount of polyethylene glycol 400;
[2]Part of the Transcutol ® HP was adjusted to compensate for the addition of the pH adjusting solution (0.5M citric acid in Transcutol ® HP). The amount of the Transcutol ® HP also includes the second addition of Transcutol ® HP (e.g., 40.50% + 4.50% by weight); and
Abbreviations: S.R. - super refined; HP - high purity; and Q.S. - quantum satis

Example 20: Ex Vivo Evaluation in Cutaneous Neurofibroma Explants

The study was conducted using a protocol similar to Example 16 with some modifications as described below.

Skin samples divided to smaller 3-4 mm pieces and placed dermal side down onto membranes. The edges of the samples were sealed with semisoft 3% agarose prepared in DMEMF-12 medium, and the apical surface was kept in contact with air to use formulations. The basal surface was in contact with the growth medium DMEMF-12 containing 10% human serum, Amphotericin B, Penicillin-Streptomycin and 1XB27. This set up enables testing of transdermal drug delivery while the tissues remain viable in the medium for the duration of the test. 3 µl of the test formulation was used.

Western Blot analysis: For immunoblotting, total skin biopsies were lysed in lysis buffer and run on Western blots. The following primary antibodies and dilutions were used: monoclonal rabbit anti-phospho-p44/42 MAPK (Erk1/2) (Thr202/Tyr204) antibody at 1:1000, monoclonal rabbit anti-p44/42 MAPK (Erk1/2) antibody at 1:1000, and beta-Actin Mouse anti-Human, Mouse, Novus Biologicals Cat #NB600501 at 1:10000. All diluted in Intercept Antibody Diluent TBS (LI-COR). The membrane was incubated with the primary antibodies overnight at 4° C. followed by three washes with 1xTBST. Secondary antibodies goat anti-rabbit IgG (H+L), LI-COR IRDye 680RD Goat anti-Rabbit IgG (H+L) and LI-COR IRDye 800CW Goat anti-Mouse IgG Secondary Antibody (0.1 mg) for beta actin diluted in Intercept Antibody Diluent TBS (LI-COR) at 1:15000 and incubated for 1-3 hours at room temperature. After three washes with 1xTBST, the blots were developed with LI-COR Oddyssey® CLx infrared imaging system.

Immunohistochemistry: Immunohistochemistry for p-ERK was performed using standard operating procedures and fully automated workflow.

Six (6) gel formulations, as shown in Table 38, were evaluated in this study. 3 µl of the test formulation was used.

TABLE 38

Composition of Six Gel Formulations

| | Compositions (wt/wt %) | | | | | |
|---|---|---|---|---|---|---|
| Components Formulation ID | Vehicle-1 | 1.003-0.1% | 1.003-0.5% | Vehicle-2 | 2.003-0.1% | 2.003-0.5% |
| [1]Compound 1.003 | 0 (none) | 0.1 | 0.5 | — | — | — |
| [1]Compound 2.003 | — | — | — | 0 (none) | 0.1 | 0.5 |
| [1]S.R. PEG-400 | 52.80 | 52.70 | 52.30 | 52.80 | 52.70 | 52.30 |
| [2]Transcutol ® HP | 45.00 | 45.00 | 45.00 | 45.00 | 45.00 | 45.00 |
| Butylated hydroxytoluene | 0.20 | 0.20 | 0.20 | 0.20 | 0.20 | 0.20 |
| Phenoxyethanol | 1.00 | 1.00 | 1.00 | 1.00 | 1.00 | 1.00 |
| 0.5M citric acid in Transcutol ® HP | | | q.s. to pH 5-6 | | | |
| HPC (Klucel ™ HF) | 1.00 | 1.00 | 1.00 | 1.00 | 1.00 | 1.00 |
| Total | 100.0 | 100.0 | 100.0 | 100.0 | 100.0 | 100.0 |

Figure 14:
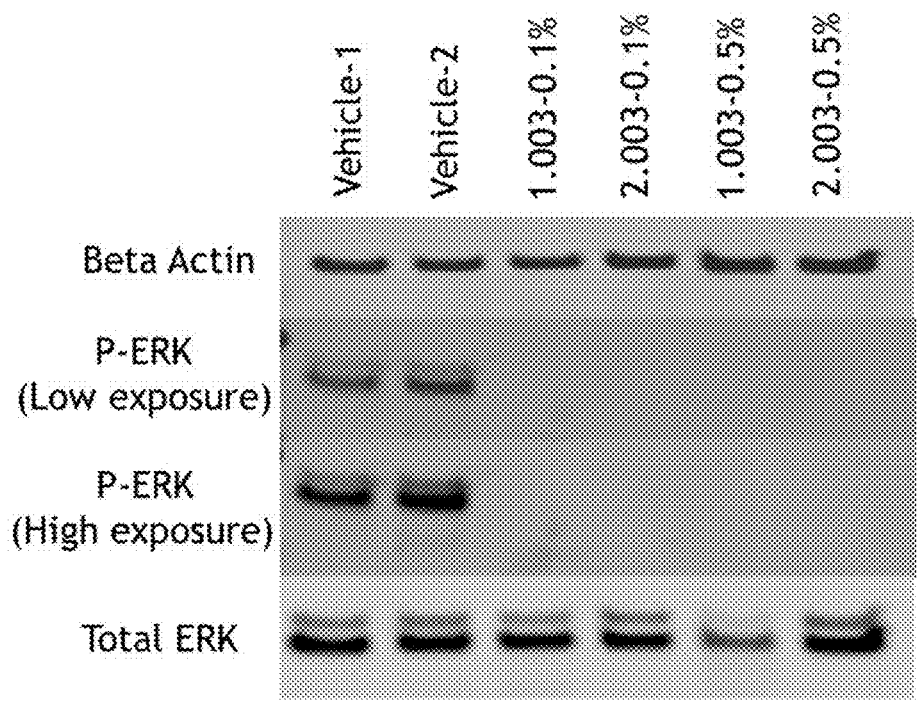
FIG. 14 shows Compounds 1.003 and 2.003 in gel formulations (1.003-0.1%), (1.003-0.5%), (2.003-0.1%), and (2.003-0.5%), respectively, penetrate human epidermis and suppress p-ERK in human cutaneous neurofibroma explants by Western Blot analysis.

[1]The amount of Compound 1.003 or 2.003 and SR PEG 400 added was adjusted based on API purity/potency;
[2]Part of the Transcutol ® HP was adjusted to compensate for the addition of the pH adjusting solution (0.5 M citric acid in Transcutol ® HP); and
Abbreviations: S.R.—super refined; HP—high purity; and Q.S.—quantum satis Results Western Blot analysis of p-ERK level showed complete suppression of p-ERK by all two dosages of Compound 1.003 and two dosage of Compound 2.003 in four formulations (1.003-0.1%), (1.003-0.5%), (2.003-0.1%), and (2.003-0.5%) (FIG. 14). p-ERK suppression was not observed in neurofibroma explants treated with the vehicle only formulations (Vehicle-1 and Vehicle-2). These data clearly demonstrate that gel formulations containing Compound 1.003 (0.1% or 0.5% by weight) and gel formulations containing Compound 2.003 (0.1% or 0.5% by weight) can penetrate human epidermis and suppress p-ERK in human cutaneous neurofibroma explants.

Figure 15:
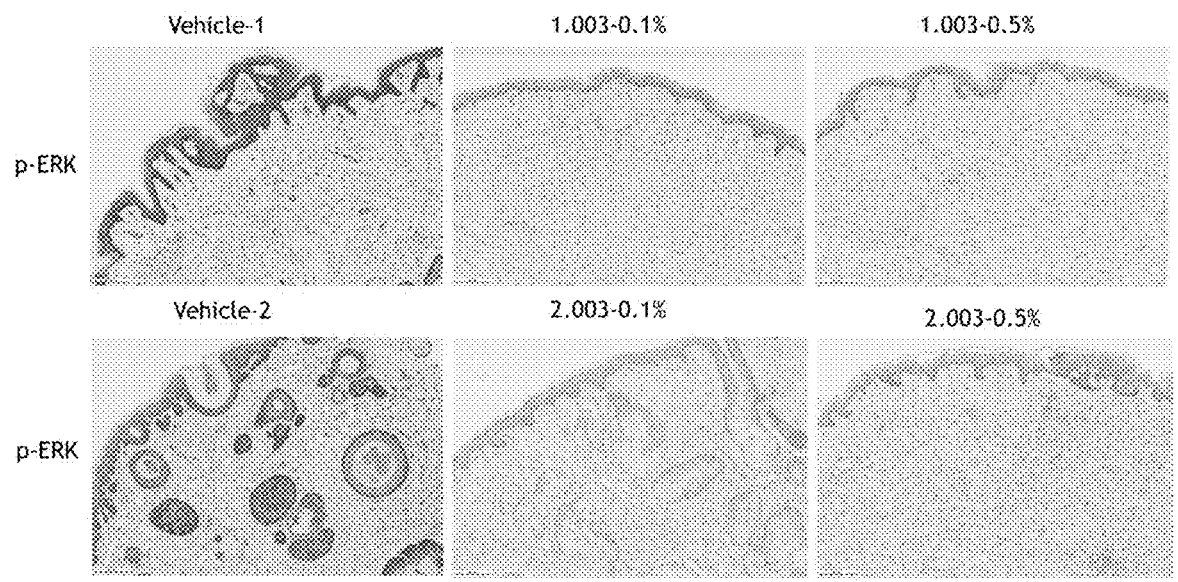
FIG. 15 shows suppression of p-ERK by Compounds 1.003 and 2.003 in gel formulations (1.003-0.1%), (1.003-0.5%), (2.003-0.1%), and (2.003-0.5%), respectively, in human cutaneous neurofibroma explants by immunohistochemistry.

Dose dependent suppression of the shared biomarker, p-ERK, by Compound 1.003 (0.1% or 0.5% by weight) and Compound 2.003 (0.1% or 0.5% by weight) in formulations was observed in human cutaneous neurofibroma explants as shown by immunohistochemistry (FIG. 15). p-ERK suppression was not observed in neurofibroma explants treated with the vehicle only formulations (Vehicle-1 and Vehicle-2).

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A gel formulation, comprising:
   a) a compound represented by formula:

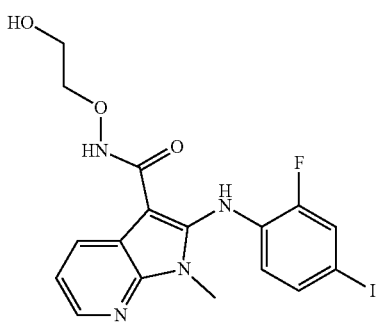 [SMILES: Cn1c(Nc2ccc(I)cc2F)c(C(=O)NOCCO)c2cccnc21]

or a pharmaceutically acceptable salt thereof;
   b) a polyethylene glycol, an antioxidant, and optionally a preservative,
   wherein
   the polyethylene glycol is PEG-400,
   the antioxidant is butylated hydroxytoluene, butylated hydroxyanisole, an ascorbyl ester, or combination thereof;
   the preservative, when present, is benzyl alcohol, phenoxyethanol, potassium sorbate, of combinations thereof;
   c) one or more organic solvents which is 2-(2-ethoxyethoxy)ethanol; and
   d) a gelling agent that is hydroxypropyl cellulose,
   wherein:
   the polyethylene glycol is present in an amount of at least about 30% by weight;
   the gelling agent has an average molecular weight of from about 80,000 Da to about 1,700,000 Da;
   the gel formulation has a pH value of no more than about 7; and
   water, when present, is no more than about 5% by weight.

2. The gel formulation of claim 1, wherein the gel formulation has a viscosity of from about 10,000 to about 200,000 cps, from about 15,000 to about 200,000 cps, from about 20,000 to about 200,000 cps, from about 25,000 to about 200,000 cps, from about 10,000 to about 100,000 cps, from about 15,000 to about 100,000 cps, from about 20,000 to about 100,000 cps, from about 25,000 to about 100,000 cps, from about 10,000 to about 50,000 cps, from about 15,000 to about 50,000 cps, from about 20,000 to about 50,000 cps, from about 25,000 to about 50,000 cps, from about 10,000 to about 40,000 cps, from about 15,000 to about 40,000 cps, from about 20,000 to about 40,000 cps, or from about 25,000 to about 40,000 cps.

3. The gel formulation of claim 2, wherein the gel formulation has a viscosity of from about 15,000 to about 50,000 cps.

4. The gel formulation of claim 1, wherein PEG-400 is present in an amount of from about 50% to about 60% by weight, based on a total weight of the formulation.

5. The gel formulation of claim 1, wherein the 2-(2-ethoxyethoxy) ethanol is present in an amount of from about 40% to about 50% by weight, based on a total weight of the formulation.

6. The gel formulation of claim 1, wherein the antioxidant is butylated hydroxytoluene in an amount of from about 0.1% to about 0.5%, from about 0.1% to about 0.4%, or from about 0.1% to about 0.3% by weight, based on a total weight of the formulation.

7. The gel formulation of claim 6, wherein butylated hydroxytoluene is present in an amount of about 0.2% by weight, based on a total weight of the formulation.

8. The gel formulation of claim 1, wherein the antioxidant is an ascorbyl ester comprising ascorbyl palmitate, which is present in an amount of from about 0.01% to about 0.1% by weight, based on a total weight of the formulation.

9. The gel formulation of claim 1, wherein the preservative, when present, is phenoxyethanol in an amount of from about 0.5% to about 5%, from about 0.5% to about 4%, from about 0.5% to about 3%, or from about 0.5% to about 2% by weight, based on a total weight of the formulation.

10. The gel formulation of claim 9, wherein phenoxyethanol is present in an amount of about 1% by weight, based on a total weight of the formulation.

11. The gel formulation of claim 1, wherein the preservative, when present, is potassium sorbate in an amount of from about 0.05% to about 0.5%, from about 0.05% to about 0.4%, from about 0.05% to about 0.3%, or from about 0.05% to about 0.2% by weight, based on a total weight of the formulation.

12. The gel formulation of claim 11, wherein potassium sorbate is present in an amount of about 0.1% by weight, based on a total weight of the formulation.

13. The gel formulation of claim 1, wherein PEG-400 is a super refined PEG-400; and/or 2-(2-ethoxyethoxy) ethanol has a purity of greater than about 99.90%.

14. The gel formulation of claim 1, wherein the hydroxypropyl cellulose has an average molecular weight of from about 850,000 Da to about 1,150,000 Da.

15. The gel formulation of claim 1, wherein the hydroxypropyl cellulose has an average molecular weight of about 1,150,000 Da and is present in an amount of from about 0.5% to about 2% by weight, based on a total weight of the formulation.

16. The gel formulation of claim 1, wherein the compound of formula (Ib) is present in an amount of from about 0.1% to about 3% by weight, based on a total weight of the formulation.

17. A gel formulation, comprising:
a) a compound represented by the formula:

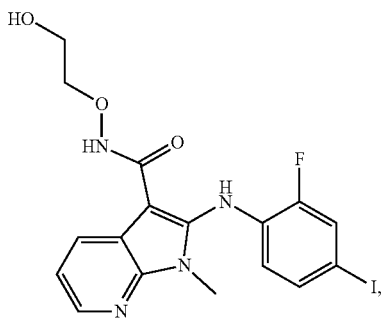 [SMILES: Cn1c(Nc2ccc(I)cc2F)c(C(=O)NOCCO)c2cccnc21]

or a pharmaceutically acceptable salt thereof;
b) PEG-400, 2-(2-ethoxyethoxy) ethanol, butylated hydroxytoluene, and potassium sorbate; and
c) a hydroxypropyl cellulose having an average molecular weight of from about 850,000 Da to about 1,150,000 Da,
wherein the gel formulation has a pH value of no more than about 7.

18. A gel formulation, comprising:
a) a compound represented by the formula:

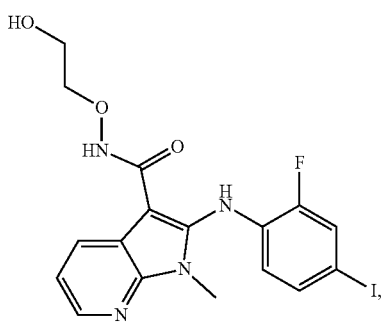 [SMILES: Cn1c(Nc2ccc(I)cc2F)c(C(=O)NOCCO)c2cccnc21]

or a pharmaceutically acceptable salt thereof,
b) PEG-400, 2-(2-ethoxyethoxy) ethanol, butylated hydroxytoluene, and phenoxyethanol; and
c) a hydroxypropyl cellulose having an average molecular weight of from about 850,000 Da to about 1,150,000 Da,
wherein the gel formulation has a pH value of no more than about 7.

19. The gel formulation of claim 18, wherein the gel formulation has a viscosity of from about 15,000 to about 50,000 cps.

20. The gel formulation of claim 17, comprising:
a) about 0.5% by weight of the compound;
b) from about 50% to about 55% by weight of the PEG-400;
c) about 45% by weight of the 2-(2-ethoxyethoxy) ethanol;
d) about 0.2% by weight of the butylated hydroxytoluene;
e) about 0.1% by weight of the potassium sorbate;
f) from about 0.5% to about 2% by weight of the hydroxypropyl cellulose having an average molecular weight of about 1,150,000 Da; and
g) citric acid, and
h) optionally from about 0.001% to about 0.05% by weight of one or more dyes, wherein the total weight of a) to h) is 100%; and the citric acid is a solution in the PEG-400 or the 2-(2-ethoxyethoxy) ethanol to adjust a pH.

21. The gel formulation of claim 17, comprising:
a) about 1.5% by weight of the compound;
b) from about 50% to about 53% by weight of the PEG-400;
c) about 45% by weight of the 2-(2-ethoxyethoxy) ethanol;
d) about 0.2% by weight of the butylated hydroxytoluene;
e) about 0.1% by weight of the potassium sorbate;
f) from about 0.5% to about 2% by weight of the hydroxypropyl cellulose having an average molecular weight of about 1,150,000 Da; and
g) citric acid,
wherein the total weight of a) to g) is 100%; and the citric acid is a solution in the PEG-400 or the 2-(2-ethoxyethoxy) ethanol to adjust a pH.

22. The gel formulation of claim 18, comprising:
a) from about 0.005% to about 3% by weight of the compound;
b) from about 50% to about 55% by weight of the PEG-400;
c) from about 40% to about 50% by weight of the 2-(2-ethoxyethoxy) ethanol;
d) from about 0.1% to about 0.3% by weight of the butylated hydroxytoluene;
e) from about 0.5% to about 2% by weight of the phenoxyethanol;
f) optionally from about 1% to about 3% PEG-1500;
g) from about 0.5% to about 2% by weight of the hydroxypropyl cellulose having an average molecular weight of about 1,150,000 Da;
h) citric acid; and
i) optionally from about 0.001% to about 0.05% by weight of one or more dyes,
wherein the total weight of a) to i) is 100%; and the citric acid is a solution in the PEG-400 or the 2-(2-ethoxyethoxy) ethanol to adjust a pH.

23. The gel formulation of claim 18, comprising:
a) about 0.5% by weight of the compound;
b) about 52% by weight of the PEG-400;
c) about 45% by weight of the 2-(2-ethoxyethoxy) ethanol;
d) about 0.2% by weight of the butylated hydroxytoluene;
e) about 1% by weight of the phenoxyethanol;
f) about 1% by weight of the hydroxypropyl cellulose having an average molecular weight of about 1,150,000 Da;
g) citric acid; and
h) optionally about 0.02% by weight of one or more dyes, wherein the total weight of a) to h) is 100%; and the citric acid is a solution in the PEG-400 or the 2-(2-ethoxyethoxy) ethanol to adjust a pH.

24. The gel formulation of claim 18, comprising:
a) about 1.5% by weight of the compound;
b) about 51% by weight of the PEG-400;
c) about 45% by weight of the 2-(2-ethoxyethoxy) ethanol;
d) about 0.2% by weight of the butylated hydroxytoluene;
e) about 1% by weight of the phenoxyethanol;
f) about 1% by weight of the hydroxypropyl cellulose having an average molecular weight of about 1,150,000 Da; and
g) citric acid,
wherein the total weight of a) to g) is 100%; and the citric acid is a solution in the PEG-400 or the 2-(2-ethoxyethoxy) ethanol to adjust a pH.

25. A method of treating a skin disorder comprising administering a gel formulation of claim 1, wherein the skin disorder is a MEK-inhibitor responsive dermal disorder or a MEK-mediated dermal disorder, a birthmark, or a skin cancer.

* * * * *